(12) United States Patent
Walsh et al.

(10) Patent No.: US 11,173,042 B2
(45) Date of Patent: Nov. 16, 2021

(54) SPINAL SURGERY DEVICES, SYSTEMS, AND METHODS

(71) Applicant: GetSet Surgical SA, Epalinges (CH)

(72) Inventors: David Walsh, Reading, MA (US); Ole Stoklund, Lausanne (CH); John Kapitan, Leicester, NC (US)

(73) Assignee: GETSET SURGICAL SA

( * ) Notice: Subject to any disclaimer, the term of this patent is extended or adjusted under 35 U.S.C. 154(b) by 26 days.

(21) Appl. No.: 16/695,952

(22) Filed: Nov. 26, 2019

(65) Prior Publication Data

US 2021/0154022 A1     May 27, 2021

(51) Int. Cl.
    *A61F 2/44*          (2006.01)
    *A61F 2/30*          (2006.01)

(52) U.S. Cl.
    CPC .......... *A61F 2/447* (2013.01); *A61F 2/30749* (2013.01); *A61F 2/442* (2013.01); *A61F 2002/30405* (2013.01); *A61F 2002/30507* (2013.01)

(58) Field of Classification Search
    CPC .......... A61F 2/44; A61F 2/442; A61F 2/4455; A61F 2/446; A61F 2/4465; A61F 2/447; A61F 2/46; A61F 2/4603; A61F 2/4611
    See application file for complete search history.

(56) References Cited

U.S. PATENT DOCUMENTS 2,796,101 A    6/1957   Hasemann
5,364,399 A    11/1994   Lowery et al.
5,423,826 A    6/1995   Coates et al.
5,549,612 A    8/1996   Yapp et al.
5,951,558 A    9/1999   Fiz
(Continued)

FOREIGN PATENT DOCUMENTS

EP      2391308 B1    12/2015
EP      2688520 B1    9/2017
(Continued)

OTHER PUBLICATIONS

International Search Report and Written Opinion dated Mar. 1, 2021 for corresponding International Application No. PCT/US2020/062421.
(Continued)

*Primary Examiner* — Eric S Gibson
(74) *Attorney, Agent, or Firm* — David Meibos; Maywood IP Law

(57) ABSTRACT

An intervertebral spacer may include a fastener channel configured to receive a fastener, a locking member channel, and a locking member. The locking member channel may include an inner wall and one or more inner wall engagement features. The locking member may include an anti-backout member, a collet retainable within the locking member channel, and one or more collet engagement features. The locking member may be rotatable within the locking member channel between an unlocked position and a locked position. The one or more collet engagement features may engage the one or more inner wall engagement features in order to retain the locking member in either the unlocked position or the locked position, such that the anti-backout member may selectively obstruct the fastener channel and prevent the fastener from backing out of the fastener channel.

19 Claims, 108 Drawing Sheets

(56) References Cited

U.S. PATENT DOCUMENTS

| | | | |
|---|---|---|---|
| 6,152,927 A | 11/2000 | Farris et al. | |
| 6,193,721 B1 | 2/2001 | Michelson | |
| 6,306,139 B1 | 10/2001 | Fuentes | |
| 6,383,186 B1 | 5/2002 | Michelson | |
| 6,428,542 B1 | 8/2002 | Michelson | |
| 6,558,432 B2 | 5/2003 | Schulte et al. | |
| 6,730,127 B2 | 5/2004 | Michelson | |
| 6,884,242 B2 | 4/2005 | LeHuec et al. | |
| 6,890,335 B2 | 5/2005 | Grabowski et al. | |
| 7,288,094 B2 | 10/2007 | Lindemann et al. | |
| 7,651,497 B2 | 1/2010 | Michelson | |
| 7,674,279 B2* | 3/2010 | Johnson | A61B 17/8042 |
| | | | 606/295 |
| 7,833,226 B2 | 11/2010 | Grabowski et al. | |
| 7,875,062 B2* | 1/2011 | Lindemann | A61B 17/8042 |
| | | | 606/295 |
| 7,901,413 B1 | 3/2011 | Lewis | |
| 7,998,180 B2 | 8/2011 | Erickson et al. | |
| 8,048,075 B2 | 11/2011 | Michelson | |
| 8,066,750 B2 | 11/2011 | Oi et al. | |
| 8,211,148 B2 | 7/2012 | Zhang et al. | |
| 8,216,285 B2 | 7/2012 | Markworth | |
| 8,246,660 B2 | 8/2012 | Boris et al. | |
| 8,262,705 B2 | 9/2012 | Bray | |
| 8,277,493 B2 | 10/2012 | Farris et al. | |
| 8,328,872 B2* | 12/2012 | Duffield | A61F 2/44 |
| | | | 623/17.16 |
| 8,348,982 B2 | 1/2013 | Baynham et al. | |
| 8,419,795 B2 | 4/2013 | Sweeney | |
| 8,439,593 B2 | 5/2013 | Slater et al. | |
| 8,480,717 B2 | 7/2013 | Michelson | |
| 8,523,920 B2 | 9/2013 | Gause et al. | |
| 8,562,655 B2 | 10/2013 | Butler | |
| 8,591,556 B2 | 11/2013 | Hansell et al. | |
| 8,613,761 B2 | 12/2013 | Lindemann et al. | |
| 8,617,222 B2 | 12/2013 | Shipp et al. | |
| 8,672,984 B2 | 3/2014 | Lindemann et al. | |
| 8,696,721 B2 | 4/2014 | Blain | |
| 8,795,341 B2 | 8/2014 | Walker et al. | |
| 8,795,373 B2* | 8/2014 | Jones | A61B 17/8042 |
| | | | 623/17.16 |
| 8,858,603 B1 | 10/2014 | Zufelt | |
| 8,858,604 B2 | 10/2014 | Biyani et al. | |
| 8,882,843 B2 | 11/2014 | Michelson | |
| 8,932,335 B2 | 1/2015 | Humphreys | |
| 8,940,030 B1 | 1/2015 | Stein et al. | |
| 8,979,910 B2 | 3/2015 | Stanaford et al. | |
| 9,005,288 B2 | 4/2015 | McCormack et al. | |
| 9,005,293 B2 | 4/2015 | Moskowitz et al. | |
| 9,017,412 B2* | 4/2015 | Wolters | A61F 2/442 |
| | | | 623/17.16 |
| 9,028,498 B2 | 5/2015 | Hershgold et al. | |
| 9,107,710 B1 | 8/2015 | Swann | |
| 9,114,023 B2 | 8/2015 | Kana et al. | |
| 9,119,682 B2 | 9/2015 | Stoll et al. | |
| 9,155,572 B2 | 10/2015 | Altarac et al. | |
| 9,179,952 B2 | 11/2015 | Biedermann et al. | |
| 9,180,020 B2 | 11/2015 | Gause et al. | |
| 9,186,189 B2 | 11/2015 | Campbell et al. | |
| 9,220,548 B2 | 12/2015 | Duong et al. | |
| 9,241,749 B2 | 1/2016 | Lombardo et al. | |
| 9,265,546 B2 | 2/2016 | Blain | |
| 9,277,943 B2 | 3/2016 | Holly et al. | |
| 9,326,803 B2 | 5/2016 | Humphreys | |
| 9,351,768 B2 | 5/2016 | Rinner et al. | |
| 9,364,340 B2* | 6/2016 | Lawson | A61F 2/4455 |
| 9,381,093 B1 | 7/2016 | Morris et al. | |
| 9,402,735 B2 | 8/2016 | McDonough et al. | |
| 9,414,935 B2 | 8/2016 | McDonough et al. | |
| 9,421,055 B2 | 8/2016 | Suh | |
| 9,445,851 B2 | 9/2016 | Walker et al. | |
| 9,451,951 B2 | 9/2016 | Sullivan et al. | |
| 9,468,534 B2 | 10/2016 | Garber et al. | |
| 9,622,875 B2 | 4/2017 | Moskowitz et al. | |
| 9,744,052 B2 | 8/2017 | Moskowitz et al. | |
| 9,814,601 B2 | 11/2017 | Moskowitz et al. | |
| 9,826,973 B2 | 11/2017 | Graul et al. | |
| 9,867,719 B2 | 1/2018 | Moskowitz et al. | |
| 9,889,022 B2 | 2/2018 | Moskowitz et al. | |
| 9,937,060 B2 | 4/2018 | Fuhrer et al. | |
| 9,980,826 B2* | 5/2018 | Martynova | A61F 2/442 |
| 2004/0133280 A1 | 7/2004 | Trieu | |
| 2006/0293668 A1 | 12/2006 | May et al. | |
| 2007/0123995 A1 | 5/2007 | Thelen et al. | |
| 2008/0033440 A1 | 2/2008 | Moskowitz et al. | |
| 2010/0016901 A1 | 1/2010 | Robinson | |
| 2010/0057206 A1* | 3/2010 | Duffield | A61F 2/30771 |
| | | | 623/17.16 |
| 2010/0292696 A1 | 11/2010 | Chantelot et al. | |
| 2012/0071933 A1 | 3/2012 | DeRidder | |
| 2012/0150301 A1 | 6/2012 | Gamache et al. | |
| 2012/0158068 A1 | 6/2012 | Humphreys | |
| 2012/0277803 A1 | 11/2012 | Remesh et al. | |
| 2013/0197588 A1 | 8/2013 | Abdou | |
| 2014/0000123 A1 | 1/2014 | Kana et al. | |
| 2014/0046377 A1 | 2/2014 | Hansell et al. | |
| 2014/0180422 A1* | 6/2014 | Klimek | A61F 2/30744 |
| | | | 623/17.16 |
| 2014/0214081 A1 | 7/2014 | Schwab et al. | |
| 2014/0257487 A1* | 9/2014 | Lawson | A61B 17/8042 |
| | | | 623/17.16 |
| 2014/0288655 A1 | 9/2014 | Parry et al. | |
| 2014/0336770 A1* | 11/2014 | Petersheim | A61F 2/447 |
| | | | 623/17.16 |
| 2014/0371859 A1* | 12/2014 | Petersheim | A61F 2/447 |
| | | | 623/17.16 |
| 2015/0025635 A1 | 1/2015 | Laubert | |
| 2015/0066096 A1 | 3/2015 | Bush, Jr. et al. | |
| 2015/0201982 A1 | 7/2015 | Altarac et al. | |
| 2016/0022335 A1 | 1/2016 | Humphreys | |
| 2016/0038309 A1 | 2/2016 | Doyle | |
| 2016/0128737 A1 | 5/2016 | Conic et al. | |
| 2016/0128746 A1 | 5/2016 | Dunaway | |
| 2016/0151171 A1* | 6/2016 | Mozeleski | A61B 17/7059 |
| | | | 623/17.16 |
| 2016/0166396 A1 | 6/2016 | McClintock | |
| 2016/0213410 A1 | 7/2016 | Humphreys | |
| 2016/0220388 A1 | 8/2016 | Flores et al. | |
| 2016/0228156 A1 | 8/2016 | Morris et al. | |
| 2016/0228165 A1 | 8/2016 | Walker et al. | |
| 2016/0235448 A1 | 8/2016 | Seex | |
| 2016/0250037 A1* | 9/2016 | Duffield | A61B 17/8042 |
| | | | 623/17.16 |
| 2016/0270832 A1 | 9/2016 | Bush, Jr. et al. | |
| 2016/0310295 A1* | 10/2016 | Reed | A61F 2/4611 |
| 2016/0324554 A1 | 11/2016 | Suh | |
| 2017/0049579 A1 | 2/2017 | Quinlan et al. | |
| 2017/0189204 A1 | 7/2017 | Riemhofer et al. | |
| 2018/0049756 A1 | 2/2018 | Livorsi et al. | |
| 2018/0055651 A1 | 3/2018 | Moskowitz et al. | |
| 2018/0318099 A1* | 11/2018 | Altarac | A61F 2/4455 |
| 2018/0318100 A1 | 11/2018 | Altarac et al. | |
| 2019/0133778 A1 | 5/2019 | Johnston | |

FOREIGN PATENT DOCUMENTS

| | | |
|---|---|---|
| JP | 2016524988 A | 8/2016 |
| WO | WO2007136452 A3 | 7/2008 |
| WO | WO2010054181 | 5/2010 |
| WO | WO2010078488 A2 | 7/2010 |
| WO | WO2013098828 A1 | 7/2013 |
| WO | WO2014094551 A1 | 6/2014 |
| WO | WO2015025108 A1 | 2/2015 |
| WO | WO2015051119 A1 | 4/2015 |

OTHER PUBLICATIONS

International Search Report and Written Opinion dated Apr. 6, 2021 for corresponding International Application No. PCT/US2020/062422.

(56) References Cited

OTHER PUBLICATIONS

International Search Report and Written Opinion dated Mar. 3, 2021 for corresponding International Application No. PCT/US2020/062424.

* cited by examiner

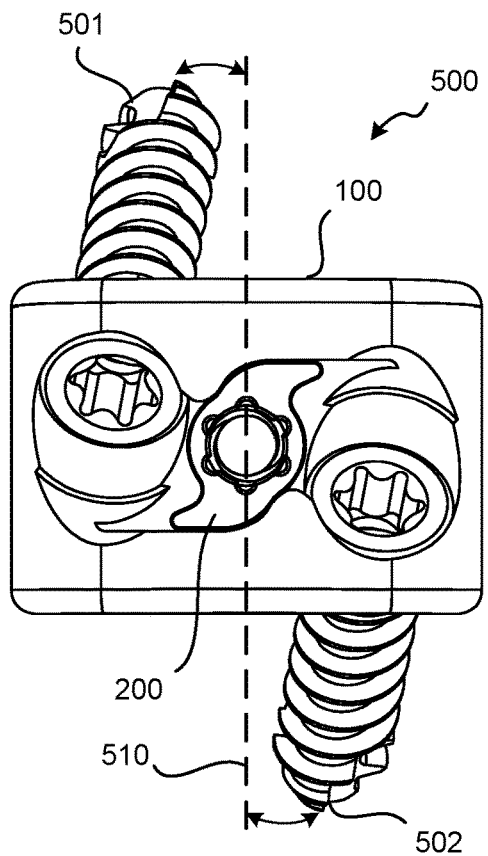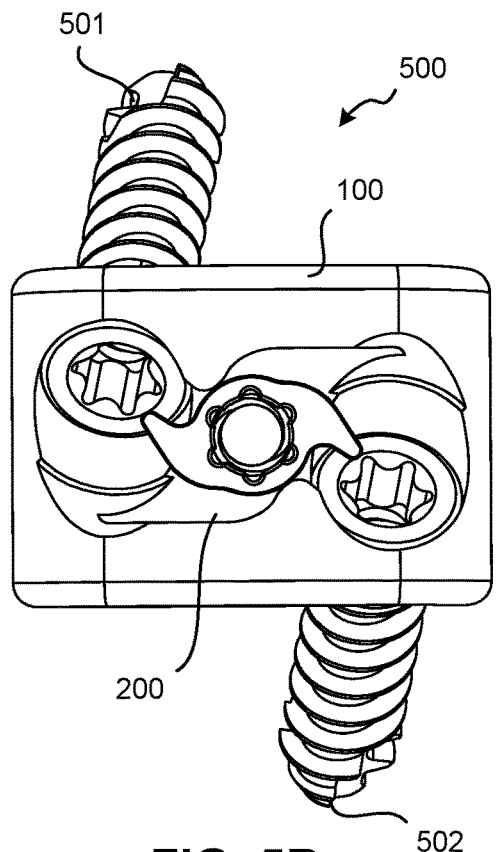
FIG. 5A  FIG. 5B
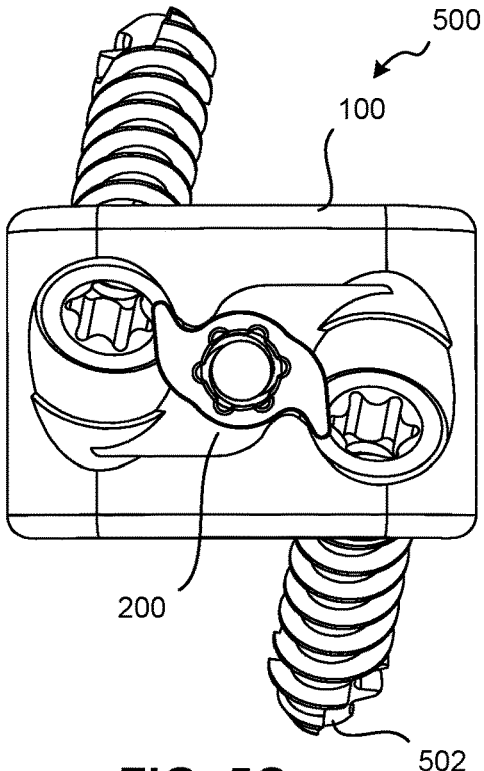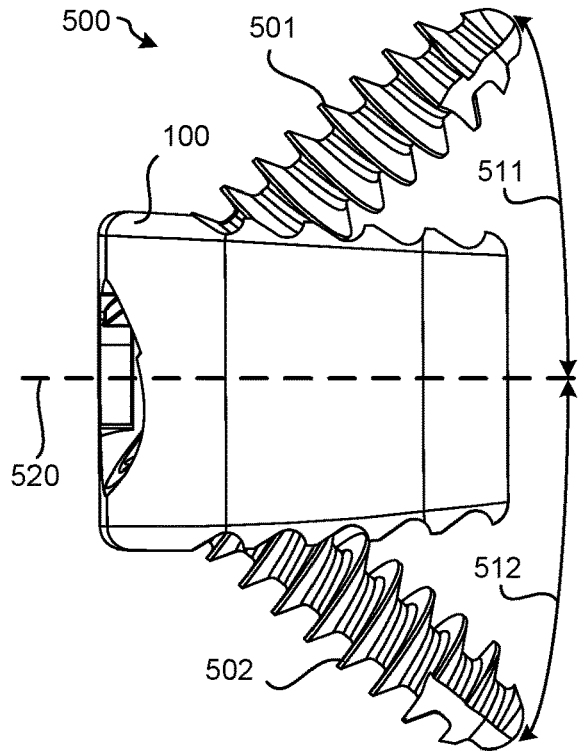
FIG. 5C  FIG. 5D

1300

1300

1400

1400

1500

1500

1800

1800

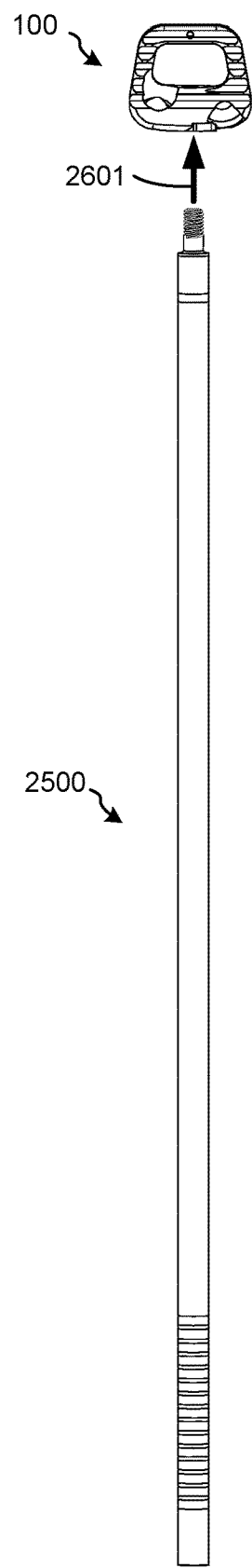 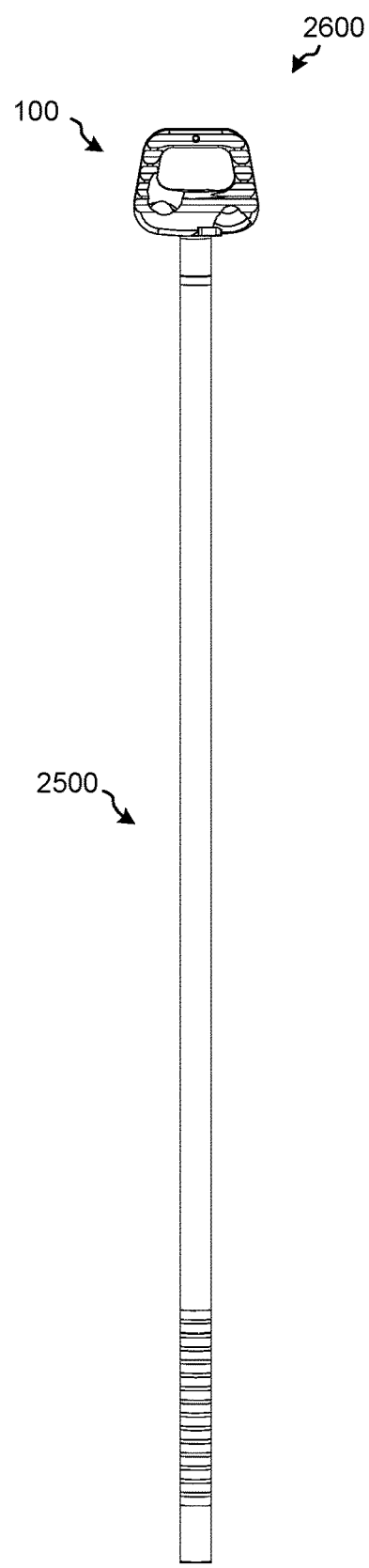
FIG. 26A  FIG. 26B

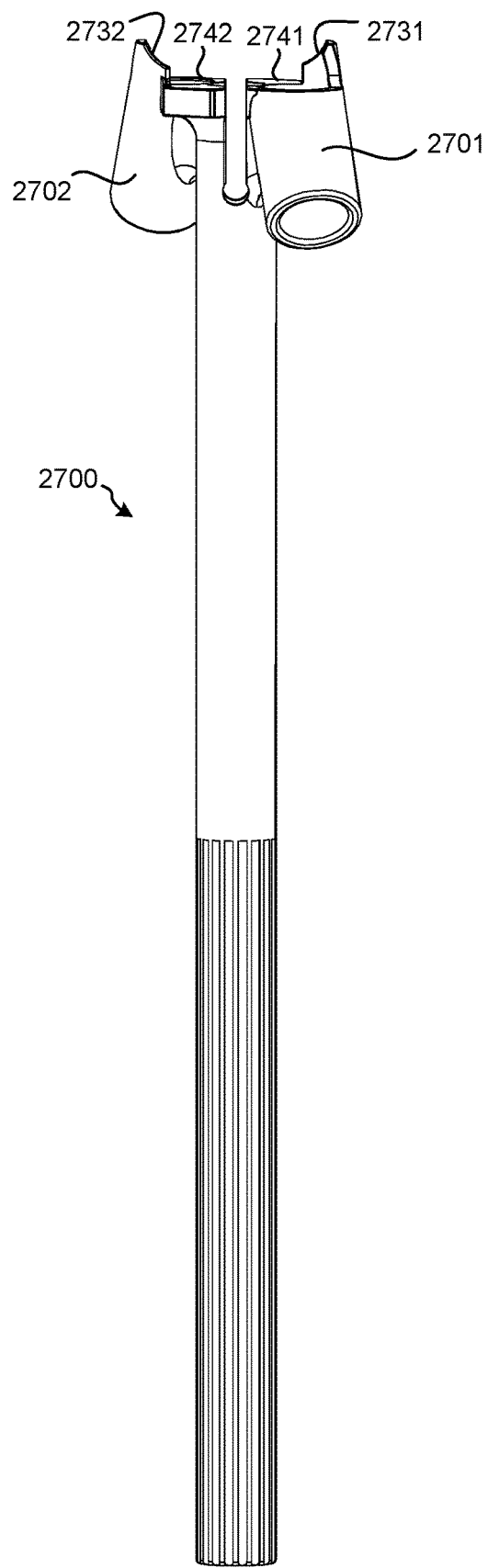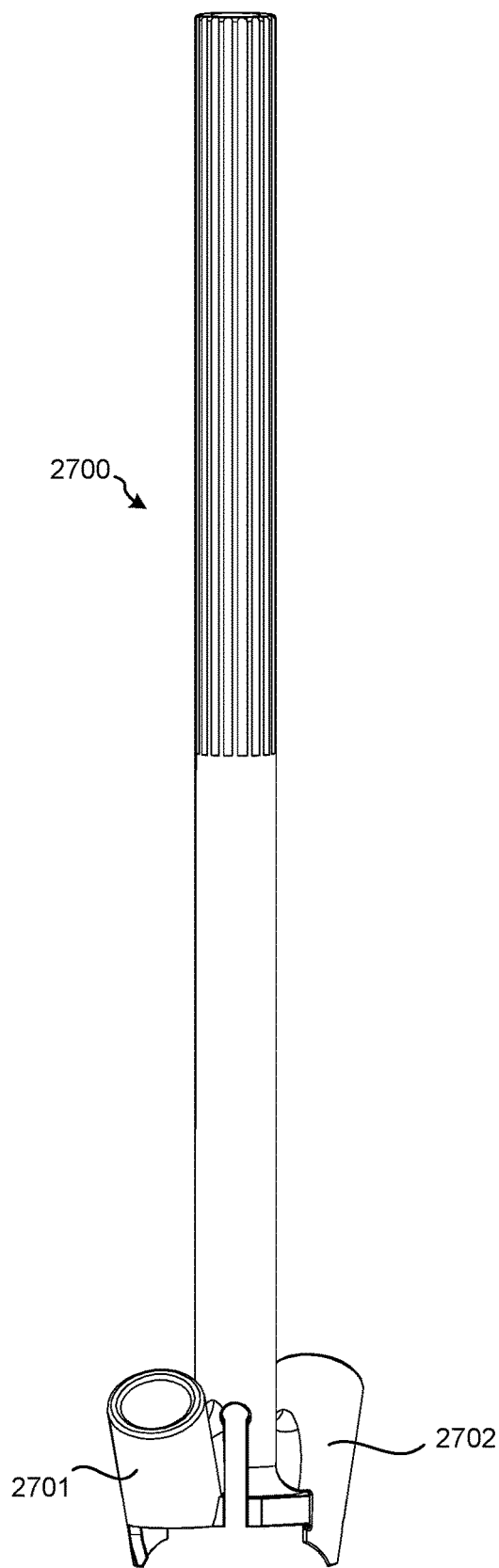
FIG. 27C  FIG. 27D

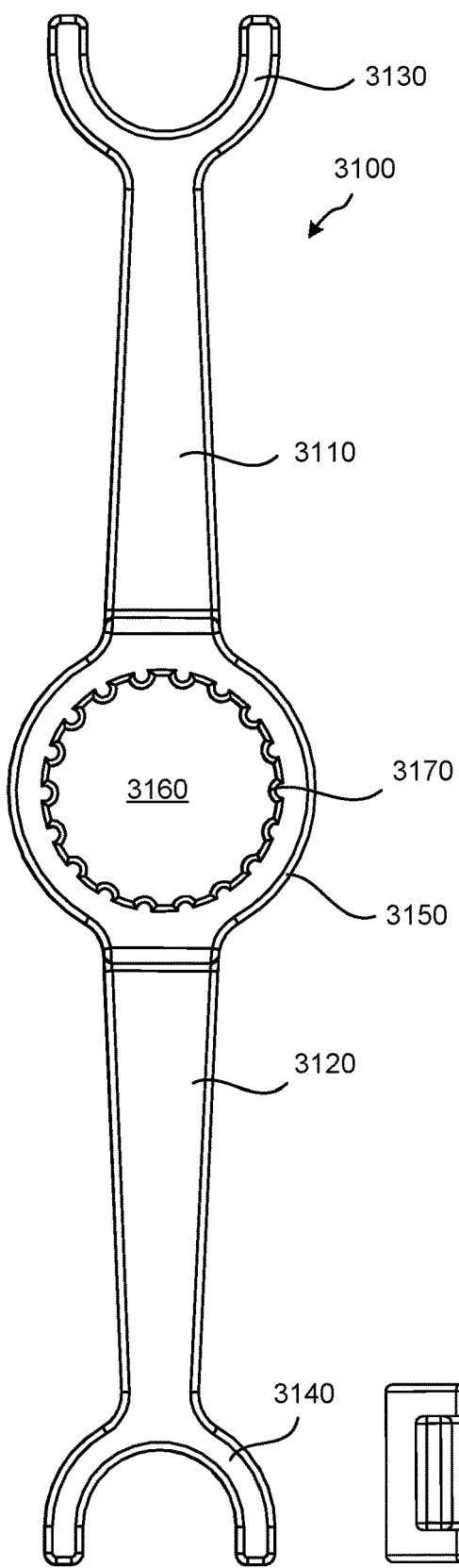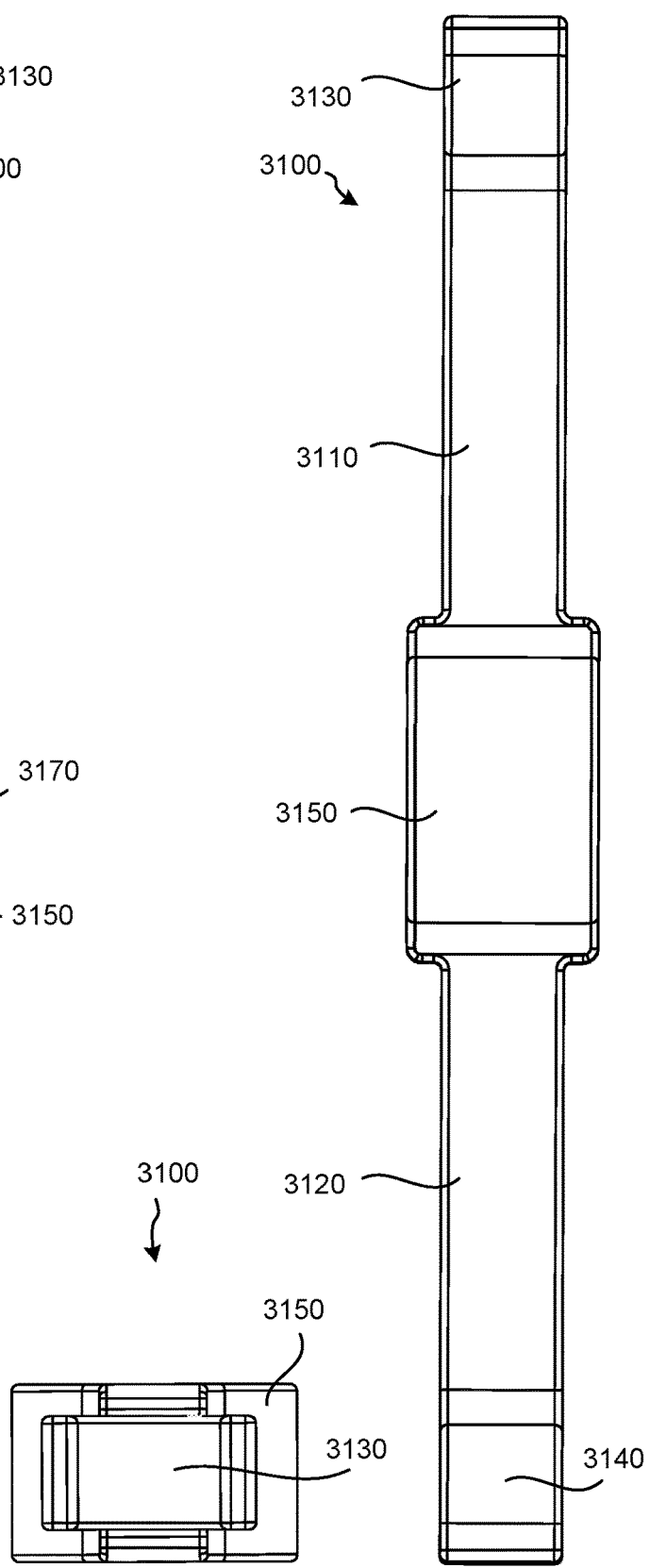
FIG. 31B   FIG. 31C   FIG. 31D

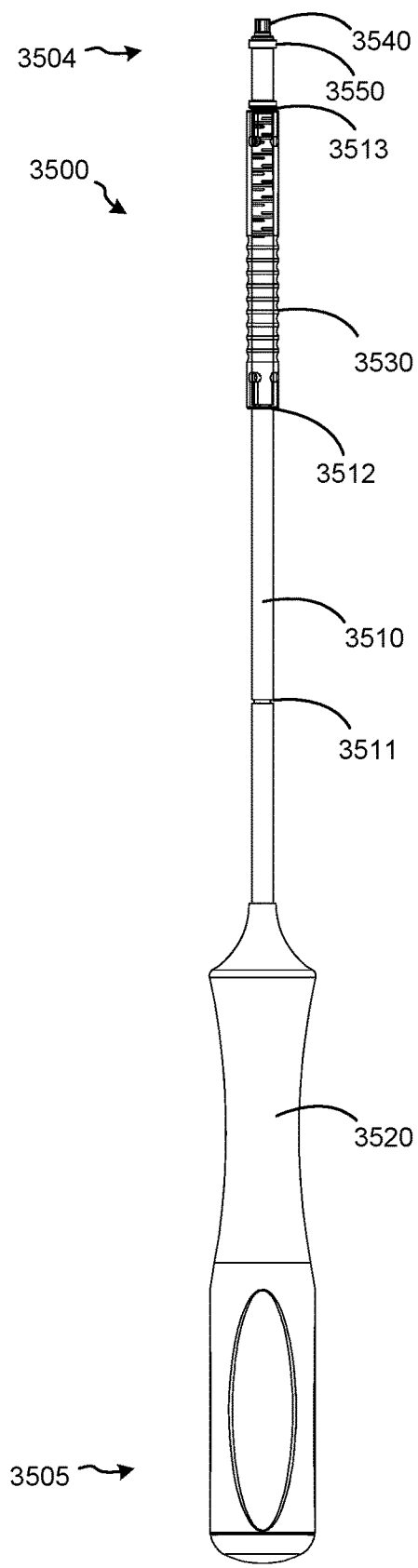
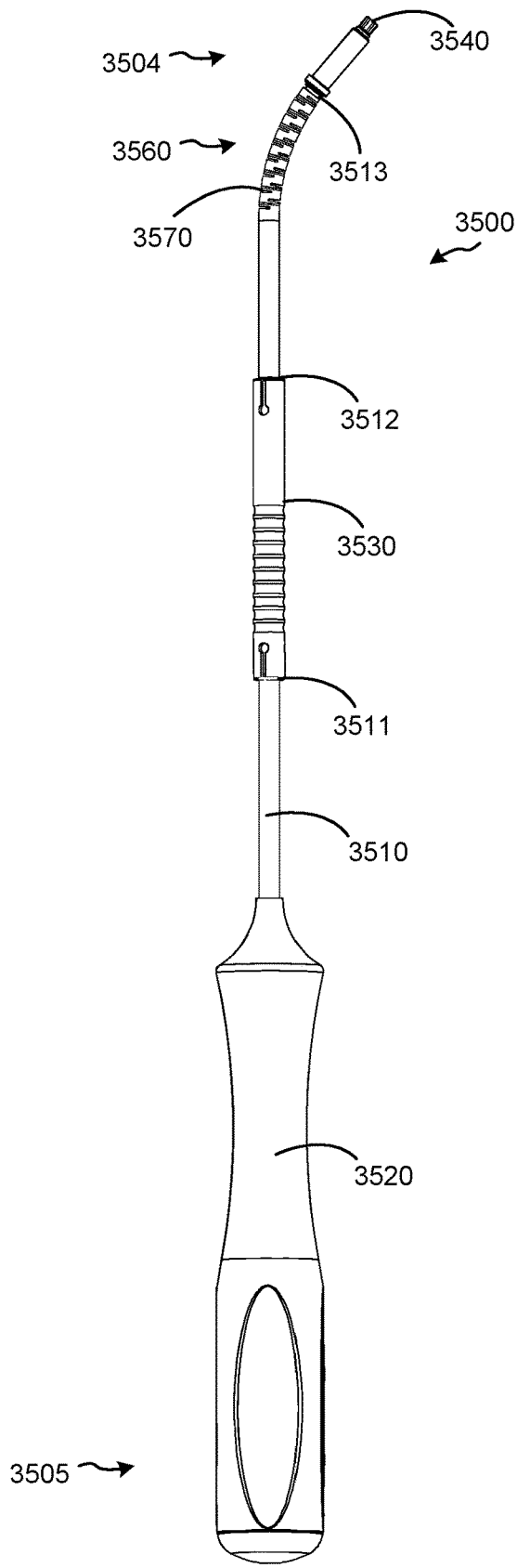
FIG. 35A  FIG. 35B

SPINAL SURGERY DEVICES, SYSTEMS, AND METHODS

TECHNICAL FIELD

The present disclosure relates to surgical devices, instruments, systems, and methods. More specifically, the present disclosure relates to improved surgical devices, instruments, systems, and methods for implanting intervertebral spacers between adjacent vertebral bodies in a patient.

BACKGROUND

Spinal fixation procedures utilizing intervertebral spacers can be used to correct spinal conditions such as degenerative disc disease, spondylolisthesis, spinal deformities, or other spinal conditions through minimally invasive or invasive spinal surgery. For example, intervertebral discs can degenerate or otherwise become damaged over time. In some instances, an intervertebral spacer can be positioned within a space previously occupied by a disc between adjacent vertebral bodies. Such intervertebral spacers can help maintain a desired spacing between adjacent vertebrae and/or promote fusion between adjacent vertebrae.

The use of bone graft and/or other materials within an intervertebral spacer can facilitate the fusion of adjacent vertebral bodies. One or more bone screws may also be utilized to help stabilize the intervertebral spacer during the fusion process. However, these bone screws may become loose over time and back out of the intervertebral spacer. Accordingly, a need exists for improved intervertebral spacers and related surgical instrumentation, tools, systems and methods.

SUMMARY

The various systems and methods of the present disclosure have been developed in response to the present state of the art, and in particular, in response to the problems and needs in the art that have not yet been fully solved by currently available surgical devices, instruments, systems, and methods for implanting intervertebral spacers between two vertebral bodies of a patient.

According to some embodiments, an intervertebral spacer assembly may include an intervertebral spacer that has a superior surface configured to engage a superior vertebral body, an inferior surface configured to engage an inferior vertebral body, and a proximal surface. The proximal surface may include a first fastener channel configured to receive a first fastener and oriented to pass through the proximal and superior surfaces of the intervertebral spacer at a first angle, a second fastener channel configured to receive a second fastener and oriented to pass through the proximal and inferior surfaces of the intervertebral spacer at a second angle, and a locking member channel intermediate the first and second fastener channels. The locking member channel may include an inner wall, an annular ridge formed in the inner wall, a first pair of recesses formed in the inner wall, and a second pair of recesses formed in the inner wall and angularly offset from the first pair of recesses about a longitudinal axis of the locking member channel. The intervertebral spacer assembly may also include a locking member comprising a first anti-backout member, a second anti-backout member, and a collet. The collet may include an annular flange that is configured to be retained by the annular ridge of the locking member channel in order to rotatably couple the locking member to the intervertebral spacer. The collet may also include a peripheral wall, a first stop protrusion projecting from a first side of the peripheral wall, and a second stop protrusion projecting from a second side of the peripheral wall, opposite the first stop protrusion. The locking member may be rotatable within the locking member channel between two stable positions including an unlocked position and a locked position. In the unlocked position, the first and second stop protrusions may protrude into the first pair of recesses in order to retain the locking member in the unlocked position, such that the first and second anti-backout members do not obstruct the first and second fastener channels. In the locked position, the first and second stop protrusions may protrude into the second pair of recesses in order to retain the locking member in the locked position, such that the first and second anti-backout members may obstruct the first and second fastener channels in order to prevent the first and second fasteners from backing out of the first and second fastener channels.

In other embodiments, an intervertebral spacer may include a superior surface configured to engage a superior vertebral body, an inferior surface configured to engage an inferior vertebral body, and a proximal end. The proximal end may include a fastener channel configured to receive a fastener and oriented to pass through the proximal end and the superior or inferior surface of the intervertebral spacer, a locking member channel, and a locking member. The locking member channel may include an inner wall and one or more inner wall engagement features. The locking member may include an anti-backout member, a collet retainable within the locking member channel, and one or more collet engagement features. The locking member may be rotatable within the locking member channel between an unlocked position and a locked position. In the unlocked position, the one or more collet engagement features may engage the one or more inner wall engagement features in order to retain the locking member in the unlocked position, independently of any additional component besides the locking member and the intervertebral spacer, such that the anti-backout member does not obstruct the fastener channel. In the locked position, the one or more collet engagement features may engage the one or more inner wall engagement features to retain the locking member in the locked position, independently of any additional component besides the locking member and the intervertebral spacer, such that the anti-backout member obstructs the fastener channel in order to prevent the fastener from backing out of the fastener channel.

In yet other embodiments, a method for preventing a fastener from backing out of an intervertebral spacer comprising a locking member channel with an inner wall having first and second recesses formed therein, and a locking member that is rotatably coupled within the locking member channel and comprises an anti-backout member and a stop protrusion configured to protrude into the first and second recesses in order to selectively retain the locking member in an unlocked position and a locked position, may include: (1) aligning a driver engagement feature of a driver tool with a driver engagement channel formed in the locking member; (2) moving the driver engagement feature into engagement with the driver engagement channel; and (3) rotating the locking member relative to the intervertebral spacer from the unlocked position to the locked position such that the locking member is retained in the locked position, independently of any additional component besides the locking member and the intervertebral spacer, such that the anti-backout member is placed in a path of the fastener to prevent the fastener from backing out of the intervertebral spacer These and other features and advantages of the present disclosure will become more fully apparent from the following description and appended claims, or may be learned by the practice of the systems and methods set forth hereinafter.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the present disclosure will be described with additional specificity and detail through use of the accompanying drawings in which:

FIG. 5A is a proximal end view of an intervertebral spacer assembly 500 including bone screws 501, 502 and a locking member 200 positioned in an unlocked position, according to an embodiment of the present disclosure;

FIG. 5B is a proximal end view of the intervertebral spacer assembly 500 of FIG. 5A with the locking member 200 positioned in a locked position;

FIG. 5C is a proximal end view of the intervertebral spacer assembly 500 of FIG. 5A with the locking member 200 positioned in an alternative locked position;

FIG. 5D is a side view of the intervertebral spacer assembly 500 of FIG. 5A;

FIG. 17H illustrates the proximal end of the intervertebral spacer 1700 of FIG. 17A;

FIG. 18A is a perspective top view of a proximal end of an intervertebral spacer 1800, according to an embodiment of the present disclosure;

FIG. 18B is a perspective top view of a distal end of the intervertebral spacer 1800 of co FIG. 18A;

FIG. 18C is a top view of the intervertebral spacer 1800 of FIG. 18A;

FIG. 18D is a bottom view of the intervertebral spacer 1800 of FIG. 18A;

FIG. 18E illustrates a first side of the intervertebral spacer 1800 of FIG. 18A;

FIG. 18F illustrates a second side of the intervertebral spacer 1800 of FIG. 18A;

FIG. 18G illustrates the distal end of the intervertebral spacer 1800 of FIG. 18A;

FIG. 18H illustrates the proximal end of the intervertebral spacer 1800 of FIG. 18A;

FIG. 19A is a perspective top view of a proximal end of an intervertebral spacer 1900, according to an embodiment of the present disclosure;

FIG. 19B is a perspective top view of a distal end of the intervertebral spacer 1900 of FIG. 19A;

FIG. 19C is a top view of the intervertebral spacer 1900 of FIG. 19A;

Figure 19A:
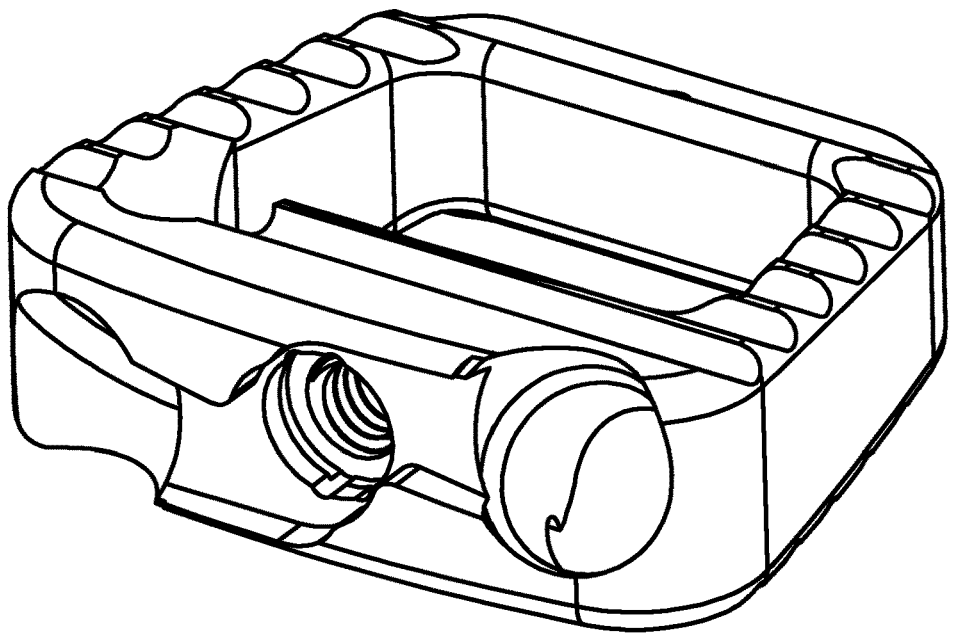
Figure 19B:
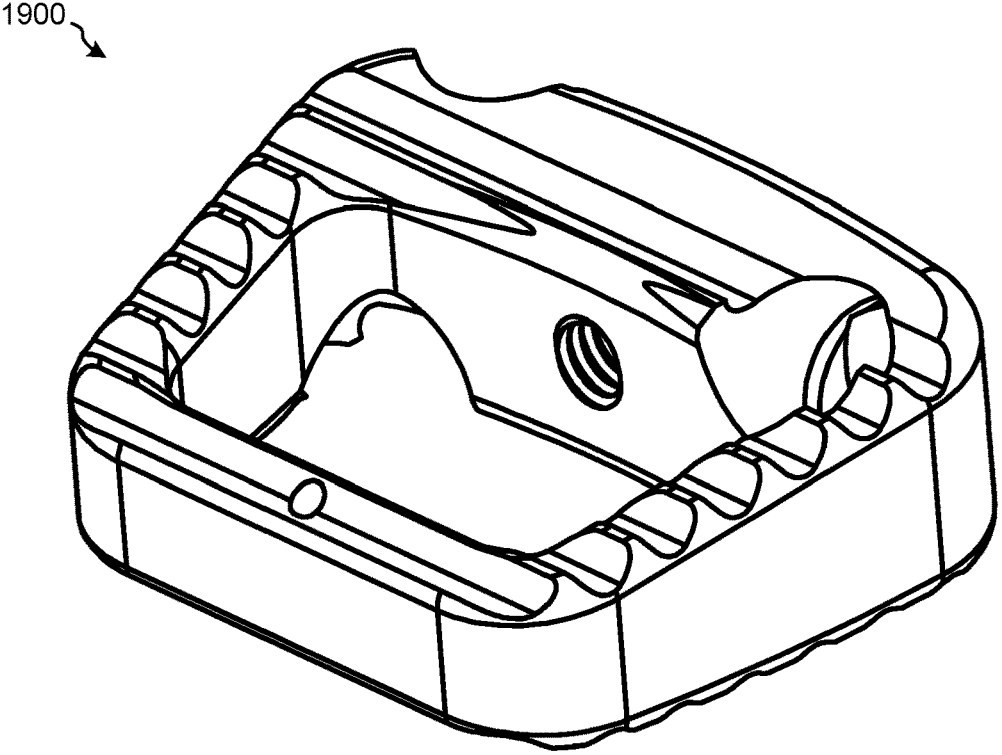
Figure 19C:
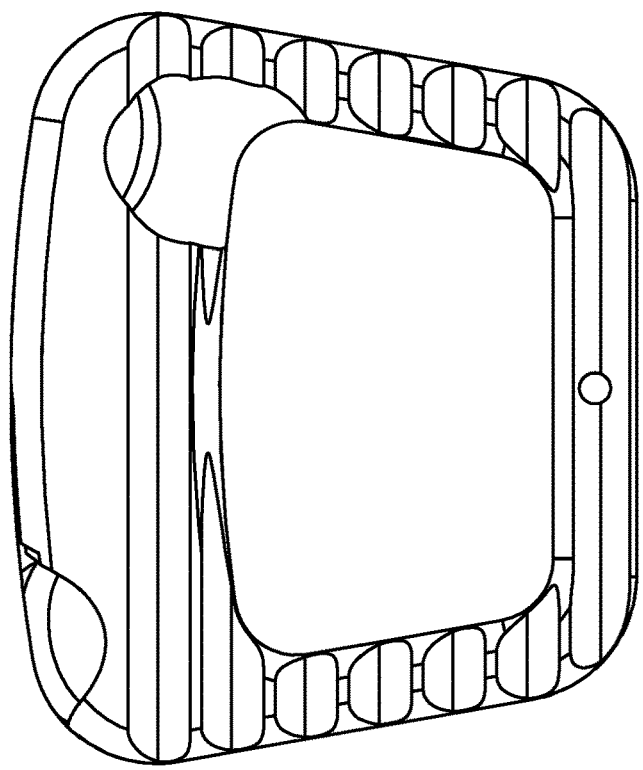
Figure 19D:
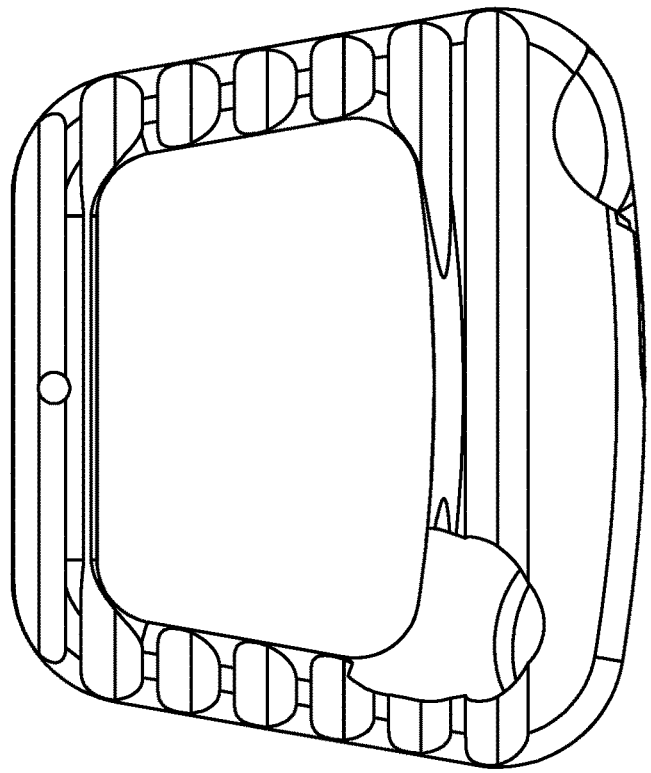
Figure 19E:
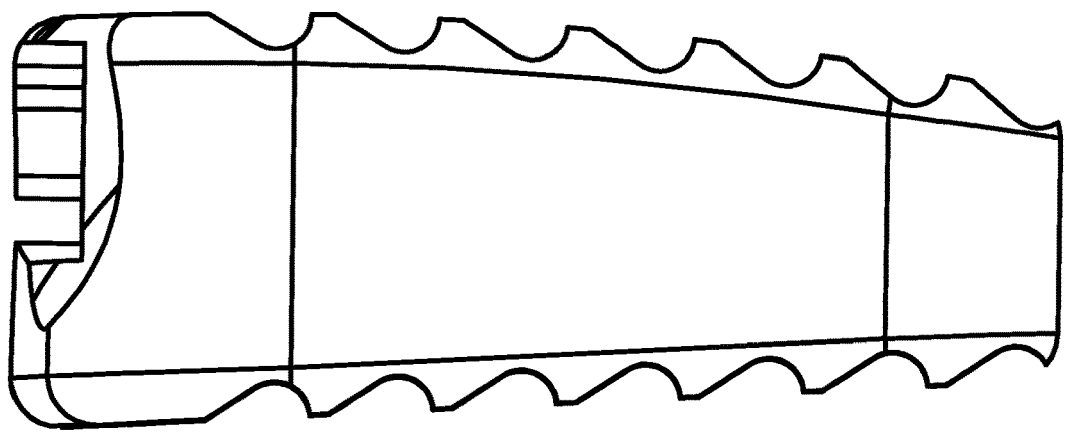
Figure 19F:
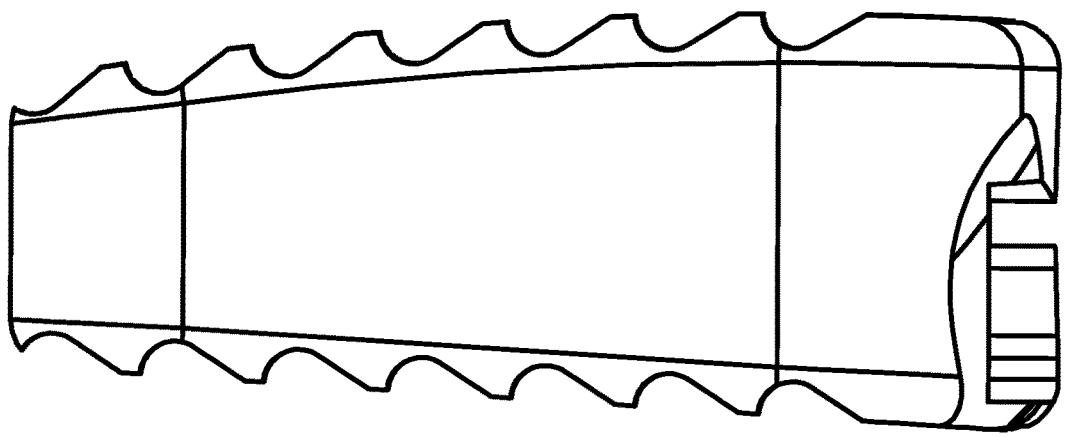
Figure 19G:
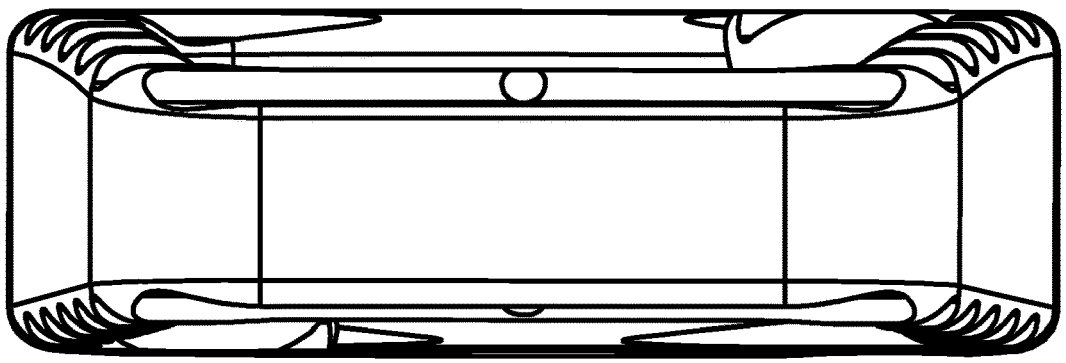
Figure 19H:
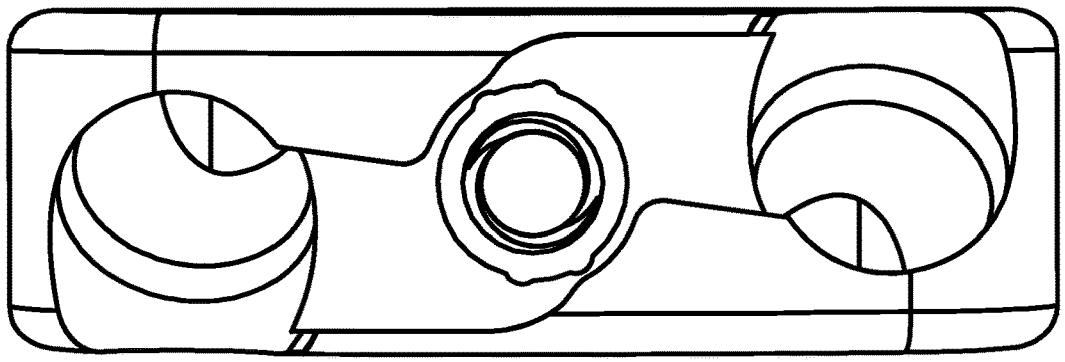
Figure 20A:
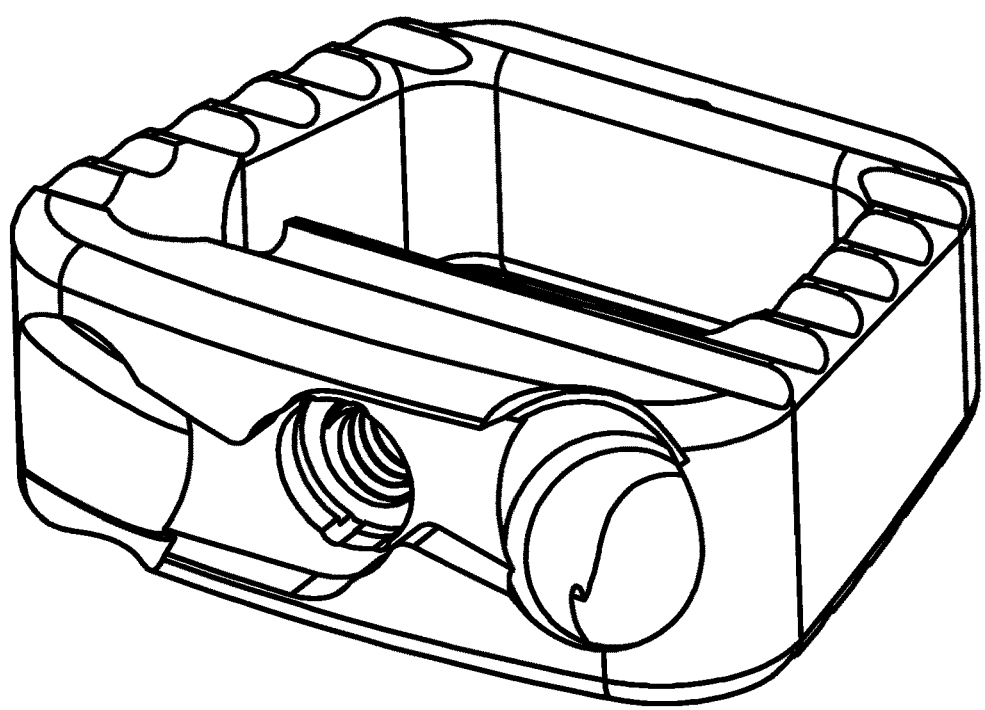
Figure 20B:
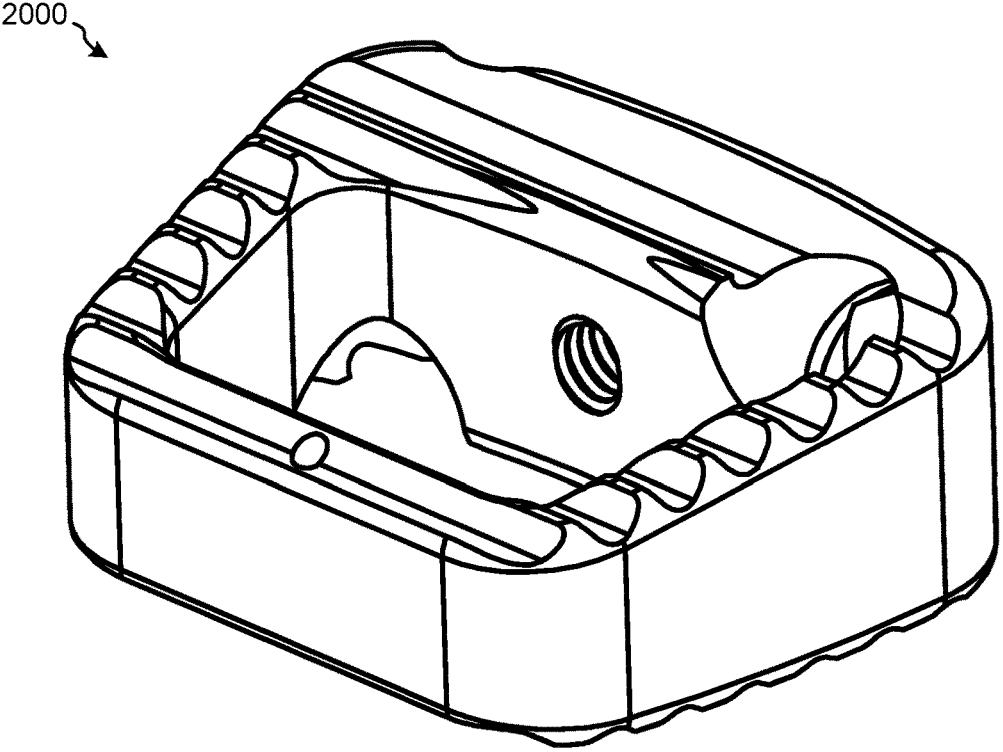
Figure 20C:
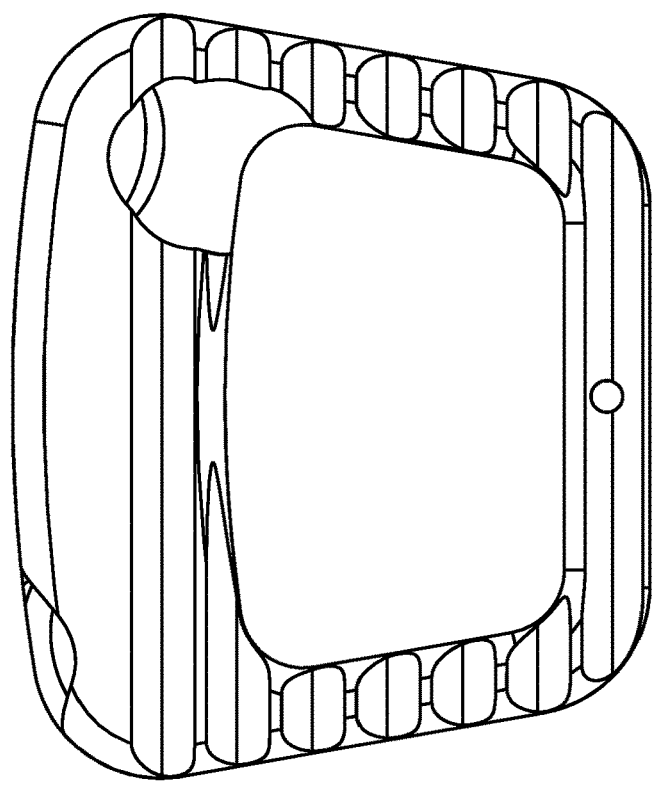
Figure 20D:
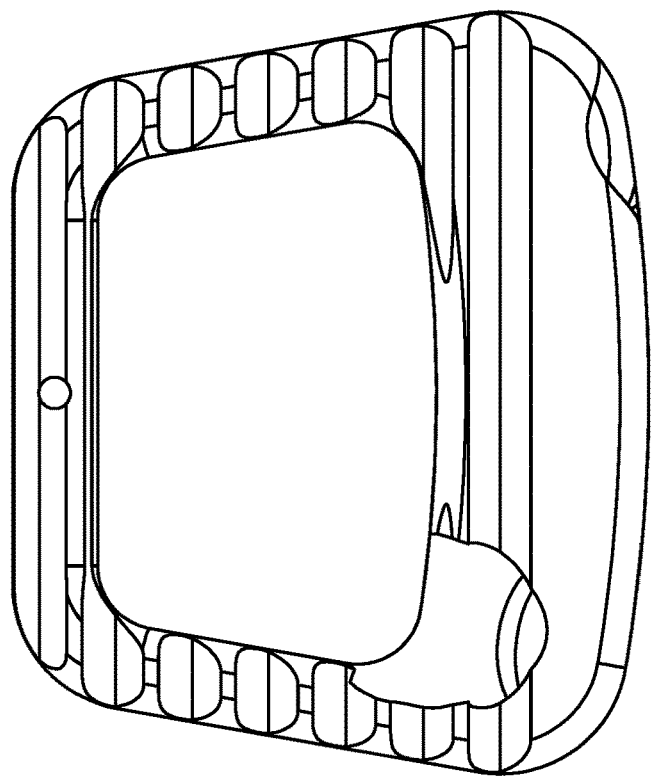
Figure 20E:
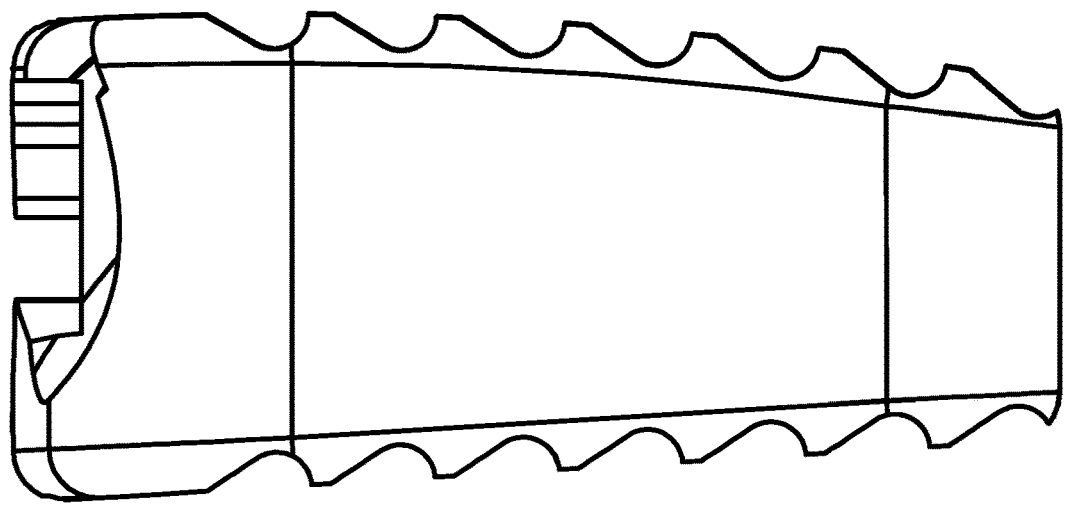
Figure 20F:
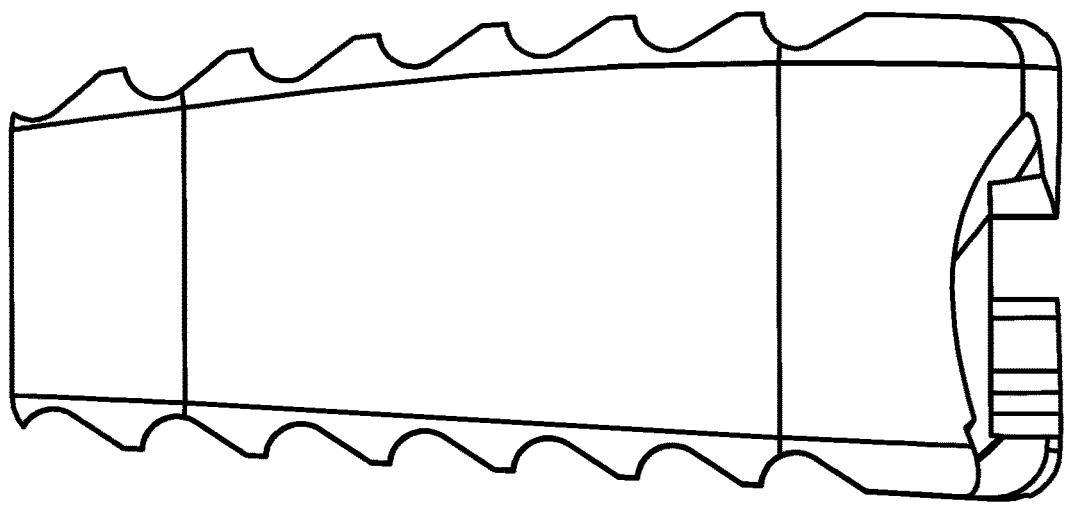
Figure 20G:
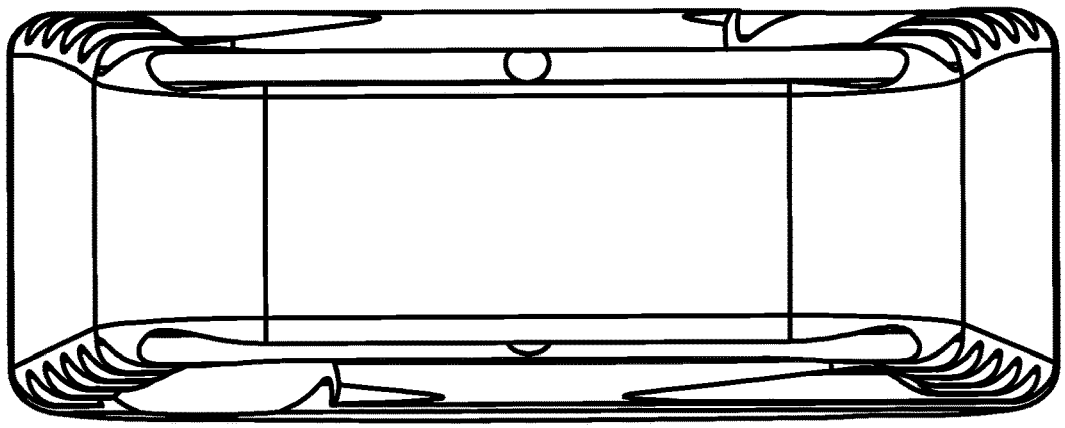
Figure 20H:
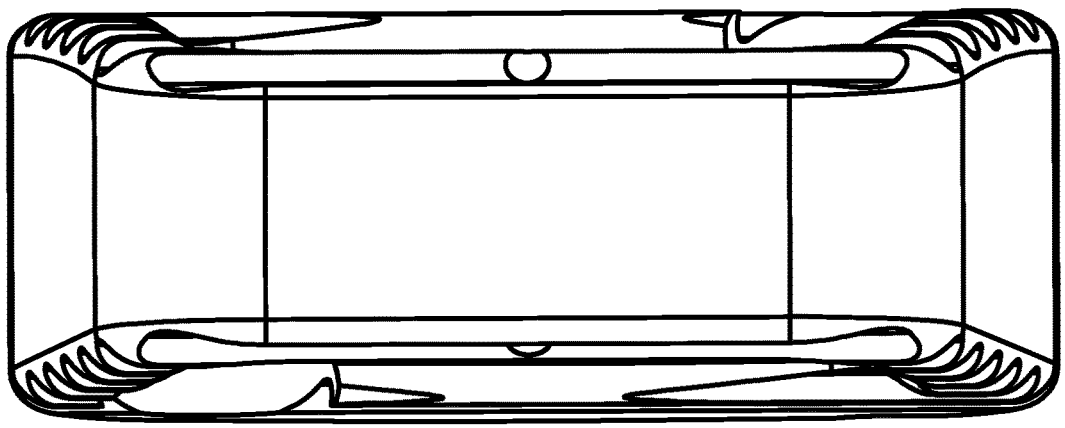
Figure 21A:
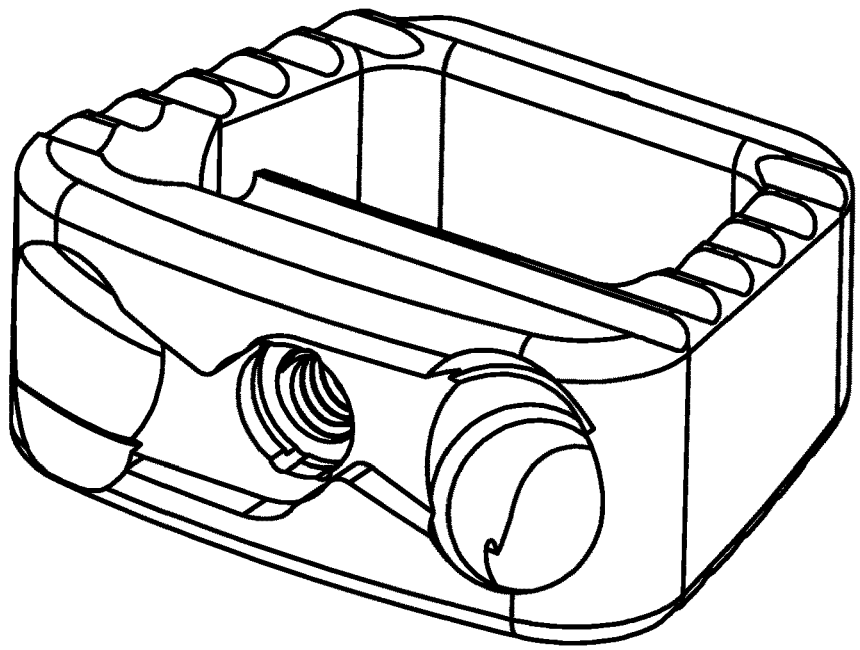
Figure 21B:
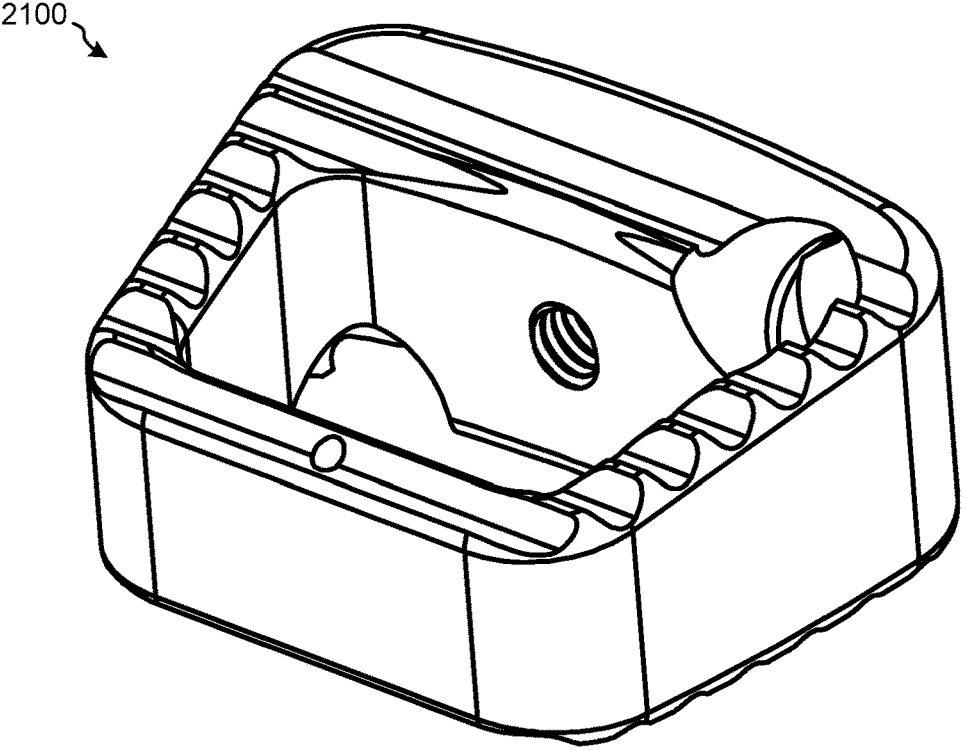
Figure 21C:
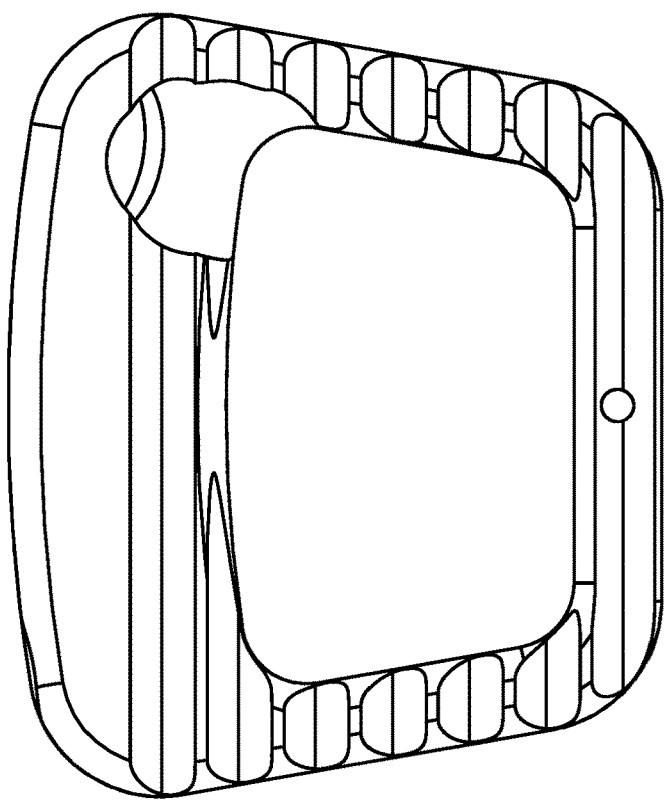
Figure 21D:
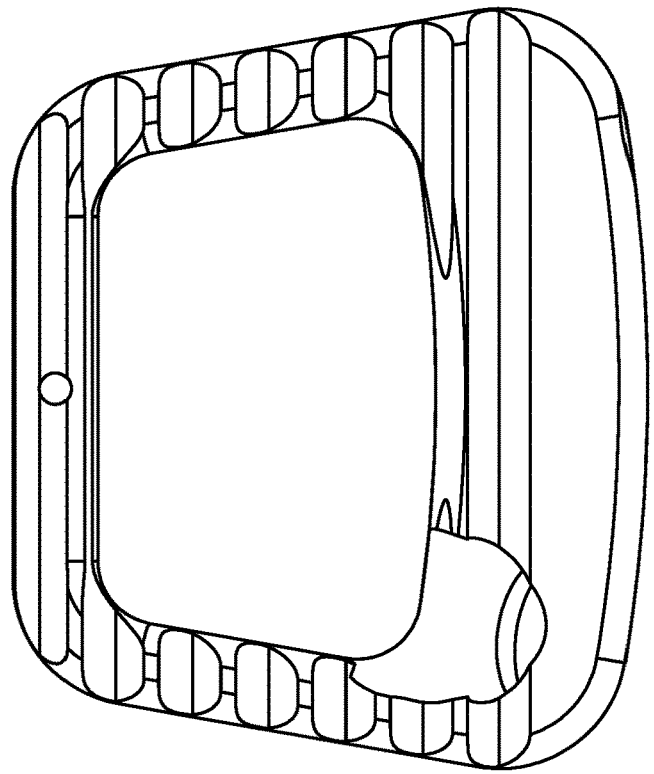
Figure 21E:
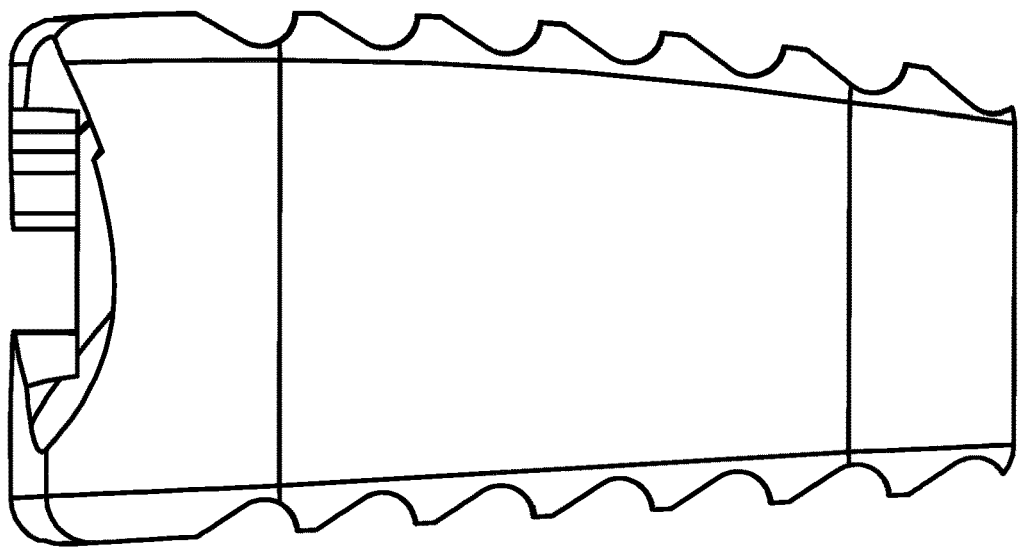
Figure 21F:
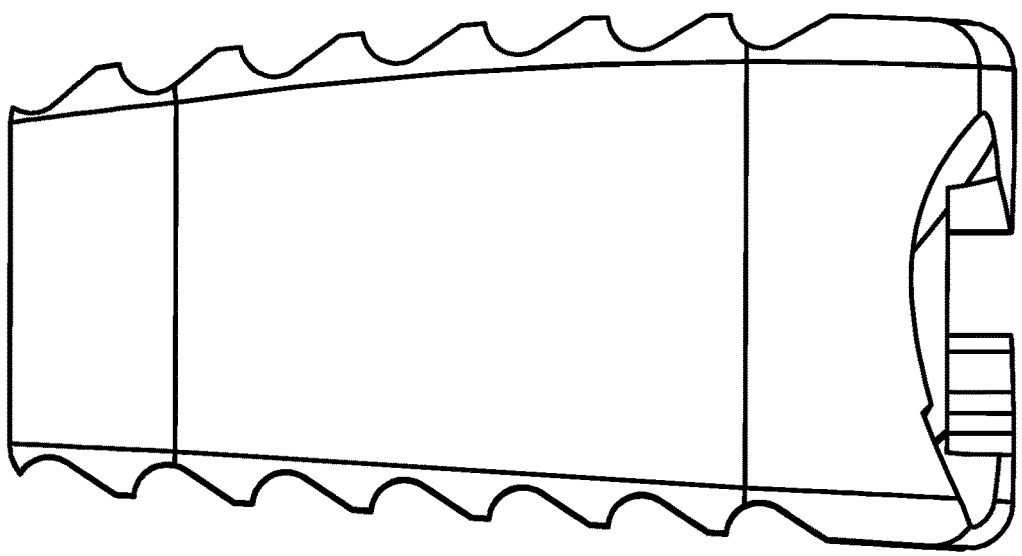
Figure 21G:
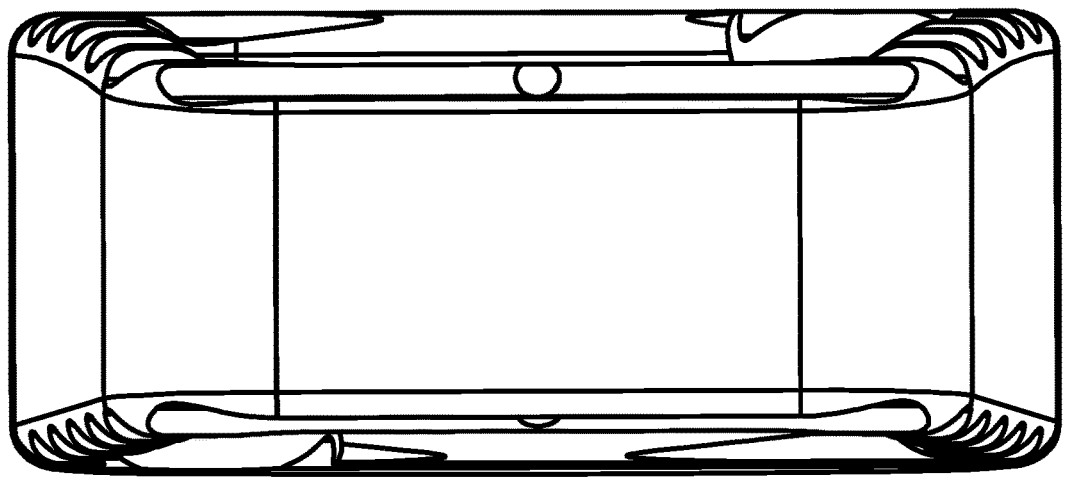
Figure 21H:
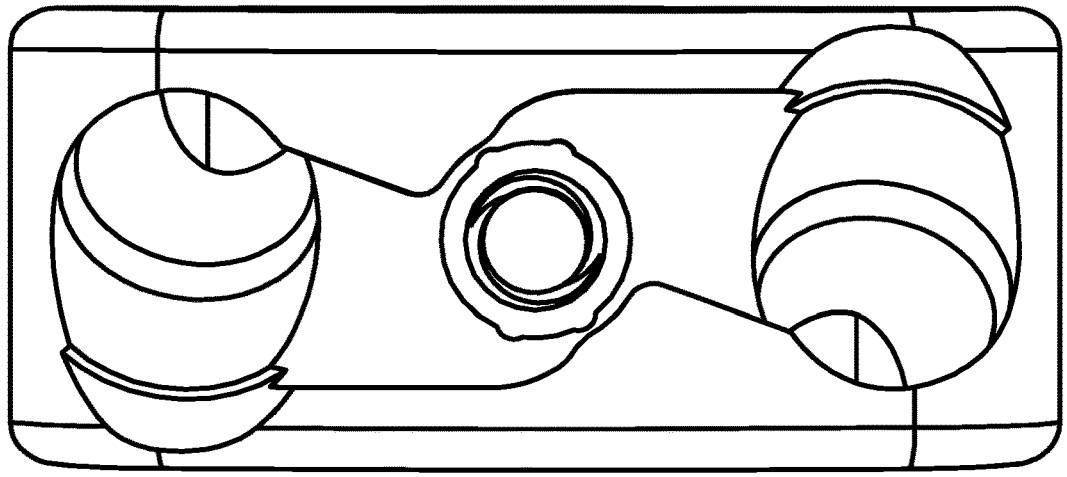
Figure 22A:
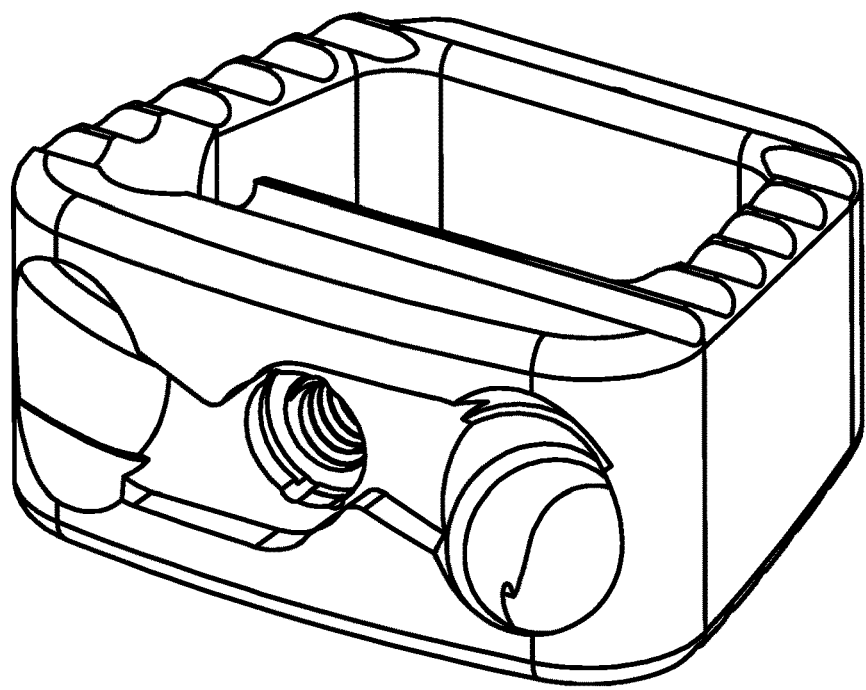
Figure 22B:
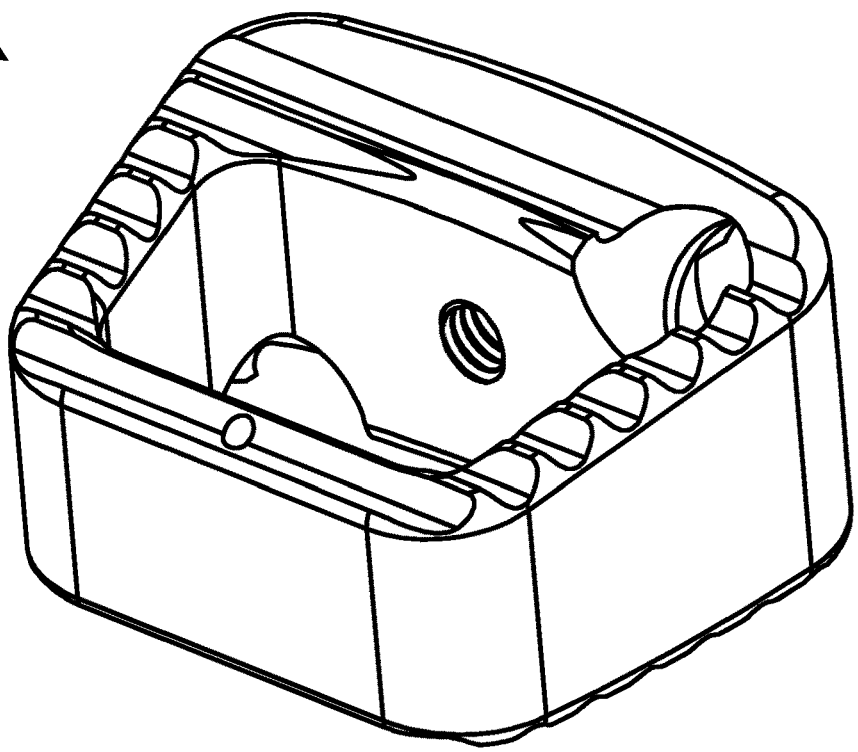
Figure 22C:
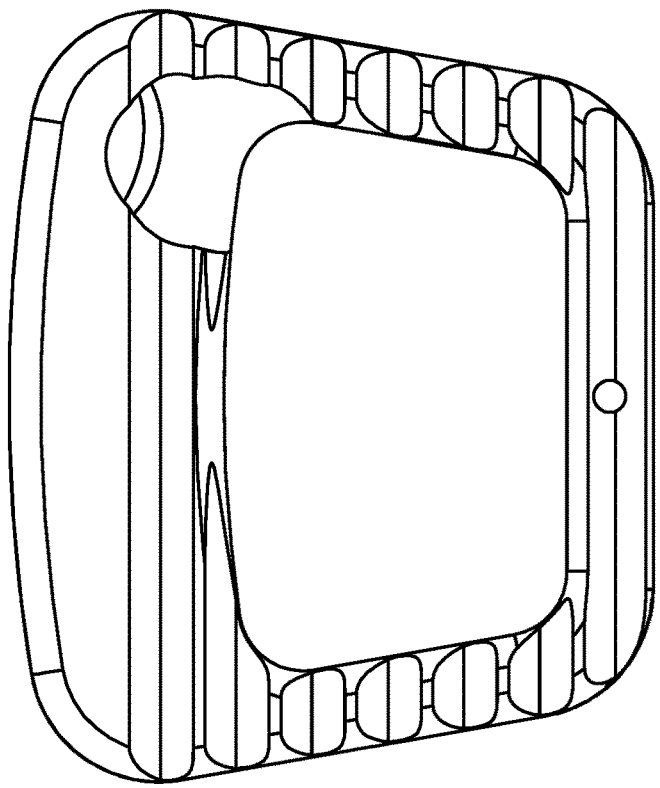
Figure 22D:
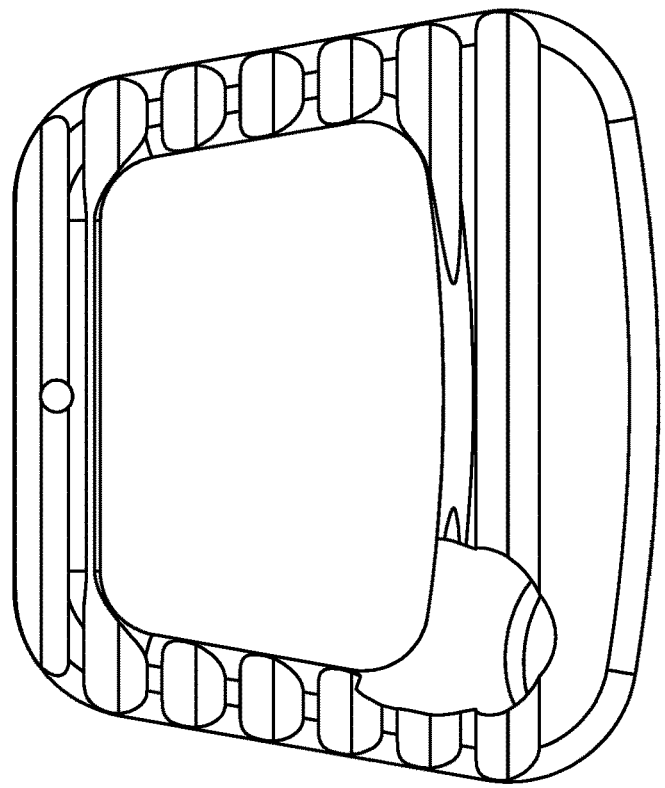
Figure 22E:
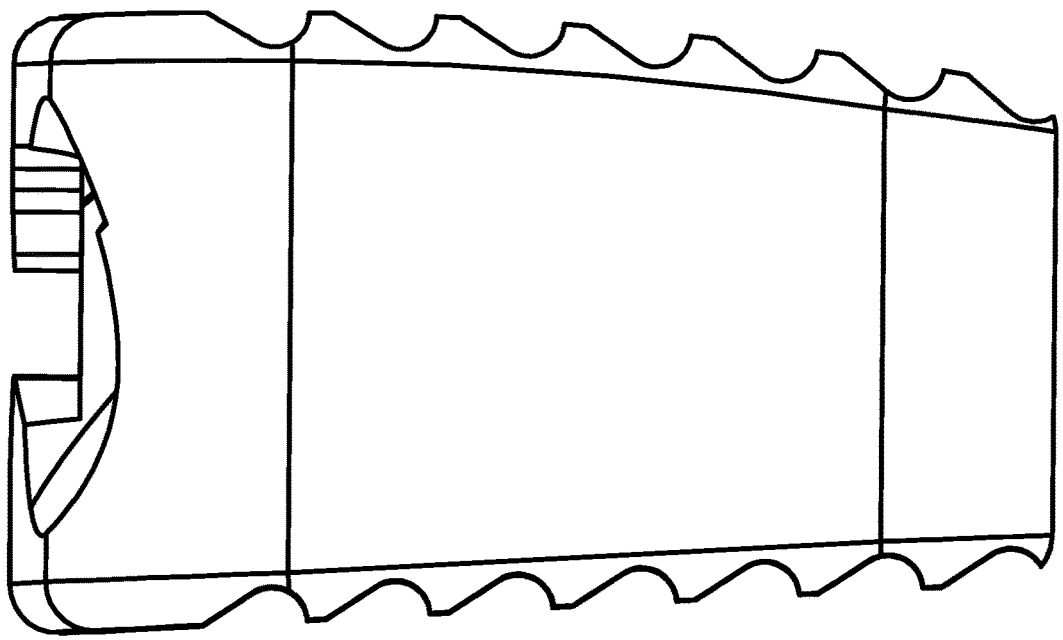
Figure 22F:
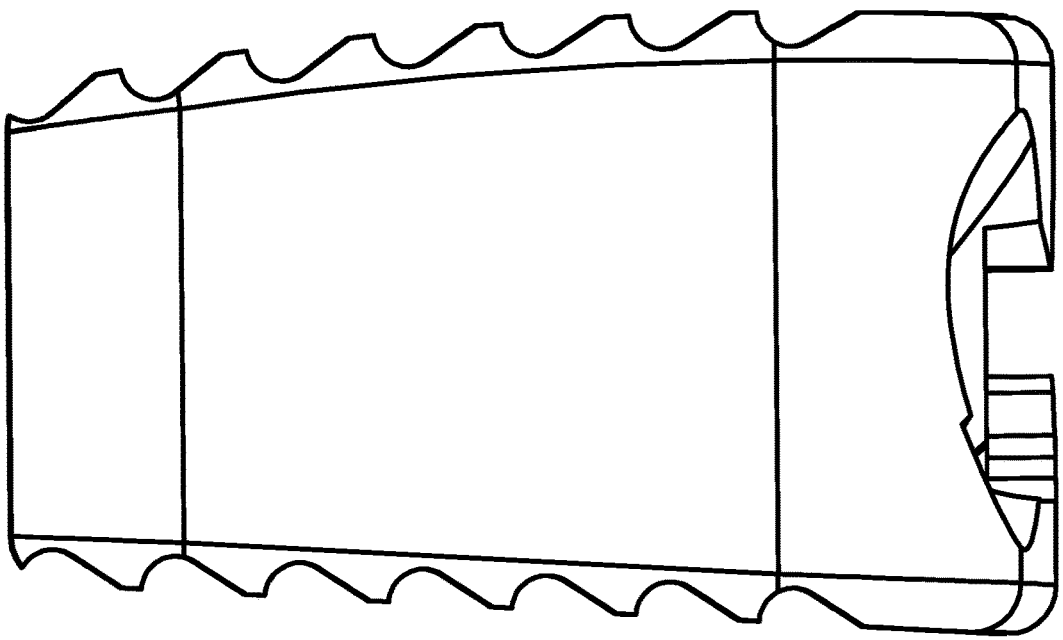
Figure 22G:
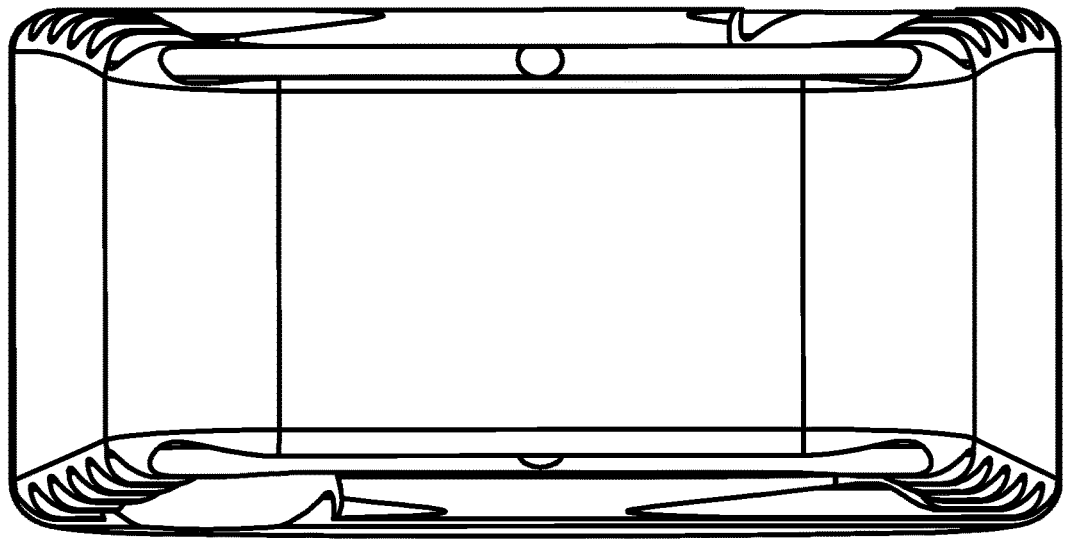
Figure 22H:
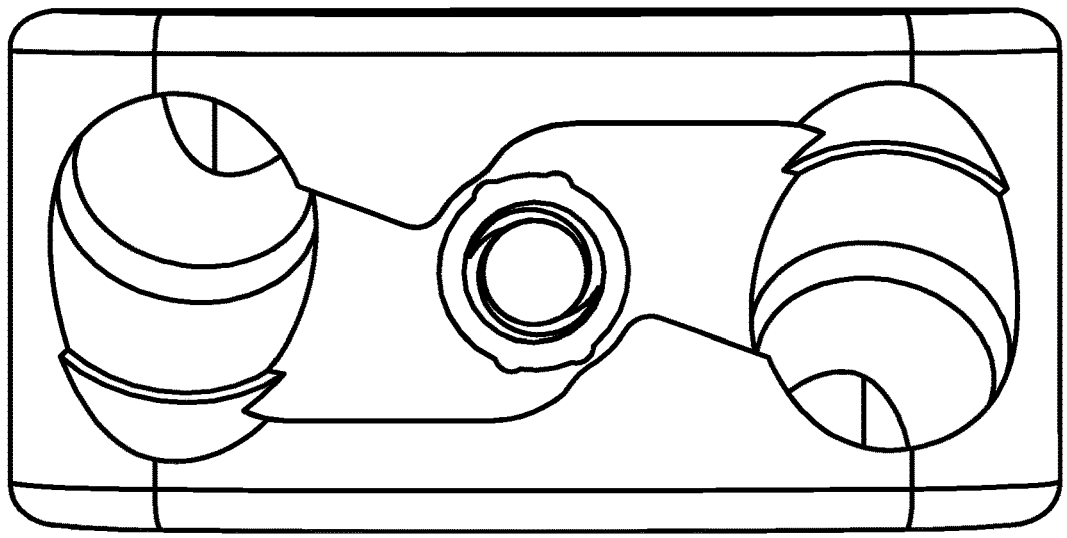
Figure 23A:
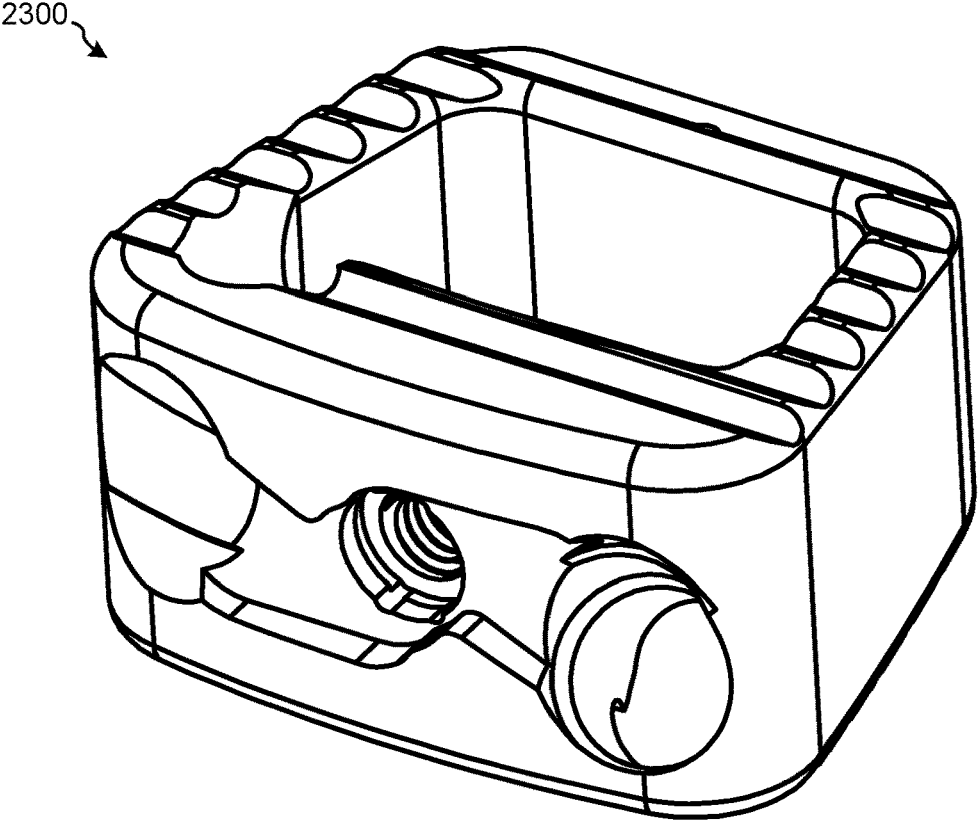
Figure 23B:
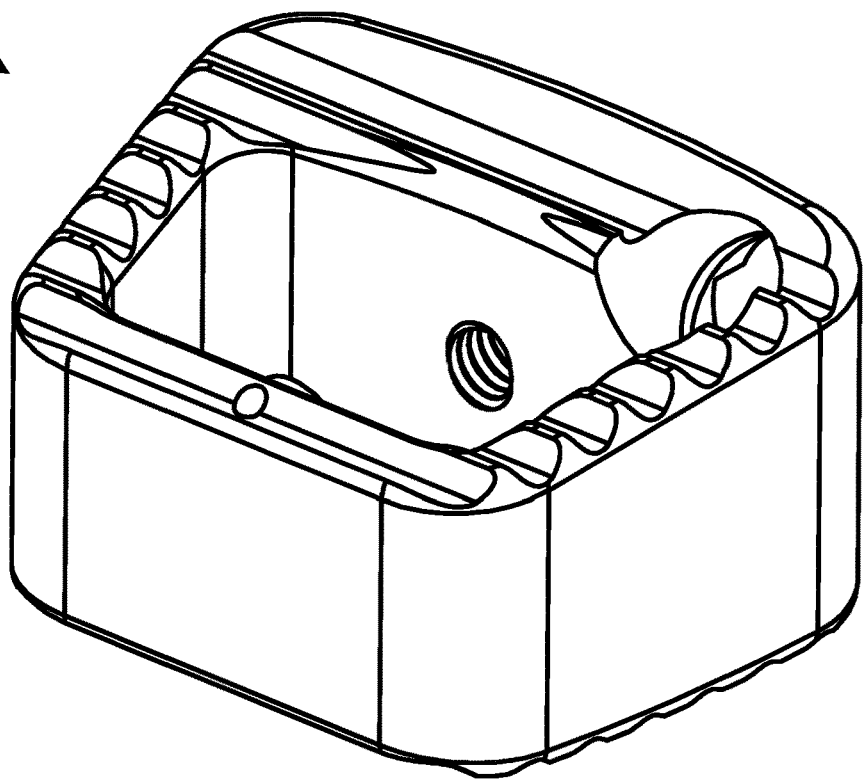
Figure 23C:
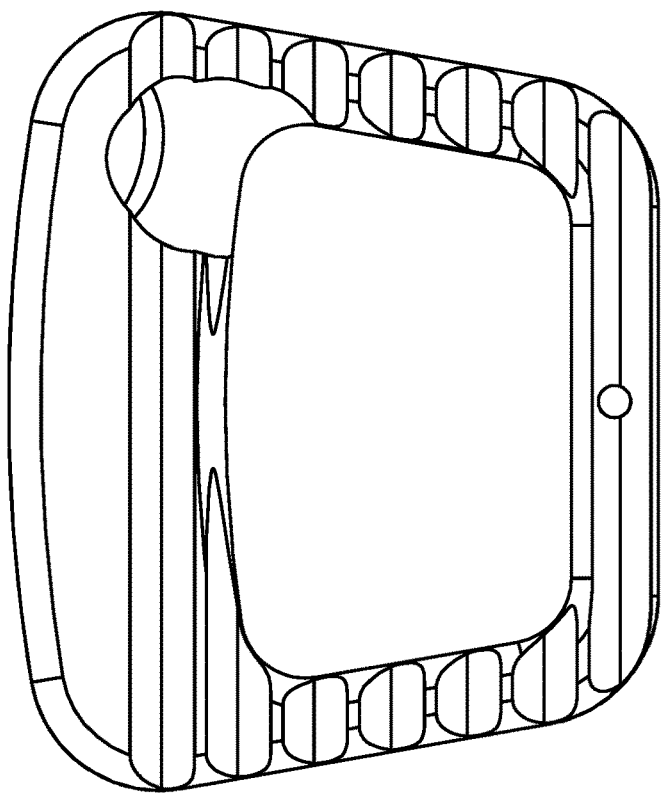
Figure 23D:
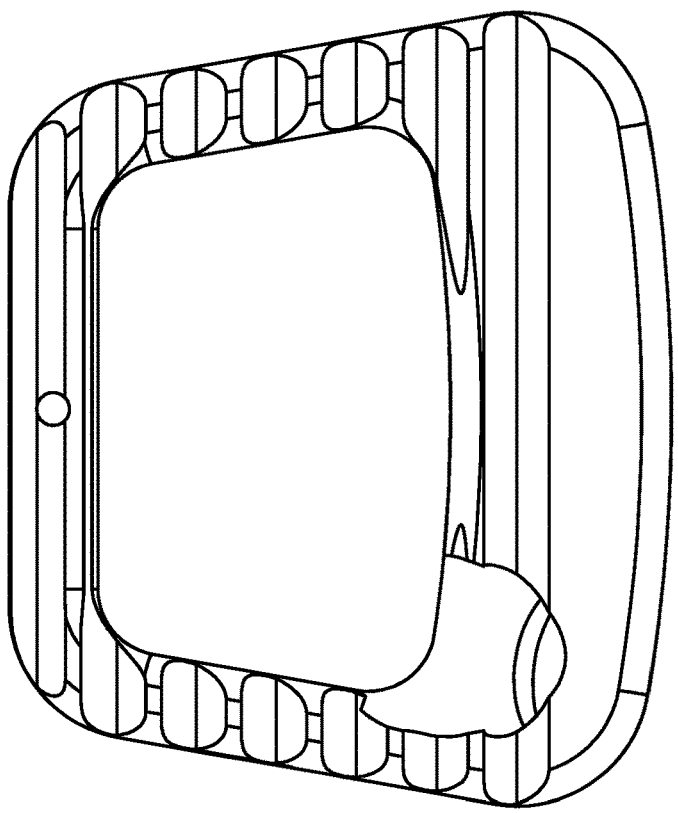
Figure 23E:
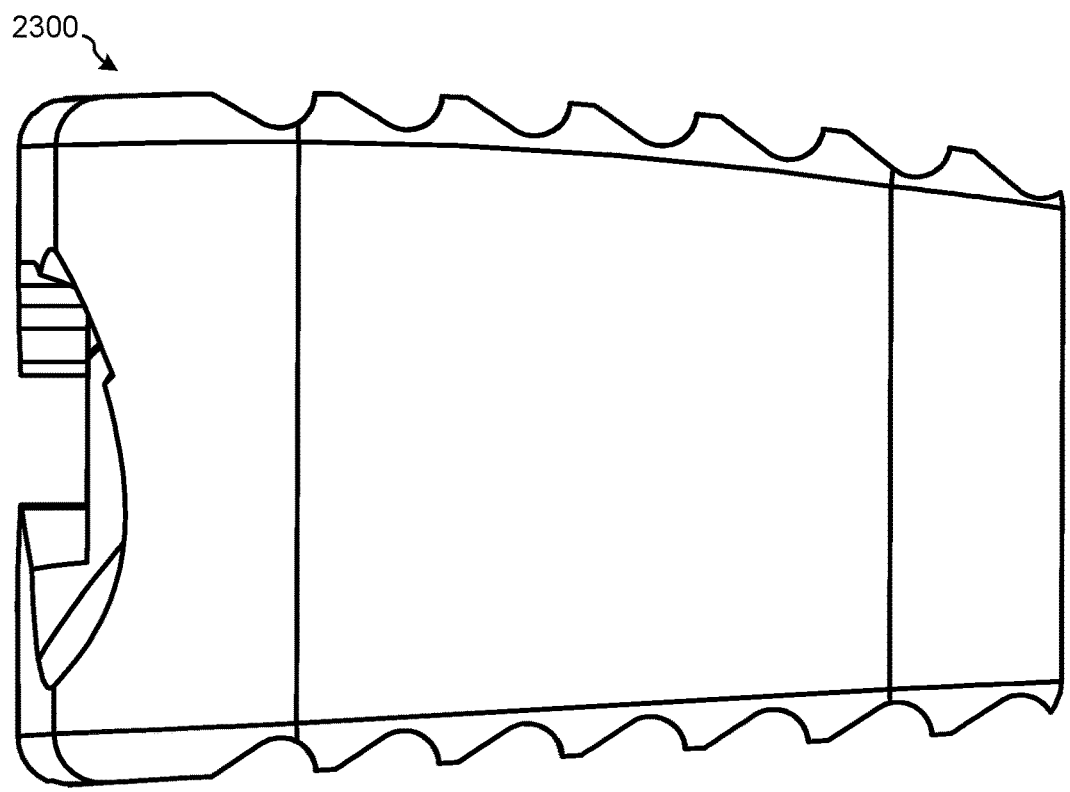
Figure 23F:
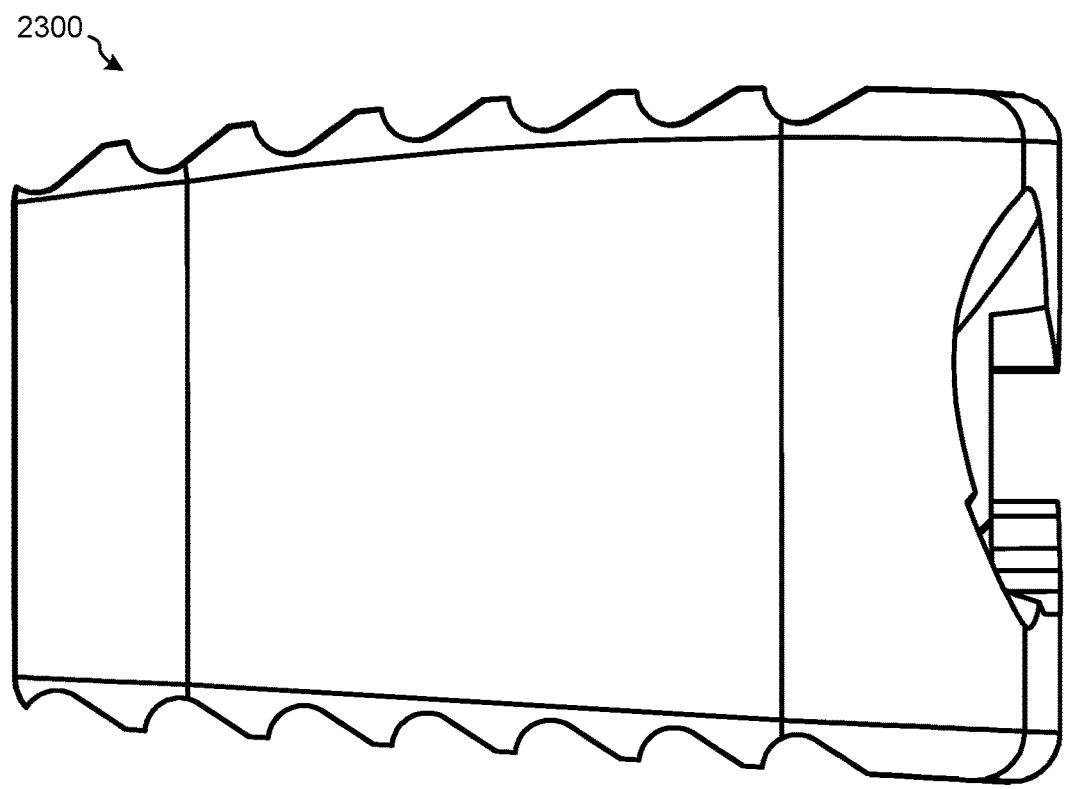
Figure 23G:
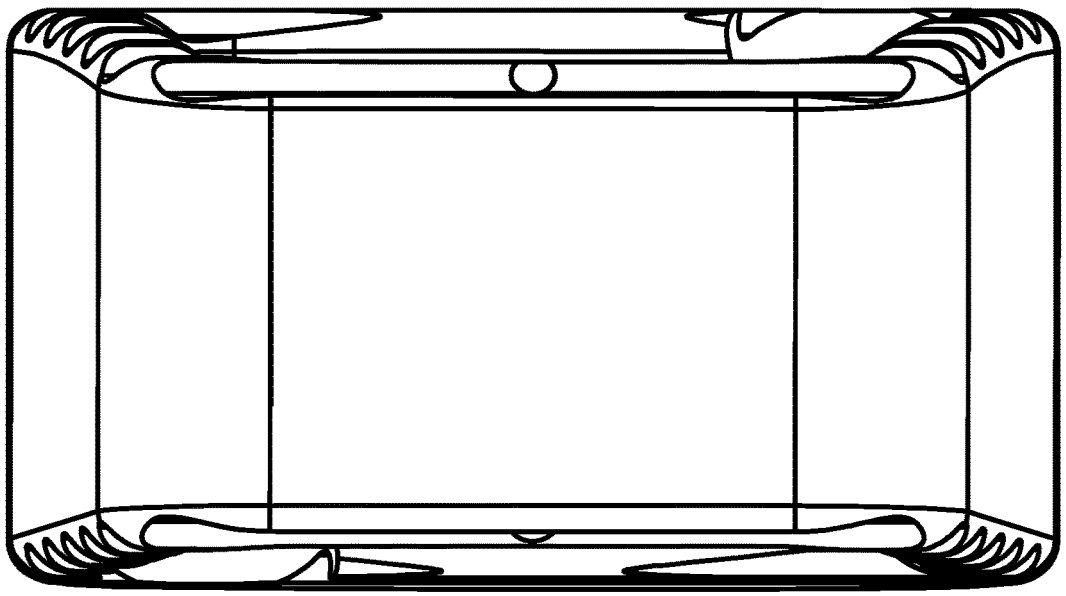
Figure 23H:
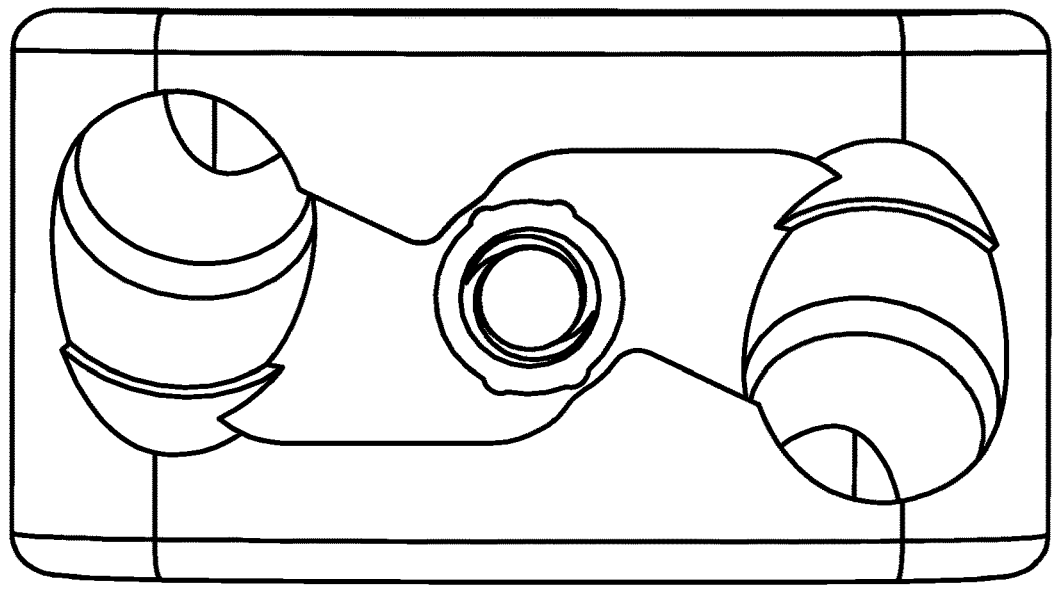
Figure 24A:
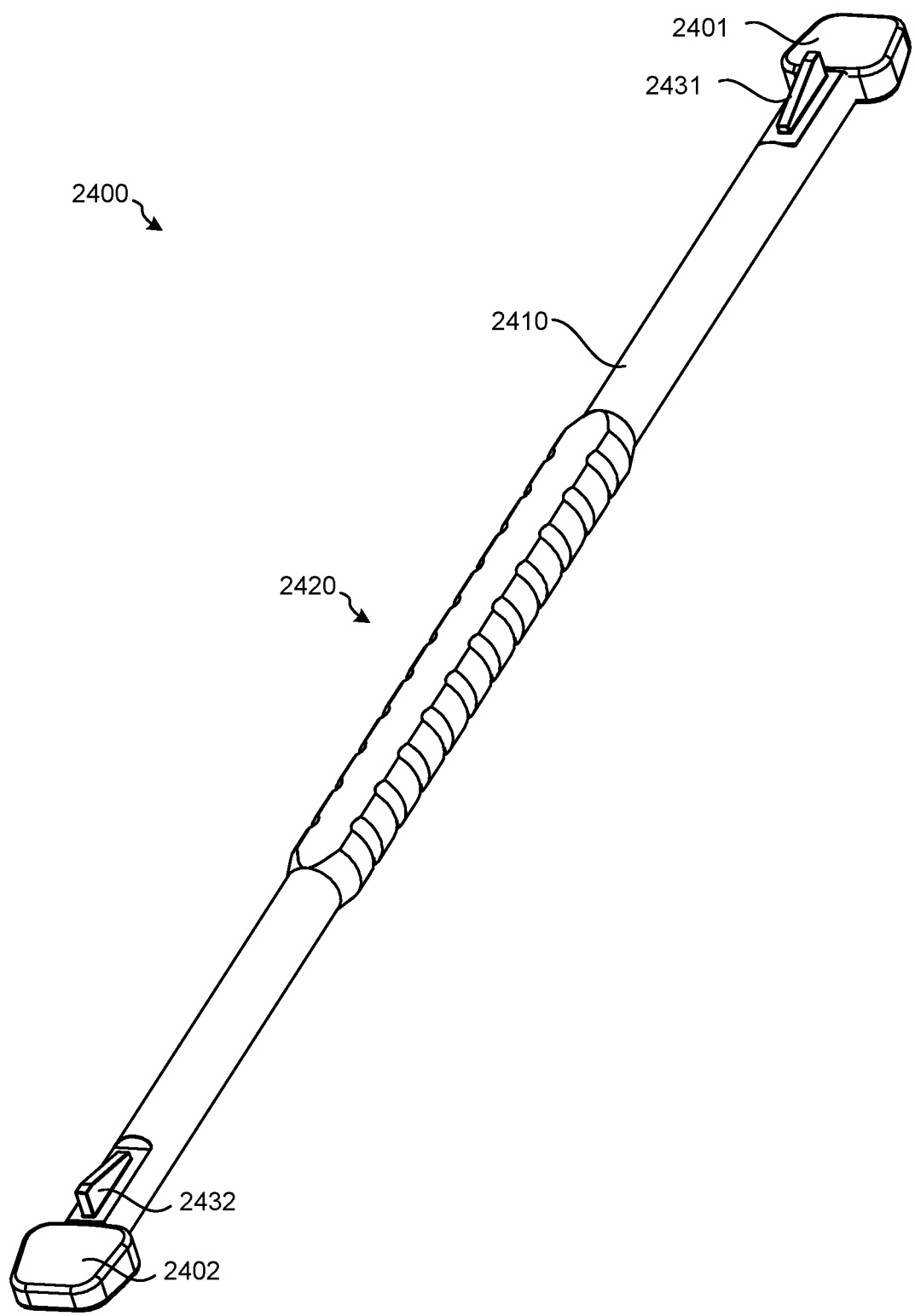
Figure 24B:
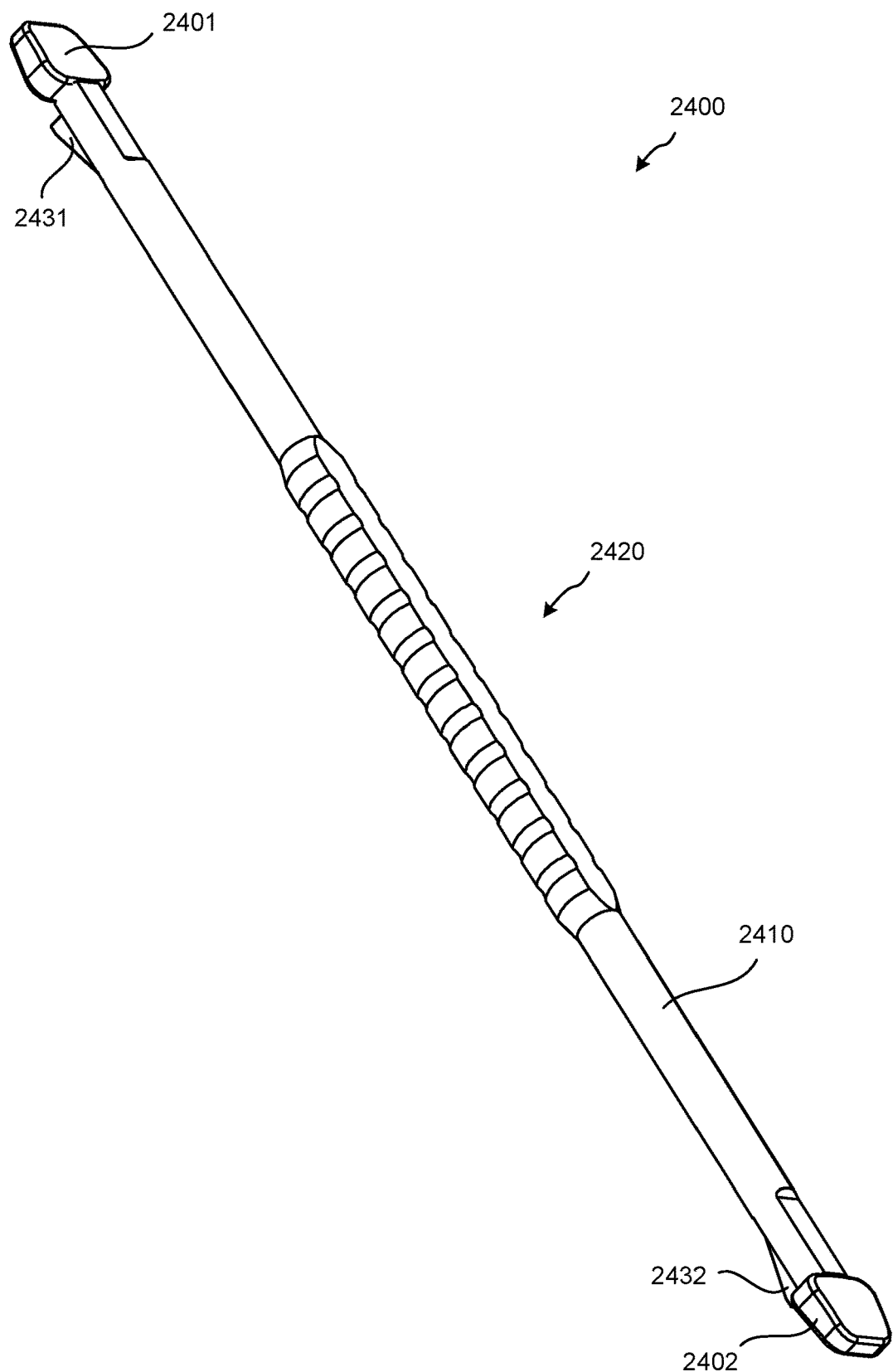
Figure 25A:
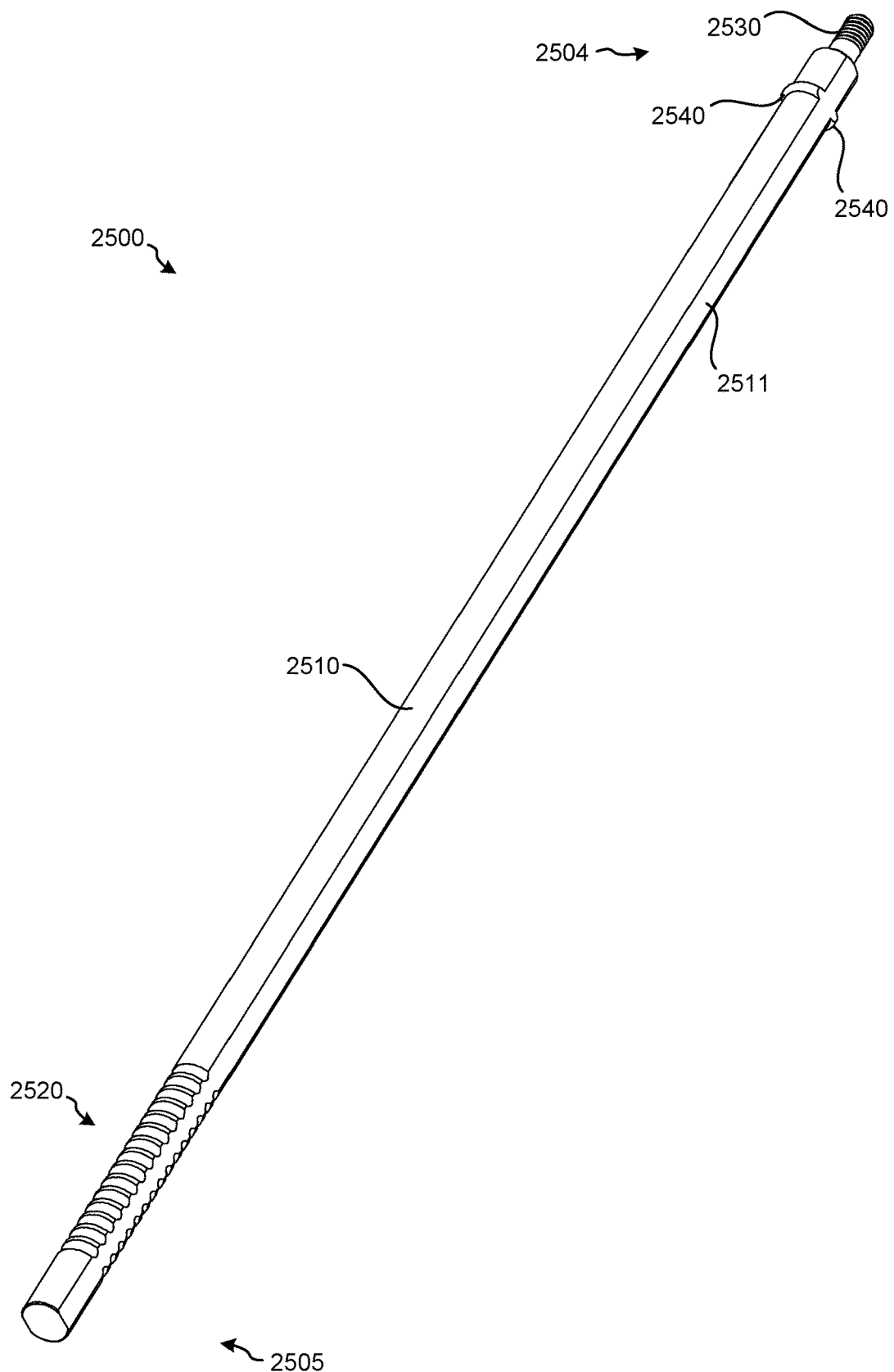
Figure 25B:
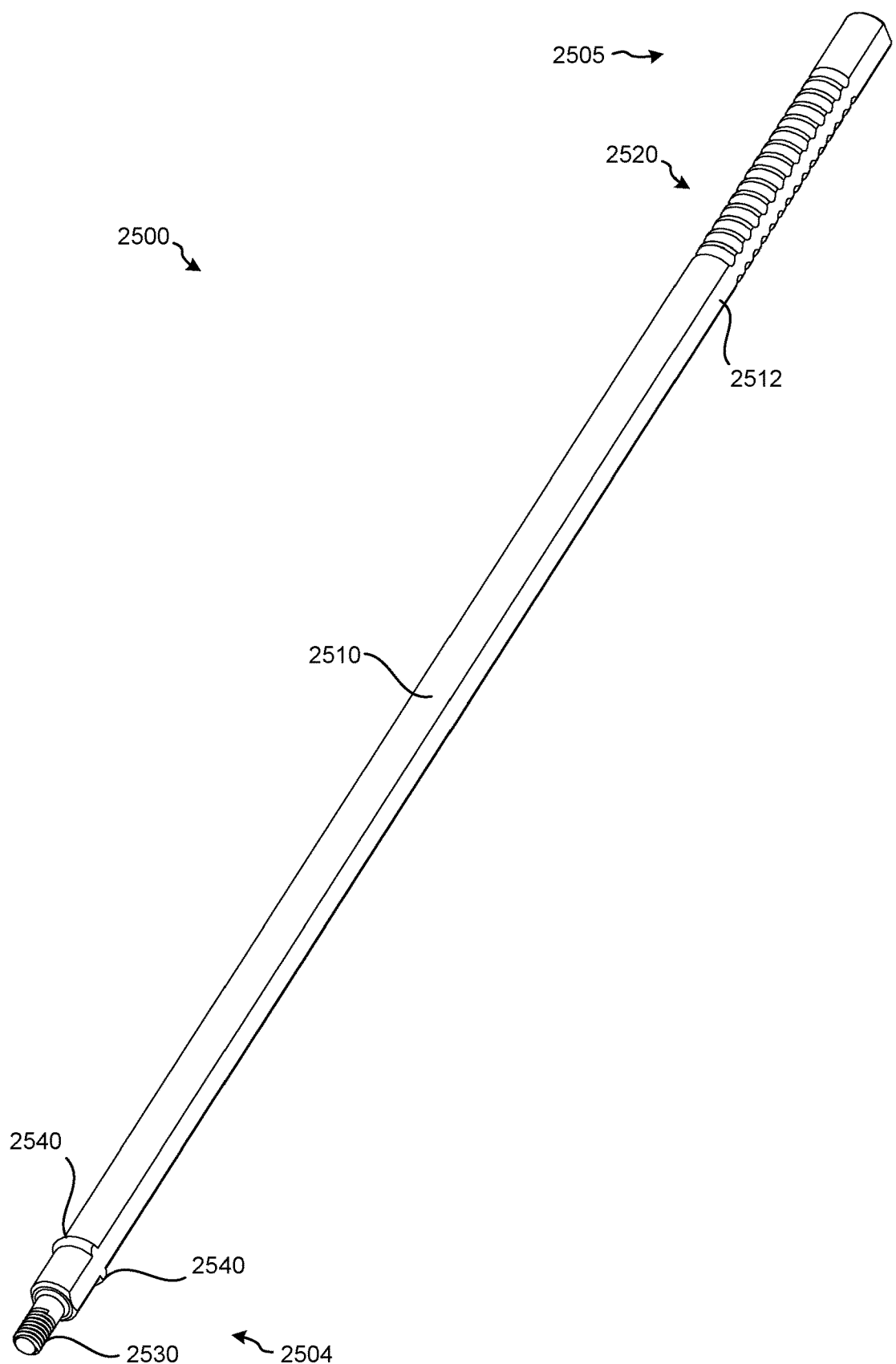
Figures 25C, 25D, 25E:
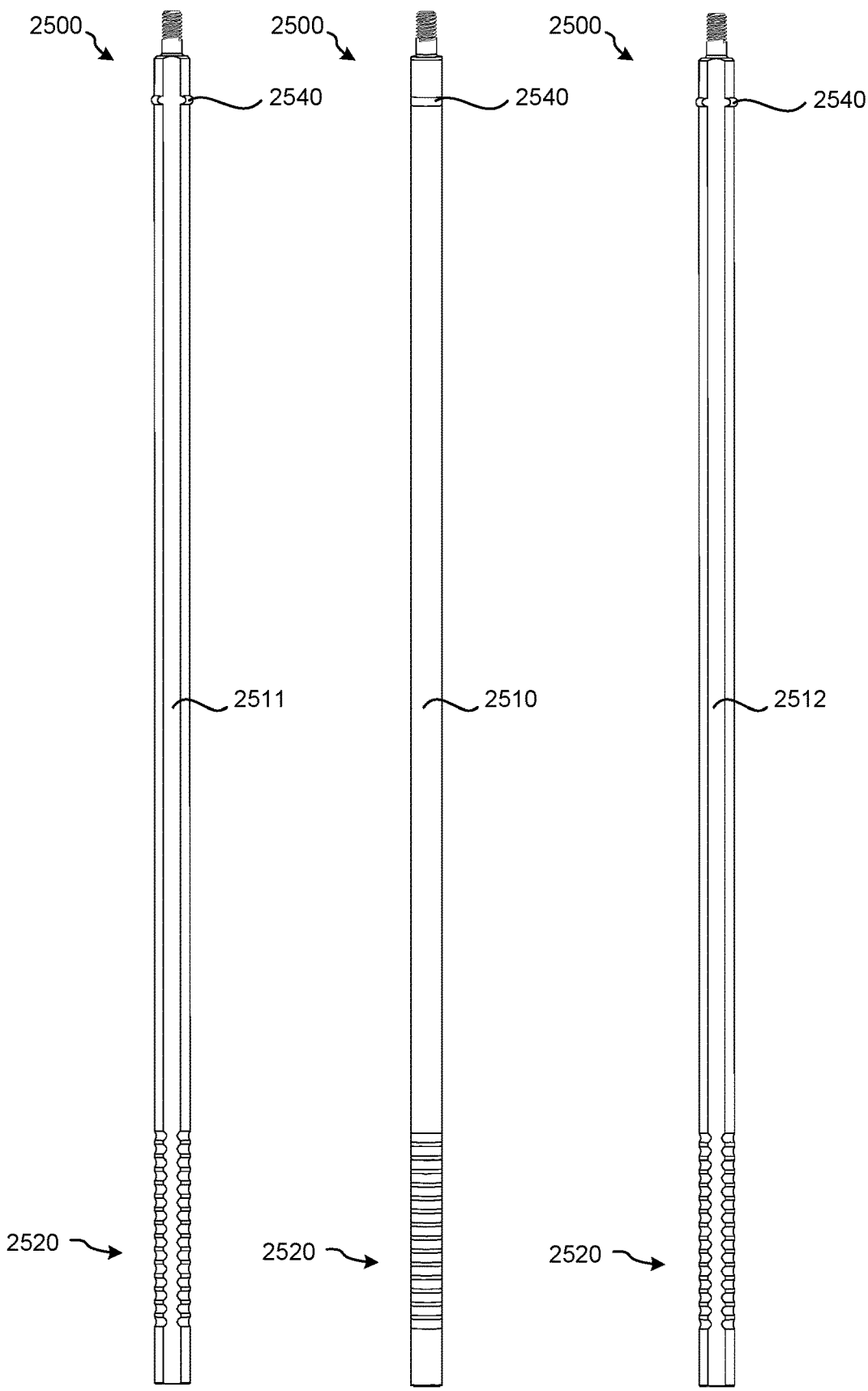
Figure 27A:
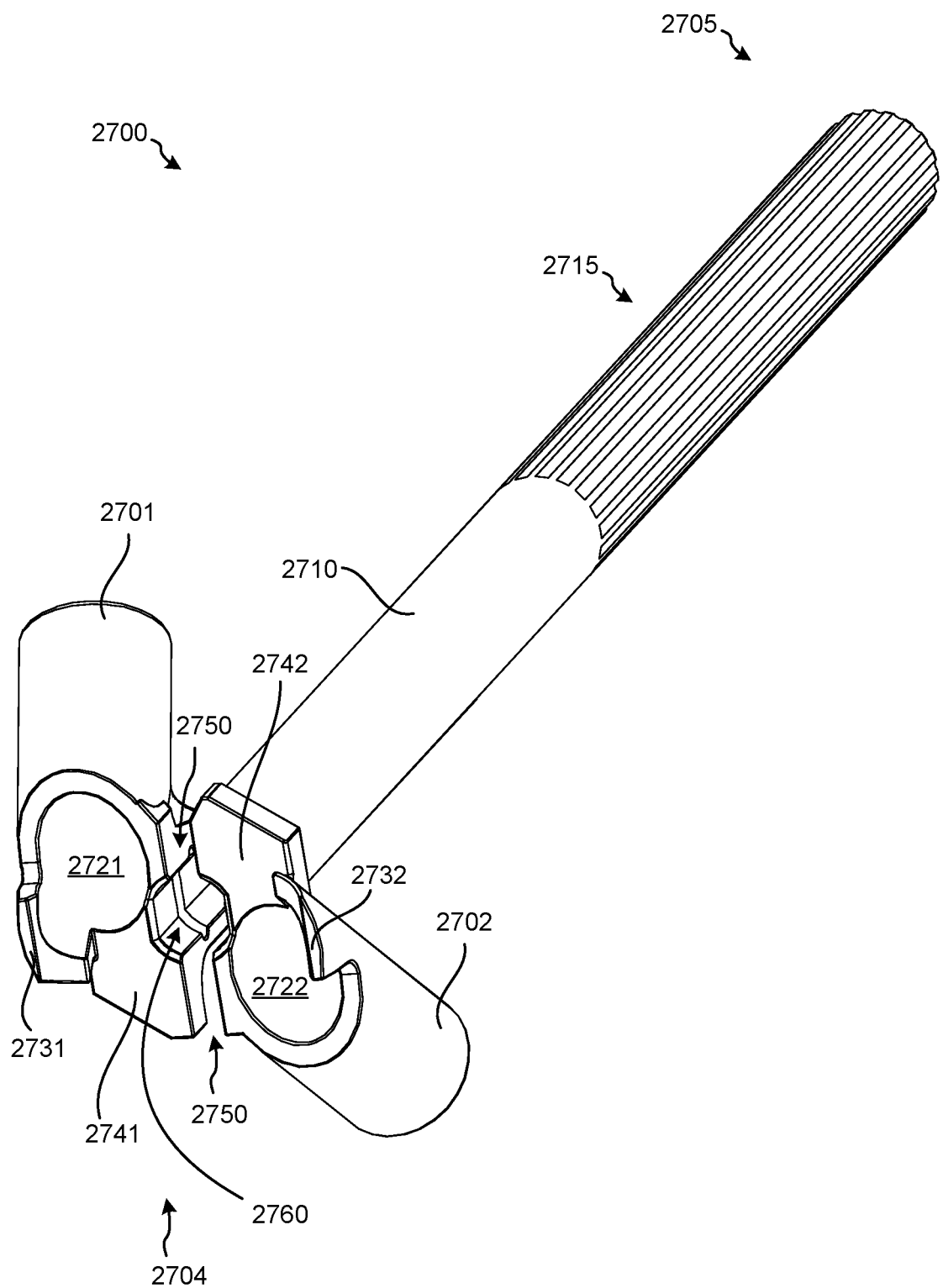
Figure 27B:
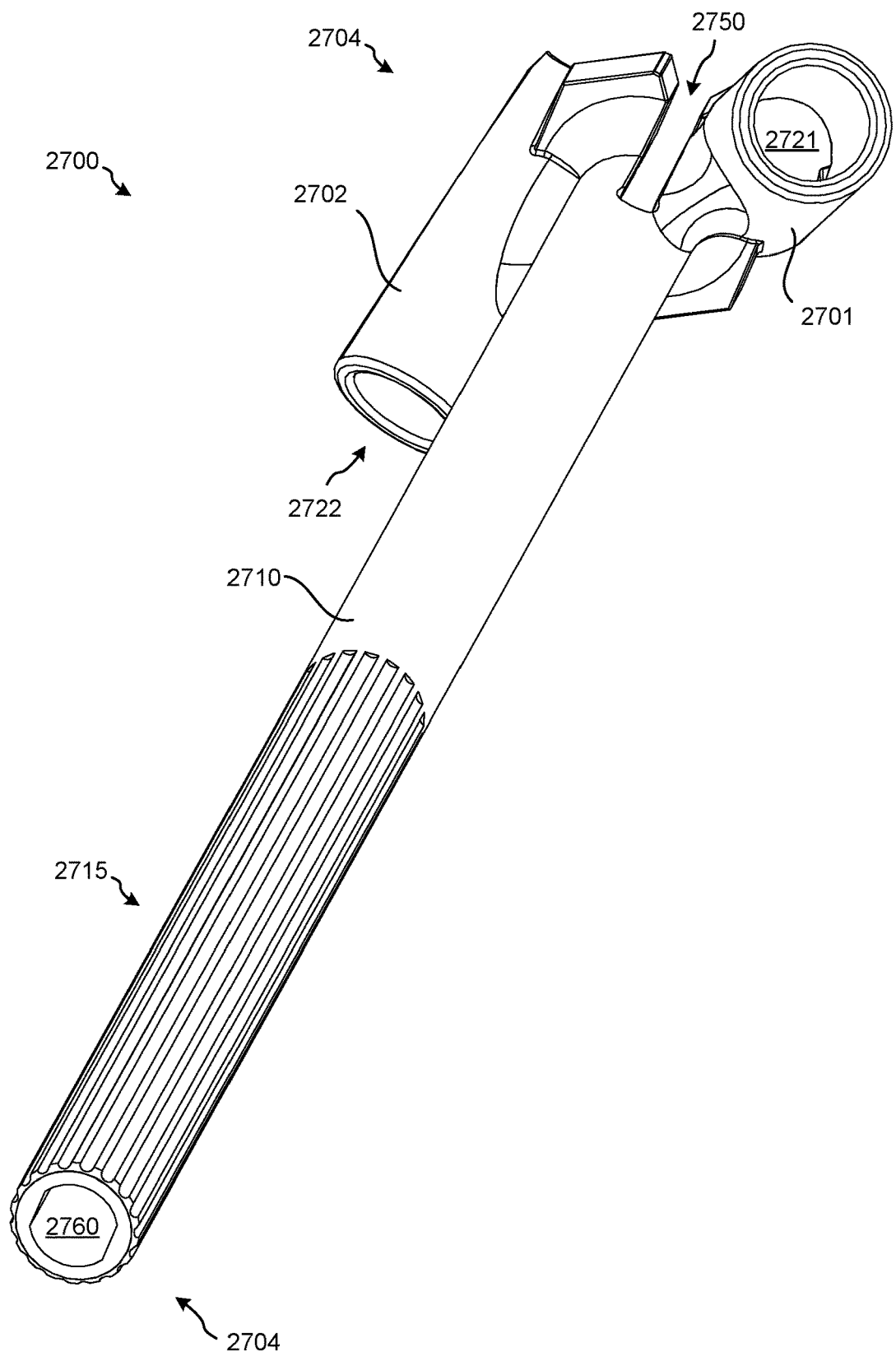
Figure 27E:
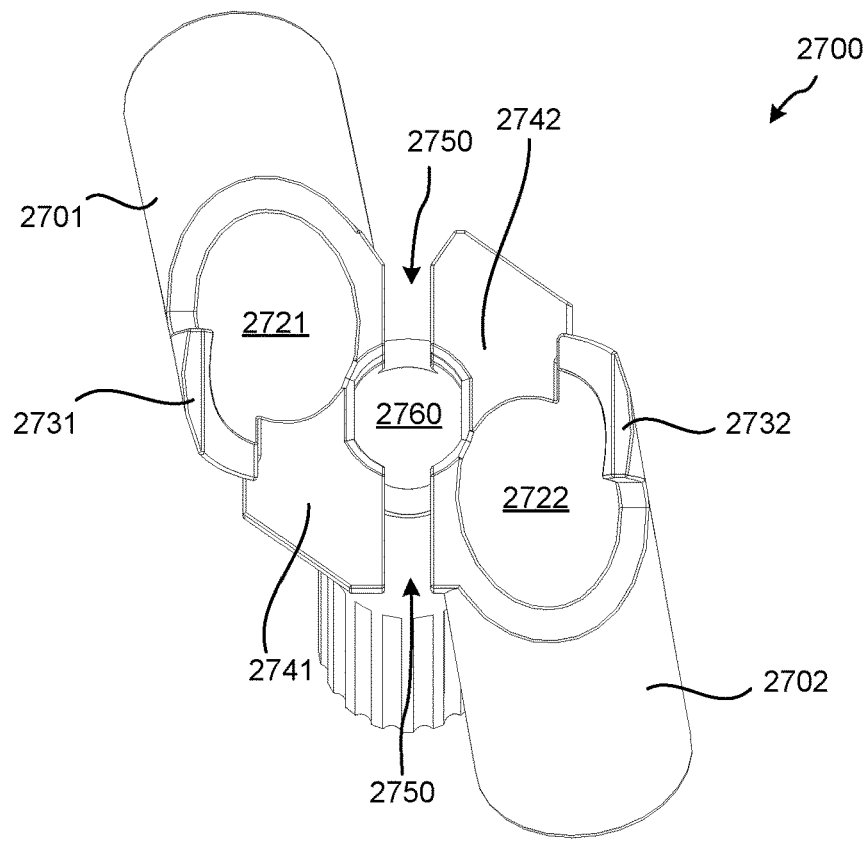
Figure 27F:
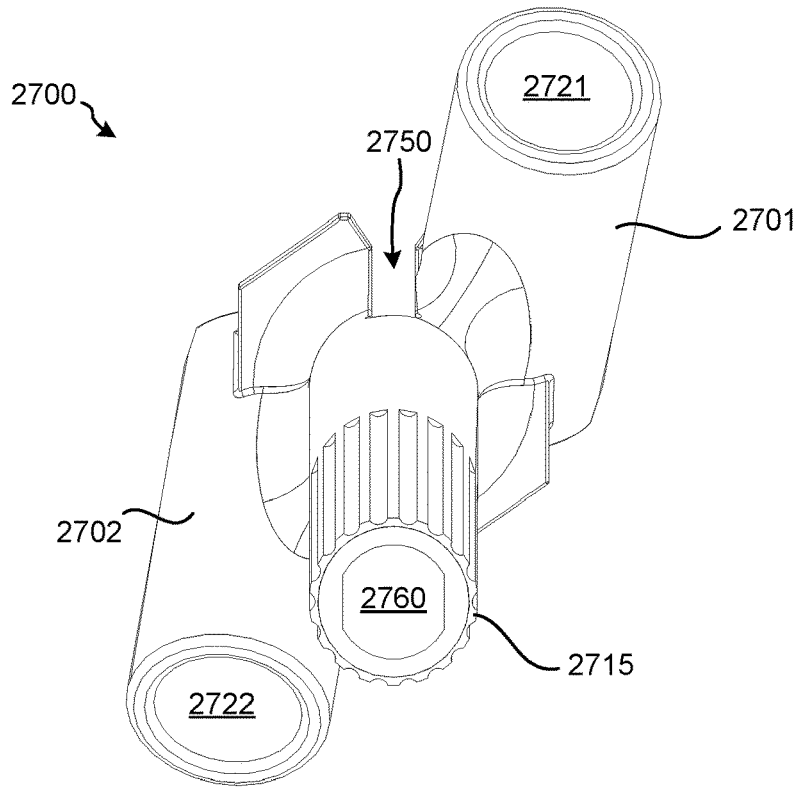
Figure 28A:
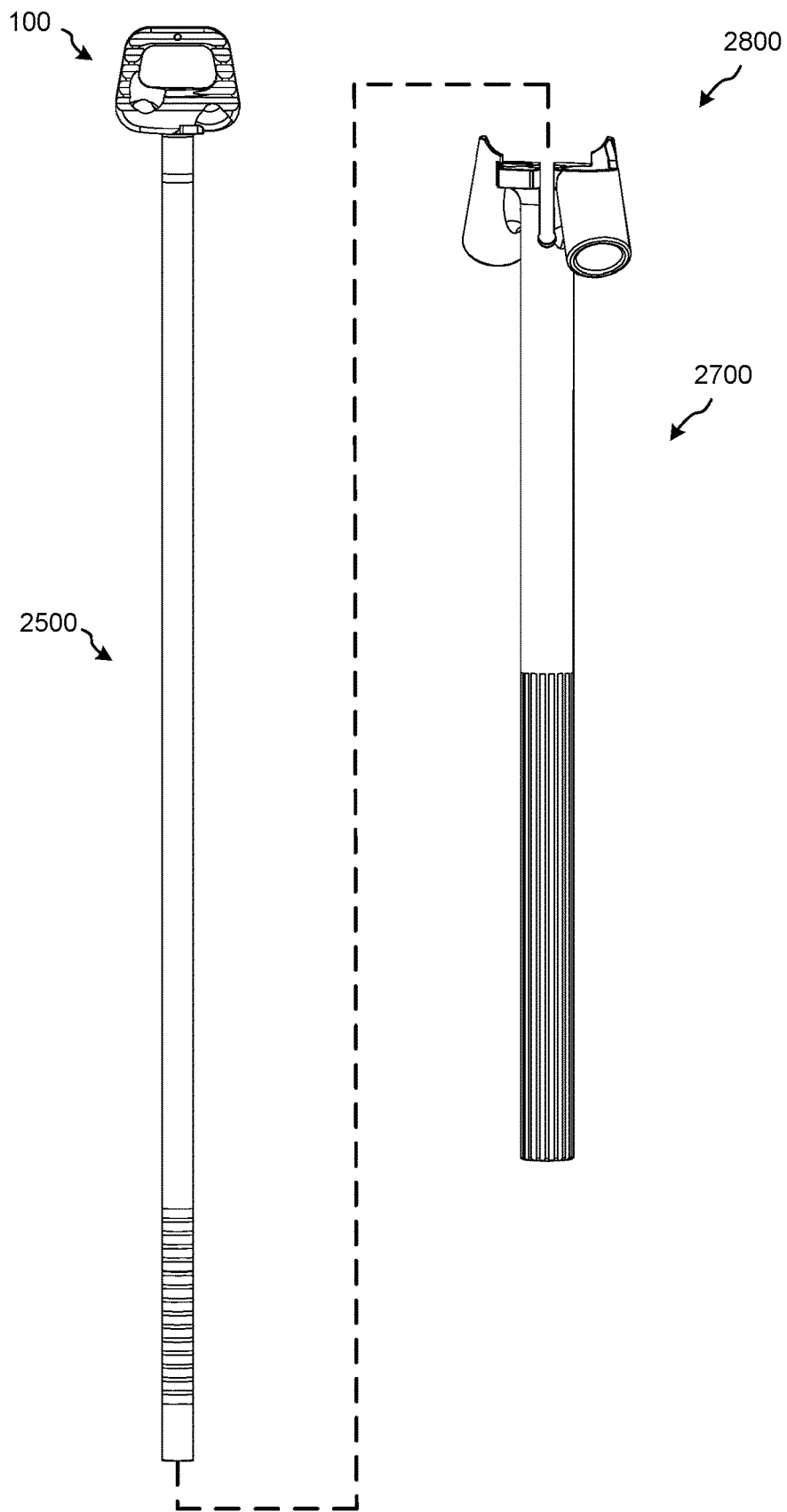
Figure 28B:
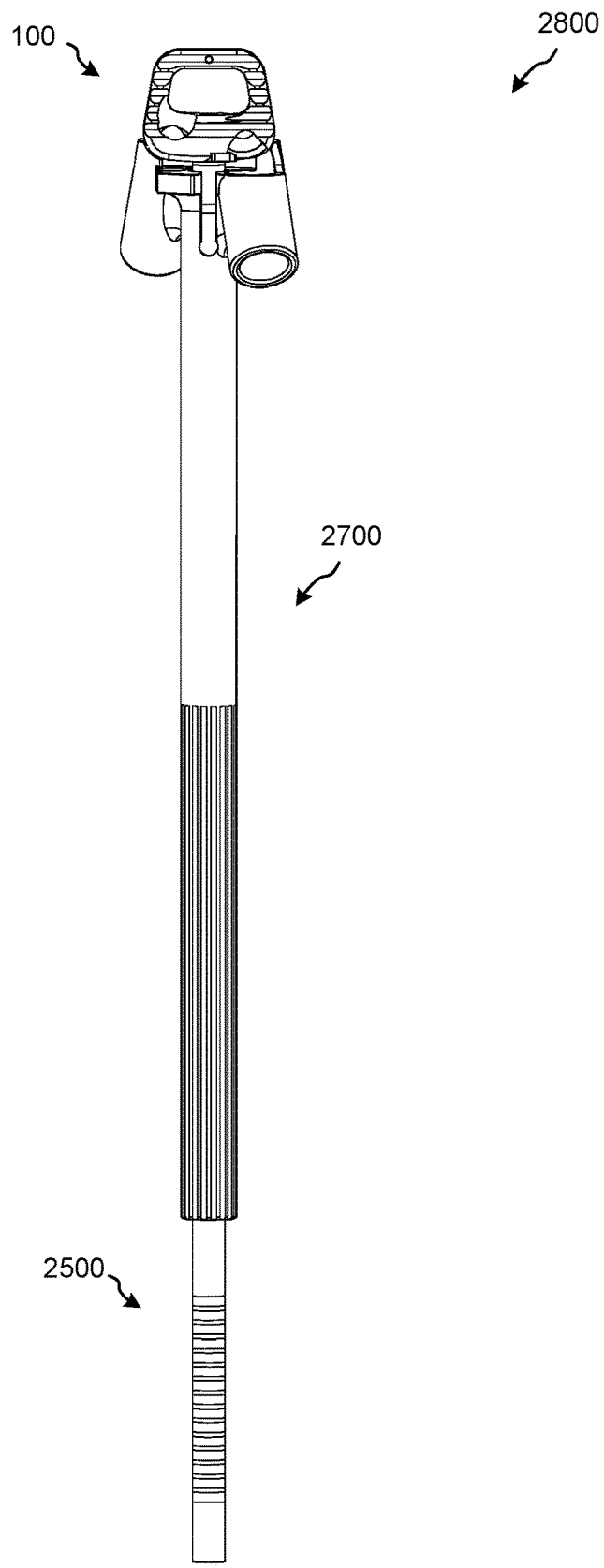
Figure 29A:
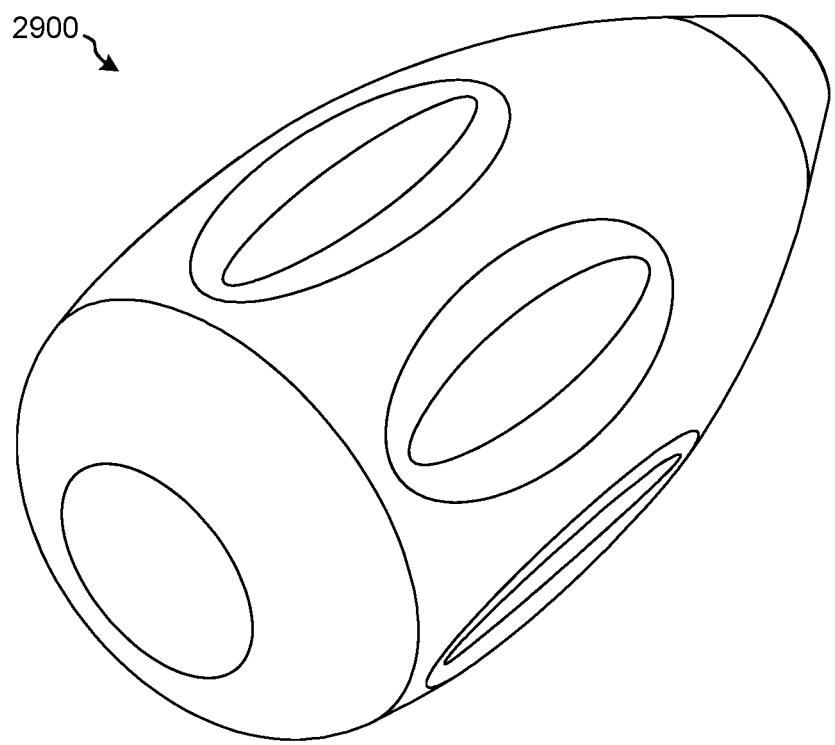
Figure 29B:
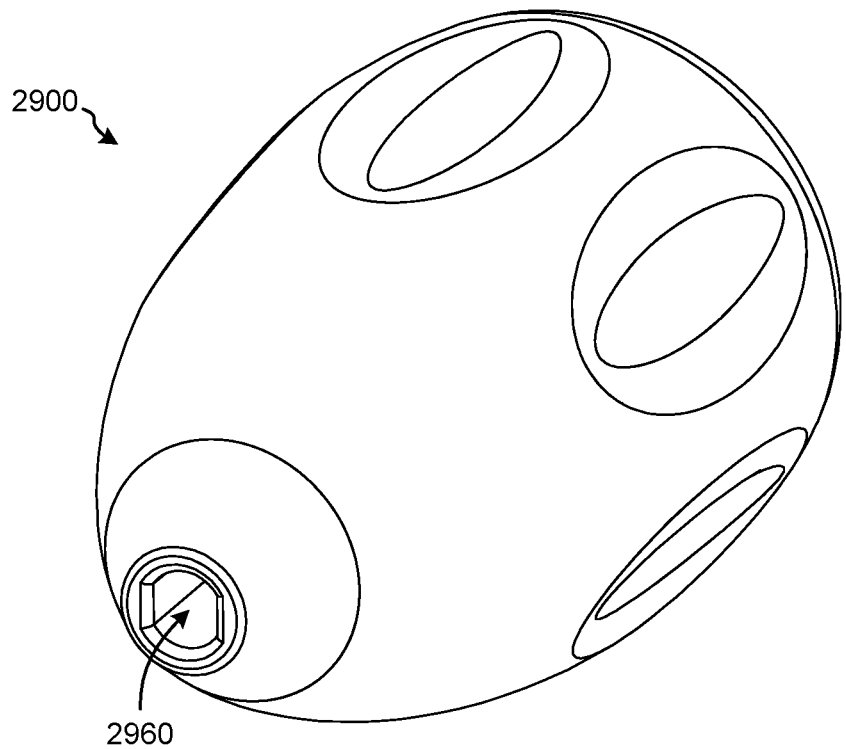
Figure 30A:
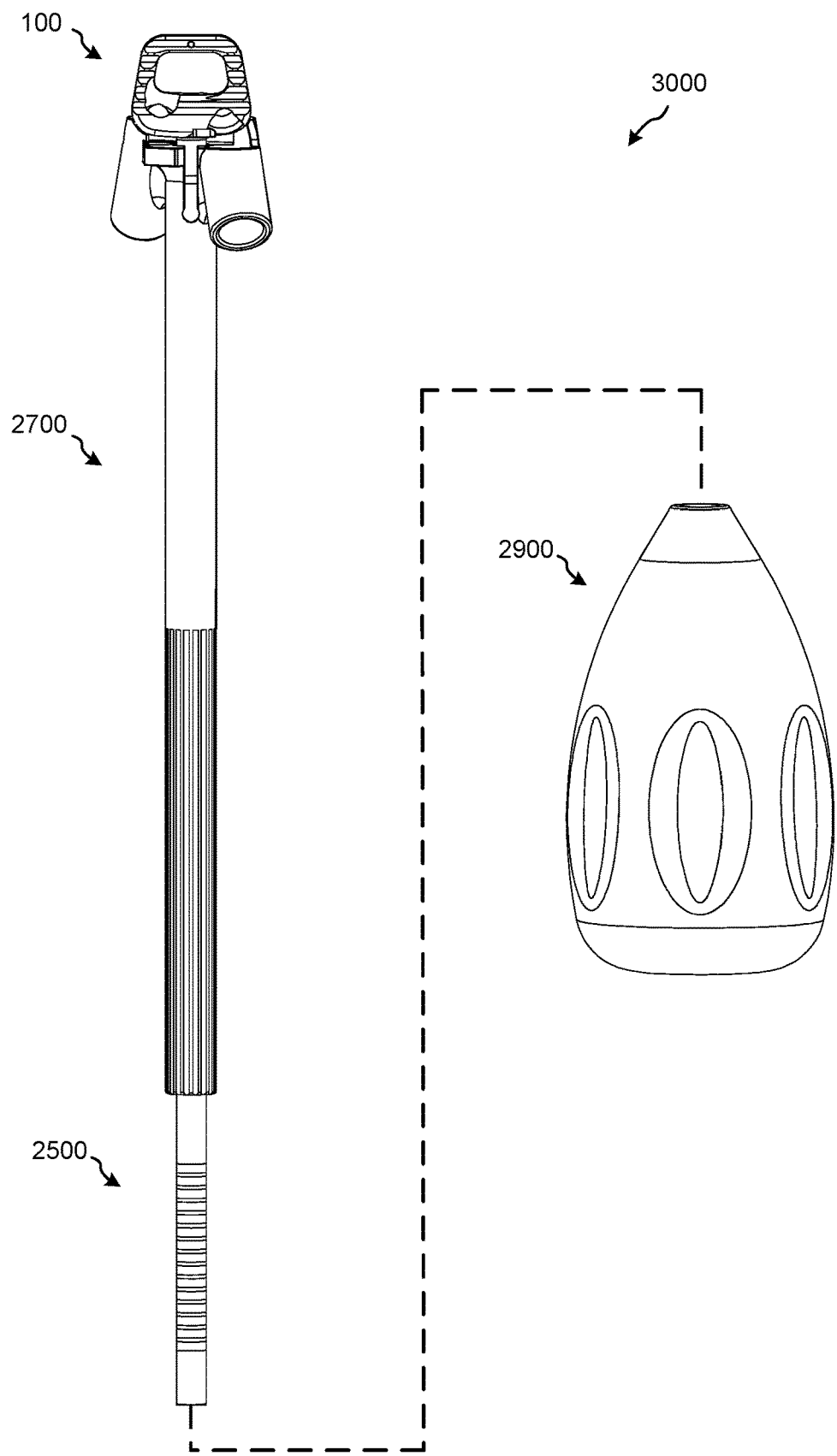
Figure 30B:
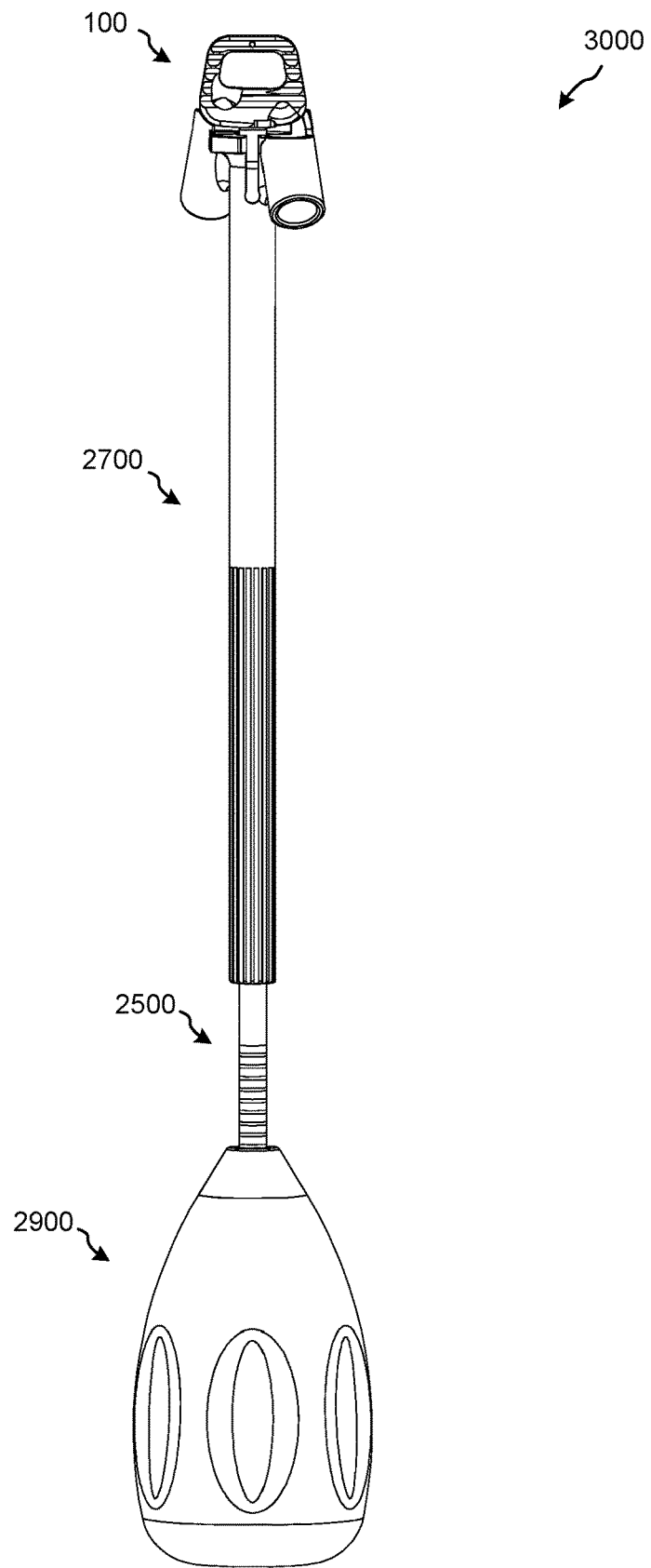
Figure 31A:
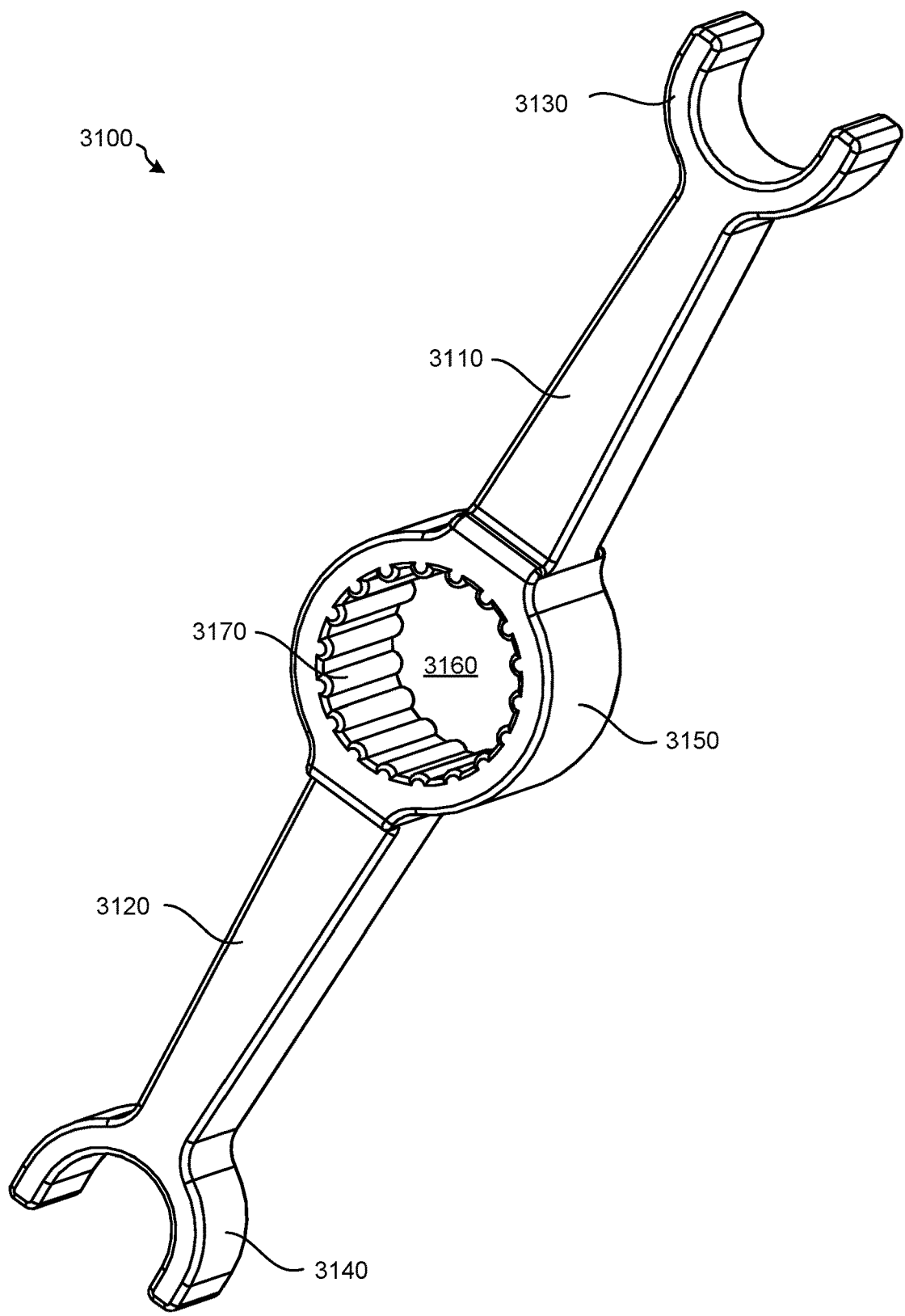
Figure 32A:
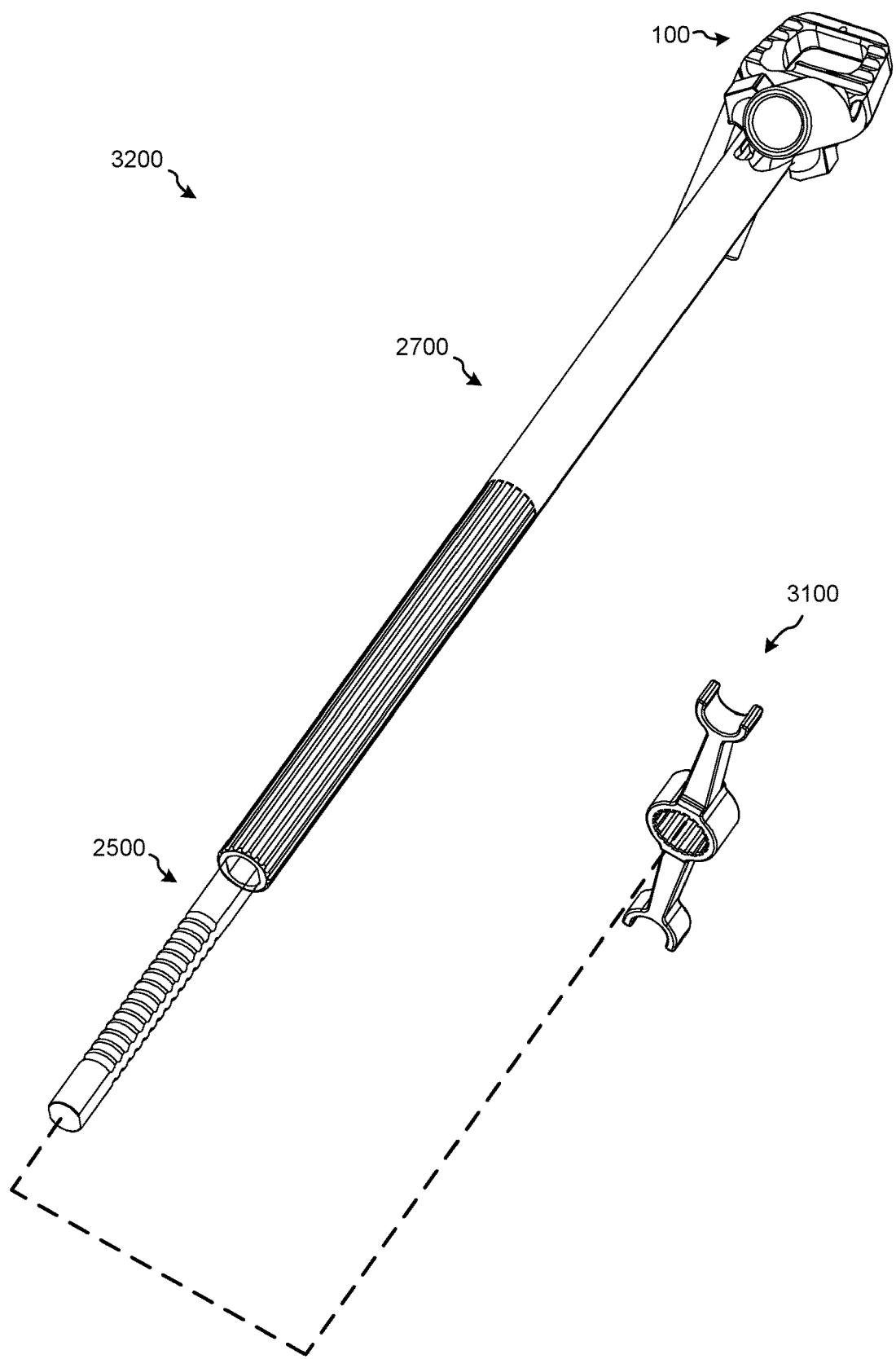
Figure 32B:
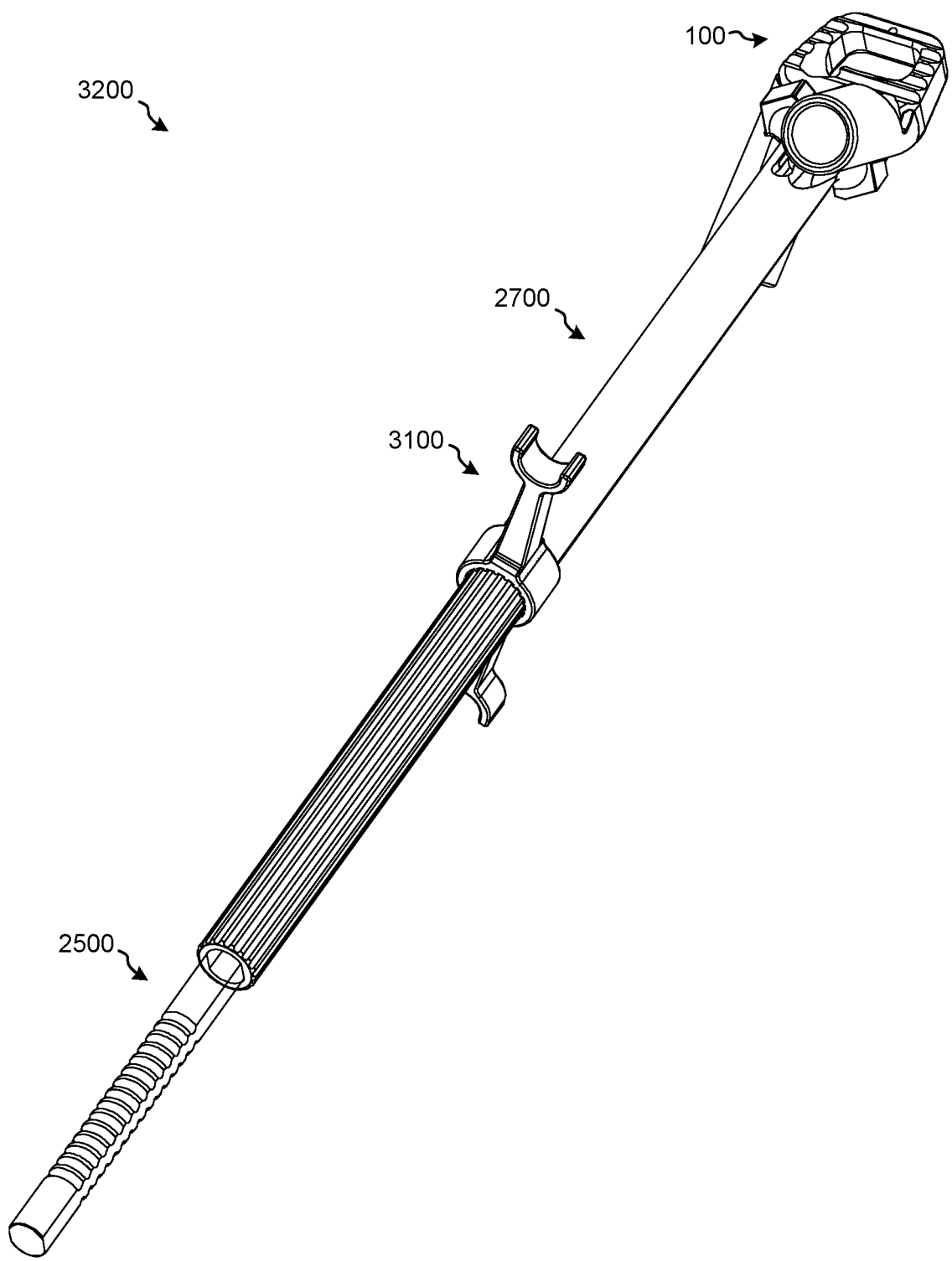
Figure 33A:
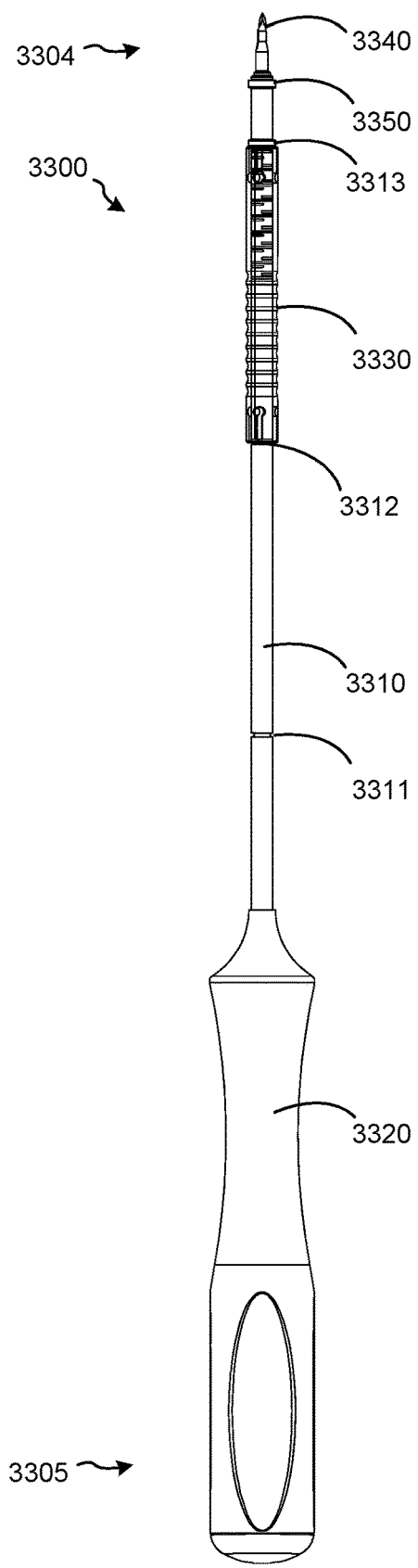
Figure 33B:
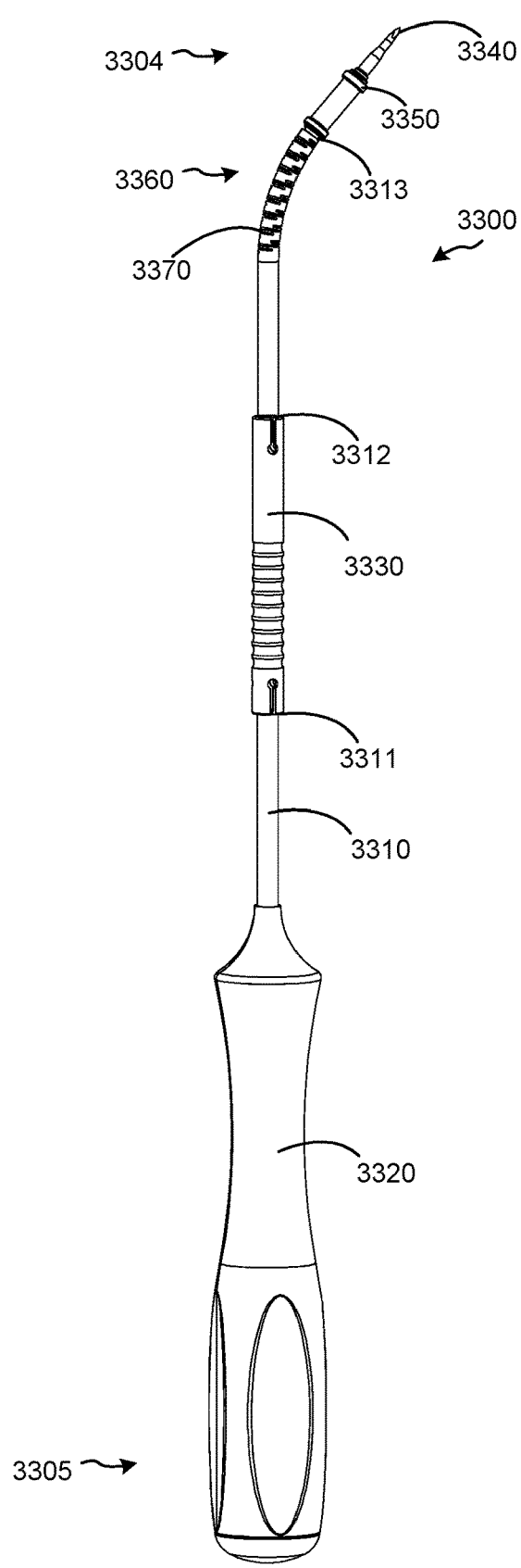
Figure 34:
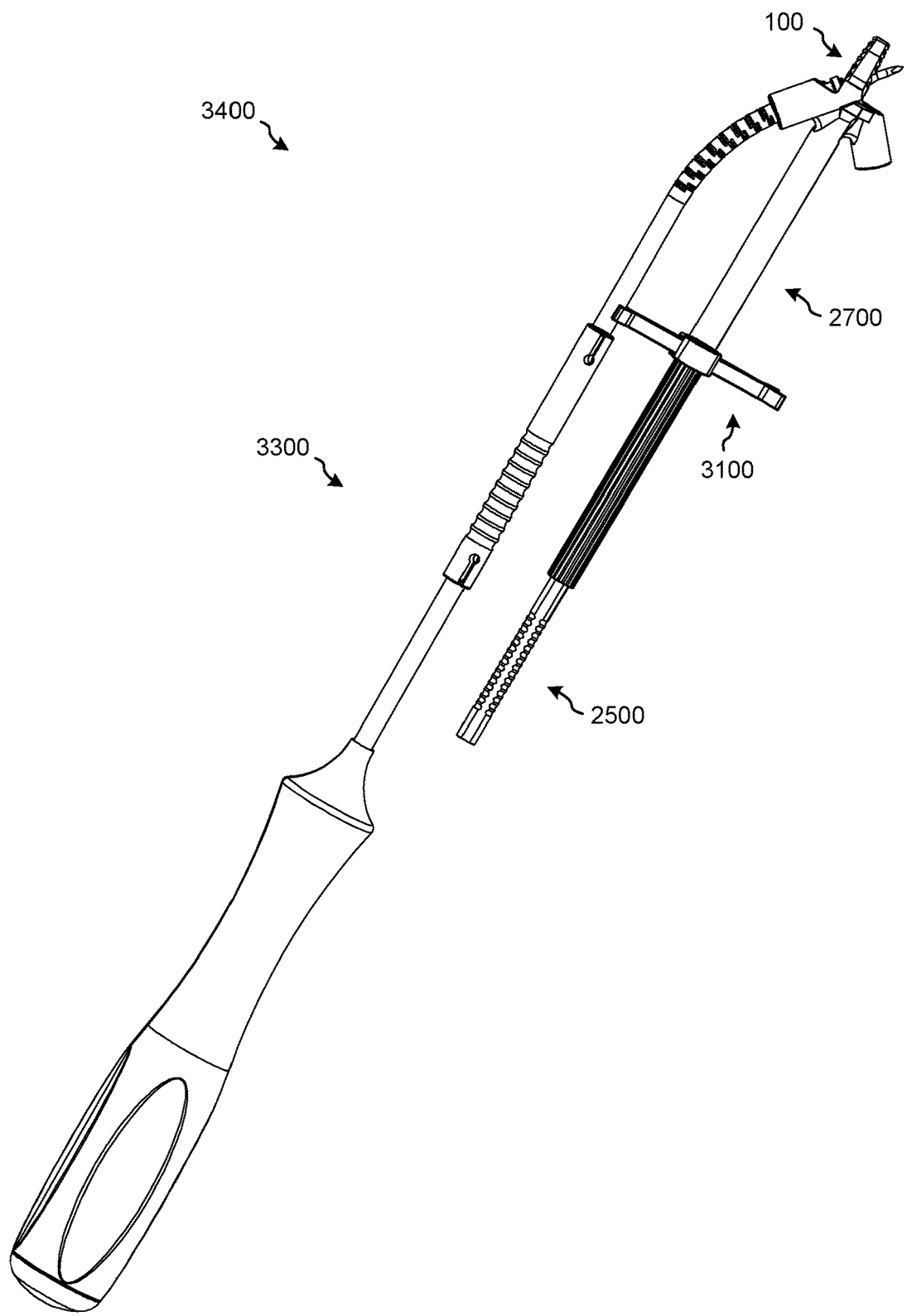
Figure 36:
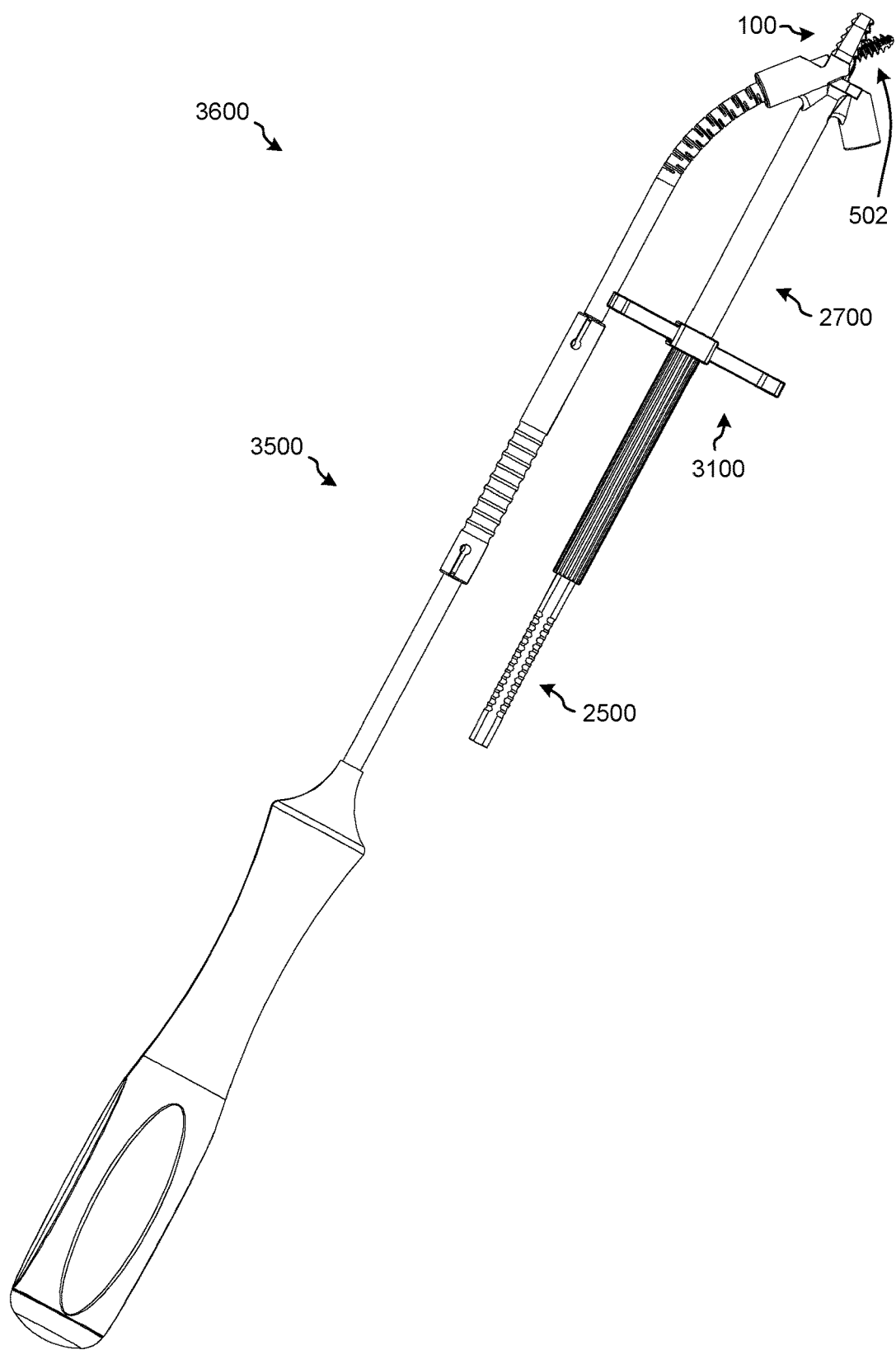
Figure 37:
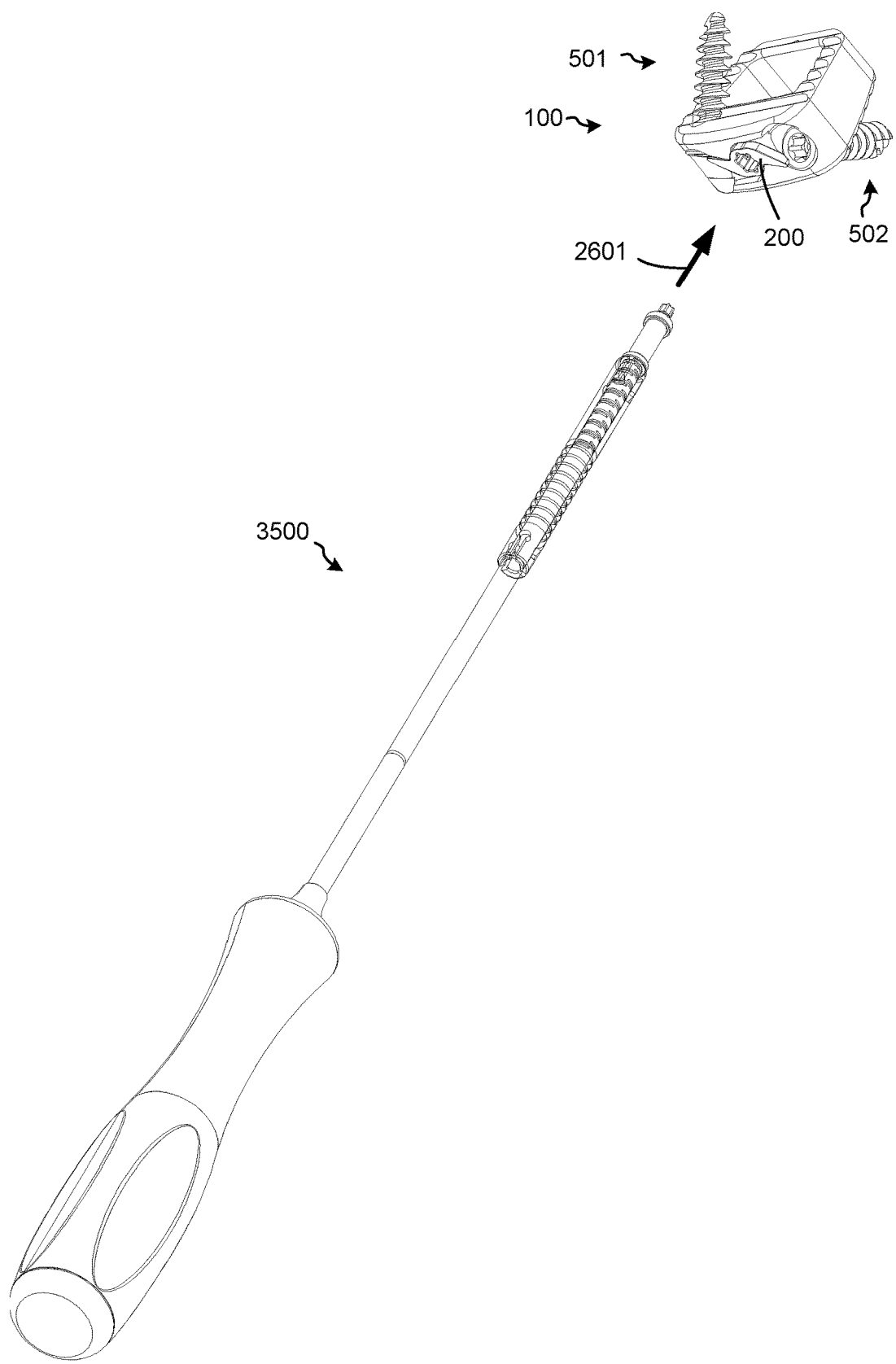
Figure 38:
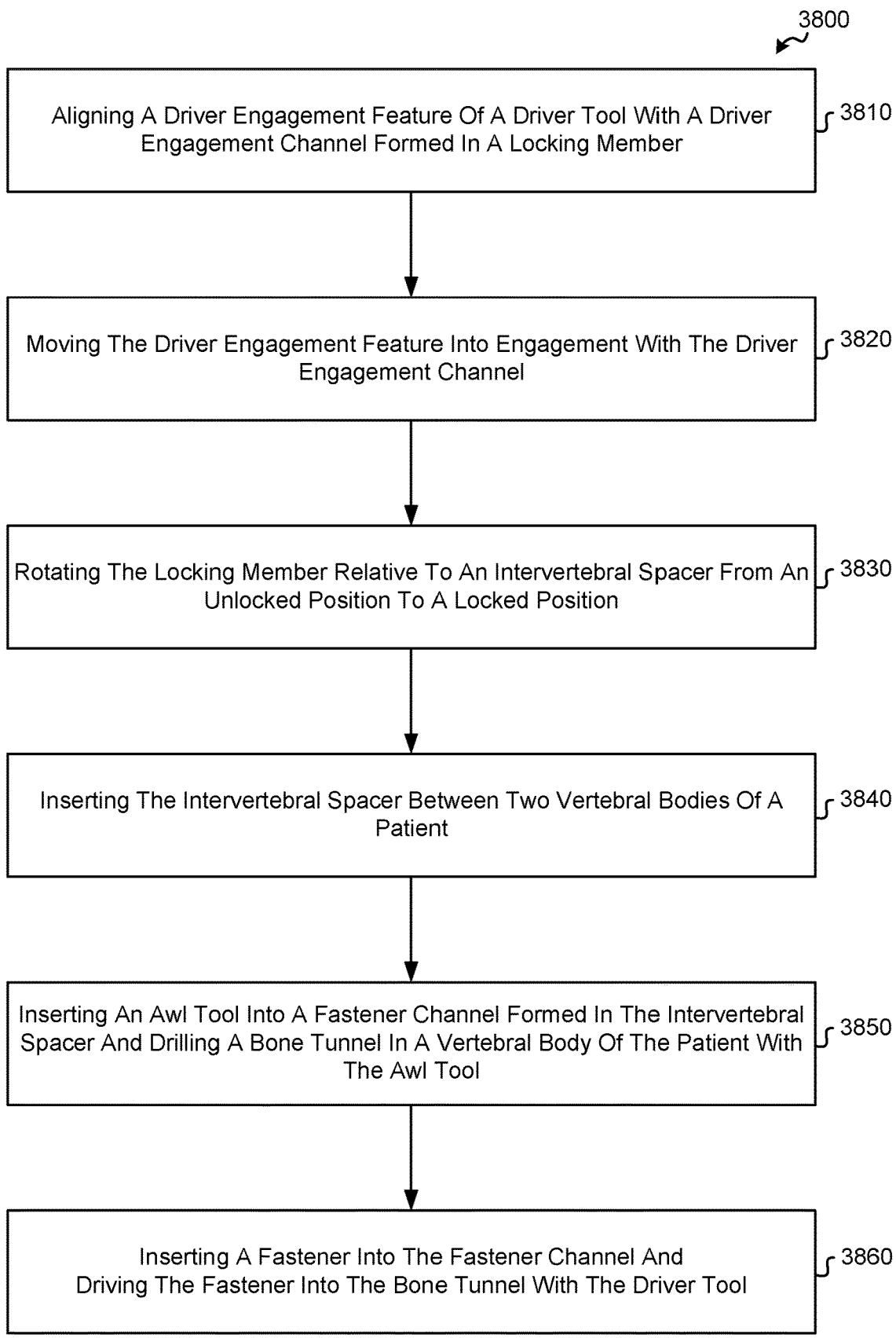

FIG. 19D is a bottom view of the intervertebral spacer 1900 of FIG. 19A;

FIG. 19E illustrates a first side of the intervertebral spacer 1900 of FIG. 19A;

FIG. 19F illustrates a second side of the intervertebral spacer 1900 of FIG. 19A;

FIG. 19G illustrates the distal end of the intervertebral spacer 1900 of FIG. 19A;

FIG. 19H illustrates the proximal end of the intervertebral spacer 1900 of FIG. 19A;

FIG. 20A is a perspective top view of a proximal end of an intervertebral spacer 2000, according to an embodiment of the present disclosure;

FIG. 20B is a perspective top view of a distal end of the intervertebral spacer 2000 of FIG. 20A;

FIG. 20C is a top view of the intervertebral spacer 2000 of FIG. 20A;

FIG. 20D is a bottom view of the intervertebral spacer 2000 of FIG. 20A;

FIG. 20E illustrates a first side of the intervertebral spacer 2000 of FIG. 20A;

FIG. 20F illustrates a second side of the intervertebral spacer 2000 of FIG. 20A;

FIG. 20G illustrates the distal end of the intervertebral spacer 2000 of FIG. 20A;

FIG. 20H illustrates the proximal end of the intervertebral spacer 2000 of FIG. 20A;

FIG. 21A is a perspective top view of a proximal end of an intervertebral spacer 2100, according to an embodiment of the present disclosure;

FIG. 21B is a perspective top view of a distal end of the intervertebral spacer 2100 of FIG. 21A;

FIG. 21C is a top view of the intervertebral spacer 2100 of FIG. 21A;

FIG. 21D is a bottom view of the intervertebral spacer 2100 of FIG. 21A;

FIG. 21E illustrates a first side of the intervertebral spacer 2100 of FIG. 21A;

FIG. 21F illustrates a second side of the intervertebral spacer 2100 of FIG. 21A;

FIG. 21G illustrates the distal end of the intervertebral spacer 2100 of FIG. 21A;

FIG. 21H illustrates the proximal end of the intervertebral spacer 2100 of FIG. 21A;

FIG. 22A is a perspective top view of a proximal end of an intervertebral spacer 2200, according to an embodiment of the present disclosure;

FIG. 22B is a perspective top view of a distal end of the intervertebral spacer 2200 of FIG. 22A;

FIG. 22C is a top view of the intervertebral spacer 2200 of FIG. 22A;

FIG. 22D is a bottom view of the intervertebral spacer 2200 of FIG. 22A;

FIG. 22E illustrates a first side of the intervertebral spacer 2200 of FIG. 22A;

FIG. 22F illustrates a second side of the intervertebral spacer 2200 of FIG. 22A;

FIG. 22G illustrates the distal end of the intervertebral spacer 2200 of FIG. 22A;

FIG. 22H illustrates the proximal end of the intervertebral spacer 2200 of FIG. 22A;

FIG. 23A is a perspective top view of a proximal end of an intervertebral spacer 2300, according to an embodiment of the present disclosure;

FIG. 23B is a perspective top view of a distal end of the intervertebral spacer 2300 of FIG. 23A;

FIG. 23C is a top view of the intervertebral spacer 2300 of FIG. 23A;

FIG. 23D is a bottom view of the intervertebral spacer 2300 of FIG. 23A;

FIG. 23E illustrates a first side of the intervertebral spacer 2300 of FIG. 23A;

FIG. 23F illustrates a second side of the intervertebral spacer 2300 of FIG. 23A;

FIG. 23G illustrates the distal end of the intervertebral spacer 2300 of FIG. 23A;

FIG. 23H illustrates the proximal end of the intervertebral spacer 2300 of FIG. 23A;

FIG. 24A is a perspective top view of a trial tool 2400, according to an embodiment of the present disclosure;

FIG. 24B is a perspective bottom view of the trial tool 2400 of FIG. 24A;

FIG. 25A is a perspective top view of an inserter tool 2500, according to an embodiment of the present disclosure;

FIG. 25B is a perspective bottom view of the inserter tool 2500 of FIG. 25A;

FIG. 25C is a top view of the inserter tool 2500 of FIG. 25A;

FIG. 25D is a side view of the inserter tool 2500 of FIG. 25A;

FIG. 25E is a bottom view of the inserter tool 2500 of FIG. 25A;

FIG. 26A illustrates an insertion assembly 2600 including the inserter tool 2500 and the intervertebral spacer 100, prior to assembly;

FIG. 26B illustrates the insertion assembly 2600, after assembly;

FIG. 27A is a perspective top view of a DTS guide 2700, according to an embodiment of the present disclosure;

FIG. 27B is a perspective bottom view of the DTS guide 2700 of FIG. 27A;

FIG. 27C is a top view of the DTS guide 2700 of FIG. 27A;

FIG. 27D is a bottom view of the DTS guide 2700 of FIG. 27A;

FIG. 27E is a proximal end view of the DTS guide 2700 of FIG. 27A;

FIG. 27F is a distal end view of the DTS guide 2700 of FIG. 27A;

FIG. 28A is an exploded view of an insertion assembly 2800 including the inserter tool 2500, the intervertebral spacer 100, and the DTS guide 2700, prior to assembly;

FIG. 28B is a top view of the insertion assembly 2800 of FIG. 28A, after assembly;

FIG. 29A is a perspective top view of a handle 2900, according to an embodiment of the present disclosure;

FIG. 29B is a perspective bottom view of the handle 2900 of FIG. 29A;

FIG. 30A is an exploded view of an insertion assembly 3000 including the inserter tool 2500, the intervertebral spacer 100, the DTS guide 2700, and the handle 2900, prior to assembly;

FIG. 30B is a top view of the insertion assembly 3000 of FIG. 30A, after assembly;

FIG. 31A is a perspective view of a U-support tool 3100, according to an embodiment of the present disclosure;

FIG. 31B is a front side view of the U-support tool 3100 of FIG. 31A;

FIG. 31C is a top view of the U-support tool 3100 of FIG. 31A;

FIG. 31D is a left side view of the U-support tool 3100 of FIG. 31A;

FIG. 32A is an exploded view of an insertion assembly 3200 including the inserter tool 2500, the intervertebral spacer 100, the DTS guide 2700, and the U-support tool 3100, prior to assembly;

FIG. 32B is a perspective view of the insertion assembly 3200 of FIG. 32A, after assembly;

FIG. 33A is a side view of a flexible awl tool 3300, according to an embodiment of the present disclosure;

FIG. 33B is a side view of the flexible awl tool 3300 of FIG. 33A, with the shaft 3310 in flexion;

FIG. 34 illustrates an insertion assembly 3400 including the inserter tool 2500, the intervertebral spacer 100, the DTS guide 2700, the U-support tool 3100, and the awl tool 3300 assembled together;

FIG. 35A is a side view of a flexible driver tool 3500, according to an embodiment of the present disclosure;

FIG. 35B is a side view of the flexible driver tool 3500 of FIG. 35A, with the shaft 3510 in flexion;

FIG. 36 illustrates an insertion assembly 3600 including the inserter tool 2500, the intervertebral spacer 100, the bone screw 502, the DTS guide 2700, the U-support tool 3100, and the driver tool 3500 assembled together;

FIG. 37 illustrates the driver tool 3500 of FIG. 35A coupling to the locking member 200 in order to rotate the locking member 200 to a locked position and prevent the bone screws 501, 502 from backing out of the intervertebral spacer 100; and FIG. 38 illustrates a flowchart of a method 3800 for preventing a fastener from backing out of an intervertebral spacer, according to an embodiment of the present disclosure.

It is to be understood that the drawings are for purposes of illustrating the concepts of the disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the Figures herein, could be arranged and designed in a wide variety of different configurations. Thus, the following more detailed description of the embodiments of the apparatus and method, as represented in the Figures, is not intended to limit the scope of the present disclosure, as claimed in this or any other application claiming priority to this application, but is merely representative of exemplary embodiments of the present disclosure.

Standard medical directions, planes of reference, and descriptive terminology are employed in this specification. For example, anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. A sagittal plane divides a body into right and left portions. A midsagittal plane divides the body into bilaterally symmetric right and left halves. A coronal plane divides a body into anterior and posterior portions. A transverse plane divides a body into superior and inferior portions. These descriptive terms may be applied to an animate or inanimate body.

The phrases "connected to," "coupled to," "engaged with," and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Figure 1A:
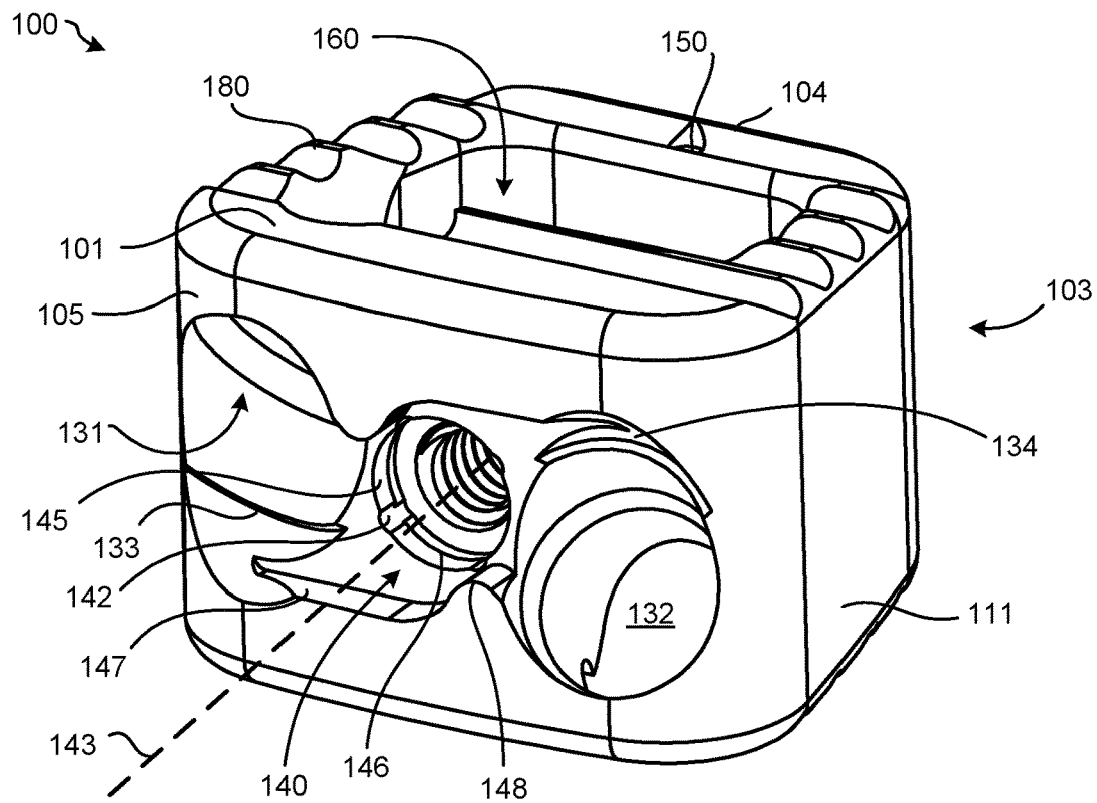
FIG. 1A is a perspective top view of a proximal end of an intervertebral spacer 100, according to an embodiment of the present disclosure.
Figure 1B:
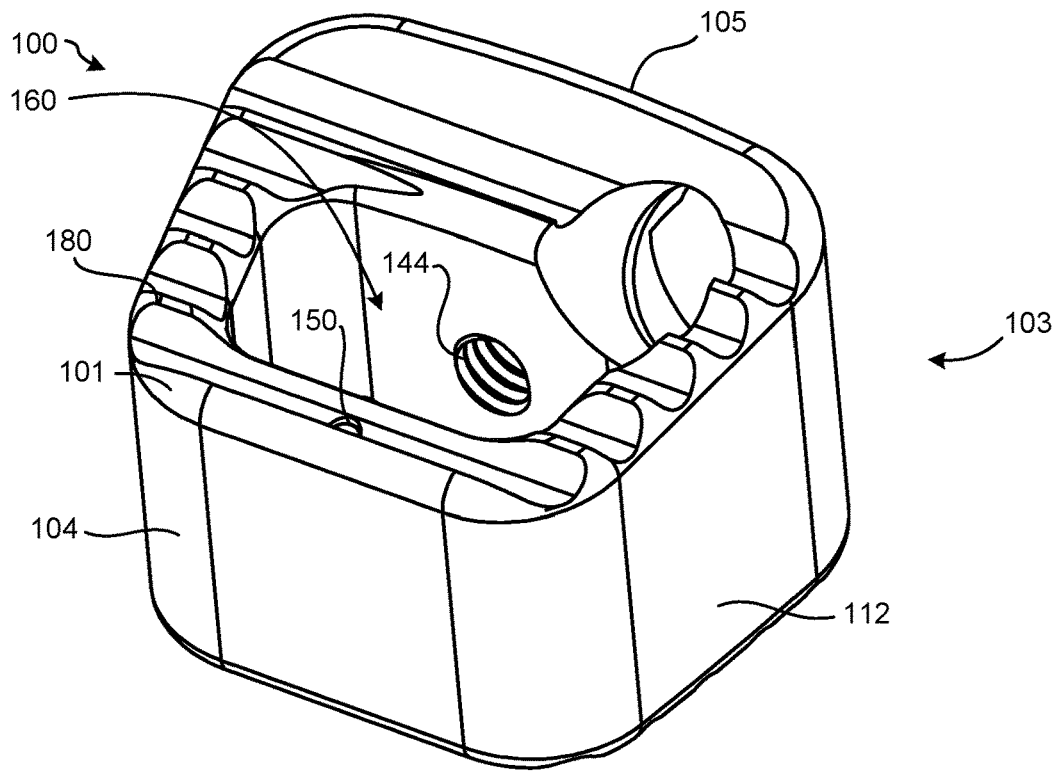
FIG. 1B is a perspective top view of a distal end of the intervertebral spacer 100 of FIG. 1A.
Figure 1C:
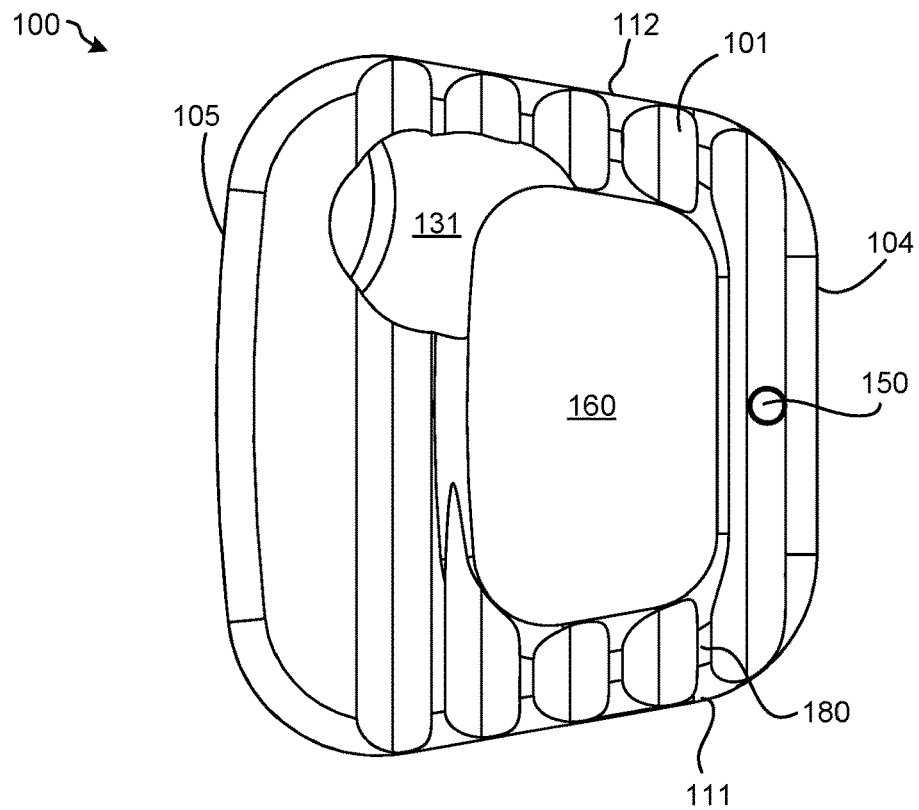
FIG. 1C is a top view of the intervertebral spacer 100 of FIG. 1A.
Figure 1D:
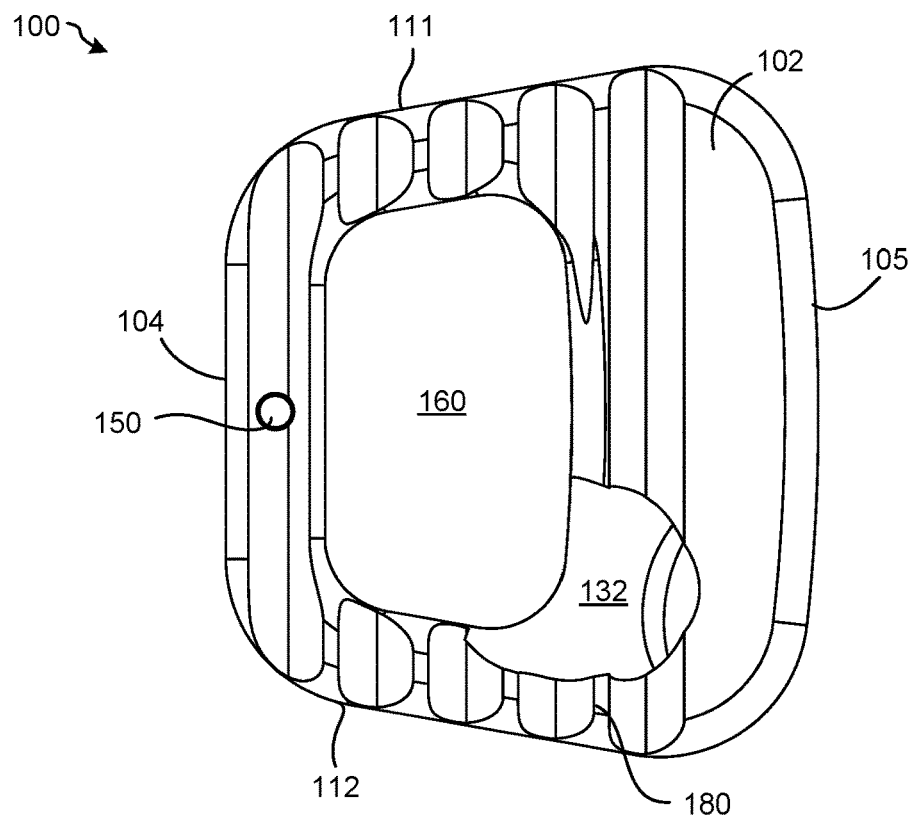
FIG. 1D is a bottom view of the intervertebral spacer 100 of FIG. 1A.
Figure 1E:
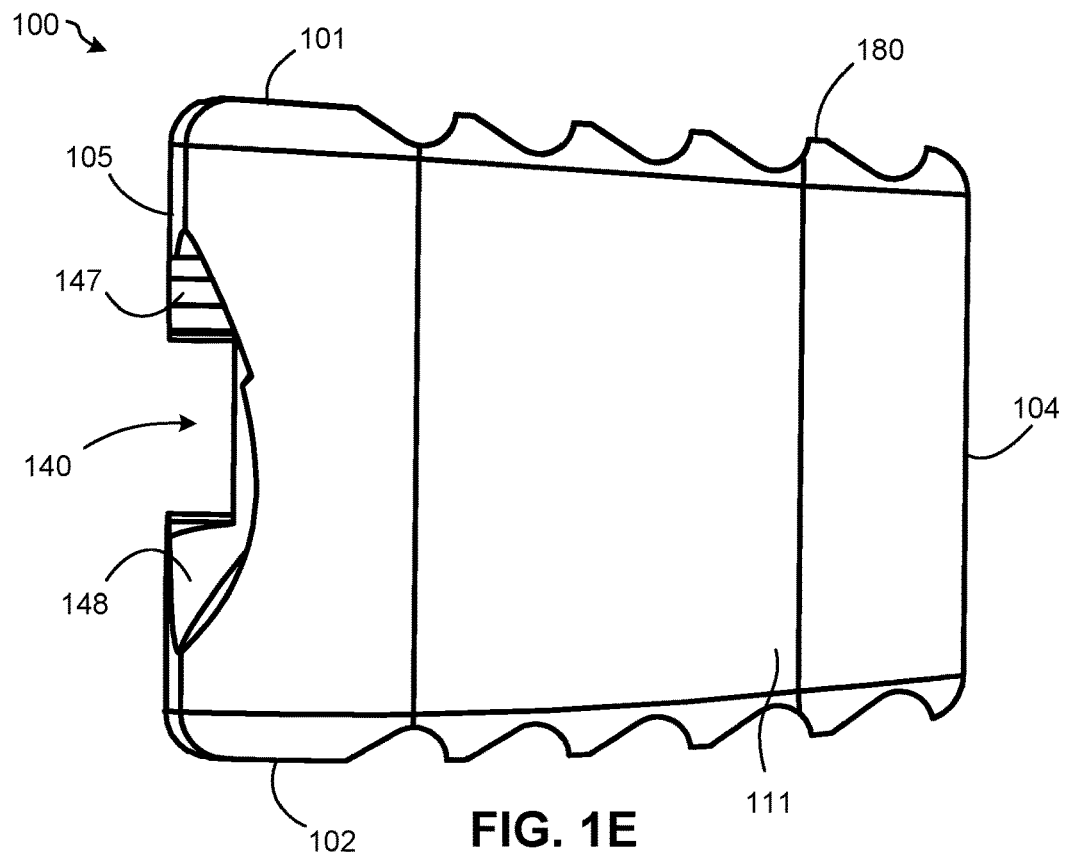
FIG. 1E illustrates a first side of the intervertebral spacer 100 of FIG. 1A.
Figure 1F:
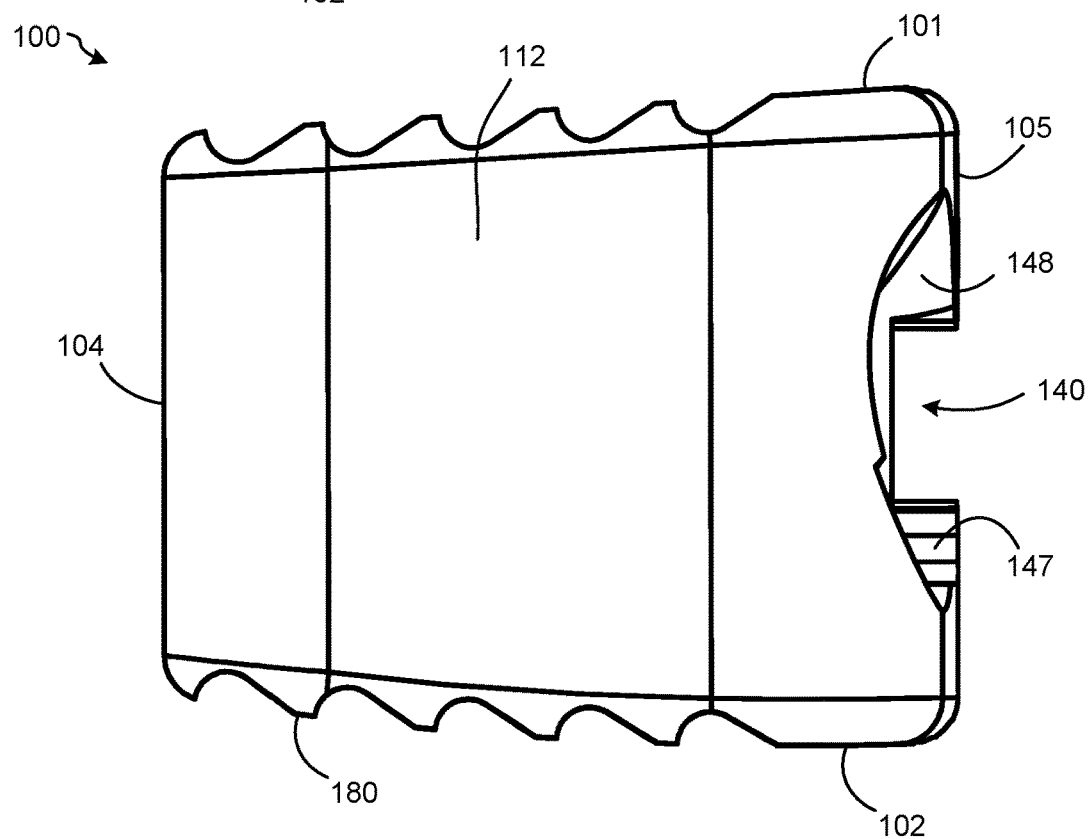
FIG. 1F illustrates a second side of the intervertebral spacer 100 of FIG. 1A.
Figure 1G:
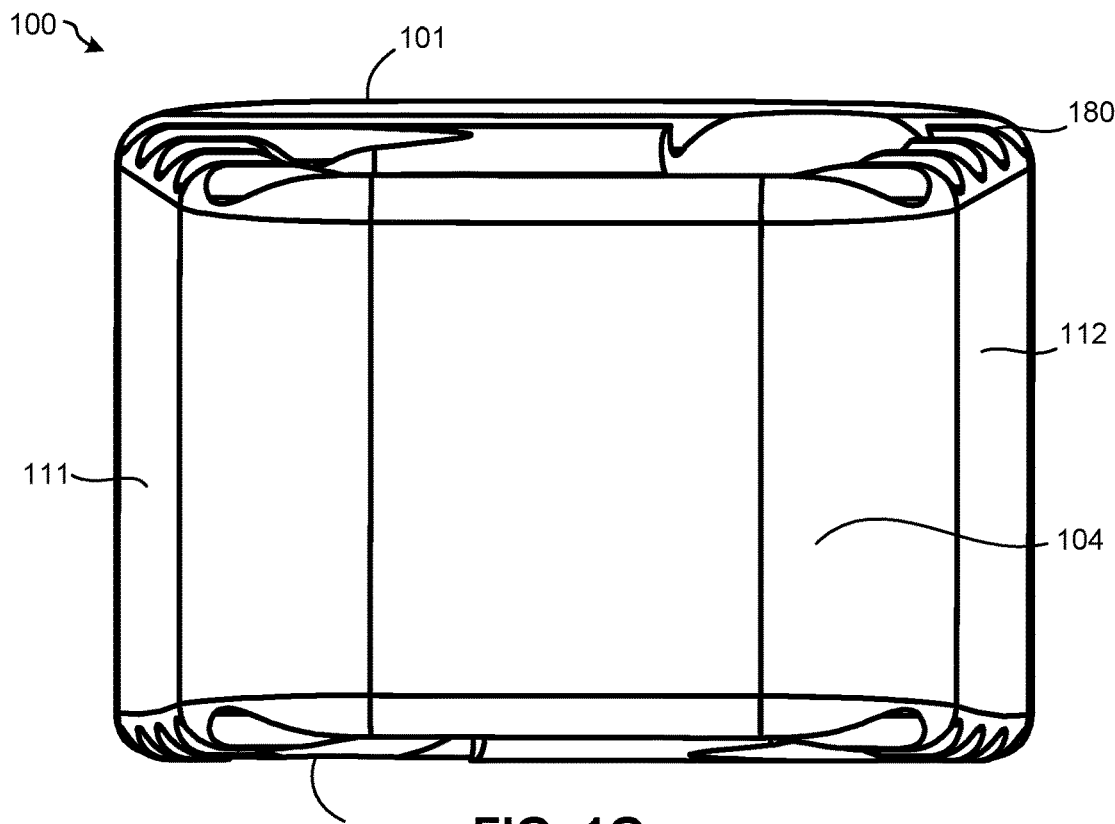
FIG. 1G illustrates the distal end of the intervertebral spacer 100 of FIG. 1A.
Figure 1H:
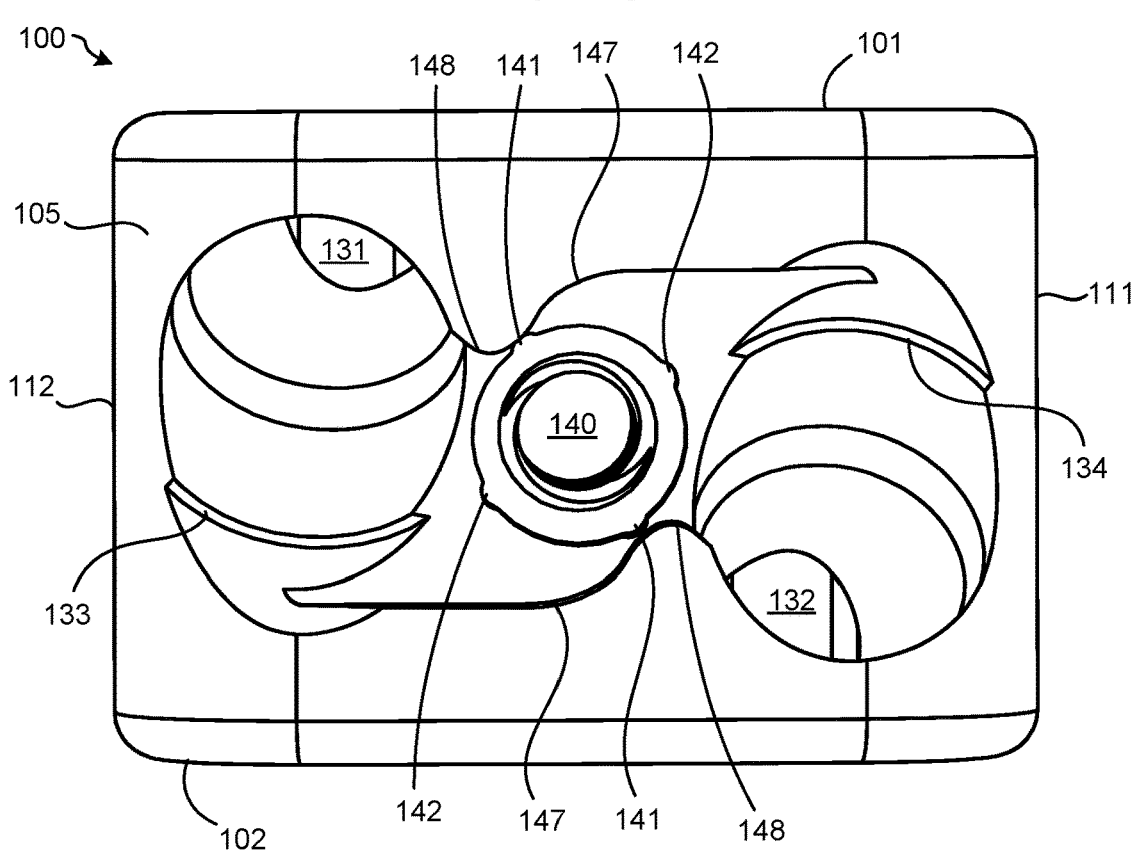
FIG. 1H illustrates the proximal end of the intervertebral spacer 100 of FIG. 1A.

FIGS. 1A-1H illustrate various views of an intervertebral spacer 100, according to an embodiment of the present disclosure. Specifically, FIG. 1A is a perspective top view of a proximal end 105 or a proximal surface of the intervertebral spacer 100; FIG. 1B is a perspective top view of a distal end 104 of the intervertebral spacer 100; FIG. 1C is a top view of the intervertebral spacer 100; FIG. 1D is a bottom view of the intervertebral spacer 100; FIG. 1E illustrates a first side 111 of the intervertebral spacer 100; FIG. 1F illustrates a second side 112 of the intervertebral spacer 100; FIG. 1G is a view of the distal end 104 of the intervertebral spacer 100; and FIG. 1H is a view of the proximal end 105 of the intervertebral spacer 100.

The intervertebral spacer 100 may generally include a superior surface 101 configured to engage a superior vertebral body (not shown), an inferior surface 102 configured to engage an inferior vertebral body (not shown), and a peripheral wall 103 extending from the superior surface 101 to the inferior surface 102. The peripheral wall 103 may generally comprise the distal end 104, the proximal end 105, the first side 111, and the second side 112 of the intervertebral spacer 100.

The intervertebral spacer 100 may include one or more bone graft channels 160 oriented to pass through opposing ends of the intervertebral spacer 100. For example, the one or more bone graft channels 160 may be formed through the superior and inferior surfaces 101, 102 of the intervertebral spacer 100. The intervertebral spacer 100 may also include one or more side bone graft channels (not shown) that may be formed in the first and second sides 111, 112 of the intervertebral spacer 100. The bone graft channel(s) may be configured to receive bone graft material (not shown) and/or other suitable materials that are known in the art. The intervertebral spacer 100 may also include one or more serrated teeth 180 formed in the superior and inferior surfaces 101, 102 of the intervertebral spacer 100. The one or more serrated teeth 180 may be configured to help stabilize the intervertebral spacer 100 between adjacent vertebral bodies during the fusion process. Moreover, bone graft and/or other suitable materials may also be placed between adjacent serrated teeth 180 of the intervertebral spacer 100 in order to enhance the fusion process and/or help stabilize the intervertebral spacer 100 between adjacent vertebral bodies during the fusion process.

Figure 3A:
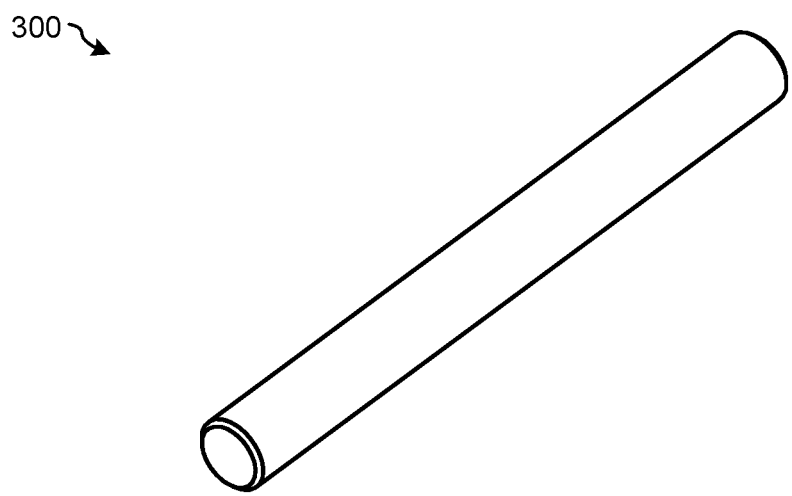
FIG. 3A is a perspective view of a radiopaque marker 300, according to an embodiment of the present disclosure.
Figure 3B:
FIG. 3B is a side view of the radiopaque marker 300 of FIG. 3A.
Figure 3C:
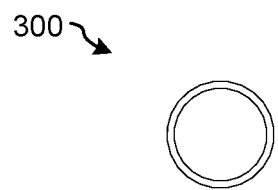
FIG. 3C is an end view of the radiopaque marker 300 of FIG. 3A.
Figure 4A:
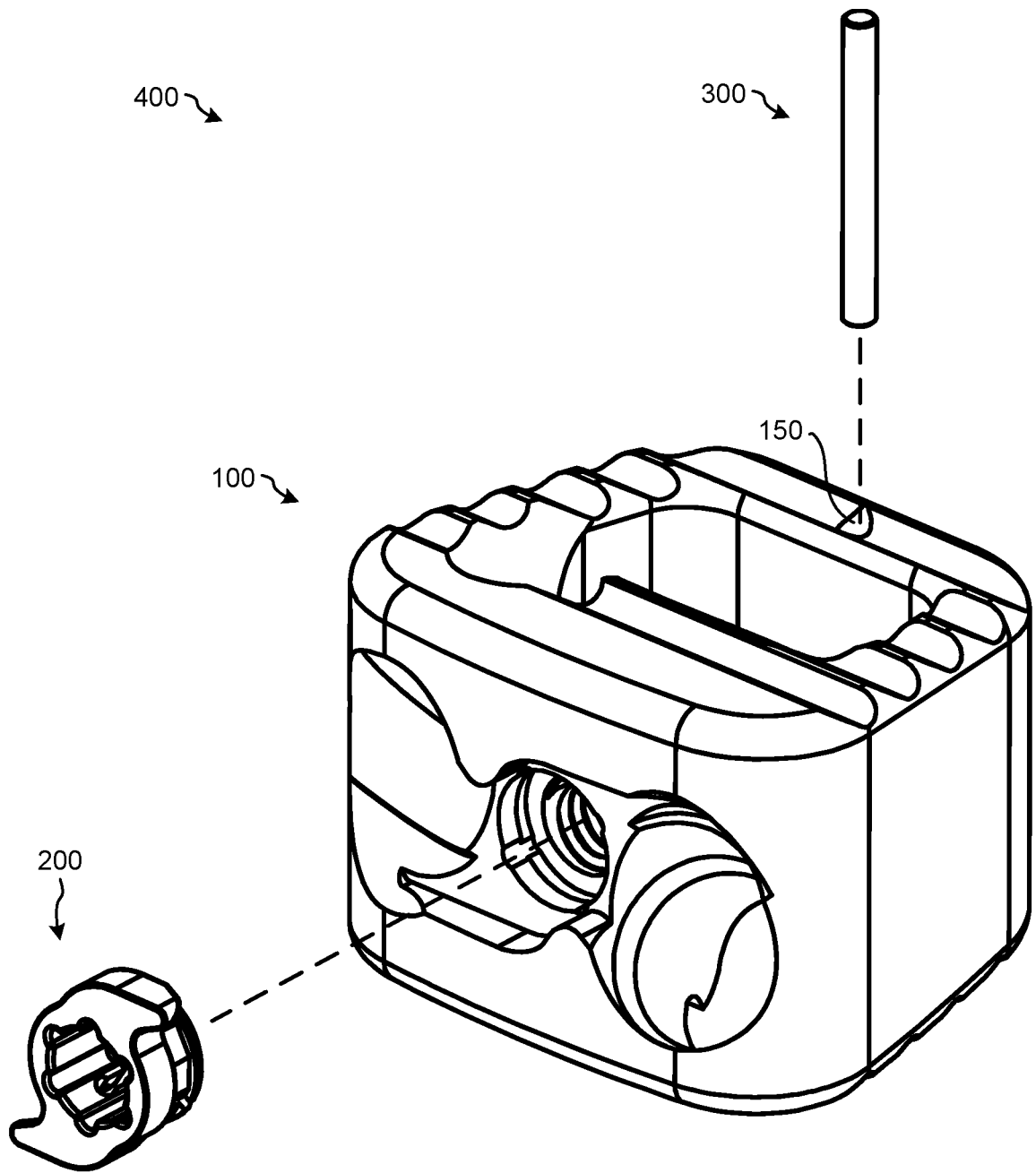
FIG. 4A is an exploded view of an intervertebral spacer assembly 400 including the intervertebral spacer 100 of FIGS. 1A-1H, the locking member 200 of FIGS. 2A-2F, and the radiopaque marker 300 of FIGS. 3A-3C.
Figure 4B:
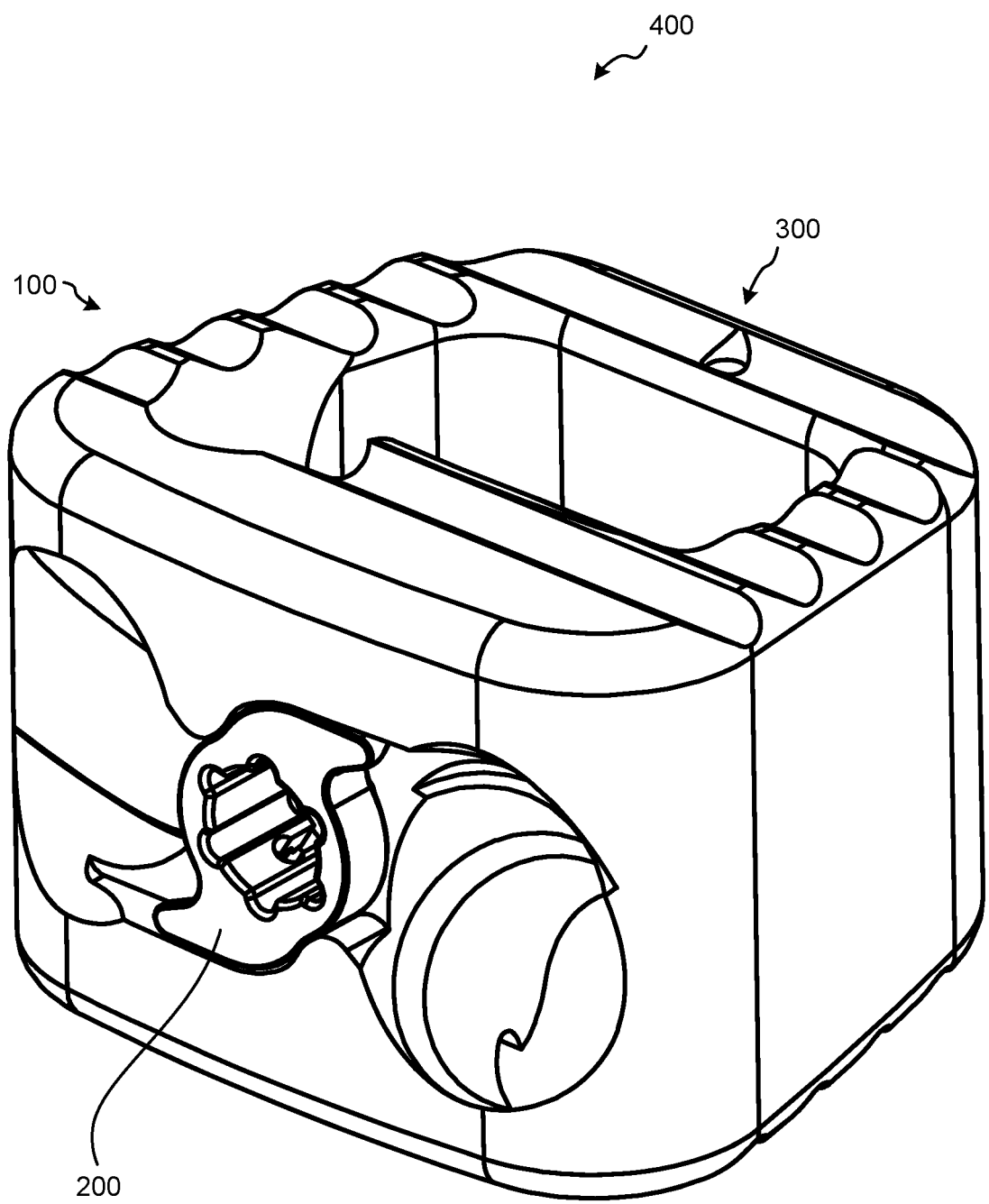
FIG. 4B is a perspective view of the intervertebral spacer assembly 400 of FIG. 4A, after assembly.
Figure 6A:
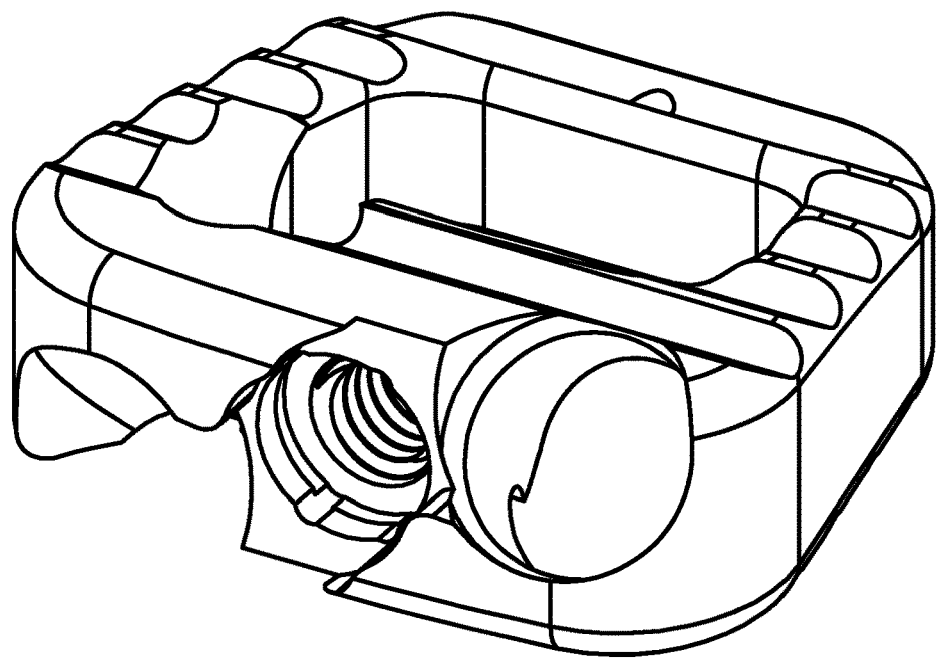
FIG. 6A is a perspective top view of a proximal end of an intervertebral spacer 600, according to an embodiment of the present disclosure.
Figure 6B:
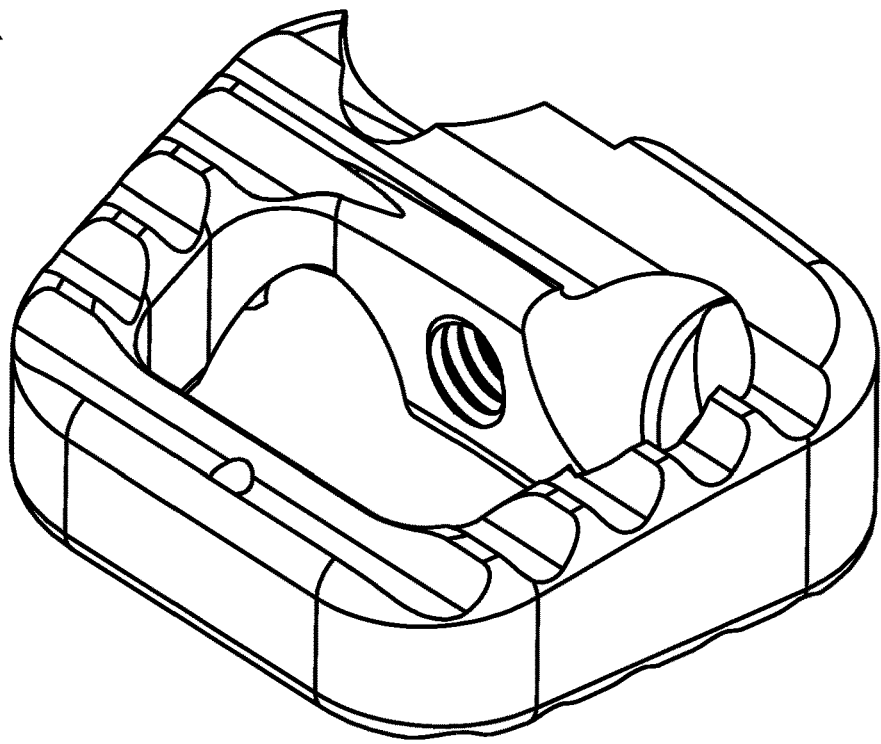
FIG. 6B is a perspective top view of a distal end of the intervertebral spacer 600 of FIG. 6A.
Figure 6C:
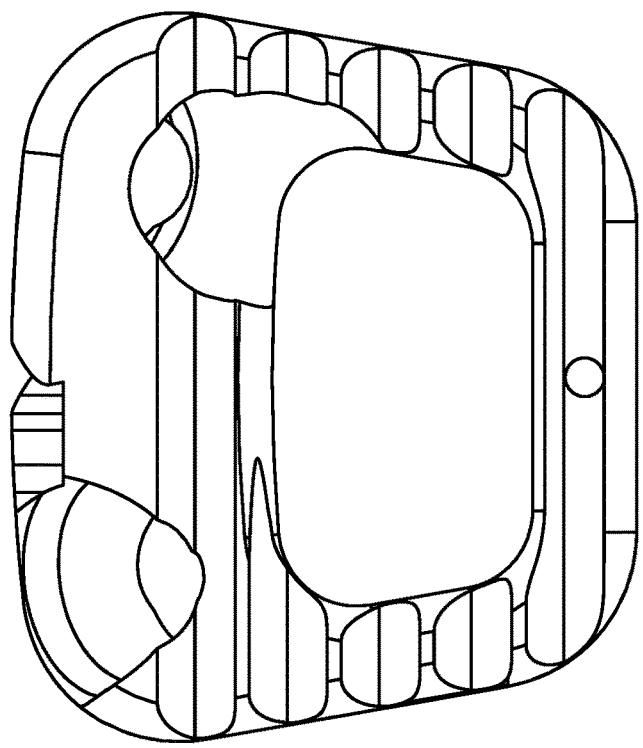
FIG. 6C is a top view of the intervertebral spacer 600 of FIG. 6A.
Figure 6D:
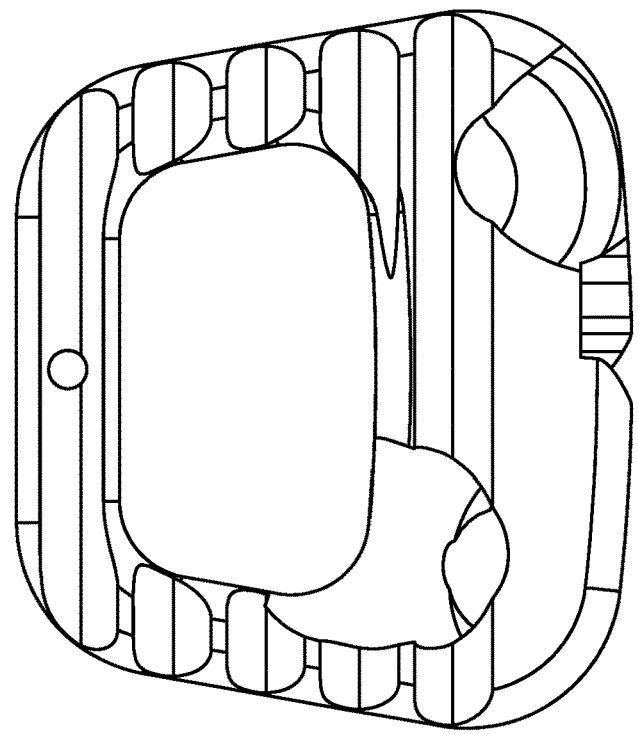
FIG. 6D is a bottom view of the intervertebral spacer 600 of FIG. 6A.
Figure 6E:
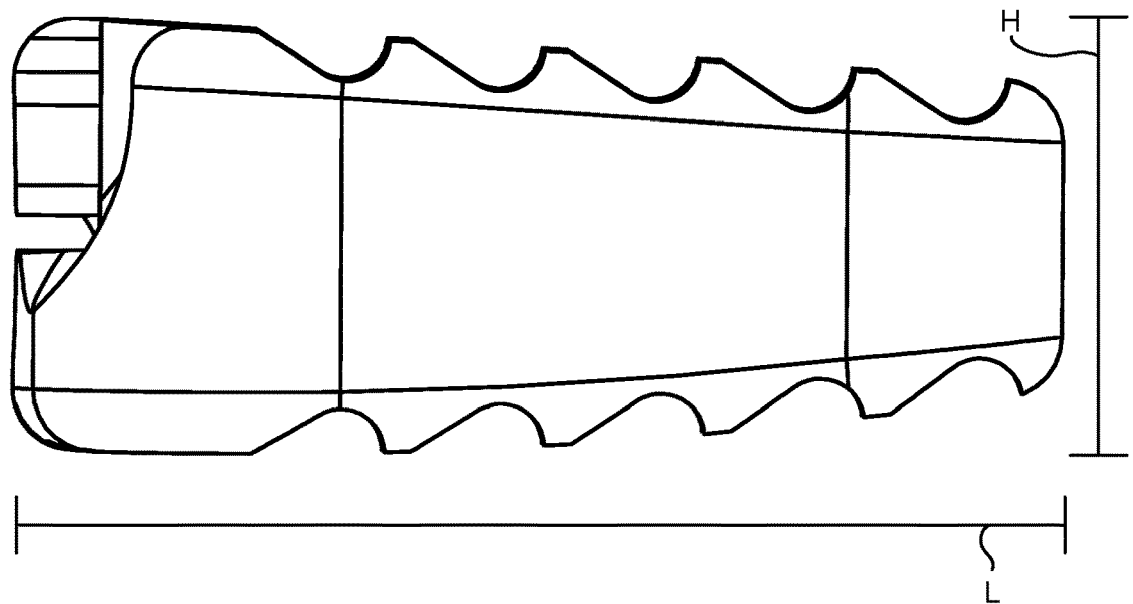
FIG. 6E illustrates a first side of the intervertebral spacer 600 of FIG. 6A.
Figure 6F:
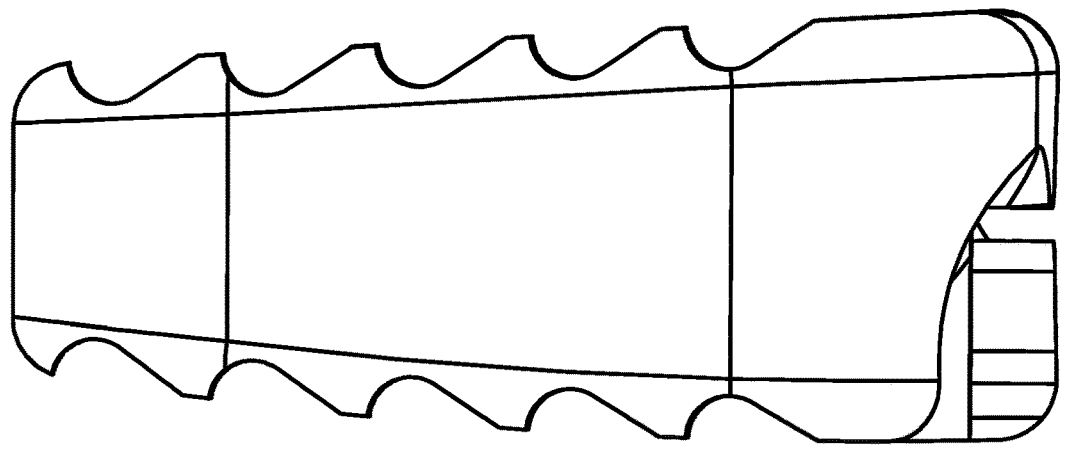
FIG. 6F illustrates a second side of the intervertebral spacer 600 of FIG. 6A.
Figure 6G:
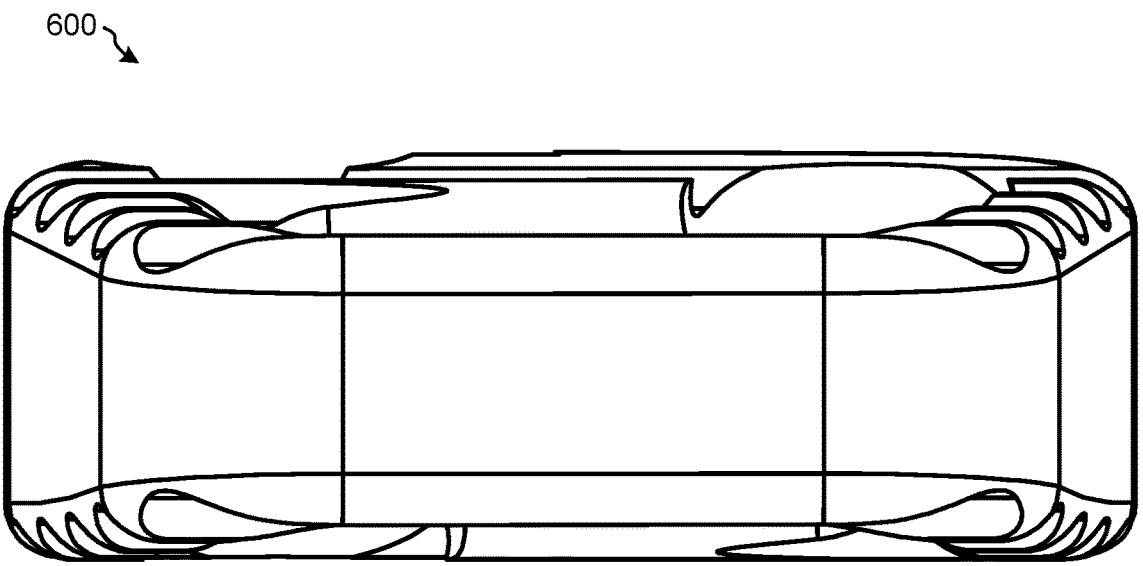
FIG. 6G illustrates the distal end of the intervertebral spacer 600 of FIG. 6A.
Figure 6H:
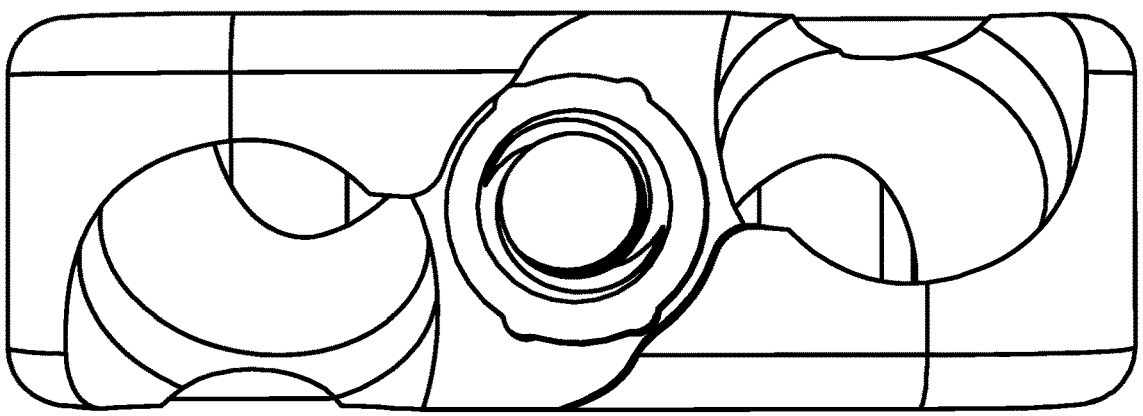
FIG. 6H illustrates the proximal end of the intervertebral spacer 600 of FIG. 6A.
Figure 7A:
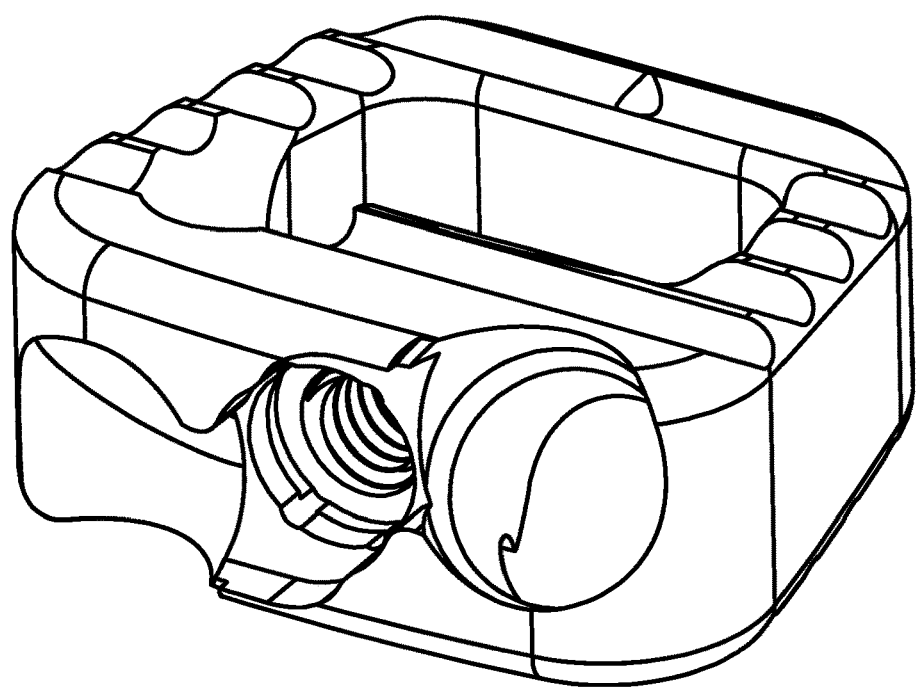
FIG. 7A is a perspective top view of a proximal end of an intervertebral spacer 700, according to an embodiment of the present disclosure.
Figure 7B:
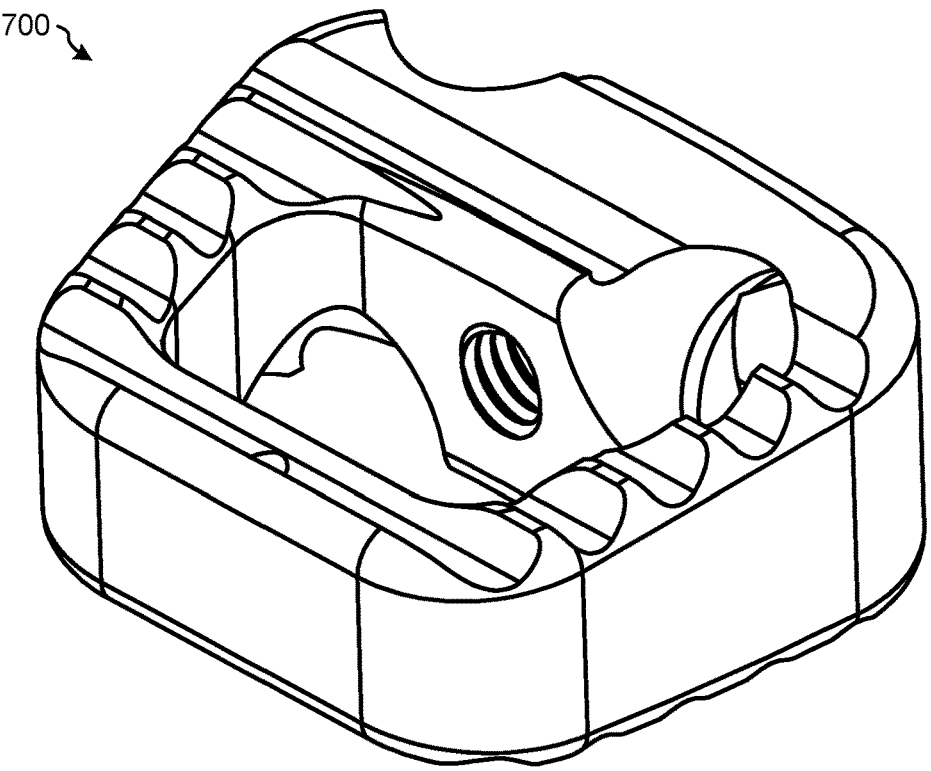
FIG. 7B is a perspective top view of a distal end of the intervertebral spacer 700 of FIG. 7A.
Figure 7C:
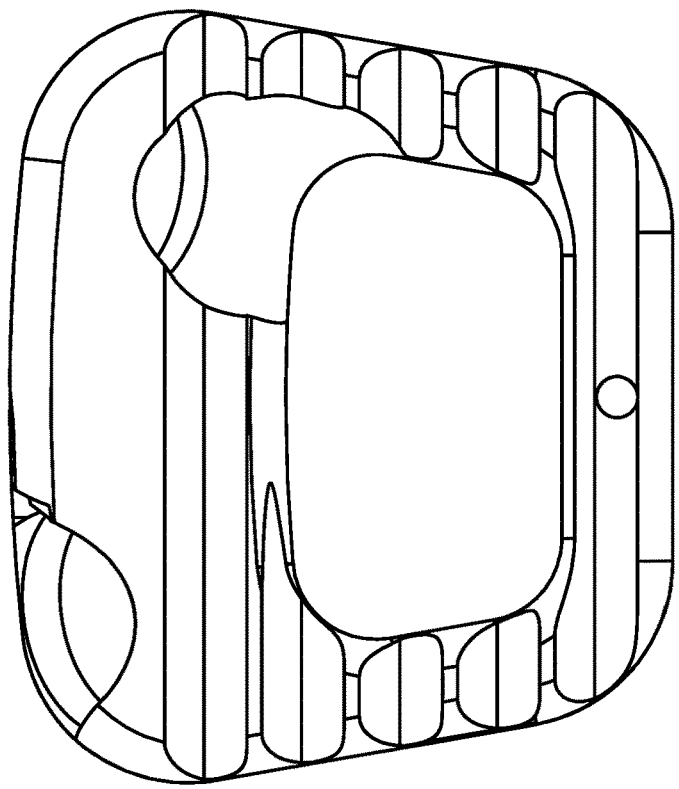
FIG. 7C is a top view of the intervertebral spacer 700 of FIG. 7A.
Figure 7D:
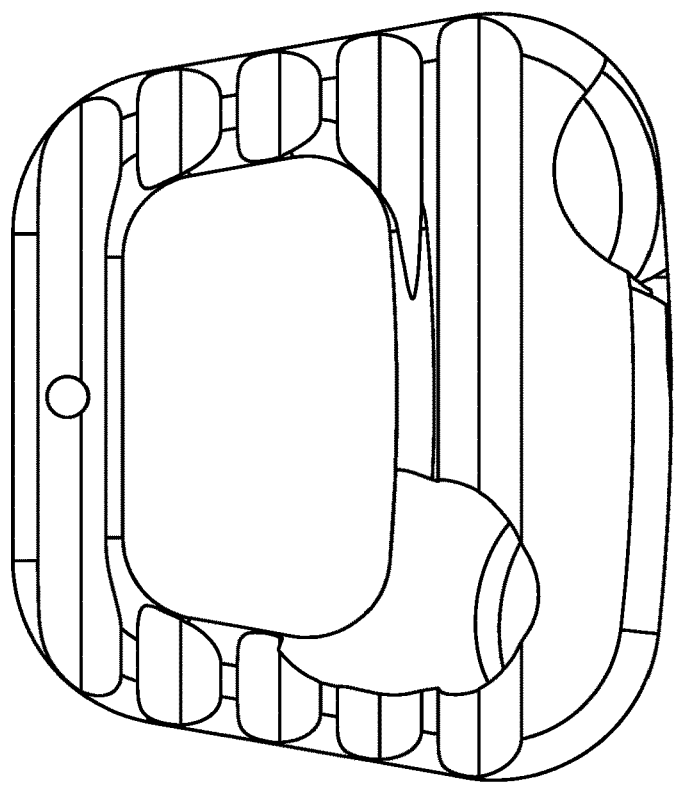
FIG. 7D is a bottom view of the intervertebral spacer 700 of FIG. 7A.
Figure 7E:
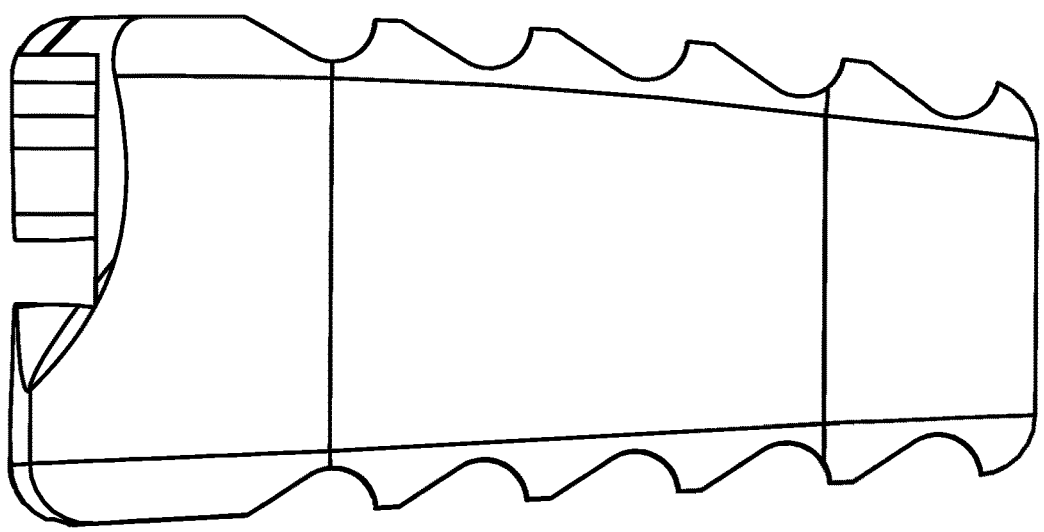
FIG. 7E illustrates a first side of the intervertebral spacer 700 of FIG. 7A.
Figure 7F:
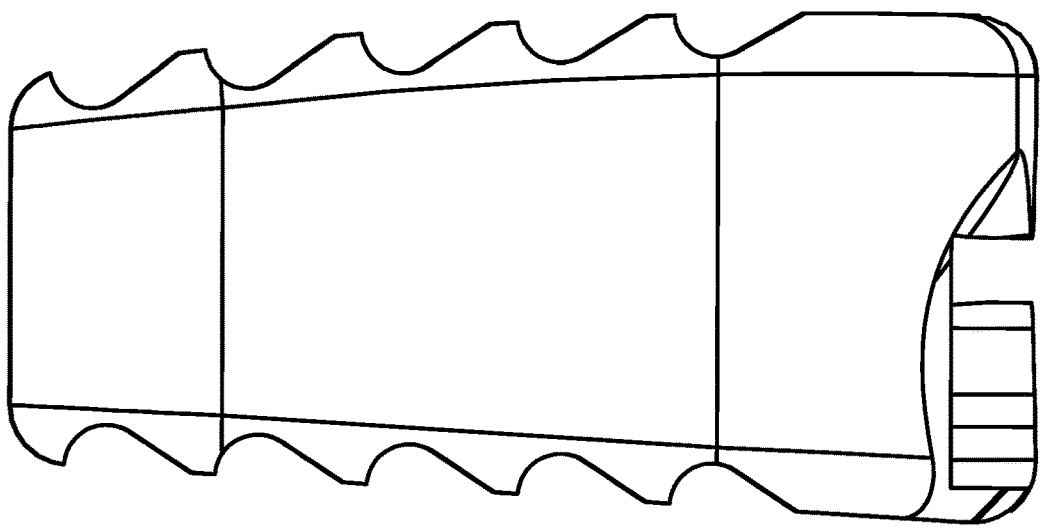
FIG. 7F illustrates a second side of the intervertebral spacer 700 of FIG. 7A.
Figure 7G:
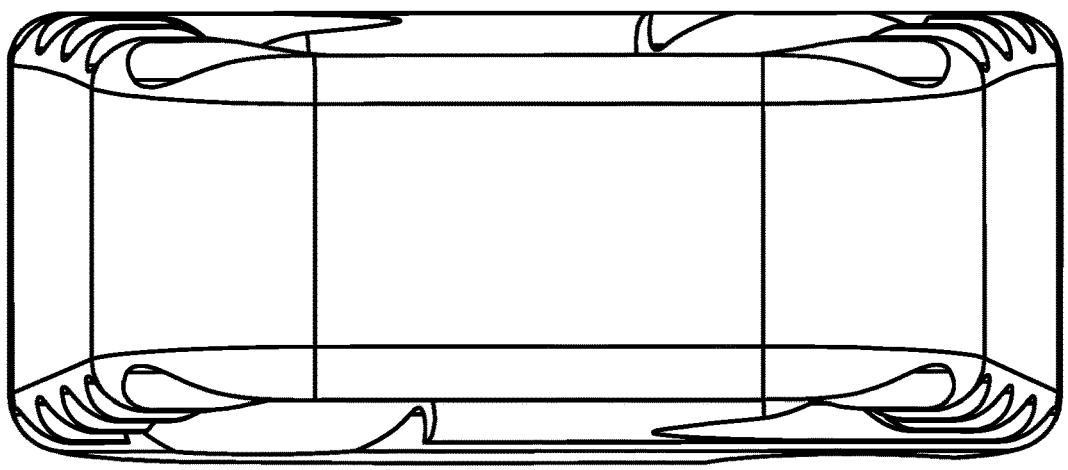
FIG. 7G illustrates the distal end of the intervertebral spacer 700 of FIG. 7A.
Figure 7H:
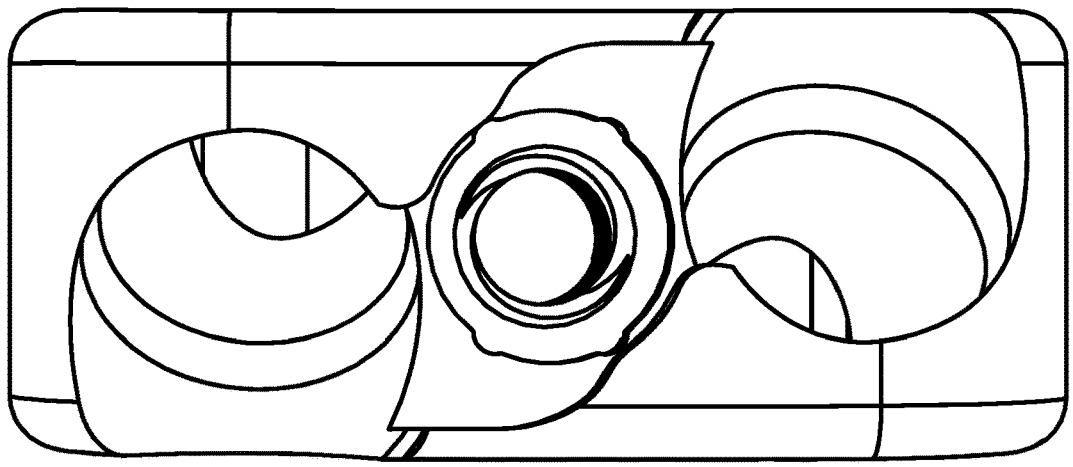
FIG. 7H illustrates the proximal end of the intervertebral spacer 700 of FIG. 7A.
Figure 8A:
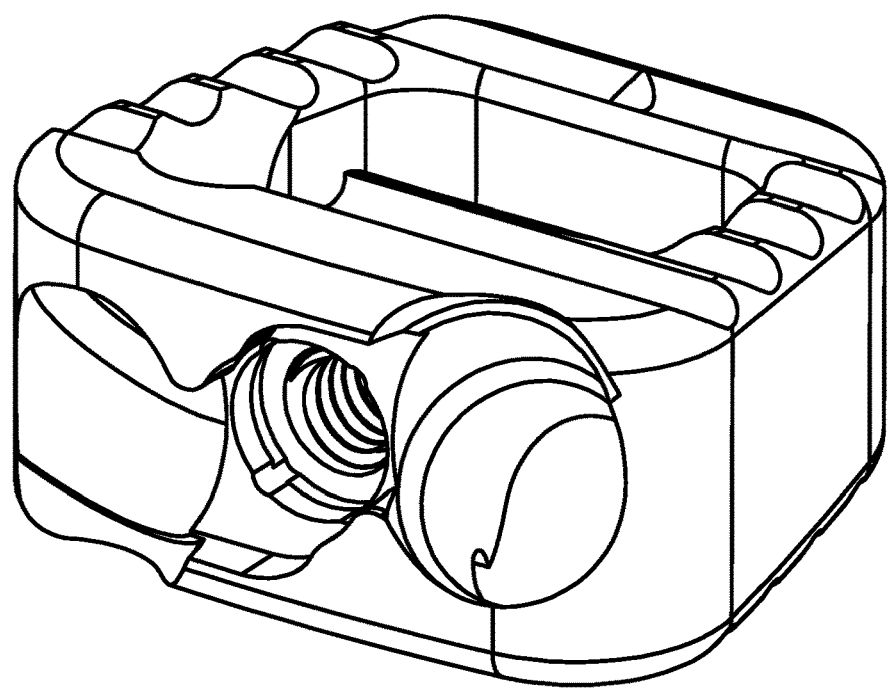
FIG. 8A is a perspective top view of a proximal end of an intervertebral spacer 800, according to an embodiment of the present disclosure.
Figure 8B:
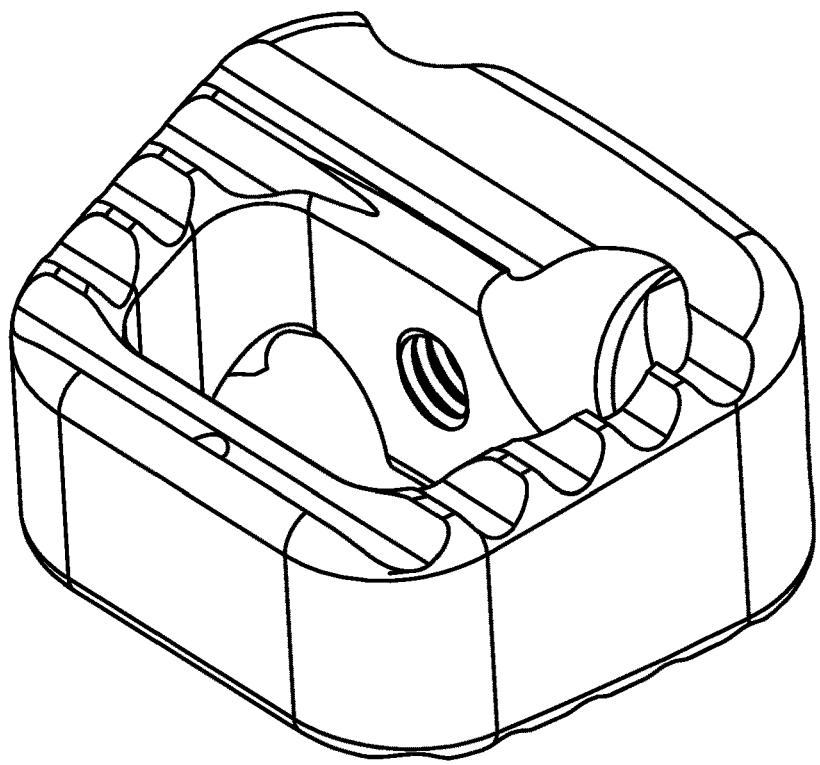
FIG. 8B is a perspective top view of a distal end of the intervertebral spacer 800 of FIG. 8A.
Figure 8C:
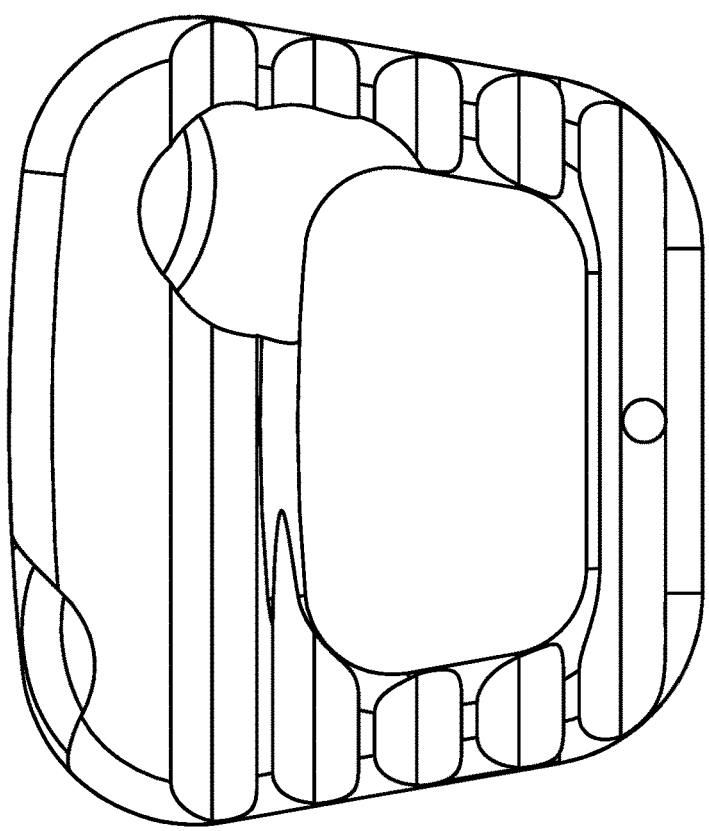
FIG. 8C is a top view of the intervertebral spacer 800 of FIG. 8A.
Figure 8D:
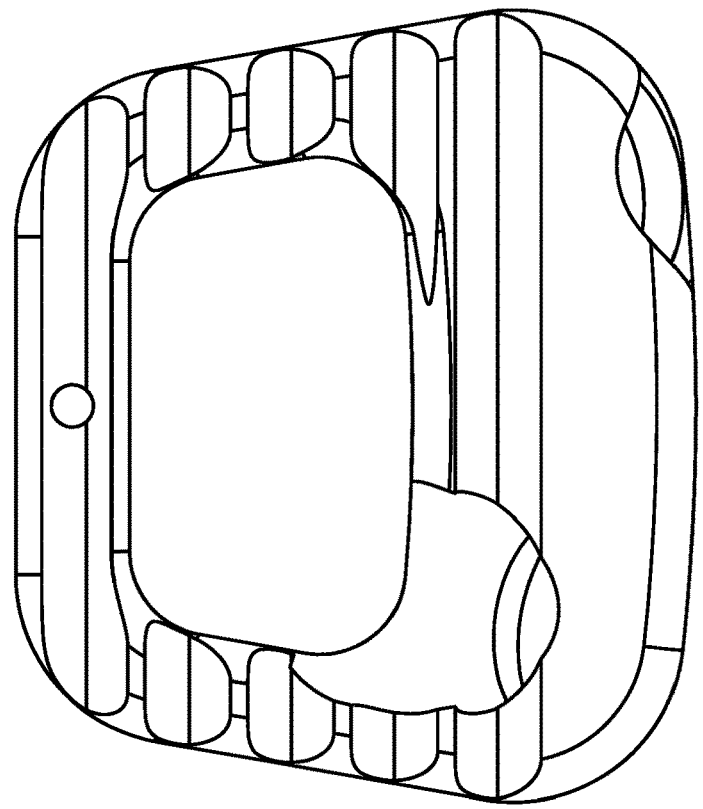
FIG. 8D is a bottom view of the intervertebral spacer 800 of FIG. 8A.
Figure 8E:
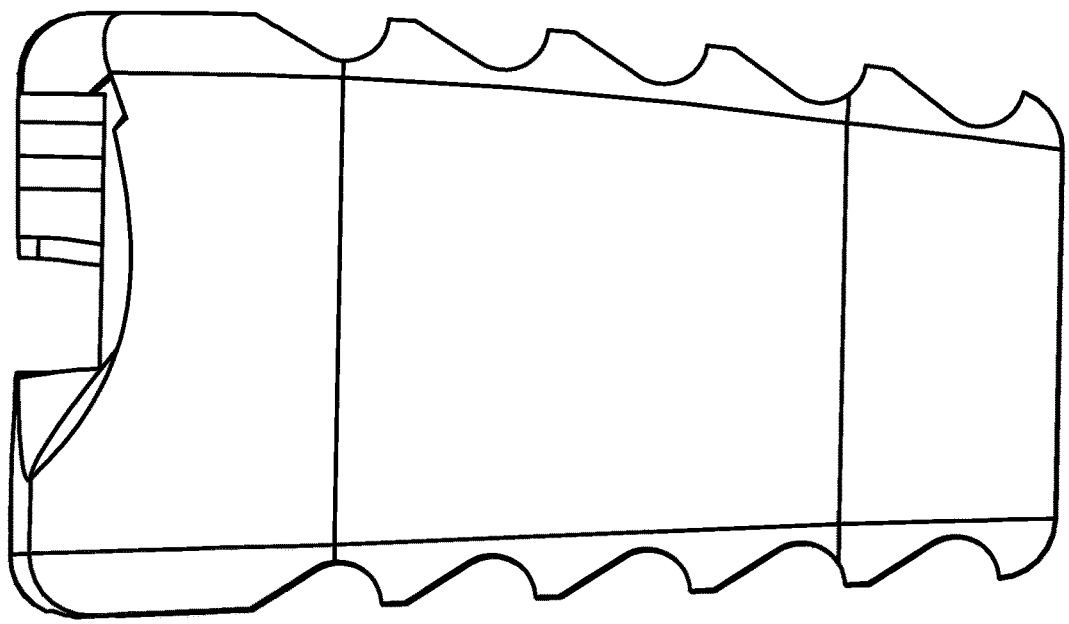
FIG. 8E illustrates a first side of the intervertebral spacer 800 of FIG. 8A.
Figure 8F:
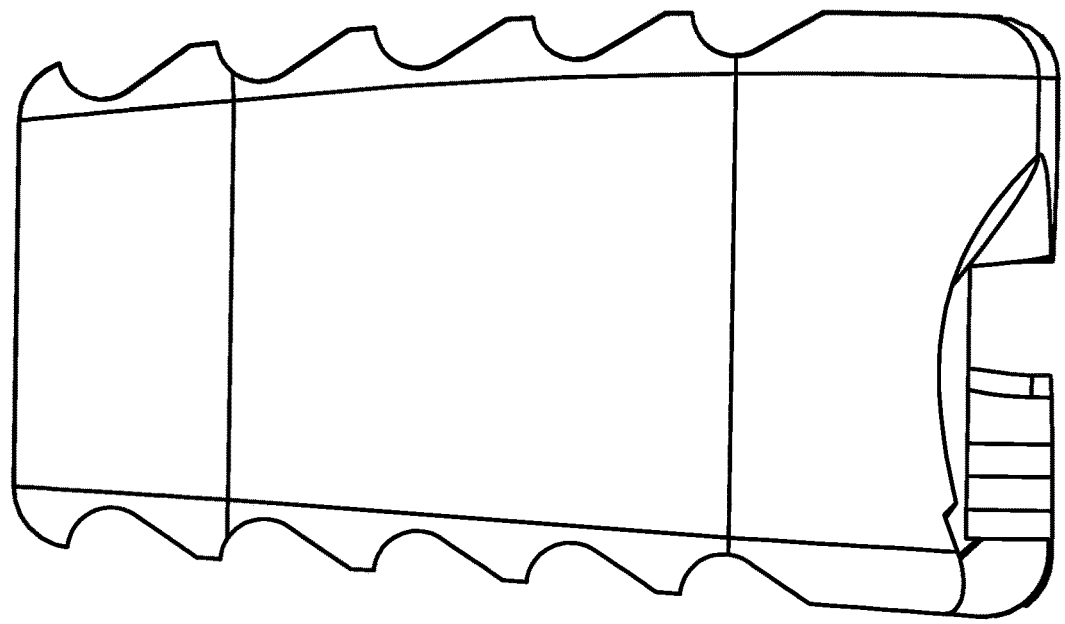
FIG. 8F illustrates a second side of the intervertebral spacer 800 of FIG. 8A.
Figure 8G:
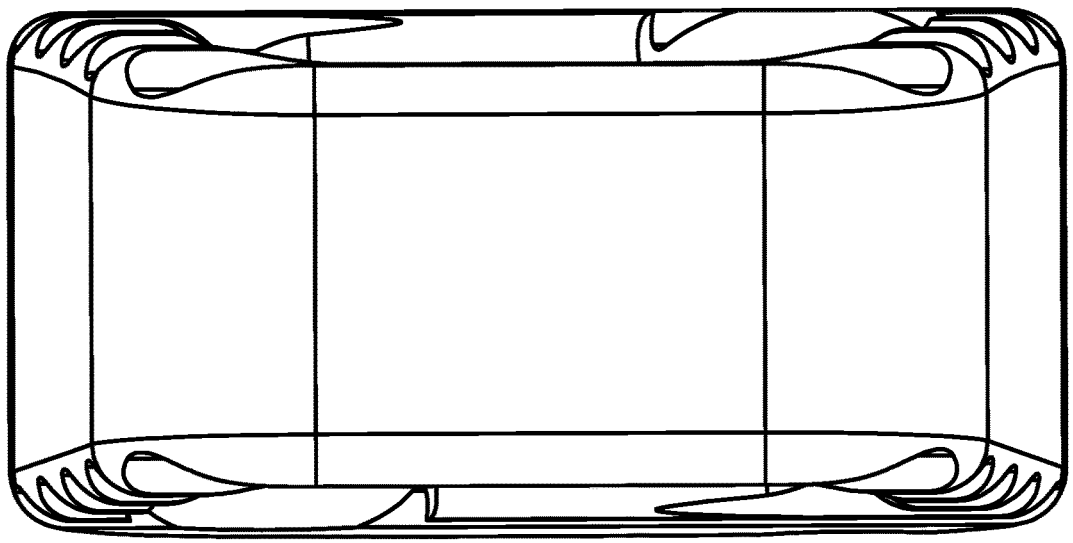
FIG. 8G illustrates the distal end of the intervertebral spacer 800 of FIG. 8A.
Figure 8H:
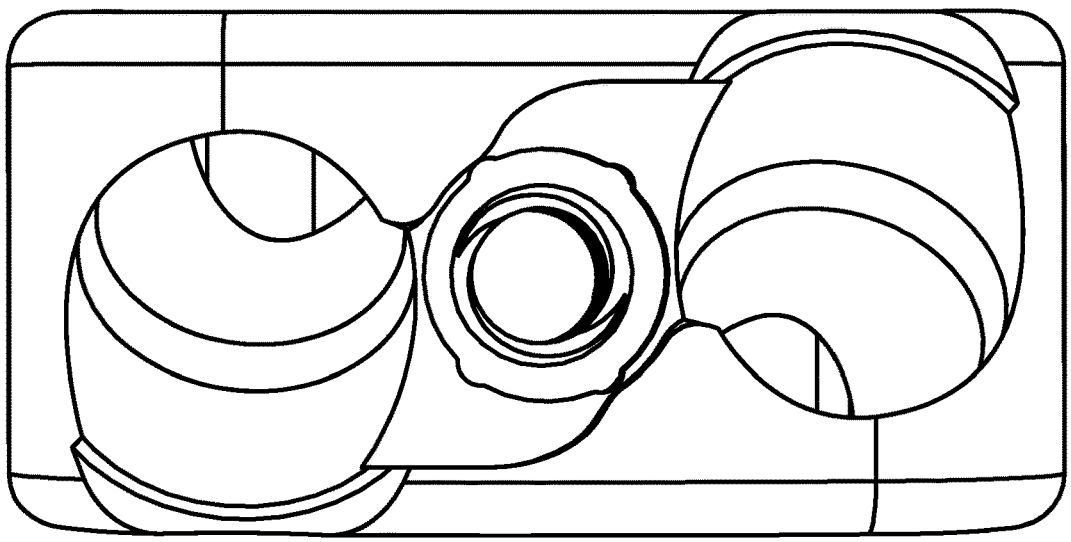
FIG. 8H illustrates the proximal end of the intervertebral spacer 800 of FIG. 8A.
Figure 9A:
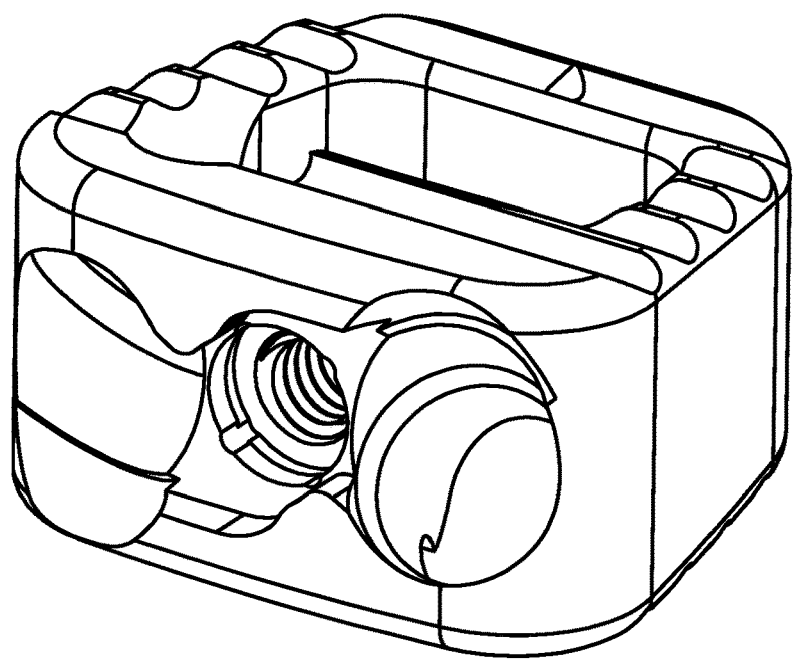
FIG. 9A is a perspective top view of a proximal end of an intervertebral spacer 900, according to an embodiment of the present disclosure.
Figure 9B:
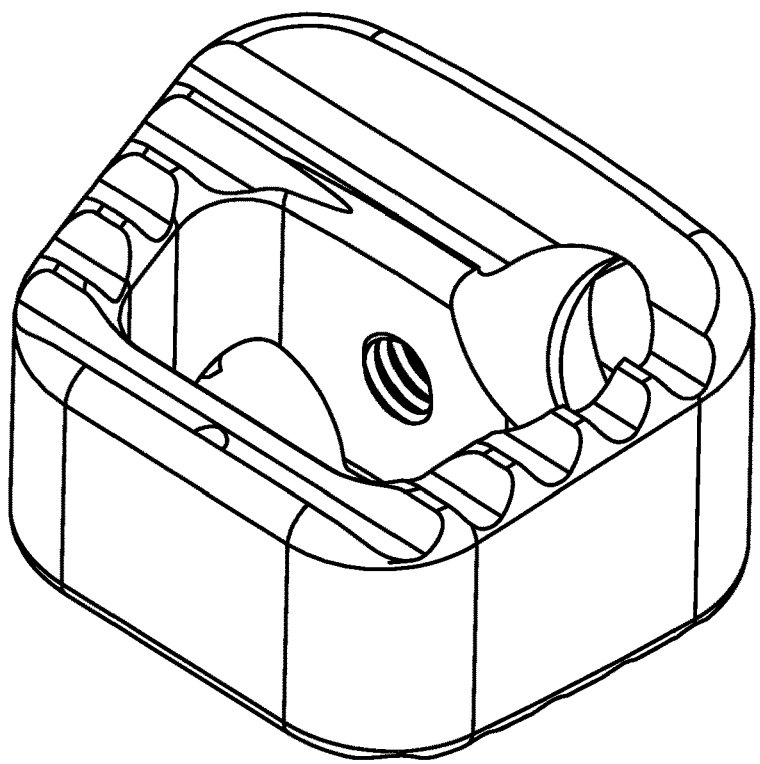
FIG. 9B is a perspective top view of a distal end of the intervertebral spacer 900 of FIG. 9A.
Figure 9C:
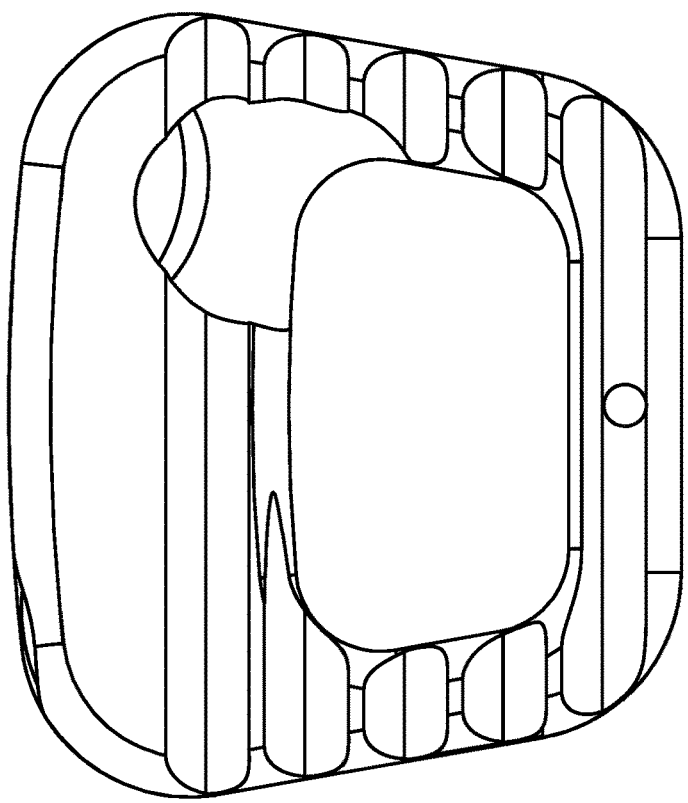
FIG. 9C is a top view of the intervertebral spacer 900 of FIG. 9A.
Figure 9D:
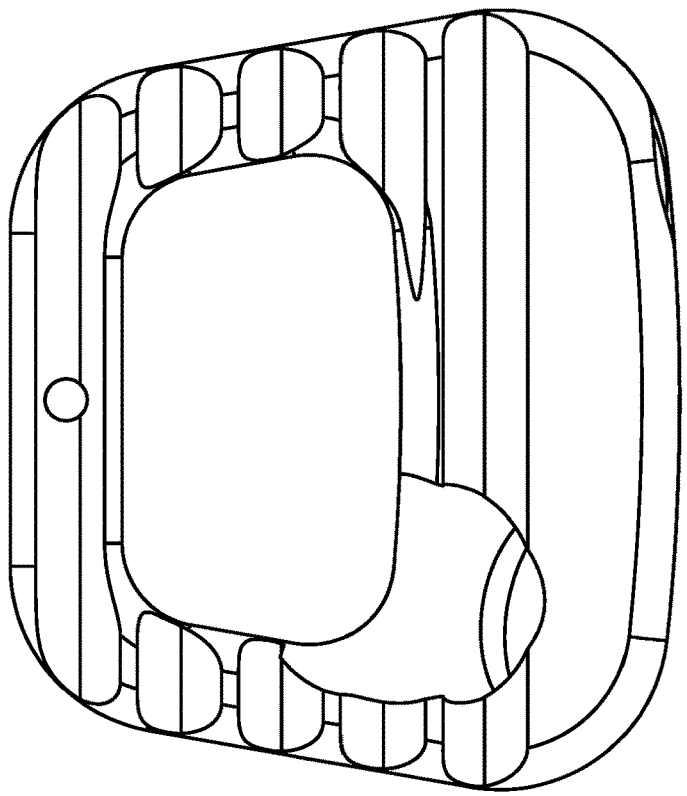
FIG. 9D is a bottom view of the intervertebral spacer 900 of FIG. 9A.
Figure 9E:
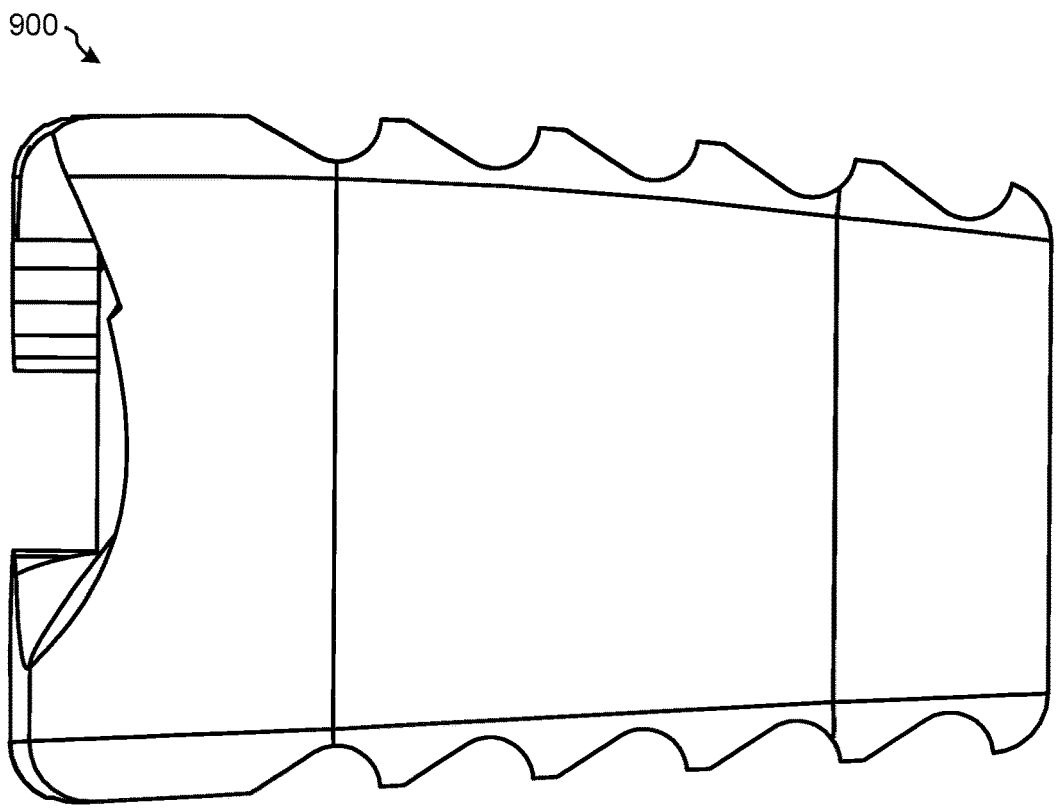
FIG. 9E illustrates a first side of the intervertebral spacer 900 of FIG. 9A.
Figure 9F:
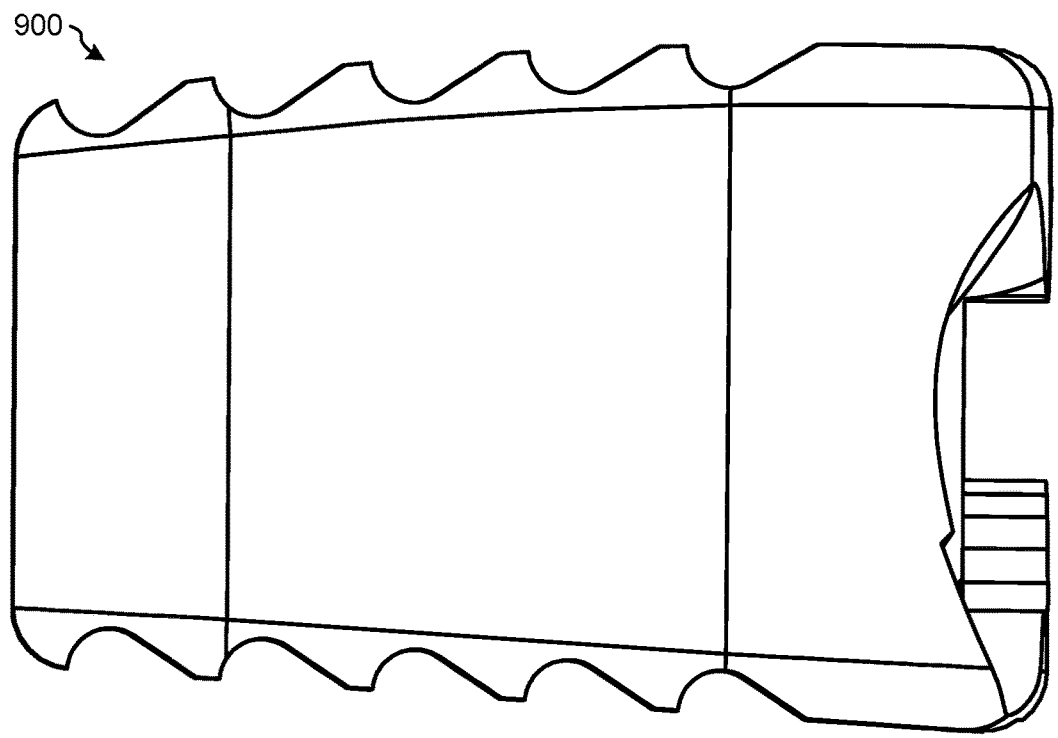
FIG. 9F illustrates a second side of the intervertebral spacer 900 of FIG. 9A.
Figure 9G:
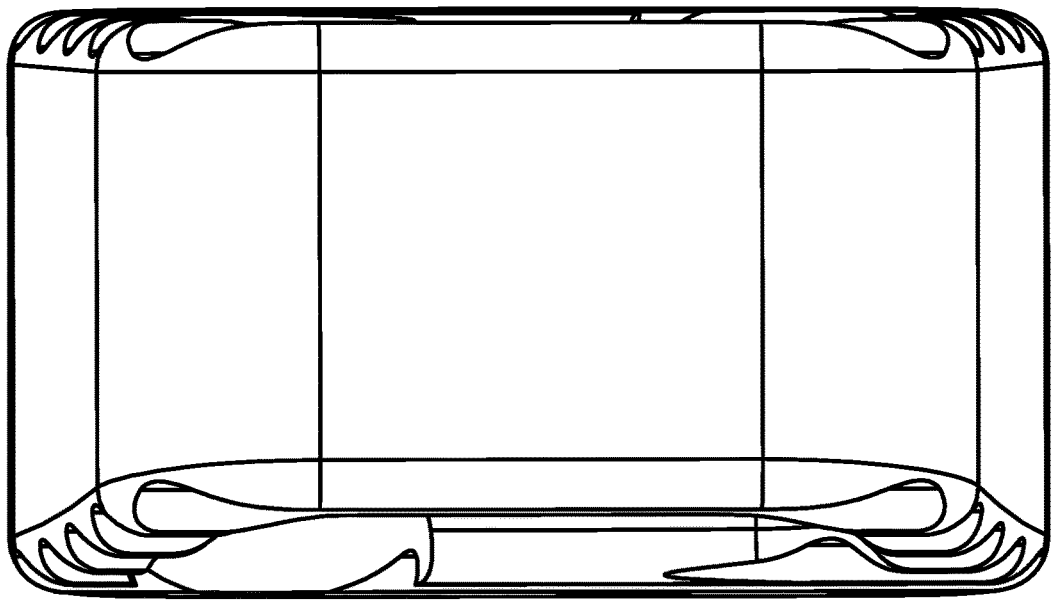
FIG. 9G illustrates the distal end of the intervertebral spacer 900 of FIG. 9A.
Figure 9H:
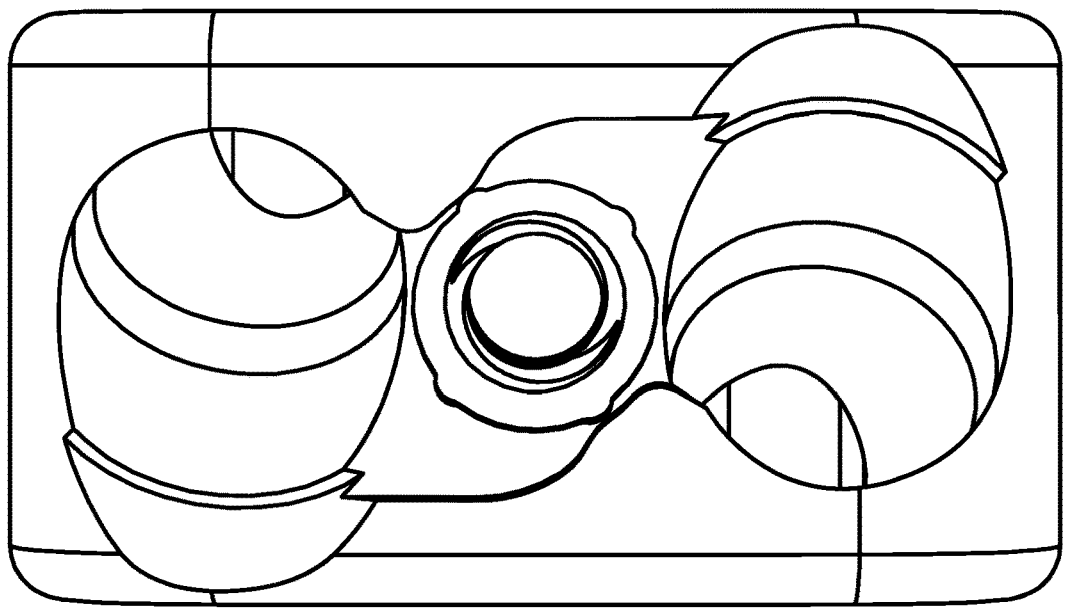
FIG. 9H illustrates the proximal end of the intervertebral spacer 900 of FIG. 9A.
Figure 10A:
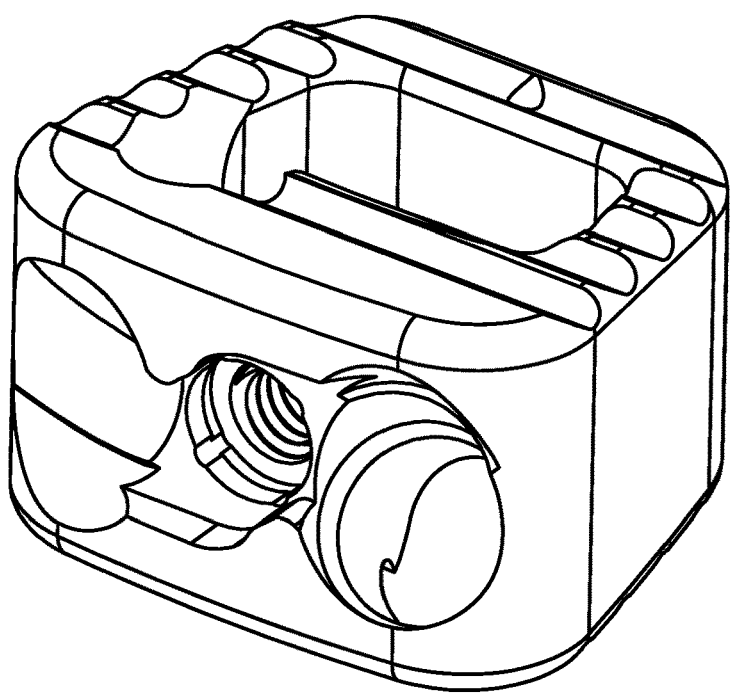
FIG. 10A is a perspective top view of a proximal end of an intervertebral spacer 1000, according to an embodiment of the present disclosure.
Figure 10B:
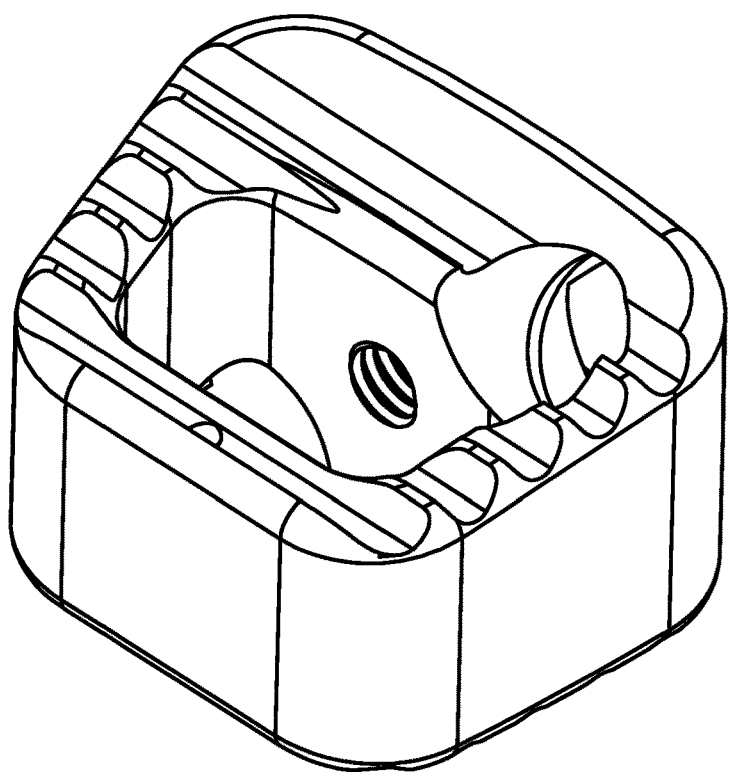
FIG. 10B is a perspective top view of a distal end of the intervertebral spacer 1000 of FIG. 10A.
Figure 10C:
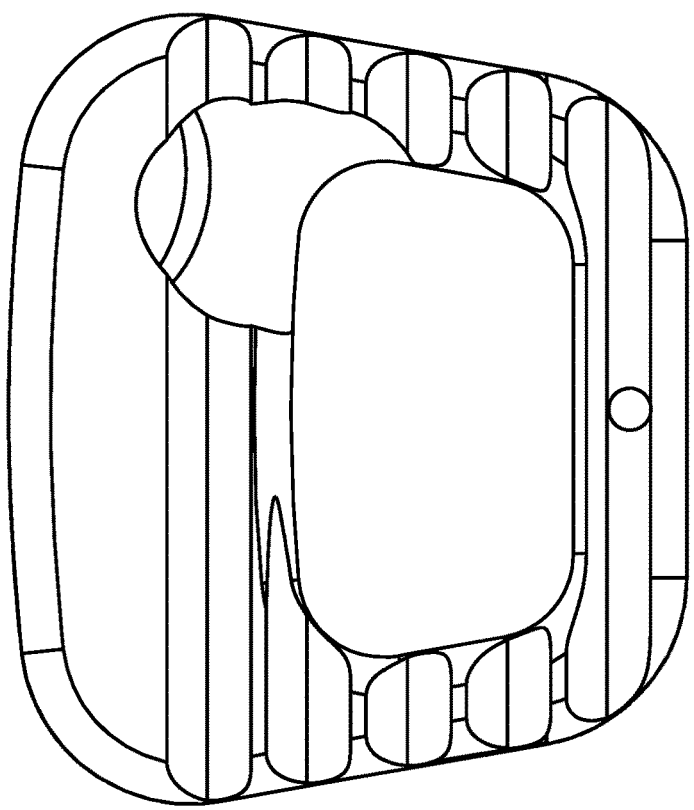
FIG. 10C is a top view of the intervertebral spacer 1000 of FIG. 10A.
Figure 10D:
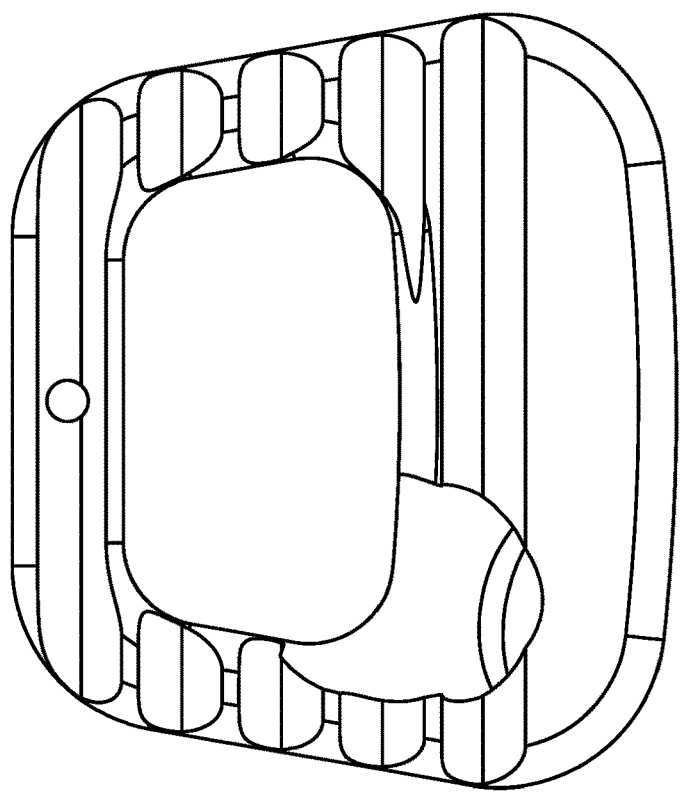
FIG. 10D is a bottom view of the intervertebral spacer 1000 of FIG. 10A.
Figure 10E:
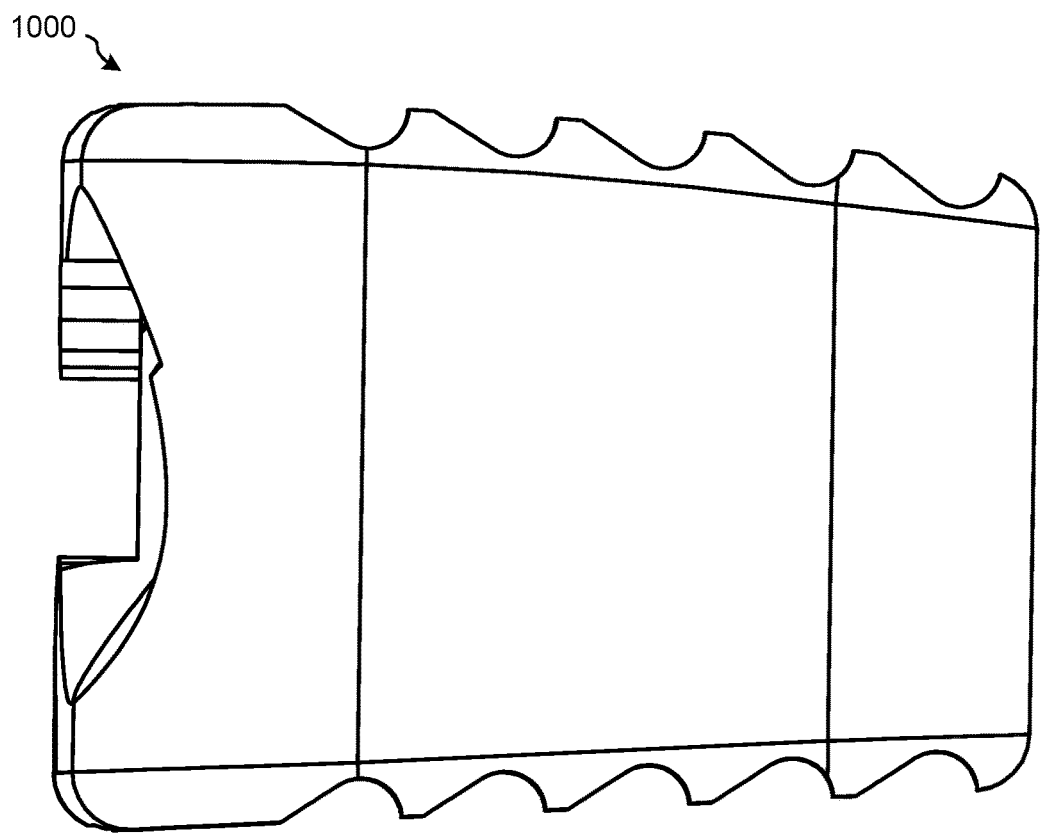
FIG. 10E illustrates a first side of the intervertebral spacer 1000 of FIG. 10A.
Figure 10F:
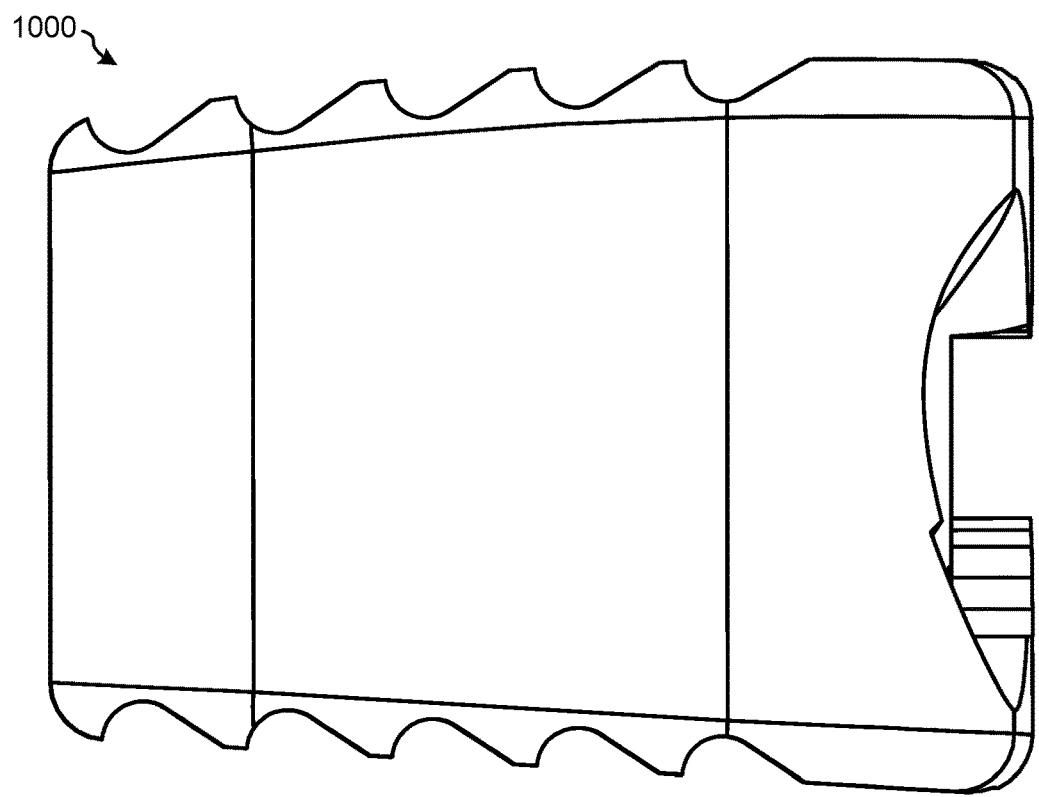
FIG. 10F illustrates a second side of the intervertebral spacer 1000 of FIG. 10A.
Figure 10G:
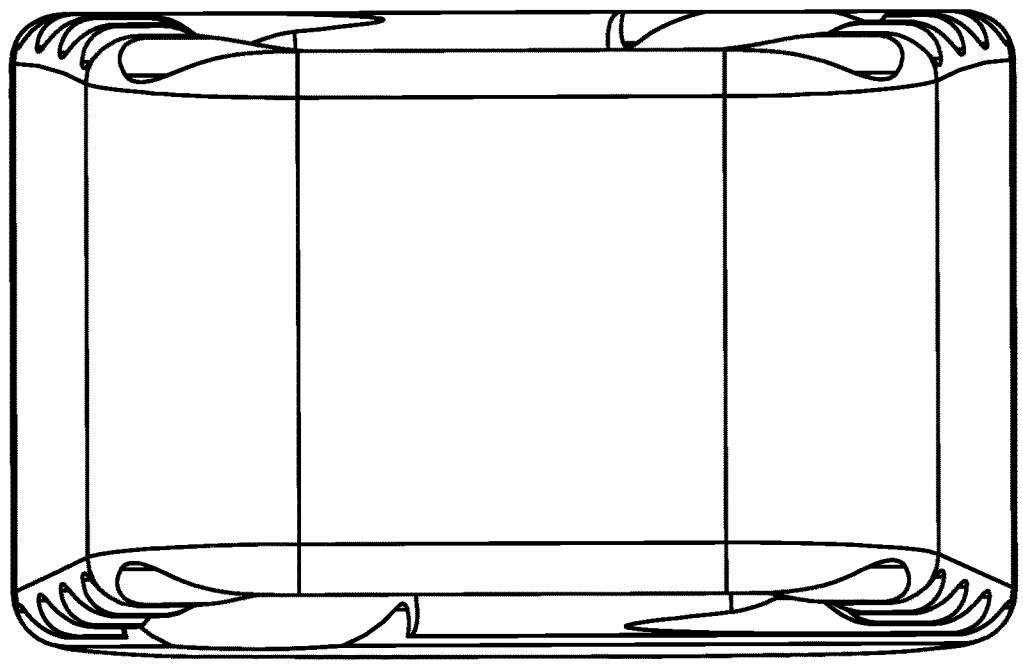
FIG. 10G illustrates the distal end of the intervertebral spacer 1000 of FIG. 10A.
Figure 10H:
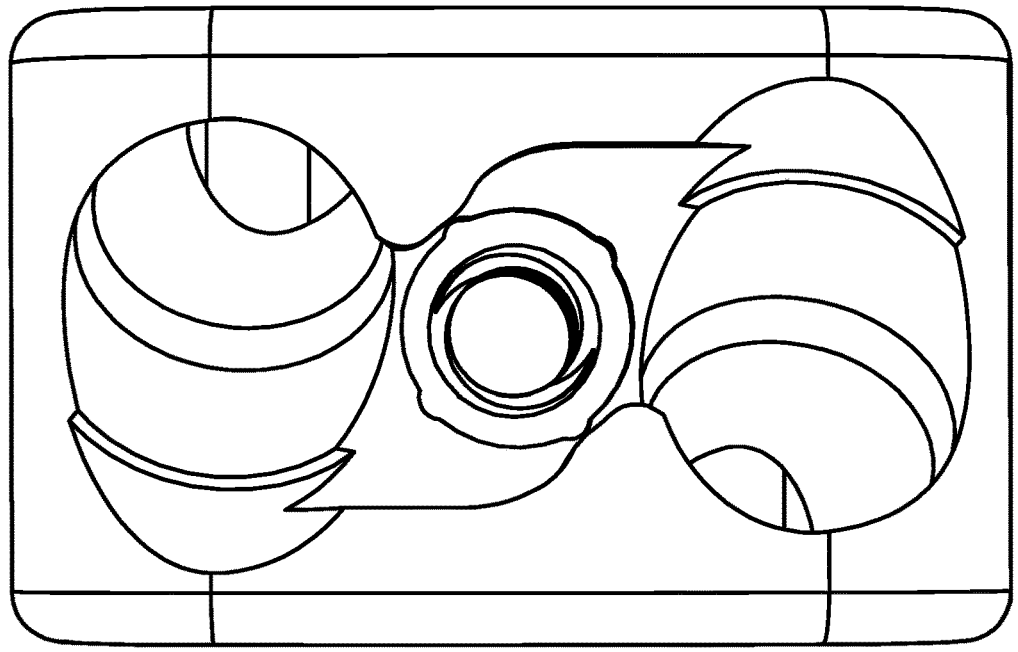
FIG. 10H illustrates the proximal end of the intervertebral spacer 1000 of FIG. 10A.
Figure 11A:
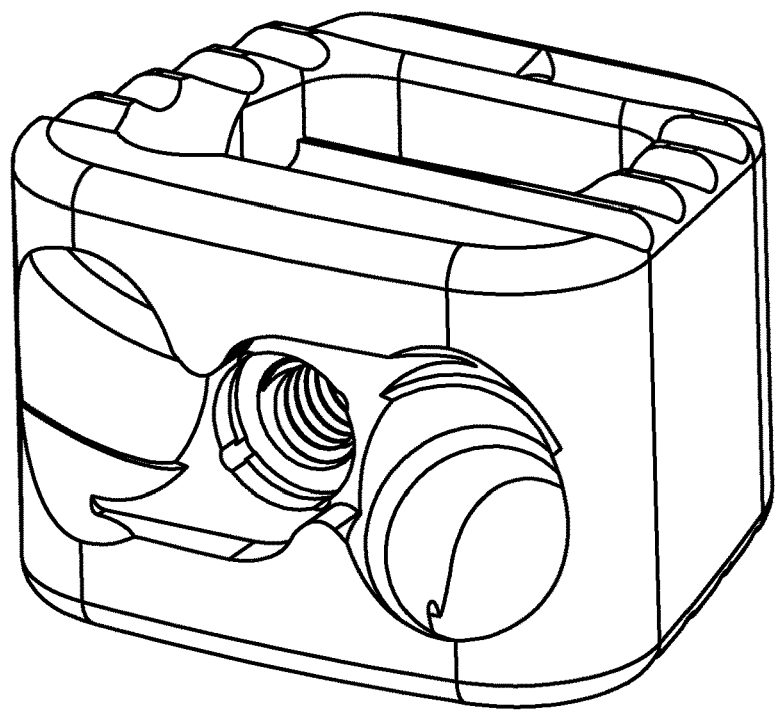
FIG. 11A is a perspective top view of a proximal end of an intervertebral spacer 1100, according to an embodiment of the present disclosure.
Figure 11B:
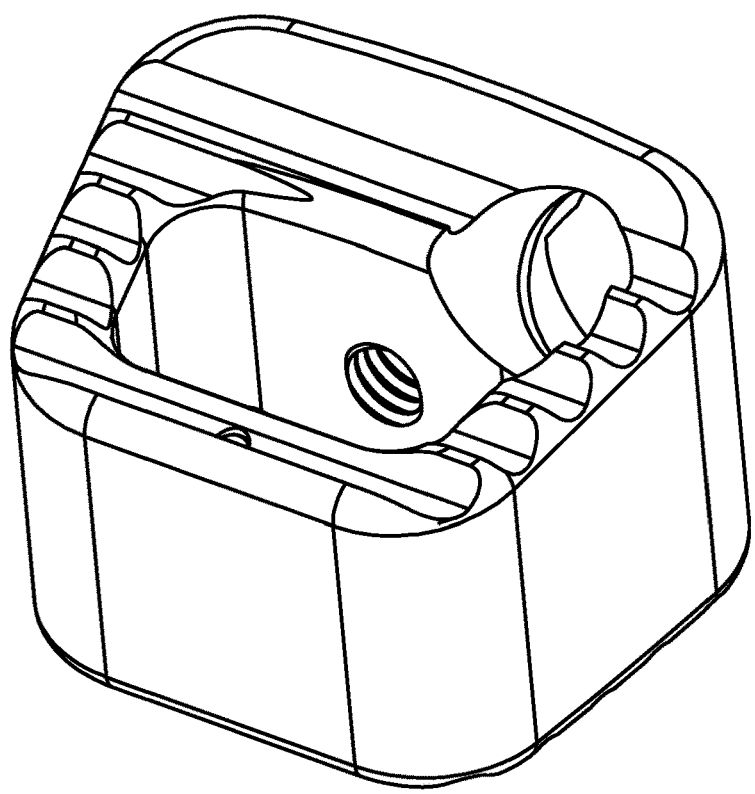
FIG. 11B is a perspective top view of a distal end of the intervertebral spacer 1100 of FIG. 11A.
Figure 11C:
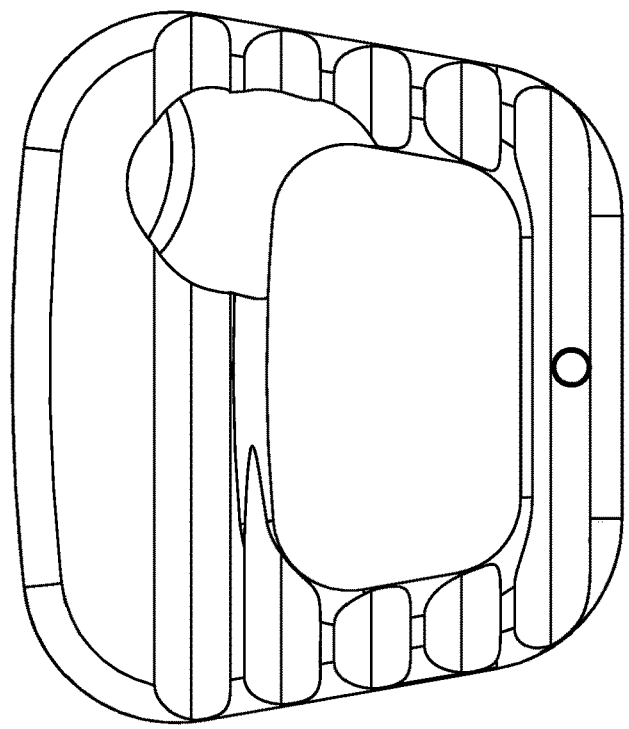
FIG. 11C is a top view of the intervertebral spacer 1100 of FIG. 11A.
Figure 11D:
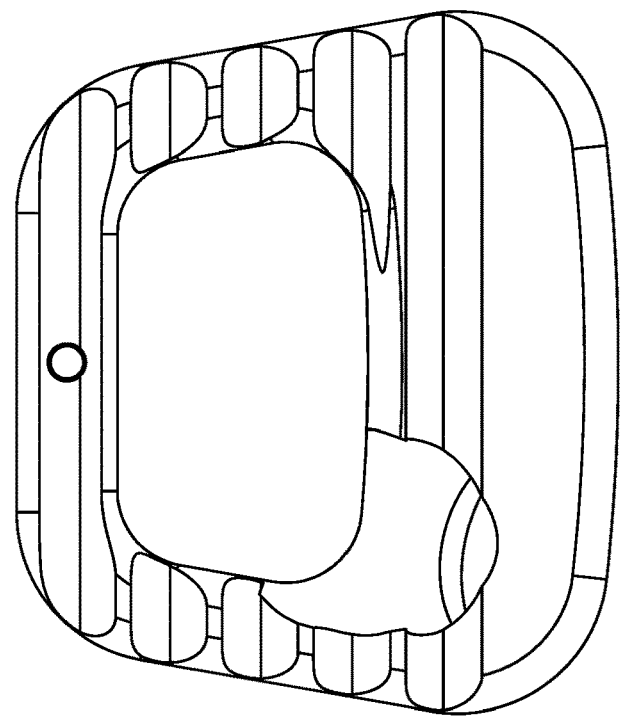
FIG. 11D is a bottom view of the intervertebral spacer 1100 of FIG. 11A.
Figure 11E:
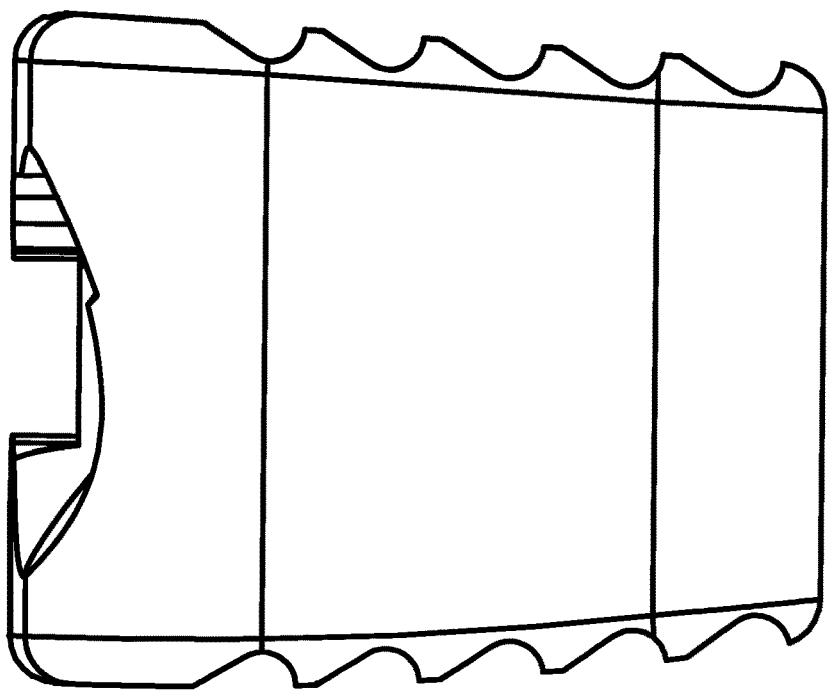
FIG. 11E illustrates a first side of the intervertebral spacer 1100 of FIG. 11A.
Figure 11F:
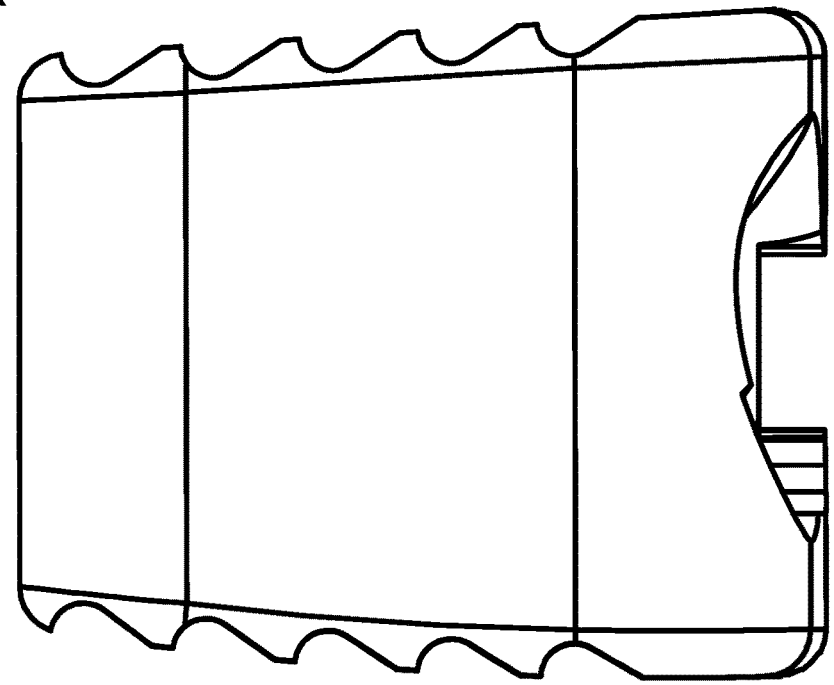
FIG. 11F illustrates a second side of the intervertebral spacer 1100 of FIG. 11A.
Figure 11G:
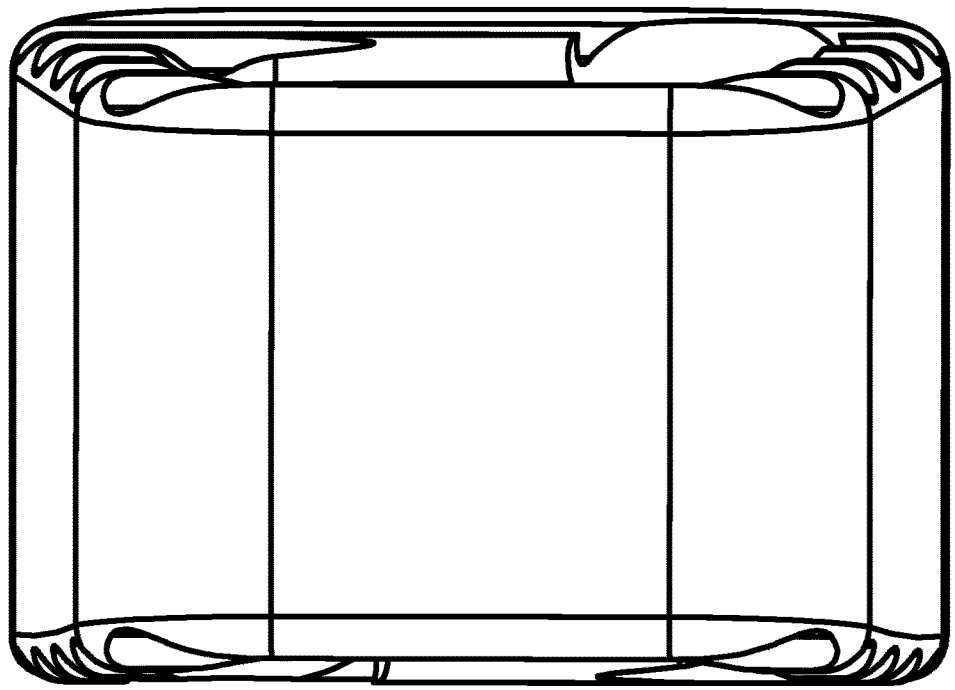
FIG. 11G illustrates the distal end of the intervertebral spacer 1100 of FIG. 11A.
Figure 11H:
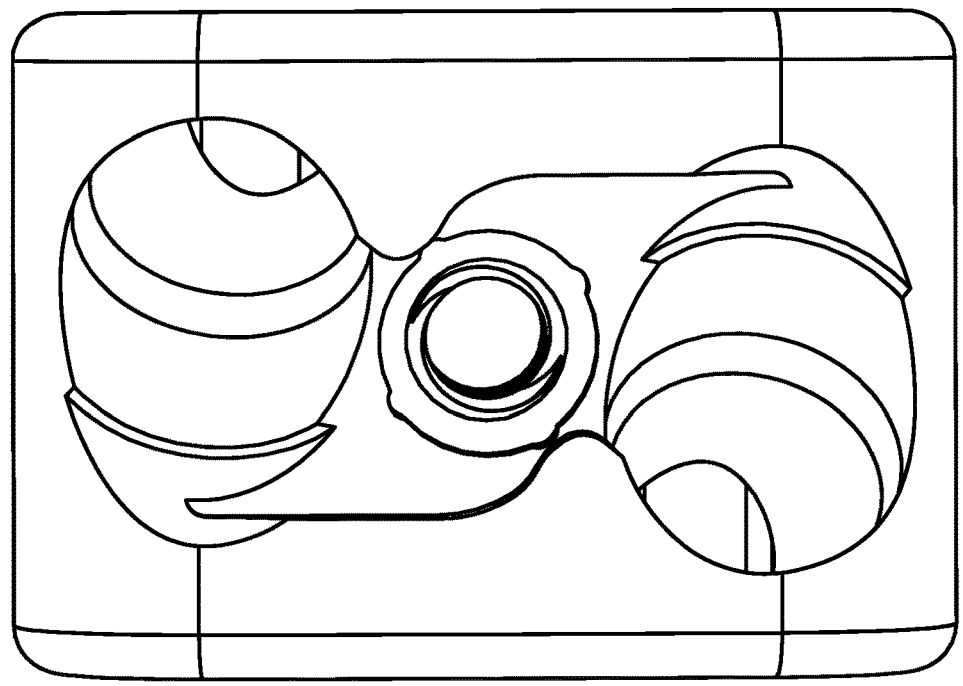
FIG. 11H illustrates the proximal end of the intervertebral spacer 1100 of FIG. 11A.
Figure 12A:
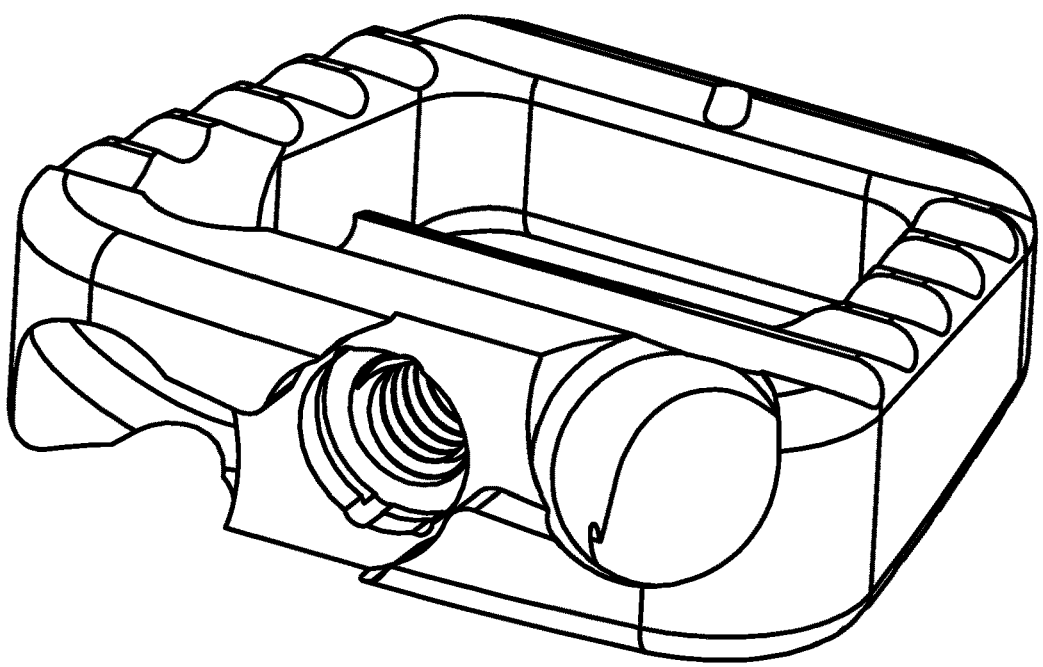
FIG. 12A is a perspective top view of a proximal end of an intervertebral spacer 1200, according to an embodiment of the present disclosure.
Figure 12B:
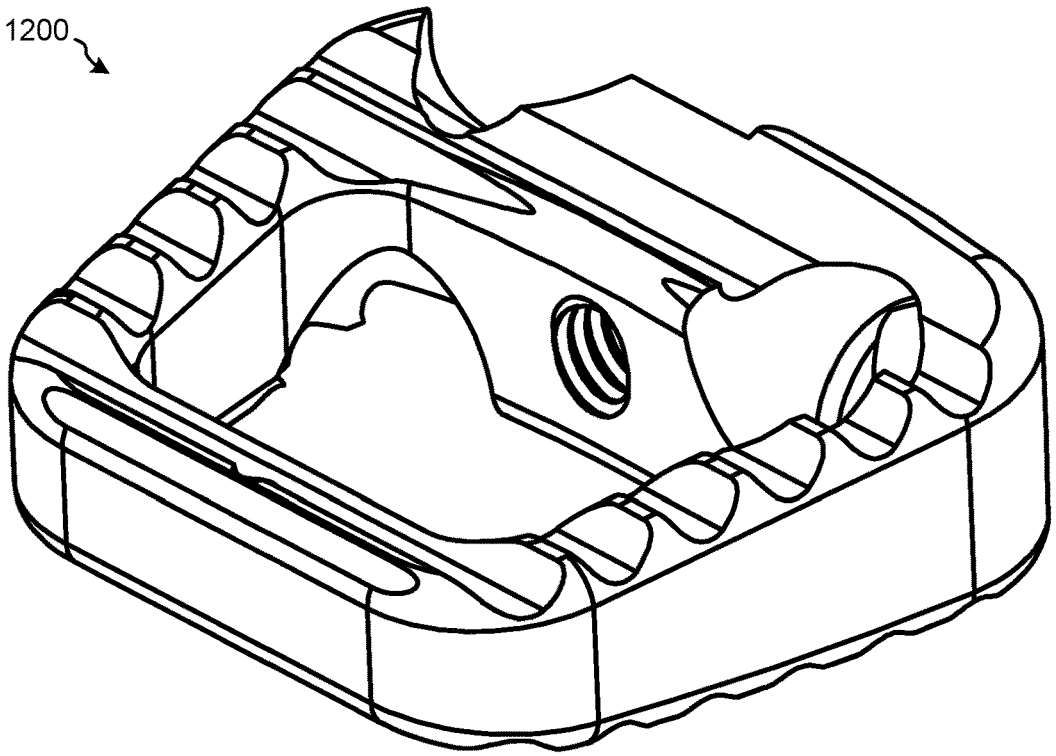
FIG. 12B is a perspective top view of a distal end of the intervertebral spacer 1200 of FIG. 12A.
Figure 12C:
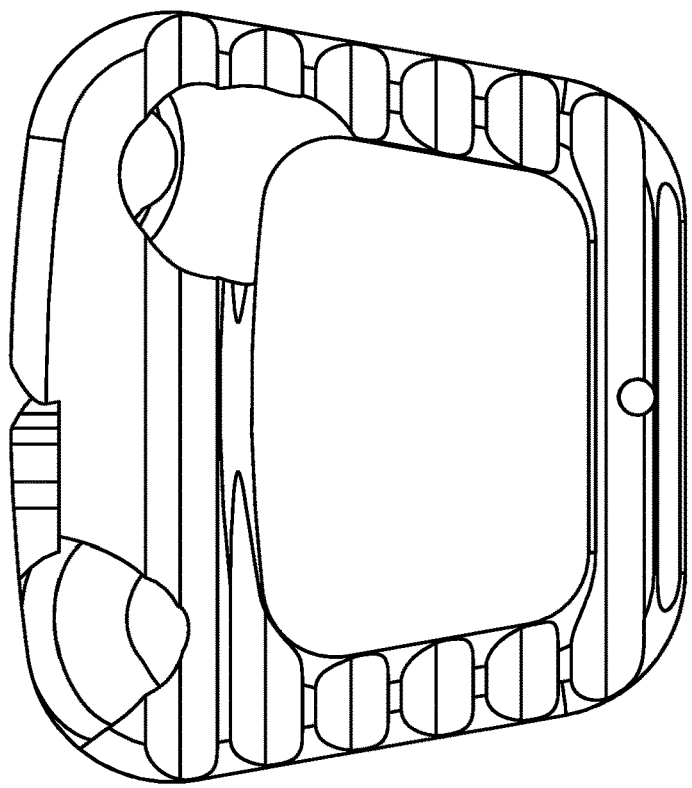
FIG. 12C is a top view of the intervertebral spacer 1200 of FIG. 12A.
Figure 12D:
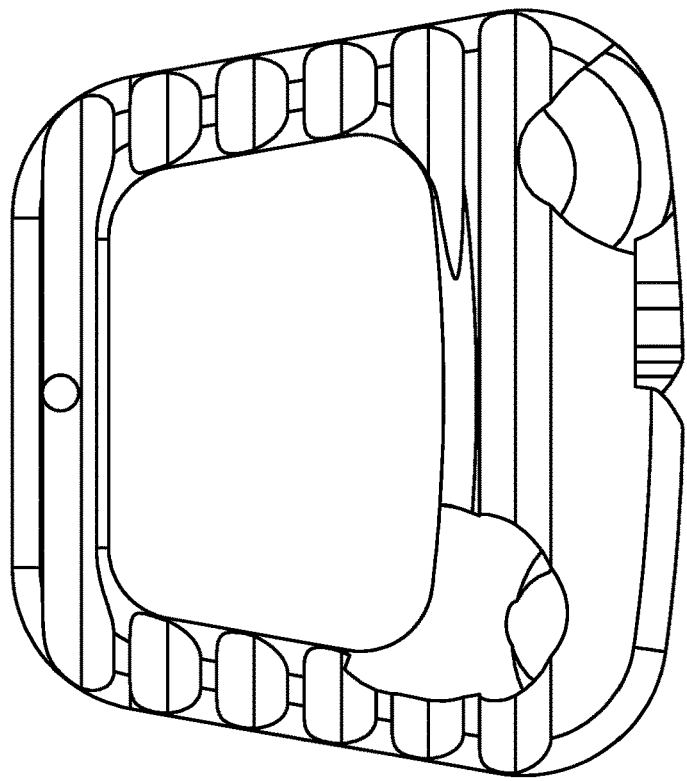
FIG. 12D is a bottom view of the intervertebral spacer 1200 of FIG. 12A.
Figure 12E:
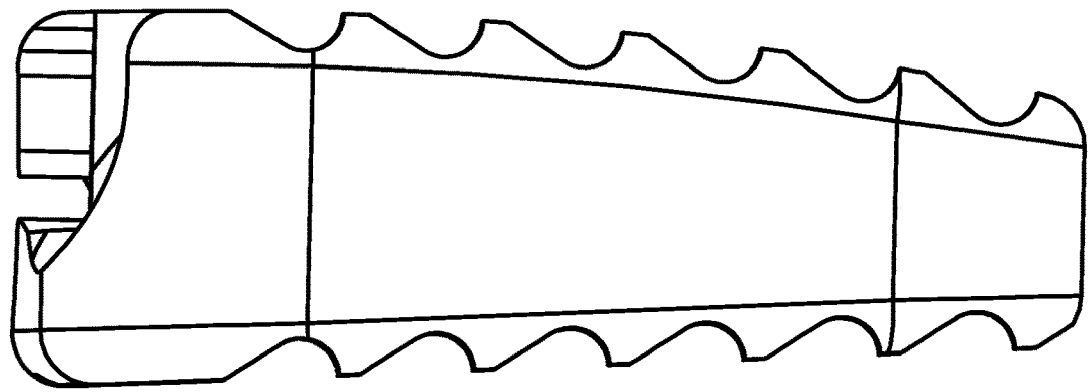
FIG. 12E illustrates a first side of the intervertebral spacer 1200 of FIG. 12A.
Figure 12F:
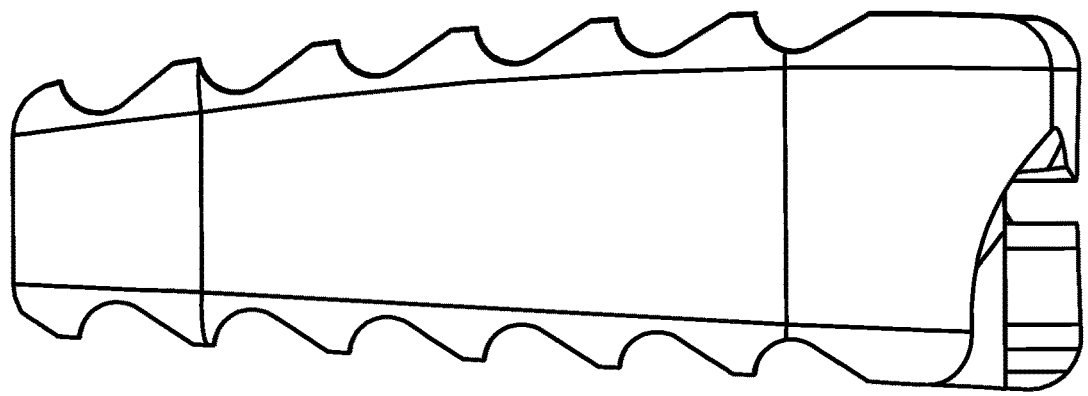
FIG. 12F illustrates a second side of the intervertebral spacer 1200 of FIG. 12A.
Figure 12G:
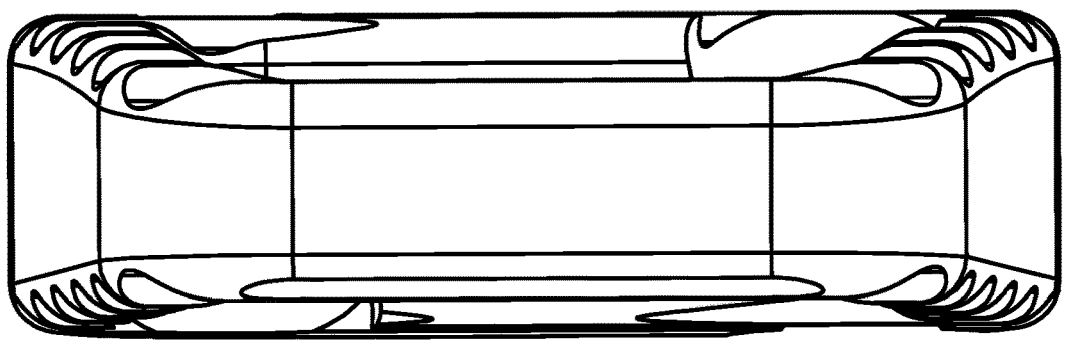
FIG. 12G illustrates the distal end of the intervertebral spacer 1200 of FIG. 12A.
Figure 12H:
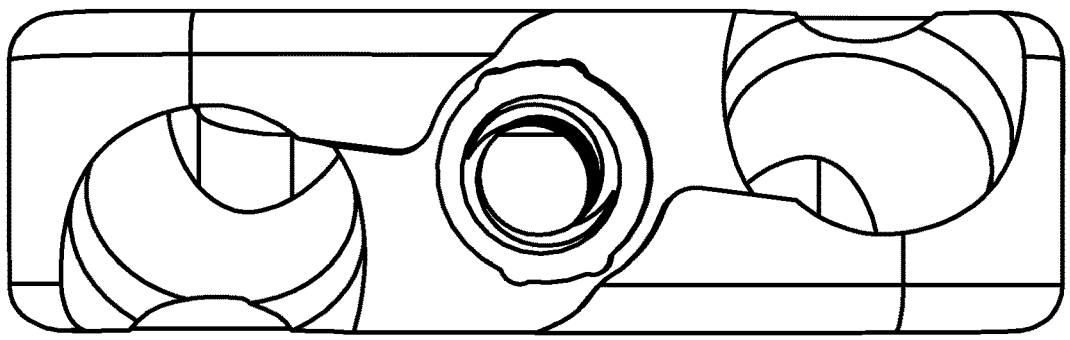
FIG. 12H illustrates the proximal end of the intervertebral spacer 1200 of FIG. 12A.
Figure 13A:
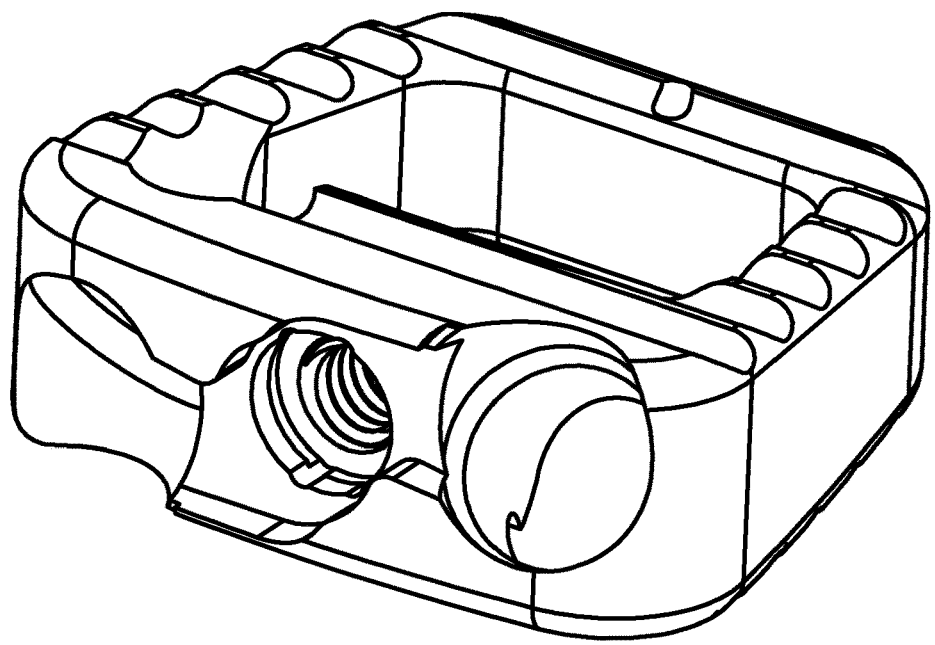
FIG. 13A is a perspective top view of a proximal end of an intervertebral spacer 1300, according to an embodiment of the present disclosure.
Figure 13B:
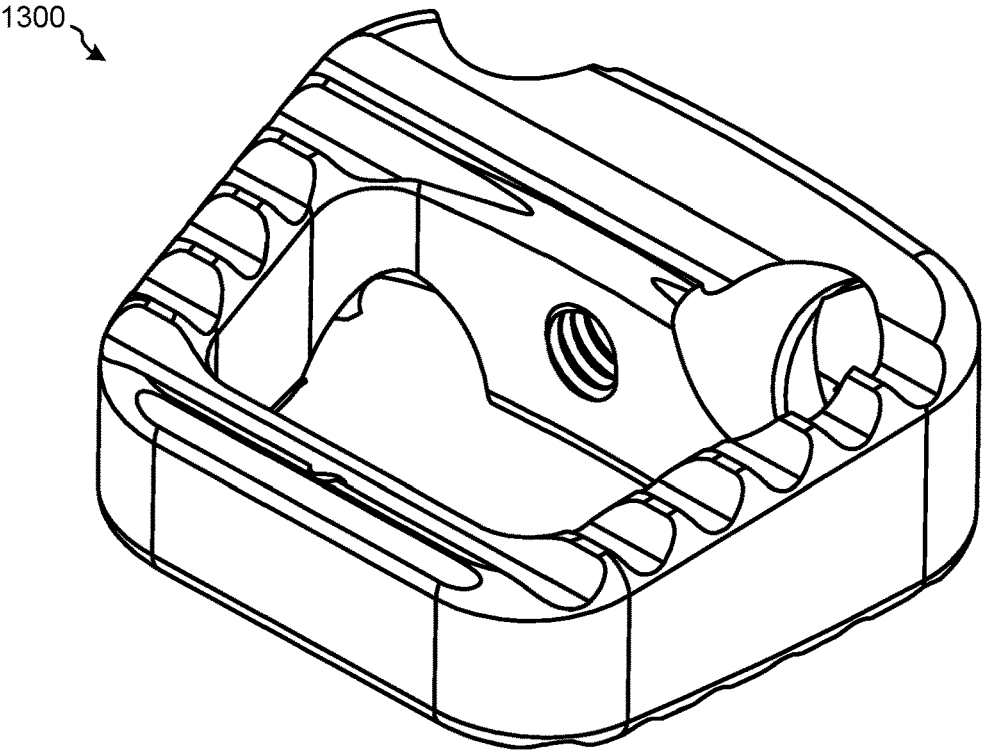
FIG. 13B is a perspective top view of a distal end of the intervertebral spacer 1300 of FIG. 13A.
Figure 13C:
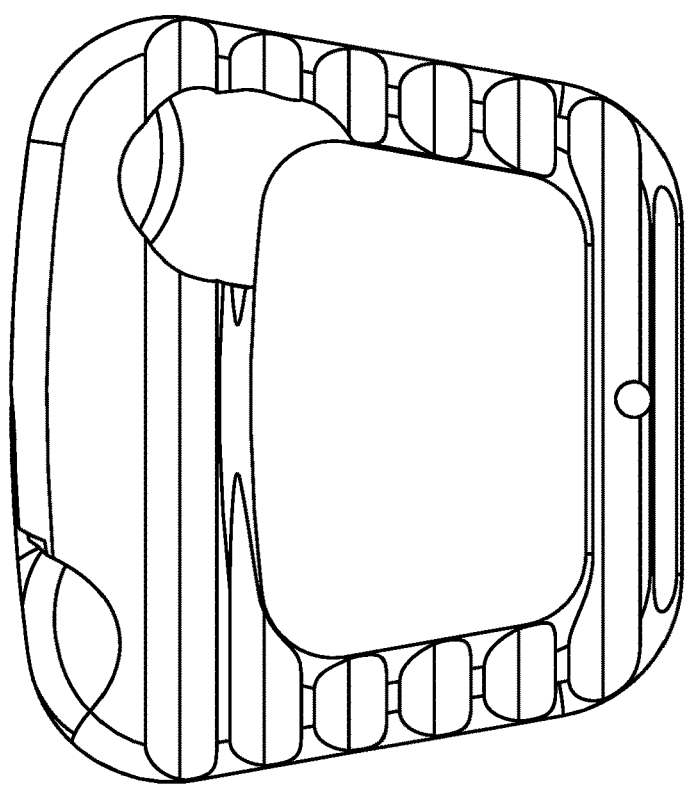
FIG. 13C is a top view of the intervertebral spacer 1300 of FIG. 13A.
Figure 13D:
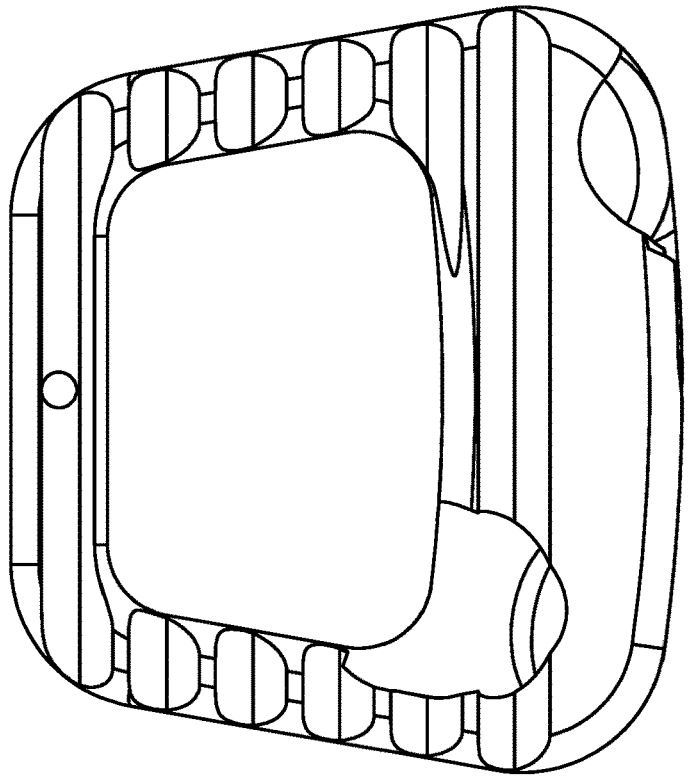
FIG. 13D is a bottom view of the intervertebral spacer 1300 of FIG. 13A.
Figure 13E:
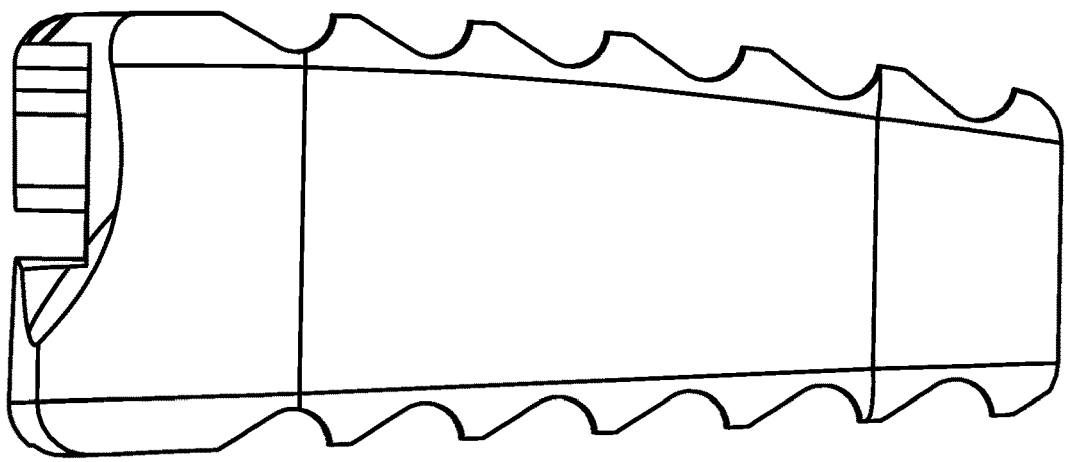
FIG. 13E illustrates a first side of the intervertebral spacer 1300 of FIG. 13A.
Figure 13F:
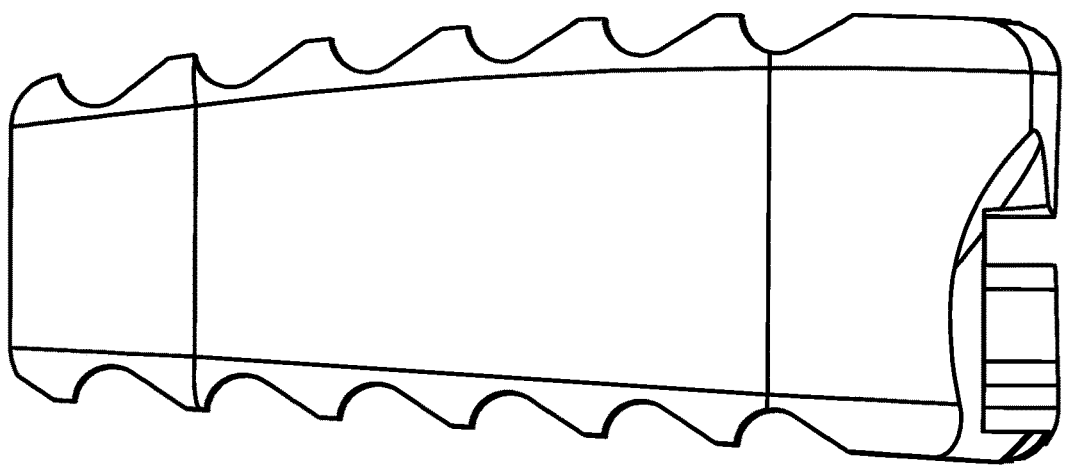
FIG. 13F illustrates a second side of the intervertebral spacer 1300 of FIG. 13A.
Figure 13G:
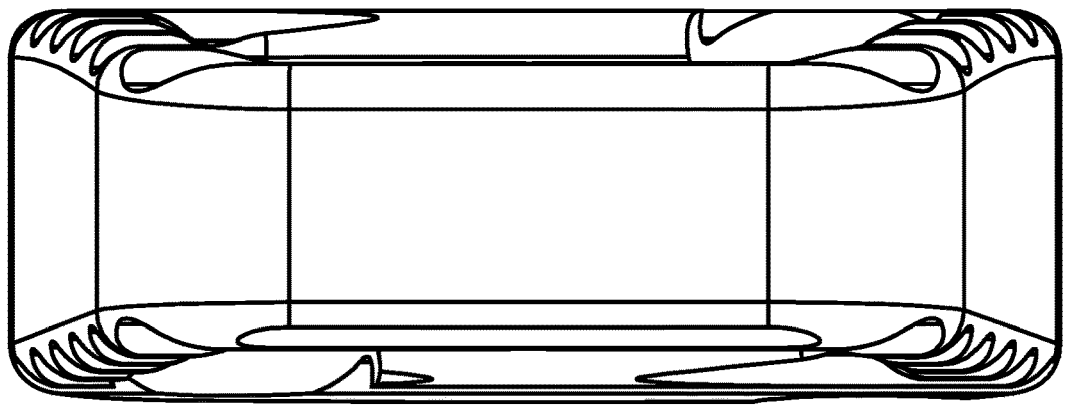
FIG. 13G illustrates the distal end of the intervertebral spacer 1300 of FIG. 13A.
Figure 13H:
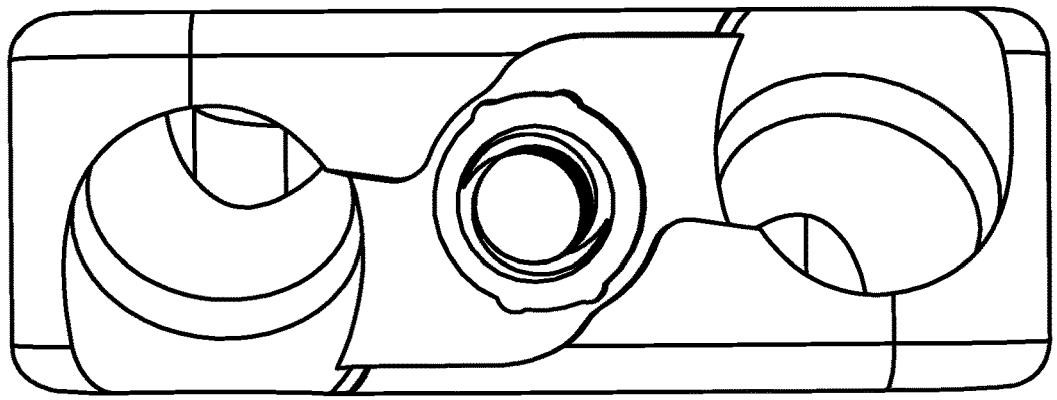
FIG. 13H illustrates the proximal end of the intervertebral spacer 1300 of FIG. 13A.
Figure 14A:
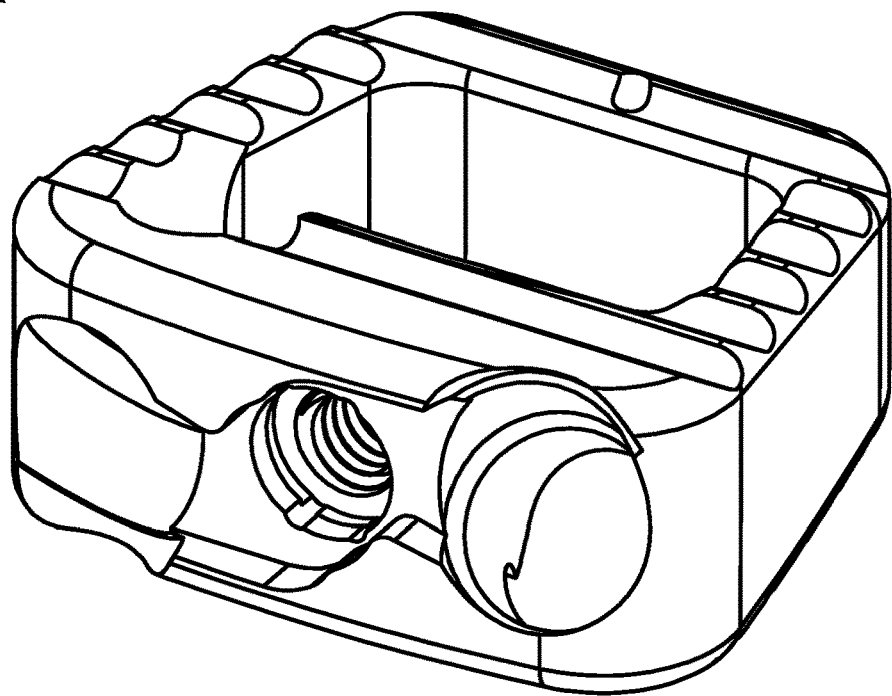
FIG. 14A is a perspective top view of a proximal end of an intervertebral spacer 1400, according to an embodiment of the present disclosure.
Figure 14B:
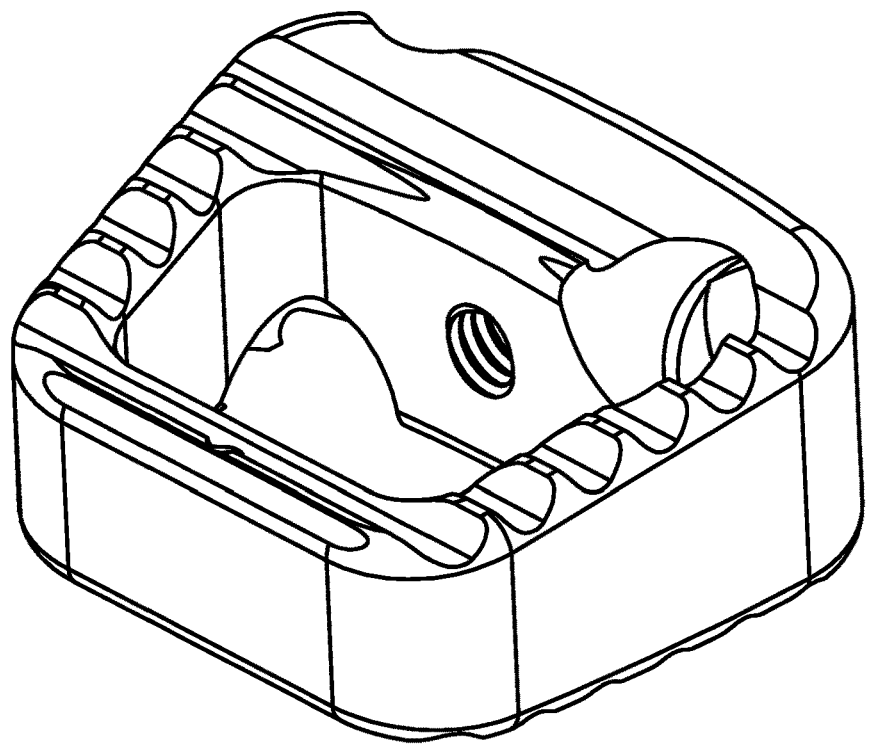
FIG. 14B is a perspective top view of a distal end of the intervertebral spacer 1400 of FIG. 14A.
Figure 14C:
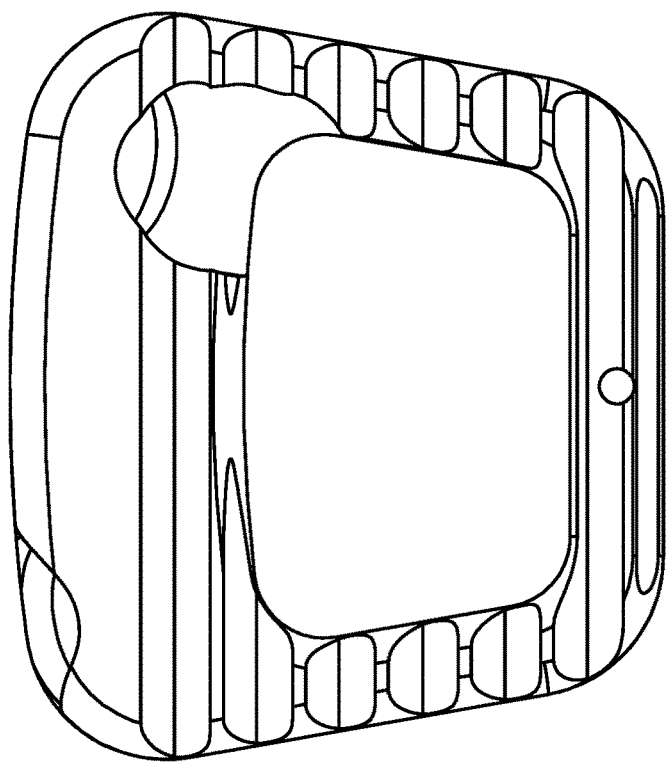
FIG. 14C is a top view of the intervertebral spacer 1400 of FIG. 14A.
Figure 14D:
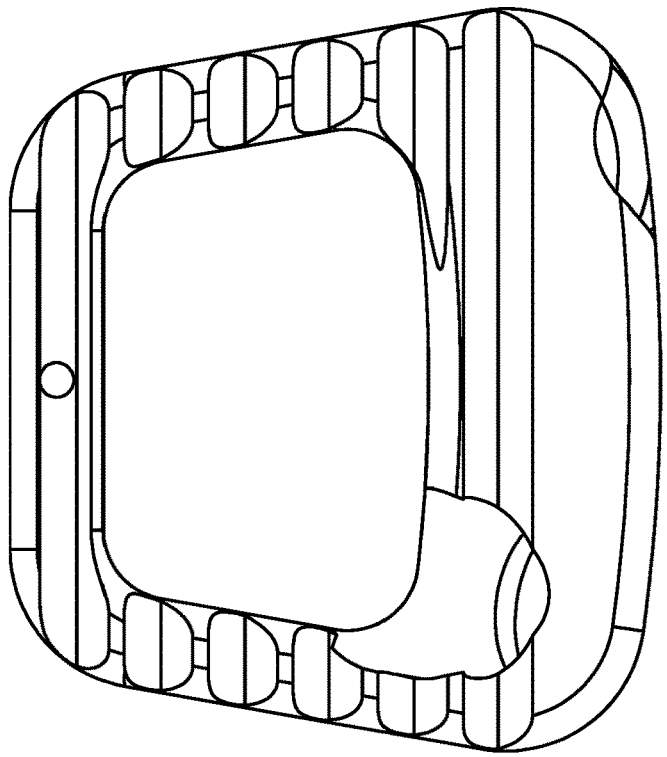
FIG. 14D is a bottom view of the intervertebral spacer 1400 of FIG. 14A.
Figure 14E:
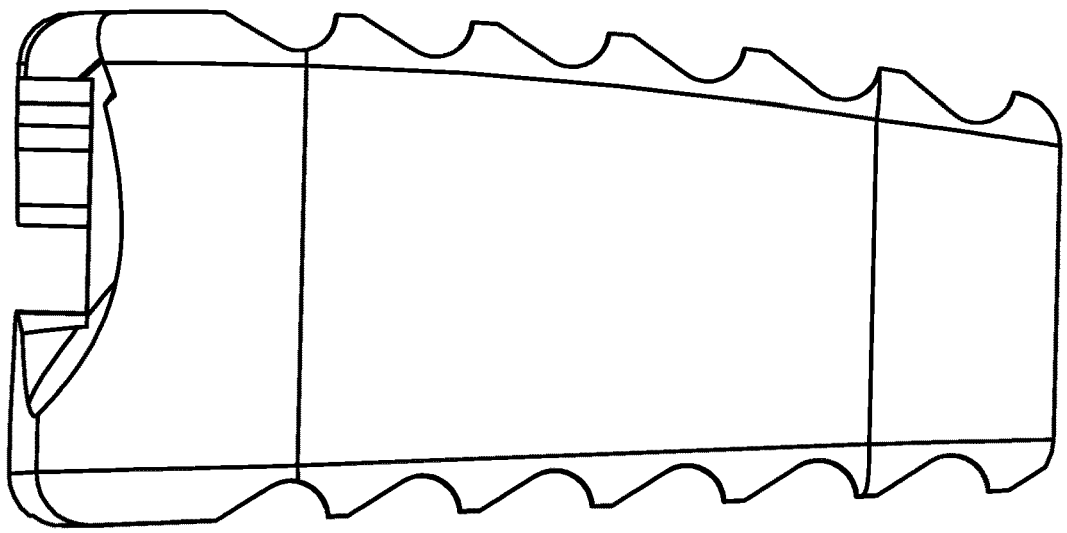
FIG. 14E illustrates a first side of the intervertebral spacer 1400 of FIG. 14A.
Figure 14F:
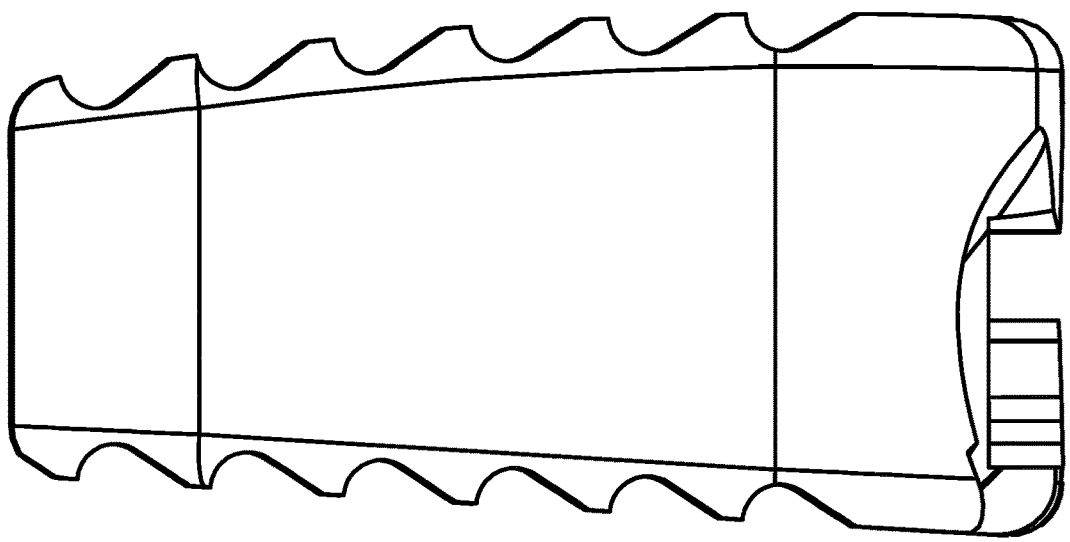
FIG. 14F illustrates a second side of the intervertebral spacer 1400 of FIG. 14A.
Figure 14G:
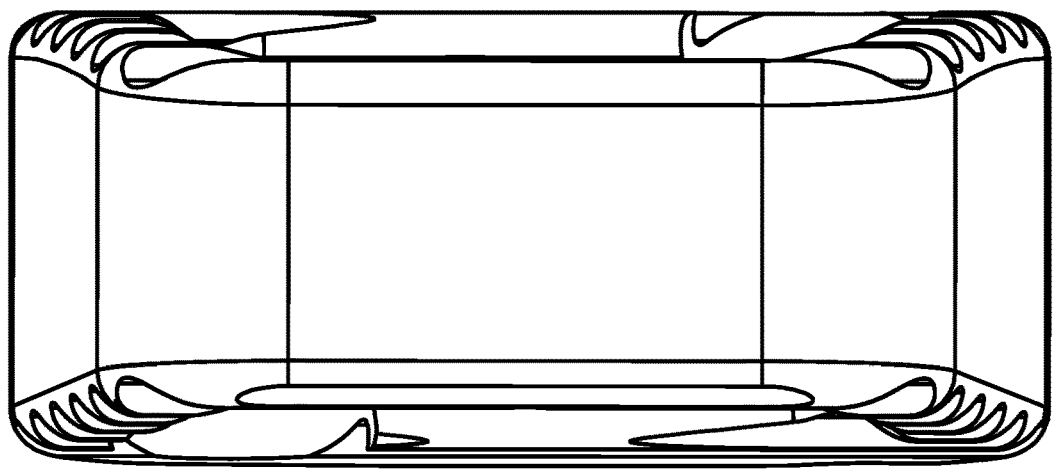
FIG. 14G illustrates the distal end of the intervertebral spacer 1400 of FIG. 14A.
Figure 14H:
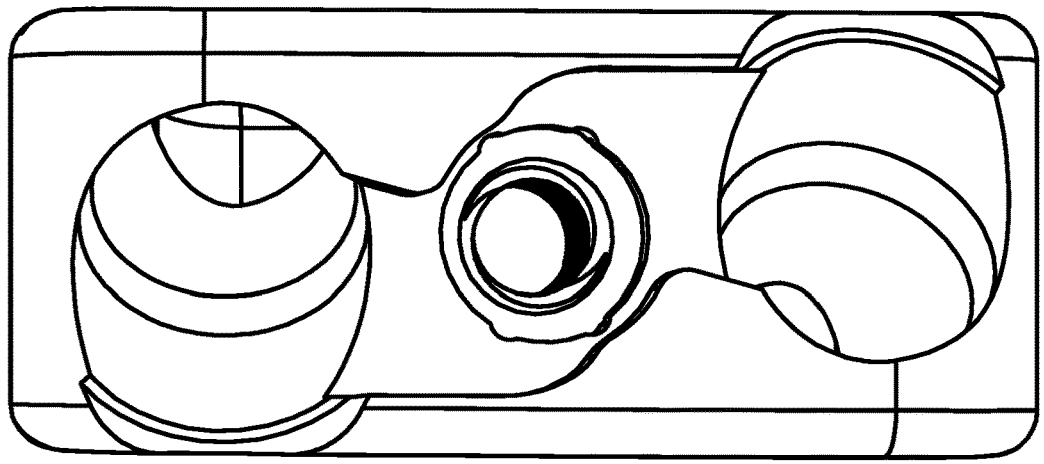
FIG. 14H illustrates the proximal end of the intervertebral spacer 1400 of FIG. 14A.
Figure 15A:
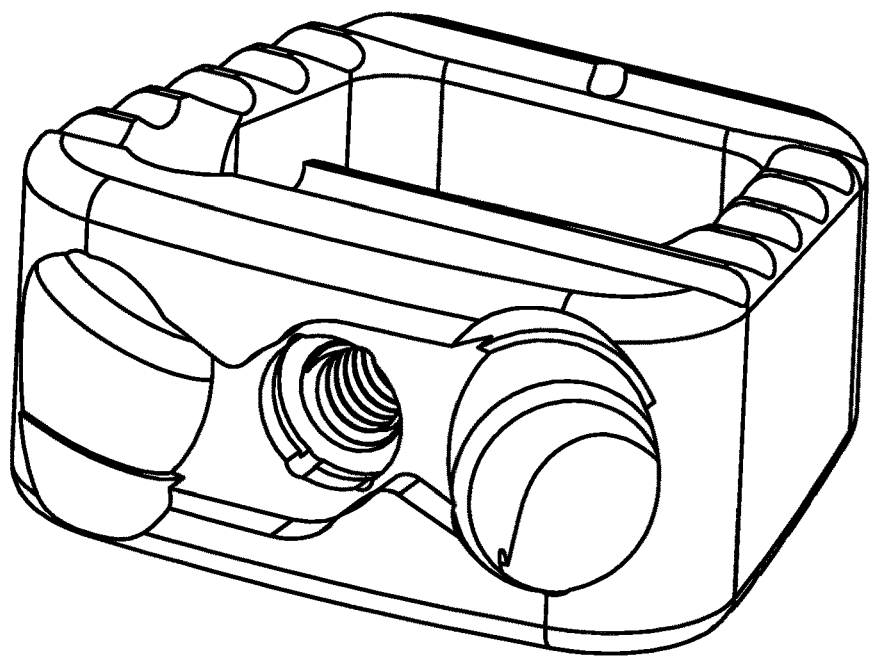
FIG. 15A is a perspective top view of a proximal end of an intervertebral spacer 1500, according to an embodiment of the present disclosure.
Figure 15B:
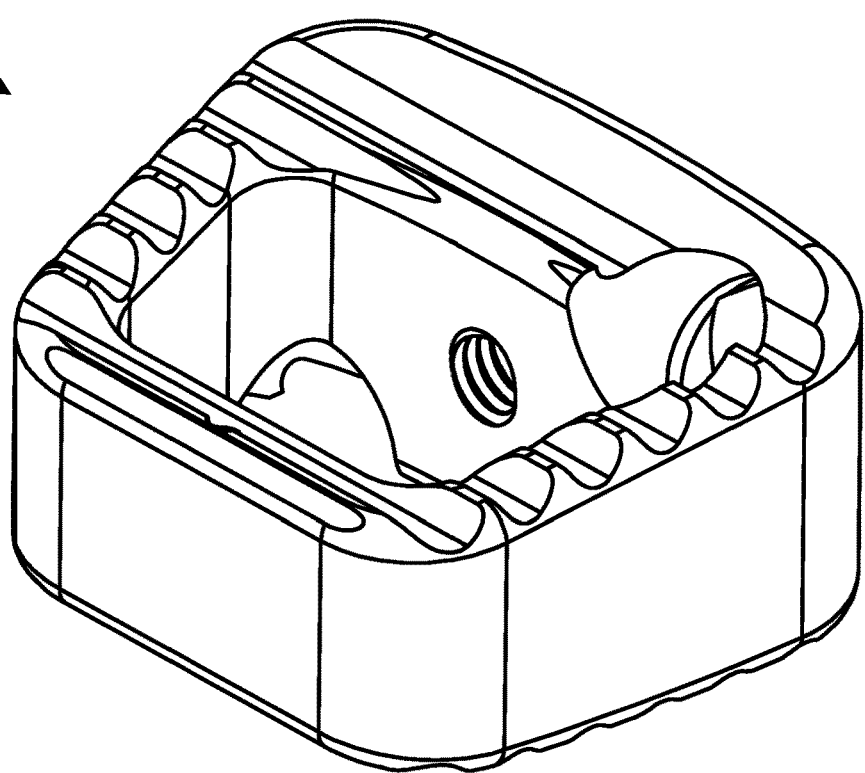
FIG. 15B is a perspective top view of a distal end of the intervertebral spacer 1500 of FIG. 15A.
Figure 15C:
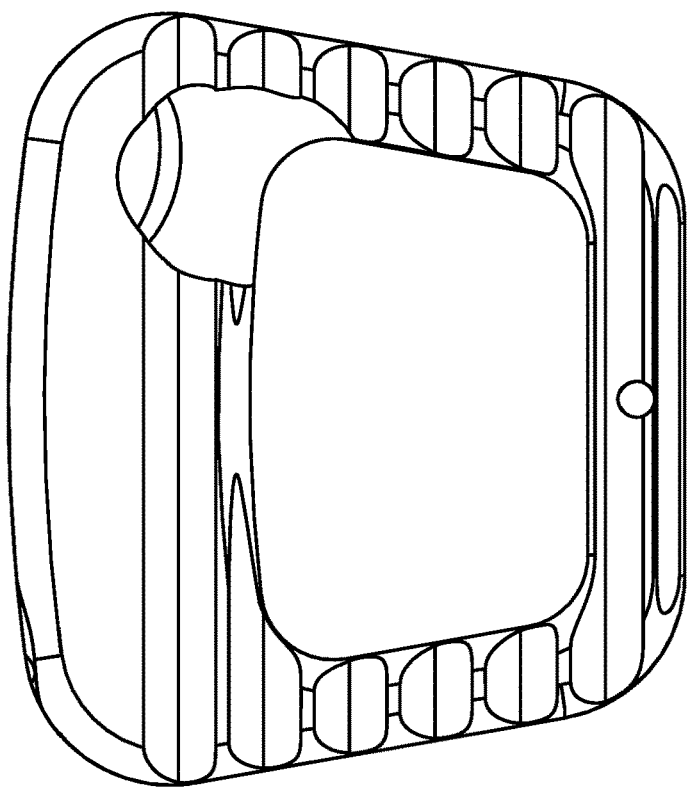
FIG. 15C is a top view of the intervertebral spacer 1500 of FIG. 15A.
Figure 15D:
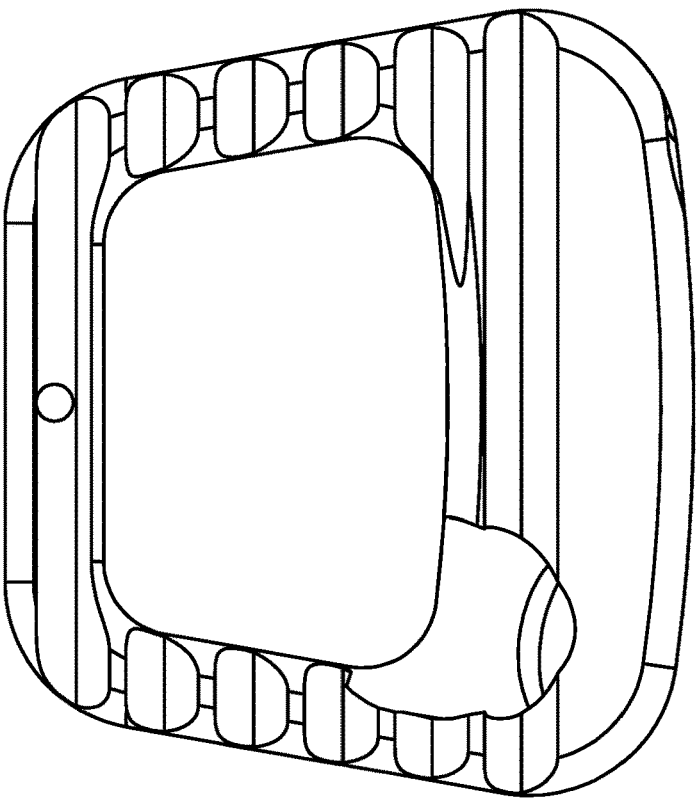
FIG. 15D is a bottom view of the intervertebral spacer 1500 of FIG. 15A.
Figure 15E:
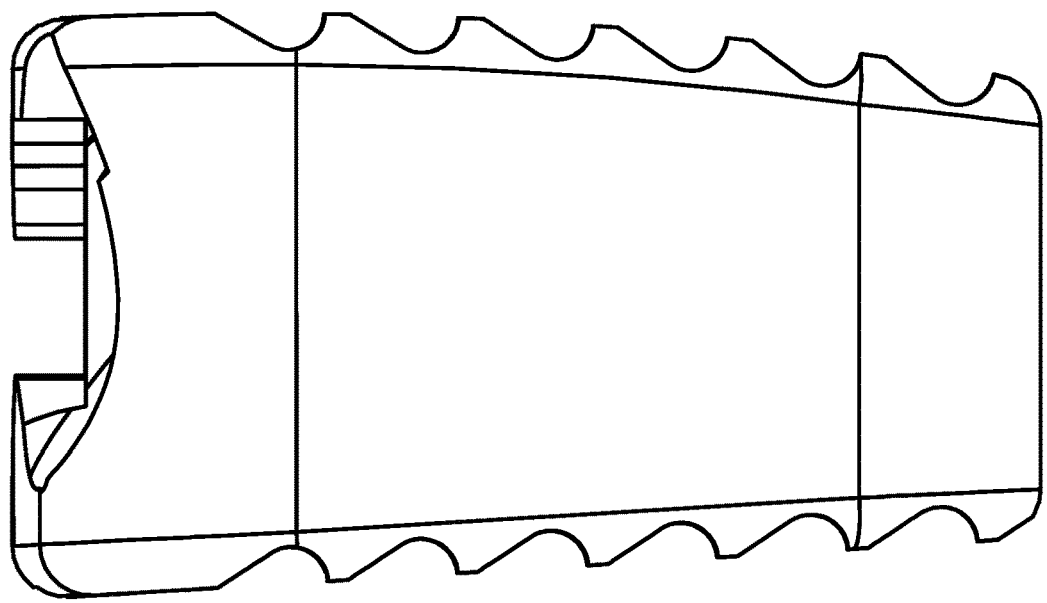
FIG. 15E illustrates a first side of the intervertebral spacer 1500 of FIG. 15A.
Figure 15F:
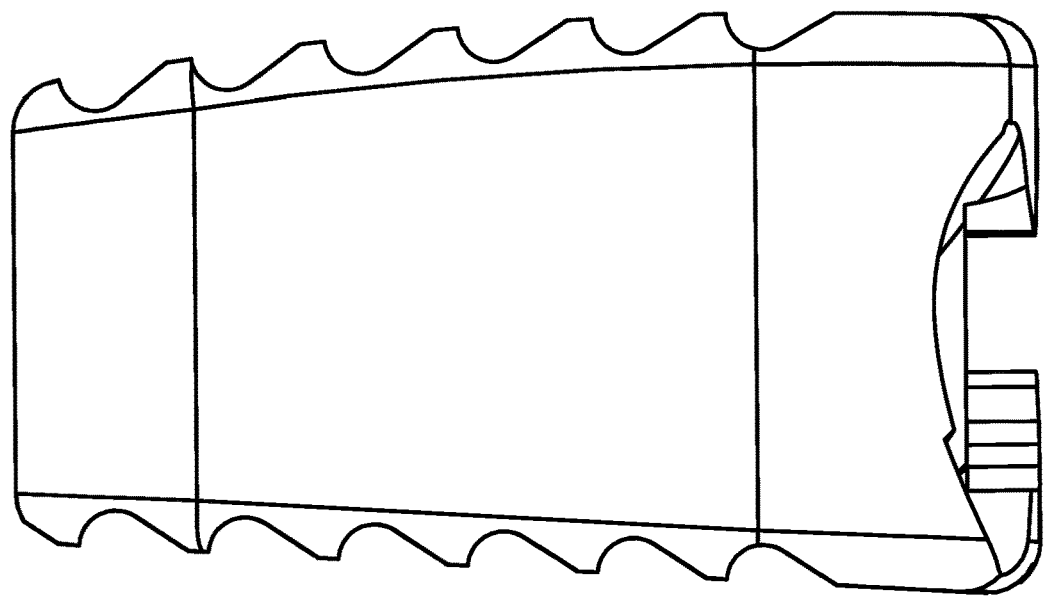
FIG. 15F illustrates a second side of the intervertebral spacer 1500 of FIG. 15A.
Figure 15G:
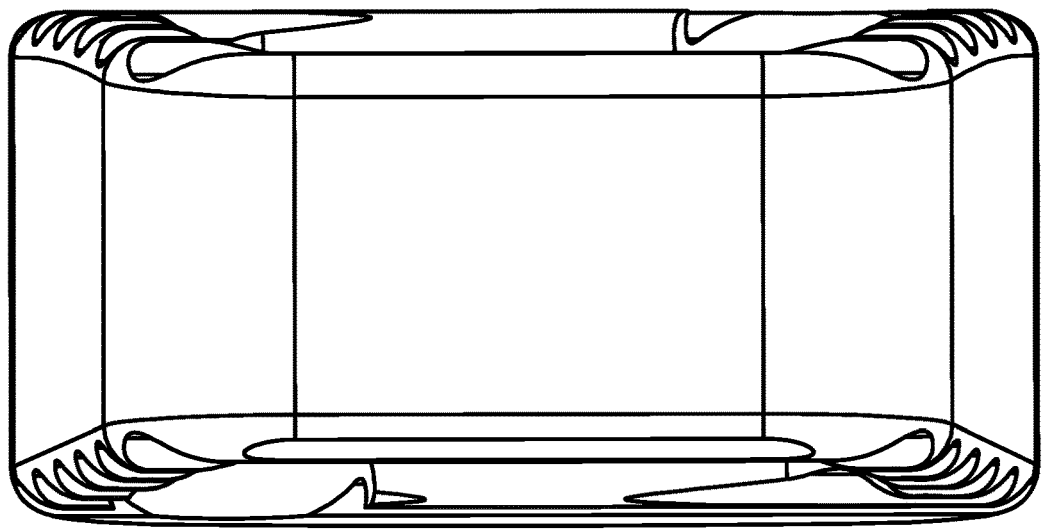
FIG. 15G illustrates the distal end of the intervertebral spacer 1500 of FIG. 15A.
Figure 15H:
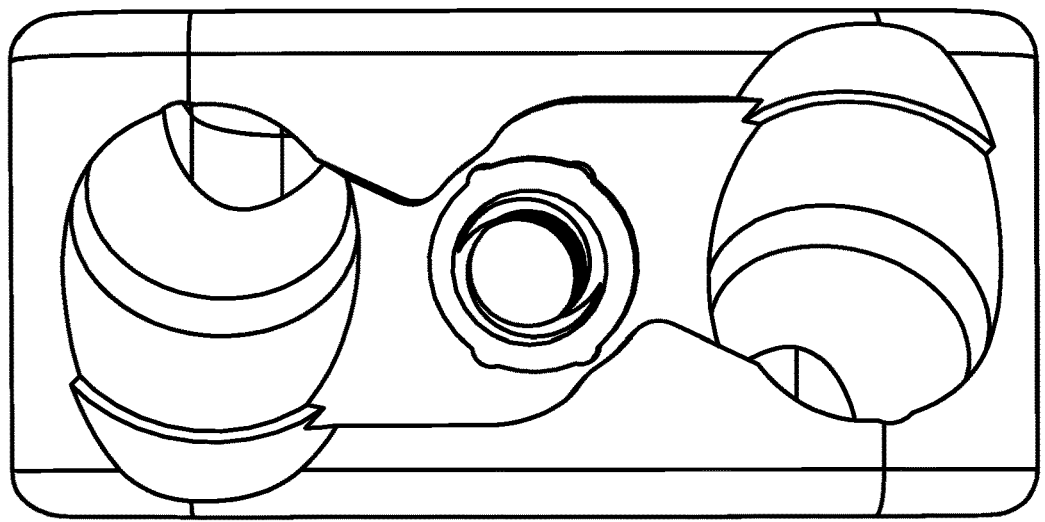
FIG. 15H illustrates the proximal end of the intervertebral spacer 1500 of FIG. 15A.
Figure 16A:
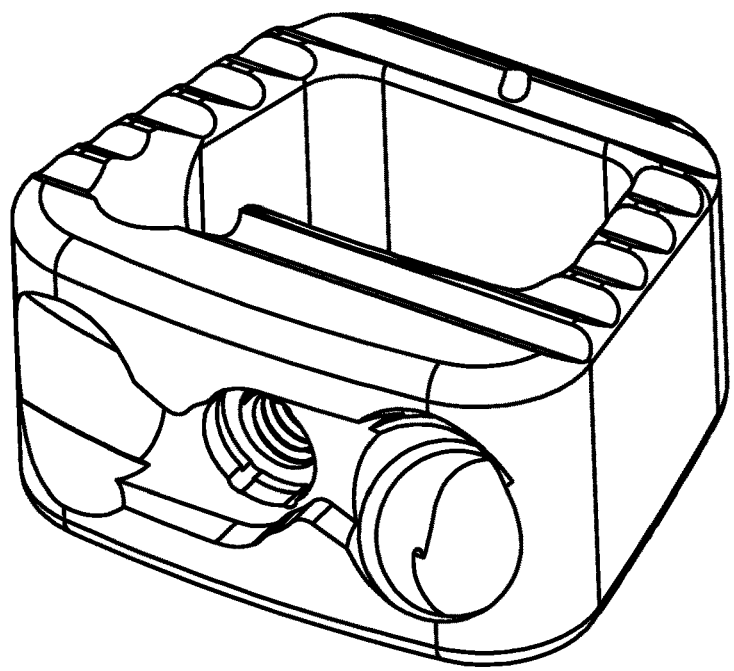
FIG. 16A is a perspective top view of a proximal end of an intervertebral spacer 1600, according to an embodiment of the present disclosure.
Figure 16B:
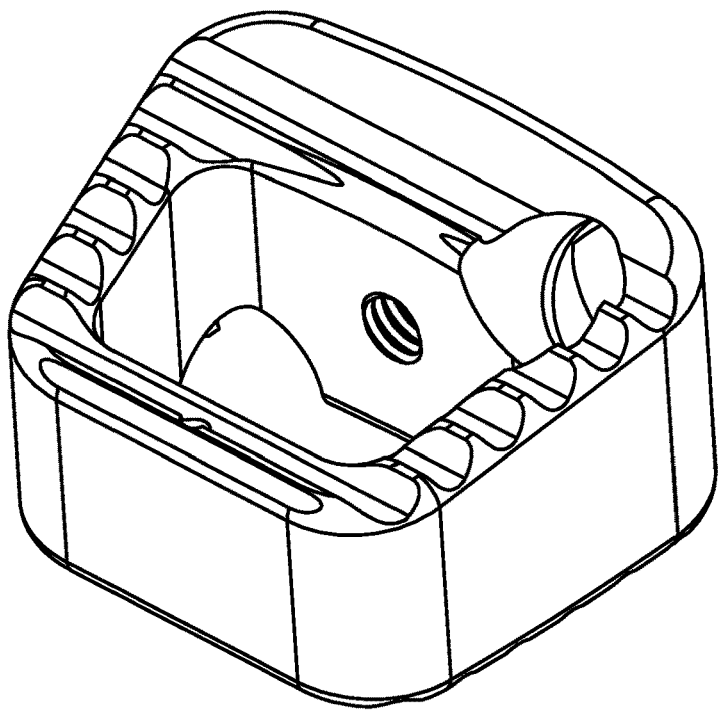
FIG. 16B is a perspective top view of a distal end of the intervertebral spacer 1600 of FIG. 16A.
Figure 16C:
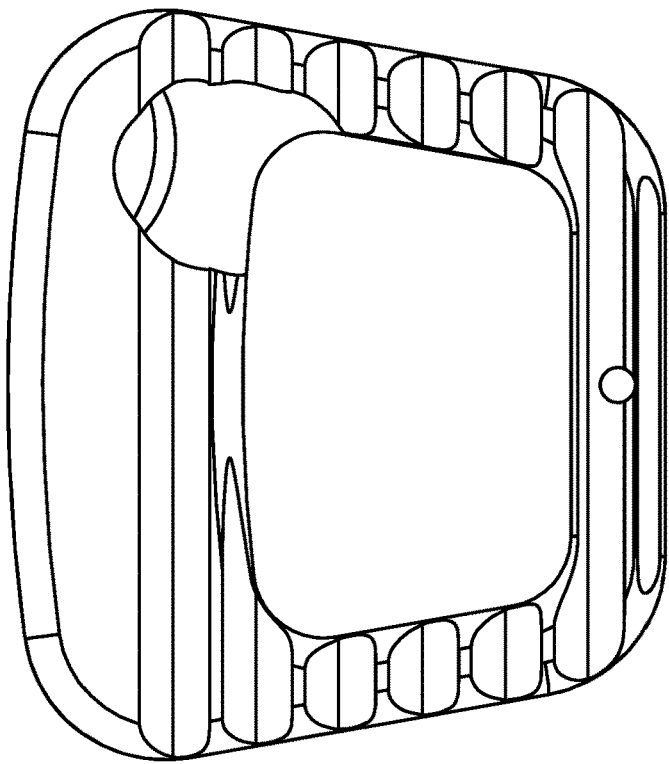
FIG. 16C is a top view of the intervertebral spacer 1600 of FIG. 16A.
Figure 16D:
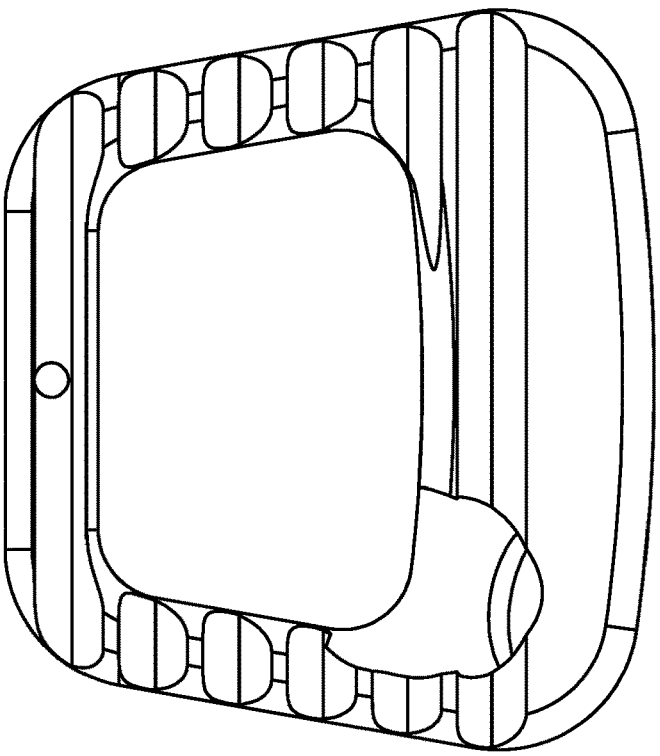
FIG. 16D is a bottom view of the intervertebral spacer 1600 of FIG. 16A.
Figure 16E:
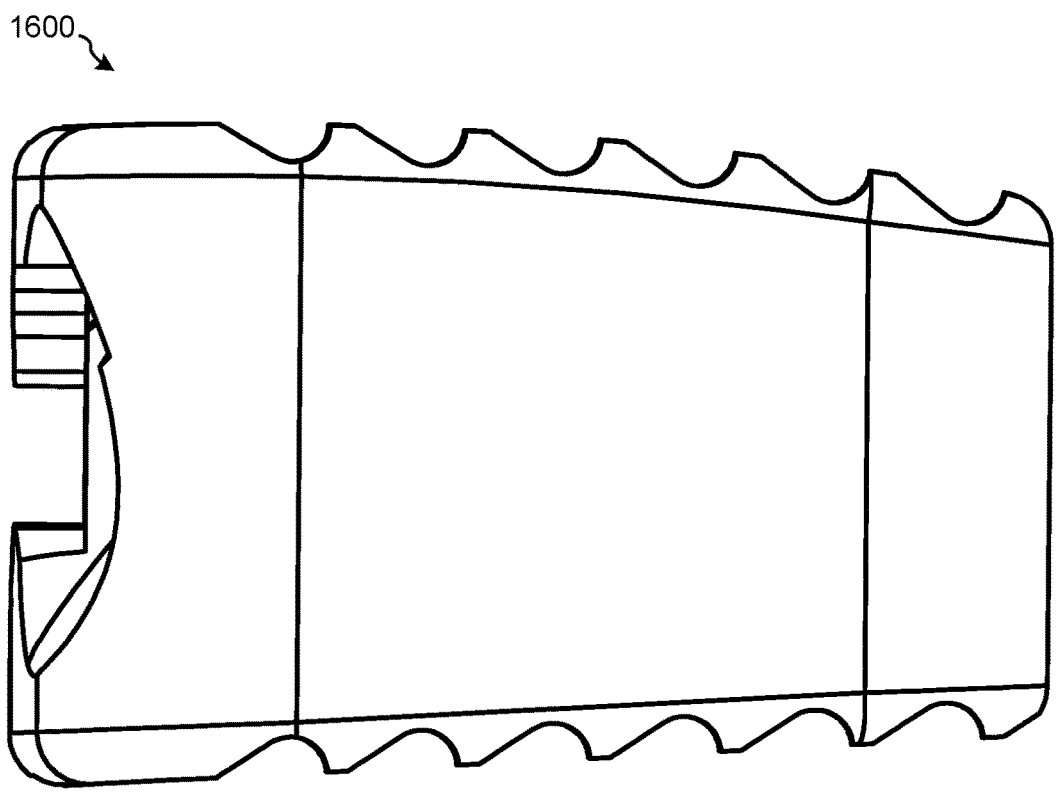
FIG. 16E illustrates a first side of the intervertebral spacer 1600 of FIG. 16A.
Figure 16F:
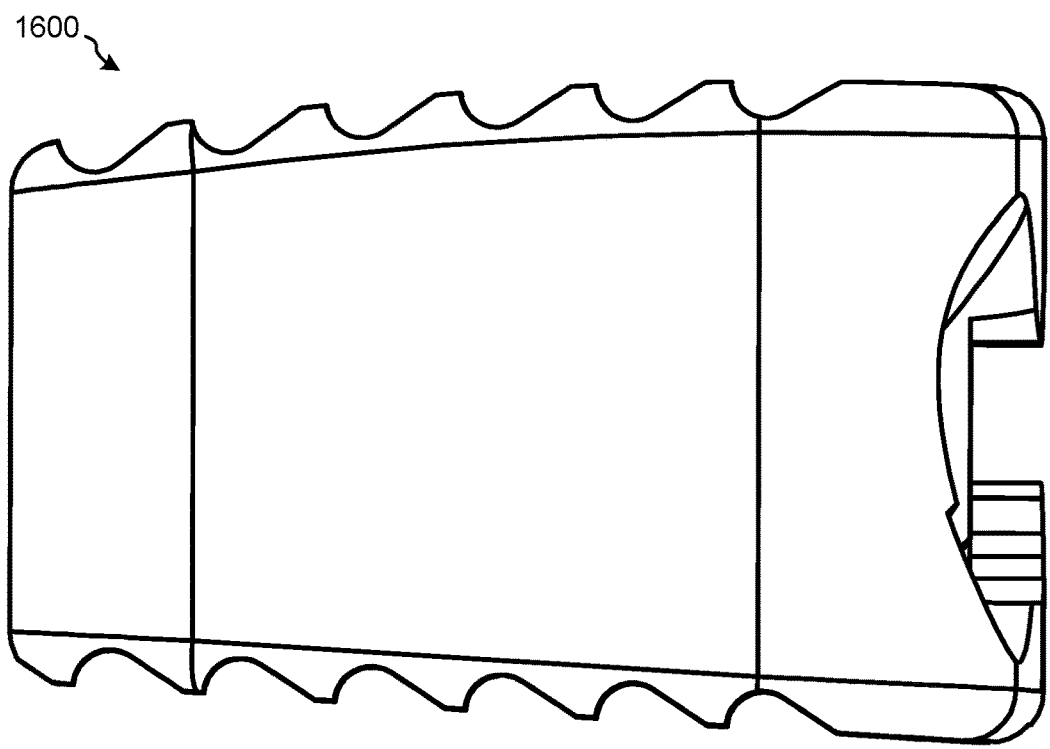
FIG. 16F illustrates a second side of the intervertebral spacer 1600 of FIG. 16A.
Figure 16G:
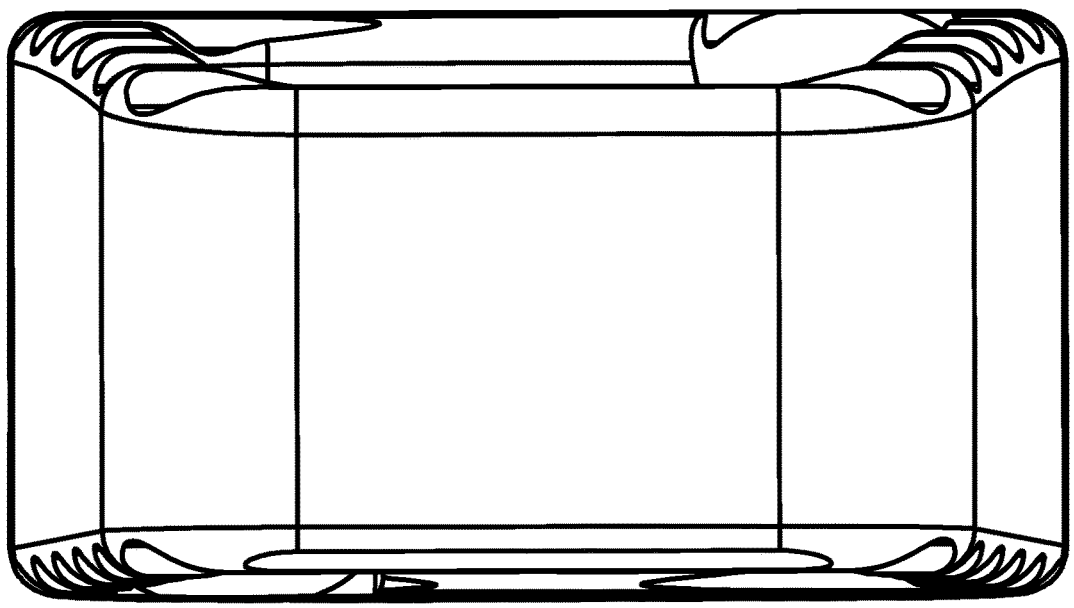
FIG. 16G illustrates the distal end of the intervertebral spacer 1600 of FIG. 16A.
Figure 16H:
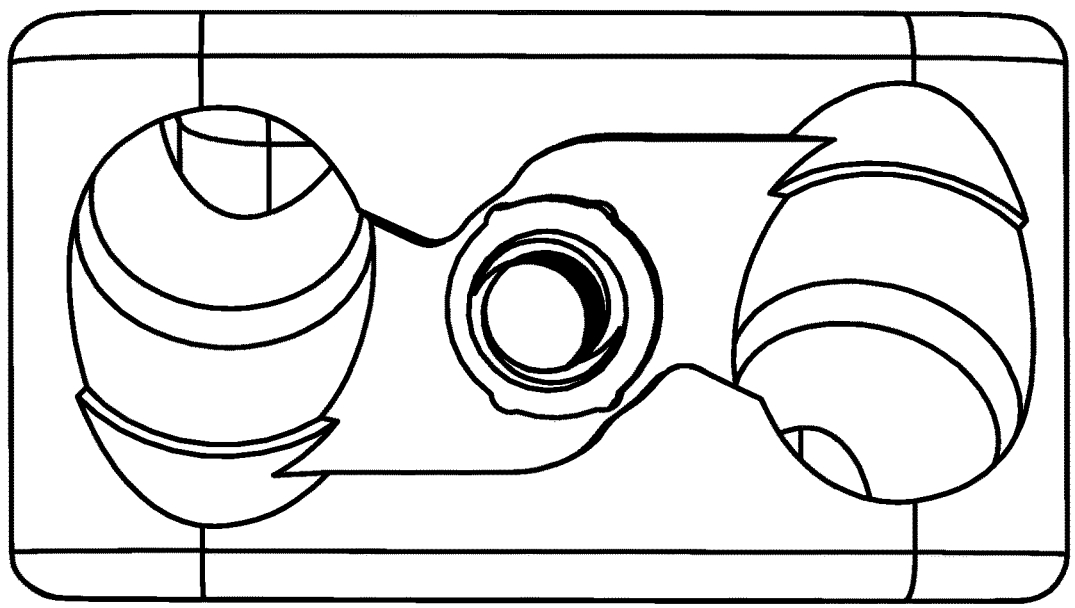
FIG. 16H illustrates the proximal end of the intervertebral spacer 1600 of FIG. 16A.
Figure 17A:
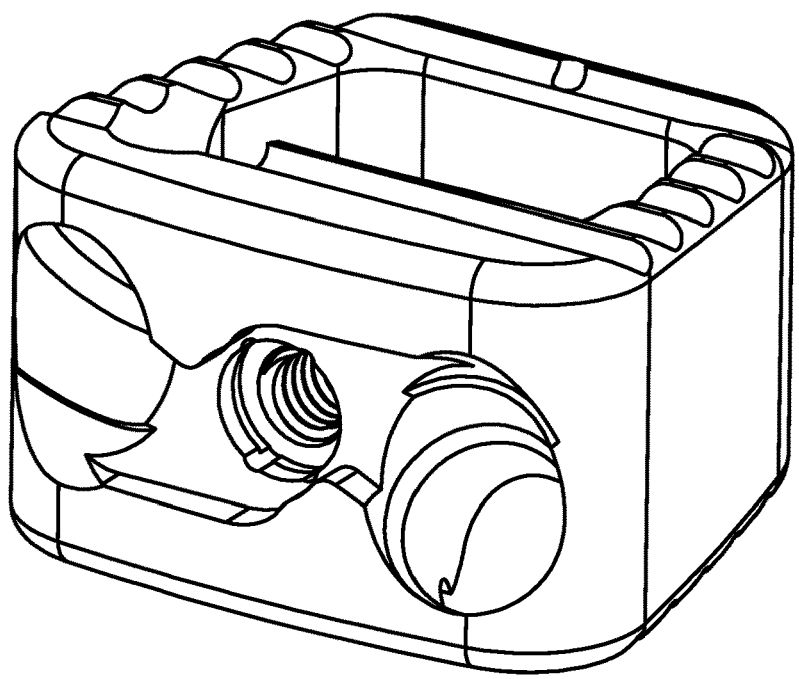
FIG. 17A is a perspective top view of a proximal end of an intervertebral spacer 1700, according to an embodiment of the present disclosure.
Figure 17B:
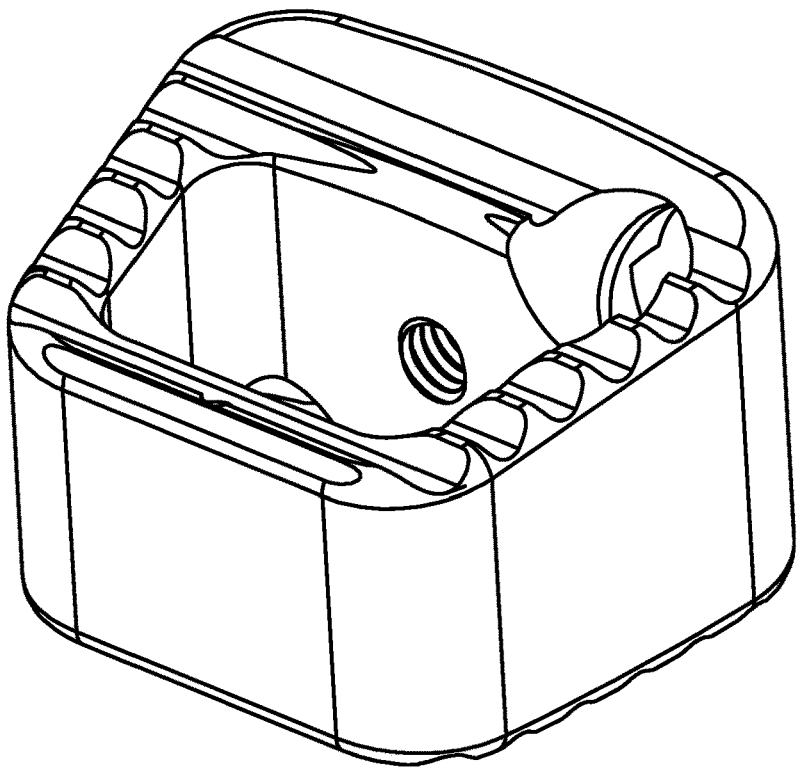
FIG. 17B is a perspective top view of a distal end of the intervertebral spacer 1700 of FIG. 17A.
Figure 17C:
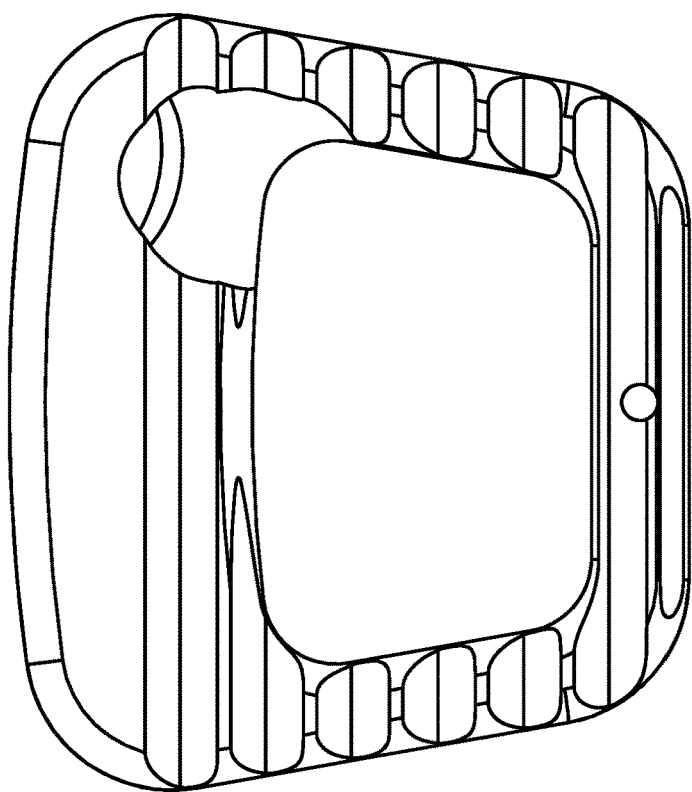
FIG. 17C is a top view of the intervertebral spacer 1700 of FIG. 17A.
Figure 17D:
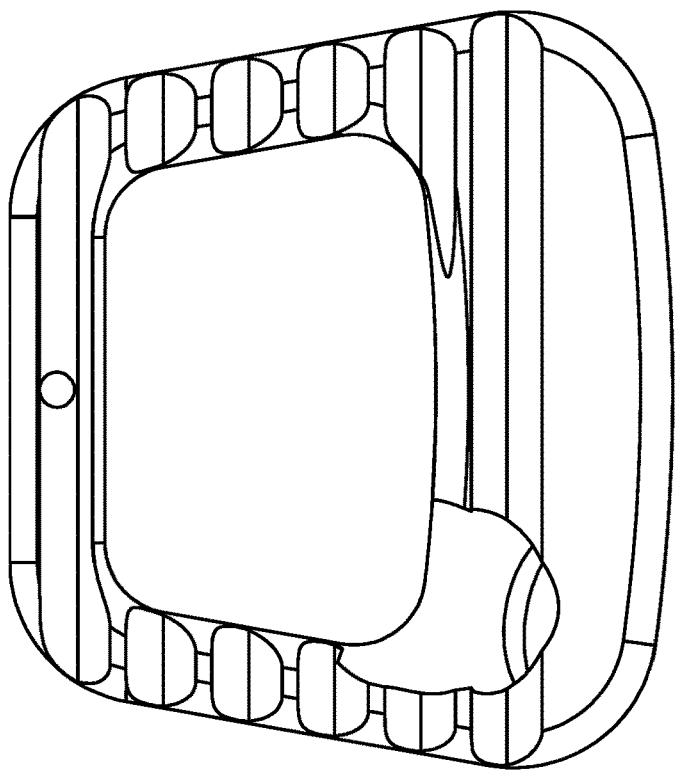
FIG. 17D is a bottom view of the intervertebral spacer 1700 of FIG. 17A.
Figure 17E:
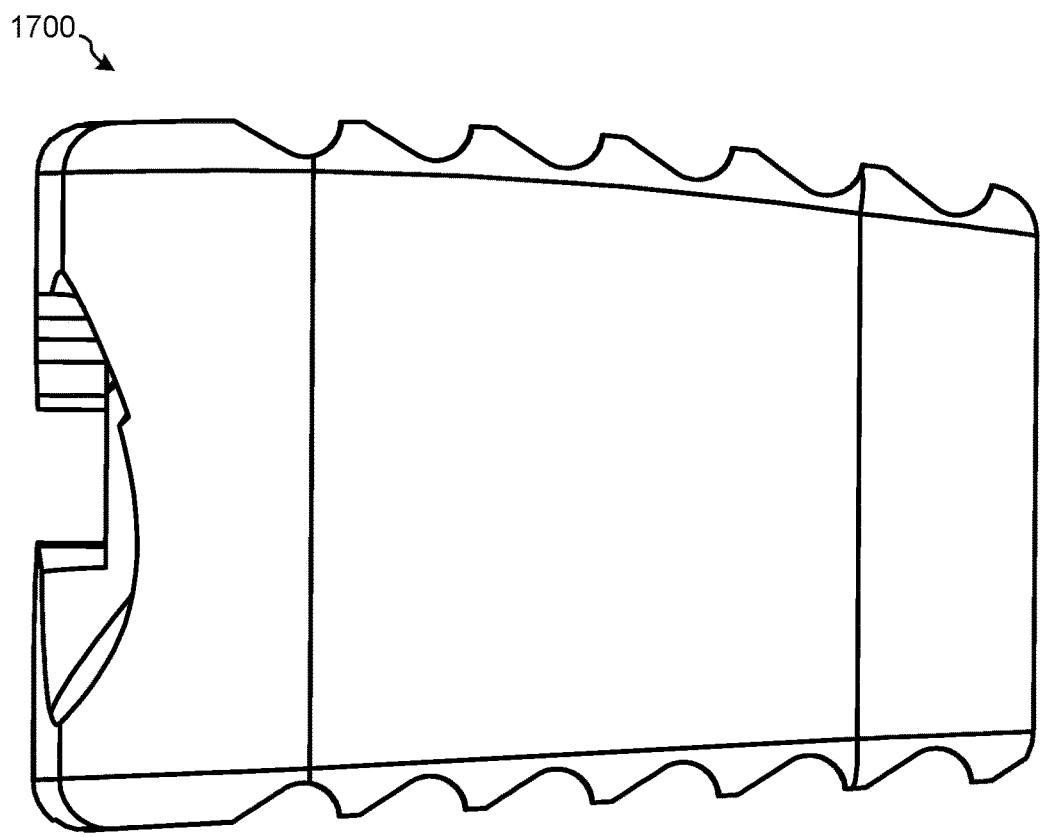
FIG. 17E illustrates a first side of the intervertebral spacer 1700 of FIG. 17A.
Figure 17F:
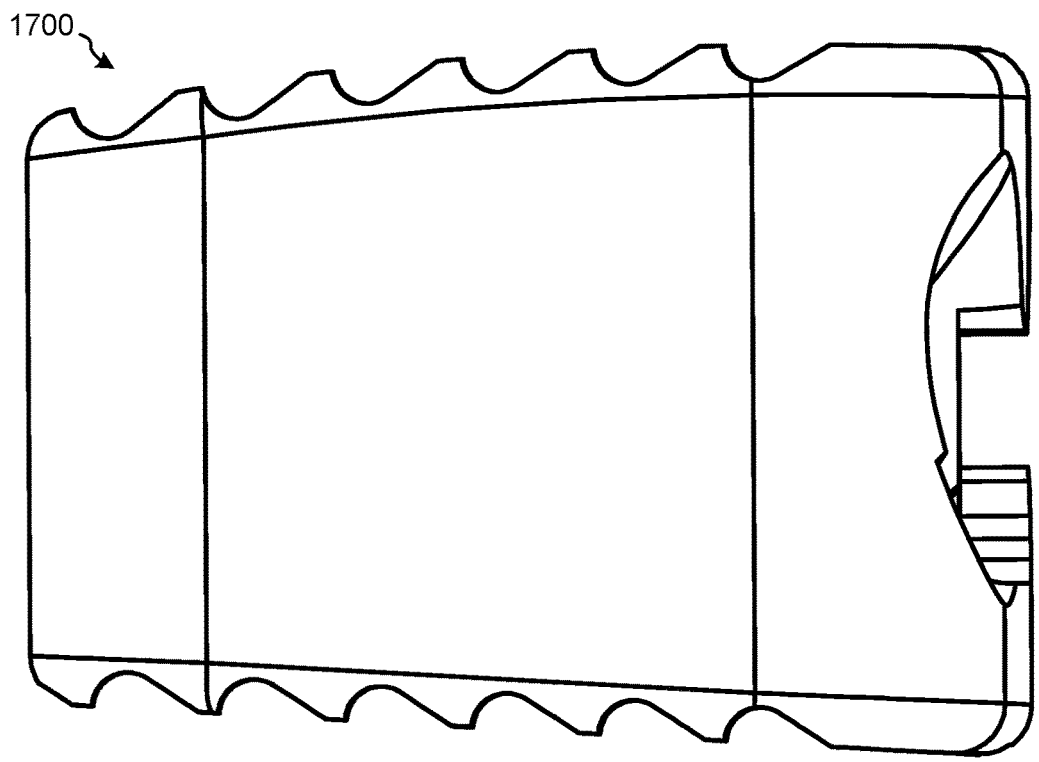
FIG. 17F illustrates a second side of the intervertebral spacer 1700 of FIG. 17A.
Figure 17G:
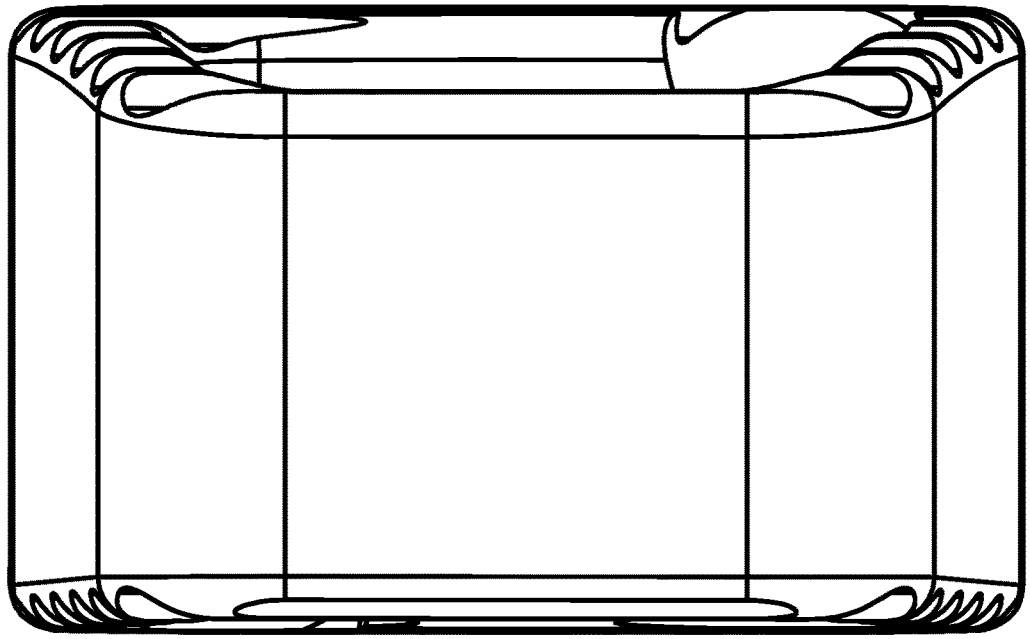
FIG. 17G illustrates the distal end of the intervertebral spacer 1700 of FIG. 17A.
Figure 17H:
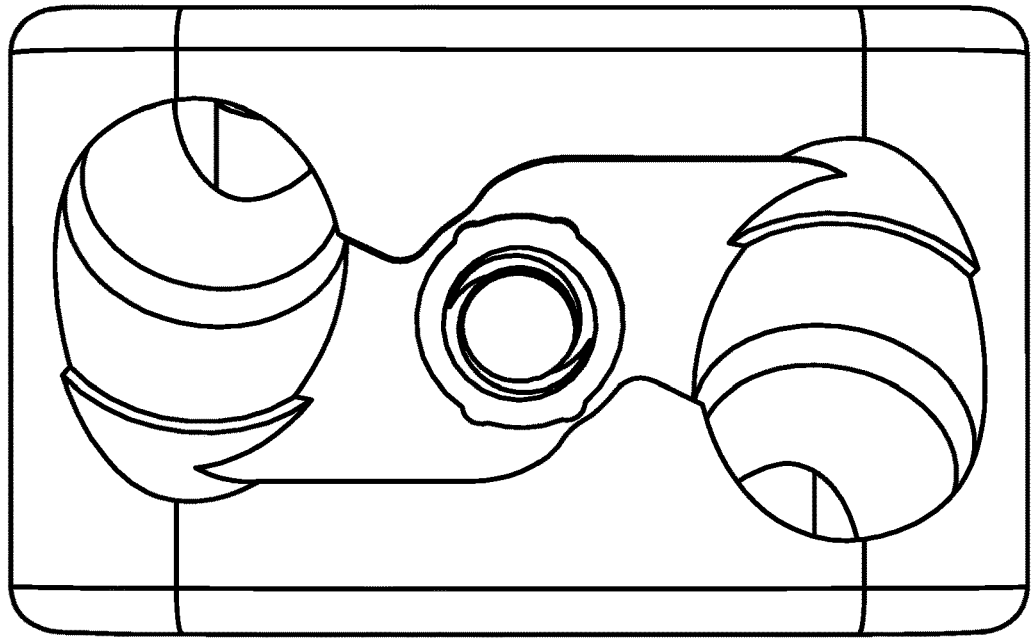
Figure 18A:
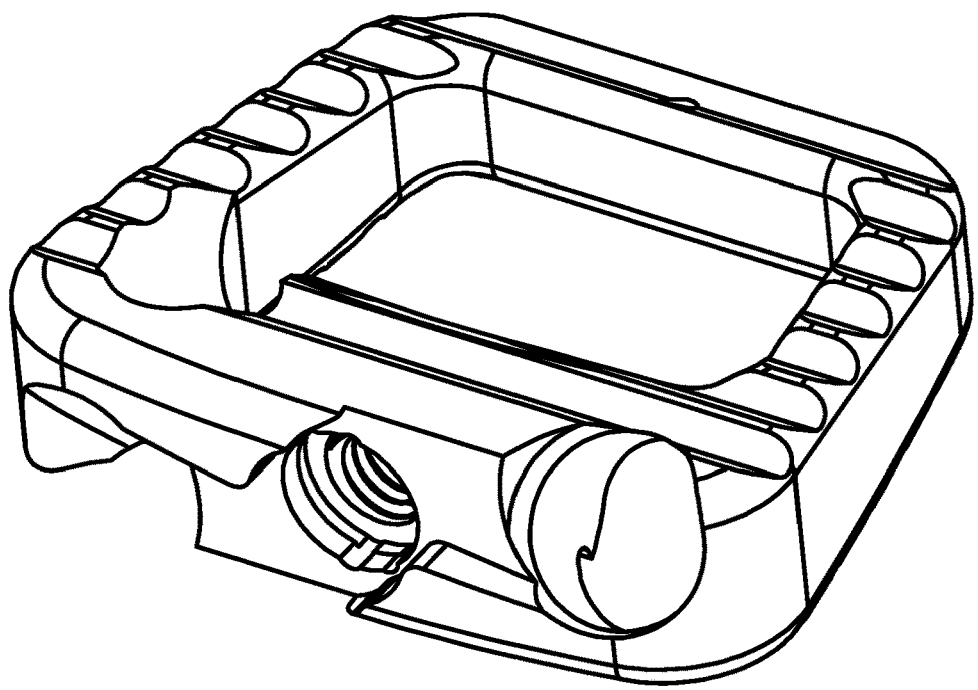
Figure 18B:
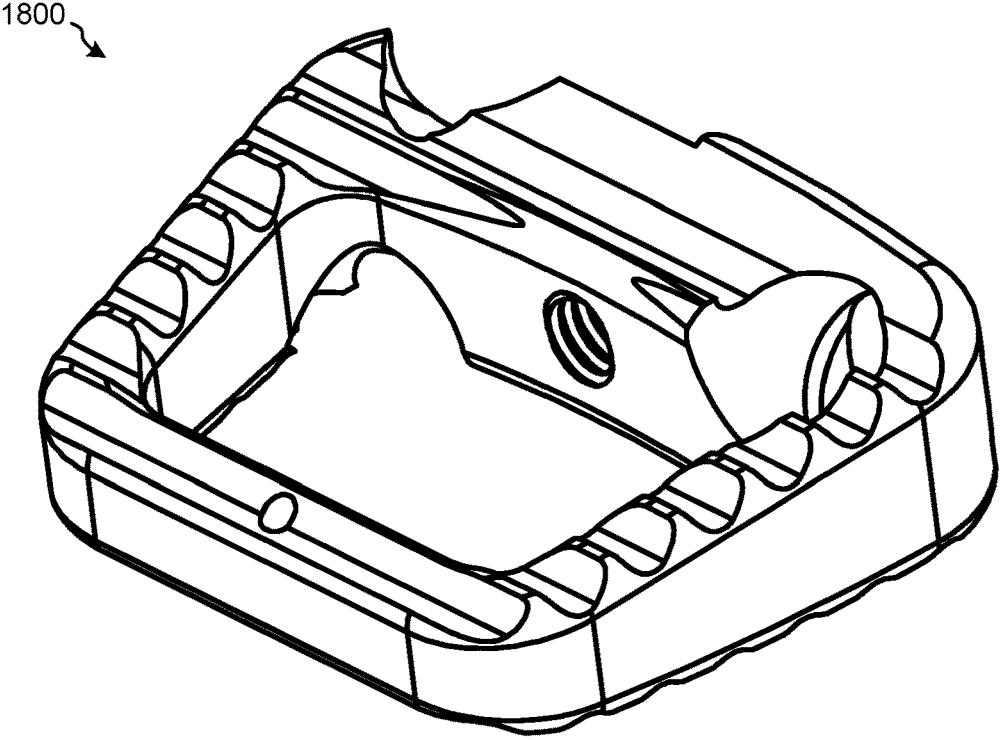
Figure 18C:
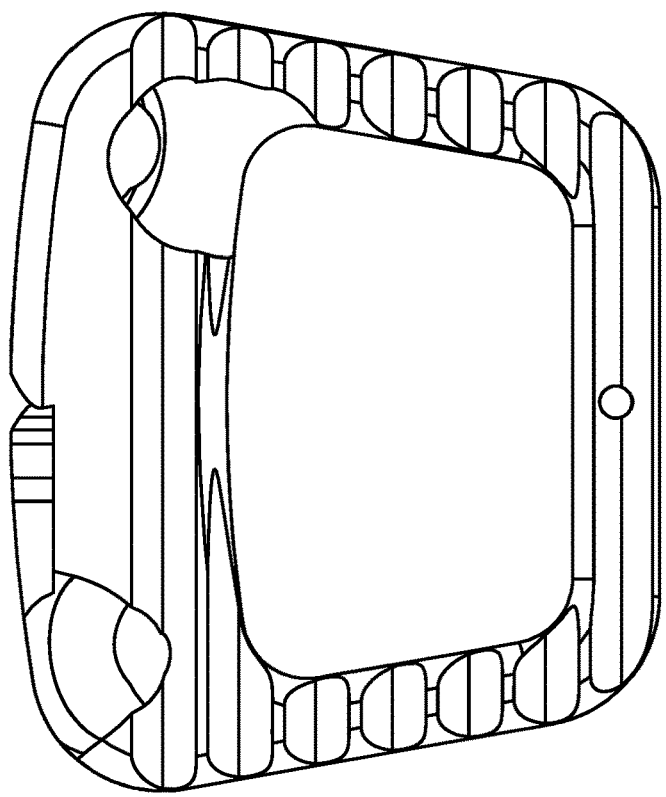
Figure 18D:
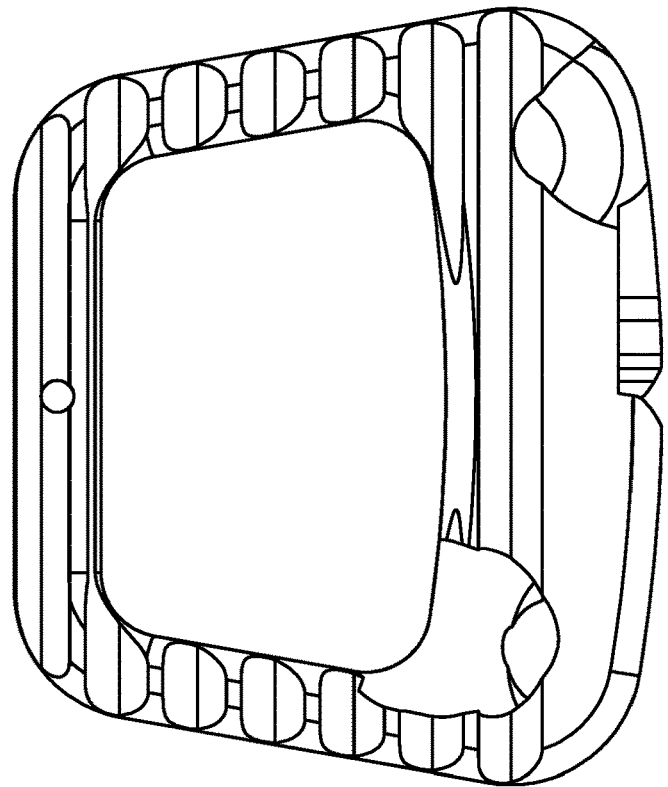
Figure 18E:
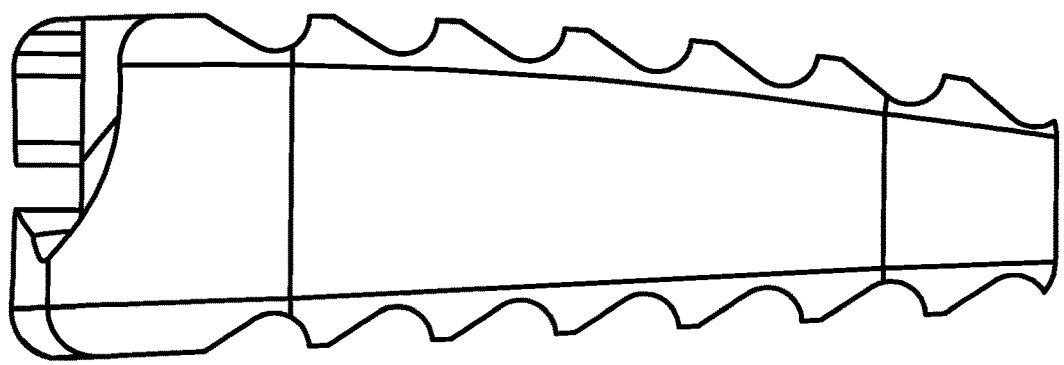
Figure 18F:
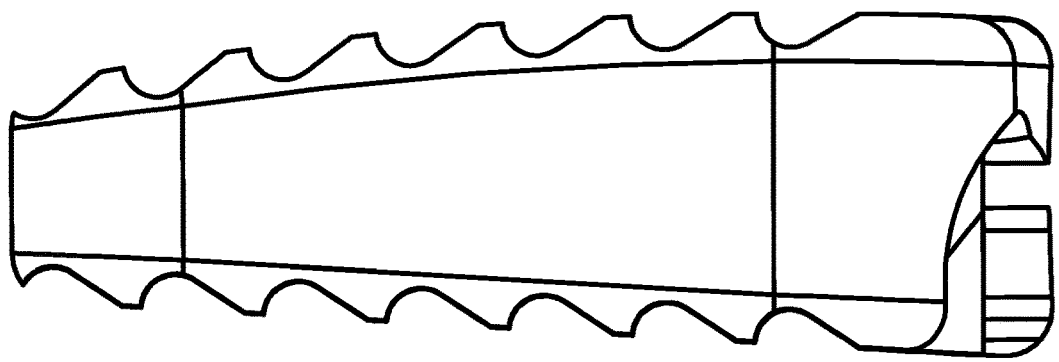
Figure 18G:
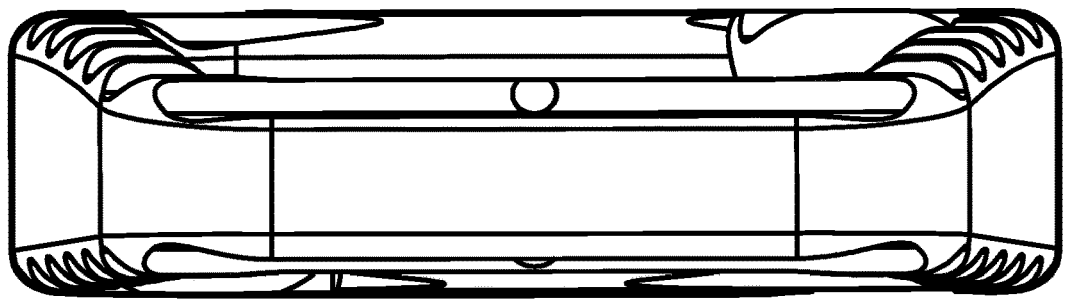
Figure 18H:
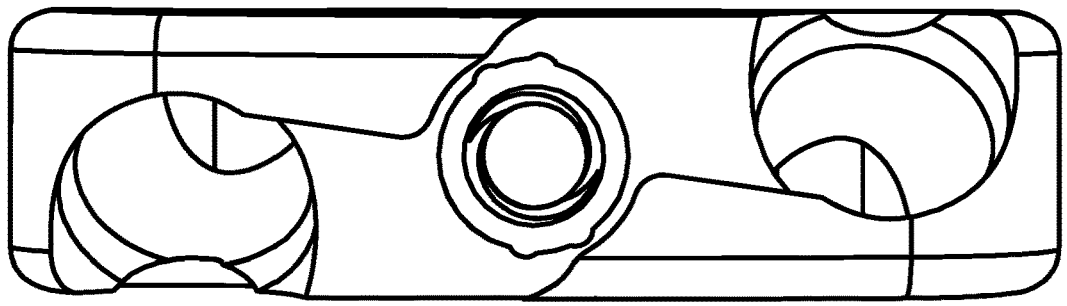

The intervertebral spacer 100 may also include one or more marker apertures 150. The one or more marker apertures 150 may be configured to receive one or more radiopaque makers 300, as can be seen in FIGS. 3A-3C. The radiopaque makers 300 may be made from any suitable radiopaque material, such as tantalum (as one non-limiting example). The one or more radiopaque makers 300 may be respectively inserted into the one or more marker apertures 150 in order to couple the one or more radiopaque makers 300 to the intervertebral spacer 100, as can be seen in the exploded view of FIG. 4A, and in the assembled view of FIG. 4B. In this manner, the one or more radiopaque makers 300 may be utilized to verify whether or not the intervertebral spacer 100 has been correctly placed between adjacent vertebral bodies via a suitable x-ray imaging process, which may be performed intraoperatively and/or postoperatively.

The proximal end 105 of the intervertebral spacer 100 may include a first fastener channel 131 configured to receive a first fastener or bone screw 501 (e.g., see FIGS. 5A-5D). The first fastener channel 131 may be oriented to pass through the proximal and superior surfaces of the intervertebral spacer 100 at a first angle 511 with respect to a mid-line 520, as shown in FIG. 5D. The proximal end 105 of the intervertebral spacer 100 may also include a second fastener channel 132 configured to receive a second fastener or bone screw 502. The second fastener channel 132 may be oriented to pass through the proximal and inferior surfaces of the intervertebral spacer 100 at a second angle 512 with respect to the mid-line 520, as shown in FIG. 5D.

In some embodiments, the first and second angles 511, 512 may be substantially equal to each other and may be between 10 and 50 degrees. In a particular embodiment, the first and second angles 511, 512 may be about 30 degrees. However, it will be understood that the first and second angles 511, 512 may utilize any angle between 0 degrees and 90 degrees.

Moreover, the first and second fastener channels 131, 132 (and thus bone screws 501, 502) may also be angled inward with respect to a mid-line 510, as shown in FIG. 5A. In at least one embodiment, the bone screws 501, 502 may be angled inward toward the mid-line 510 by about 5 degrees. However, it will be understood that the bone screws 501, 502 may be angled inward toward the mid-line 510, or outward away from the mid-line 510, according to any angle.

The first and second first fastener channels 131, 132 may also comprise a first depth stop 133 and a second depth stop 134. The first and second depth stops 133, 134 may prevent an awl tool and a drill tool from penetrating too far within the first and second first fastener channels 131, 132, as will be discussed in more detail with respect to FIGS. 33A-36.

The proximal end 105 of the intervertebral spacer 100 may also include a locking member channel 140 intermediate the first and second fastener channels 131, 132. The locking member channel 140 may include an inner wall 145, an annular ridge 146 formed in the inner wall 145, a first pair of recesses 141 formed in the inner wall 145, and a second pair of recesses 142 formed in the inner wall 145. The second pair of recesses 142 may be angularly offset from the first pair of recesses 141 about a longitudinal axis 143 of the locking member channel 140 (see FIGS. 1A and 1H). In some embodiments, the second pair of recesses 142 may be angularly offset from the first pair of recesses 141 by about 30 degrees. In some embodiments, the second pair of recesses 142 may be angularly offset from the first pair of recesses 141 by about 90 degrees. In some embodiments, the second pair of recesses 142 may be angularly offset from the first pair of recesses 141 at any angle between 10 and 170 degrees. However, it will be also understood that the second pair of recesses 142 may be angularly offset from the first pair of recesses 141 at any angle between 0 and 360 degrees. The locking member channel 140 may also include first threading 144 configured to engage second threading formed on an inserter tool, as will be discussed below with respect to FIGS. 25A-26B.

The proximal end 105 of the intervertebral spacer 100 may also include a first pair of stop surfaces 147 configured to prevent a locking member 200 from rotating in a first direction (e.g., counter clockwise) past an unlocked position (see FIG. 5A), and a second pair of stop surfaces 148 configured to prevent the locking member from rotating in a second direction (e.g., clockwise) past a locked position (see FIG. 5C).

Figure 2A:
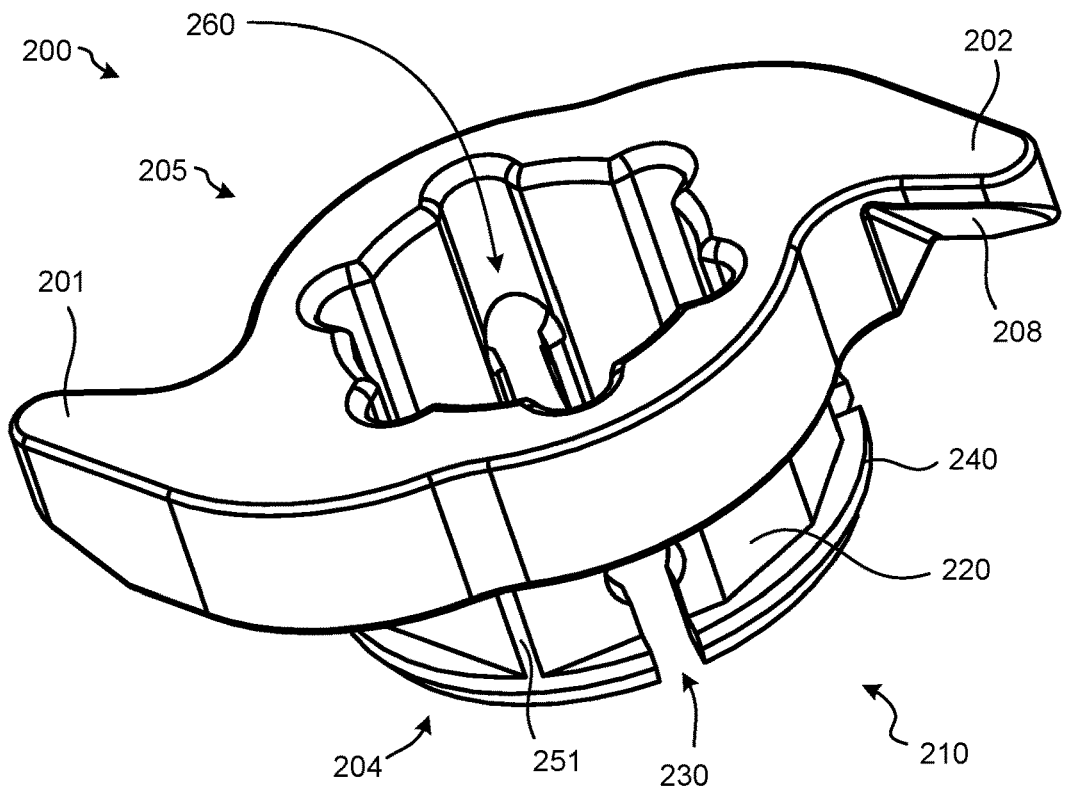
FIG. 2A is a perspective top view of a locking member 200, according to an embodiment of the present disclosure.
Figure 2B:
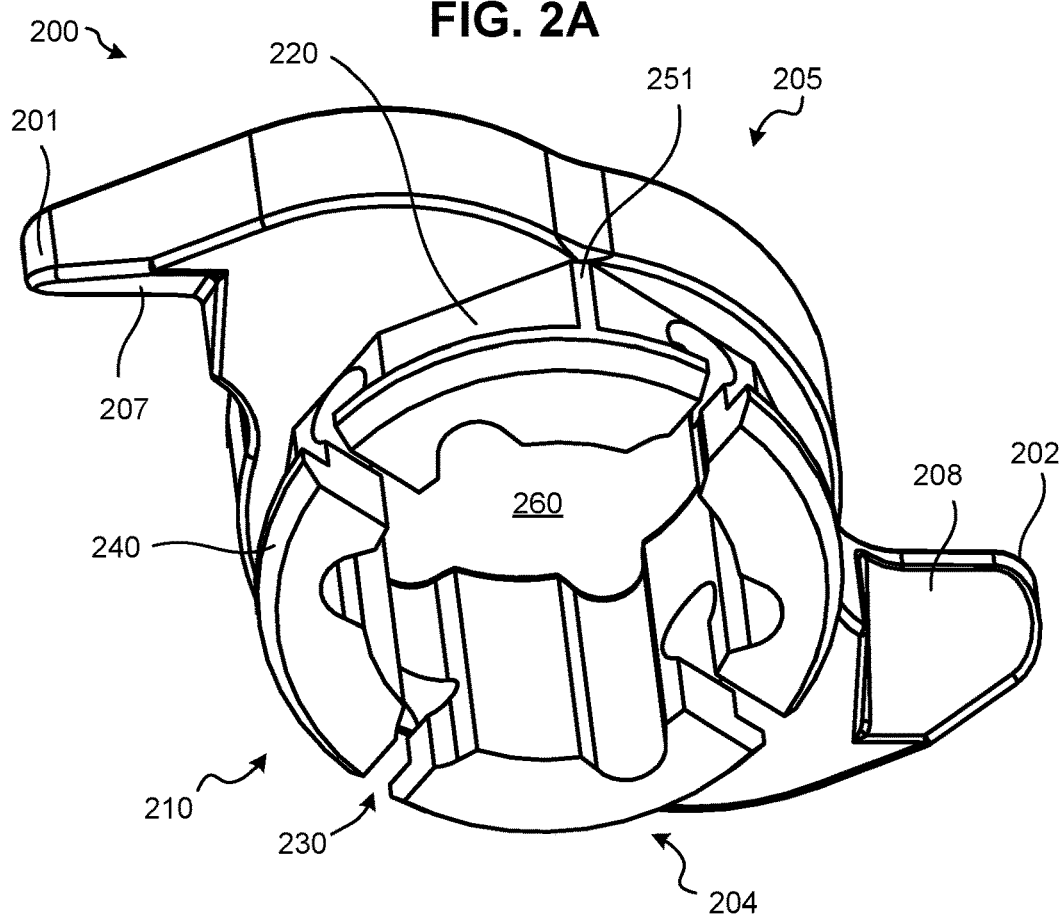
FIG. 2B is a perspective bottom view of the locking member 200 of FIG. 2A.
Figure 2C:
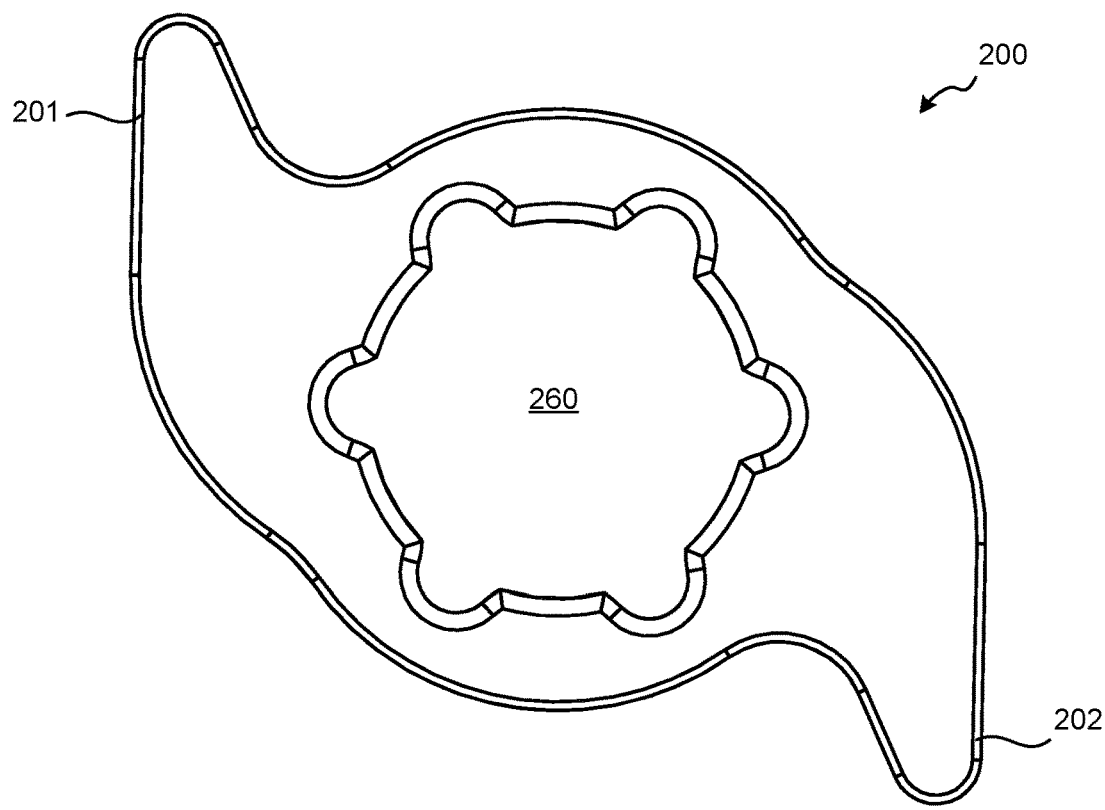
FIG. 2C is a top view of the locking member 200 of FIG. 2A.
Figure 2D:
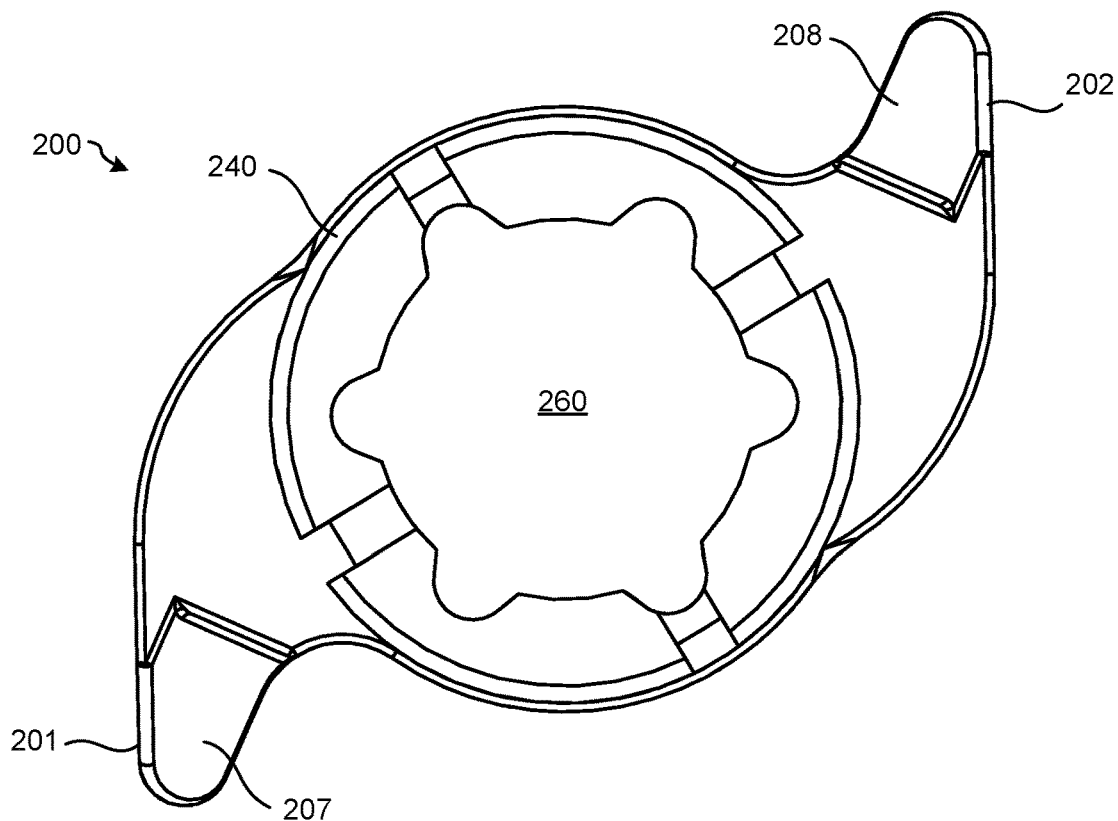
FIG. 2D is a bottom view of the locking member 200 of FIG. 2A.
Figure 2E:
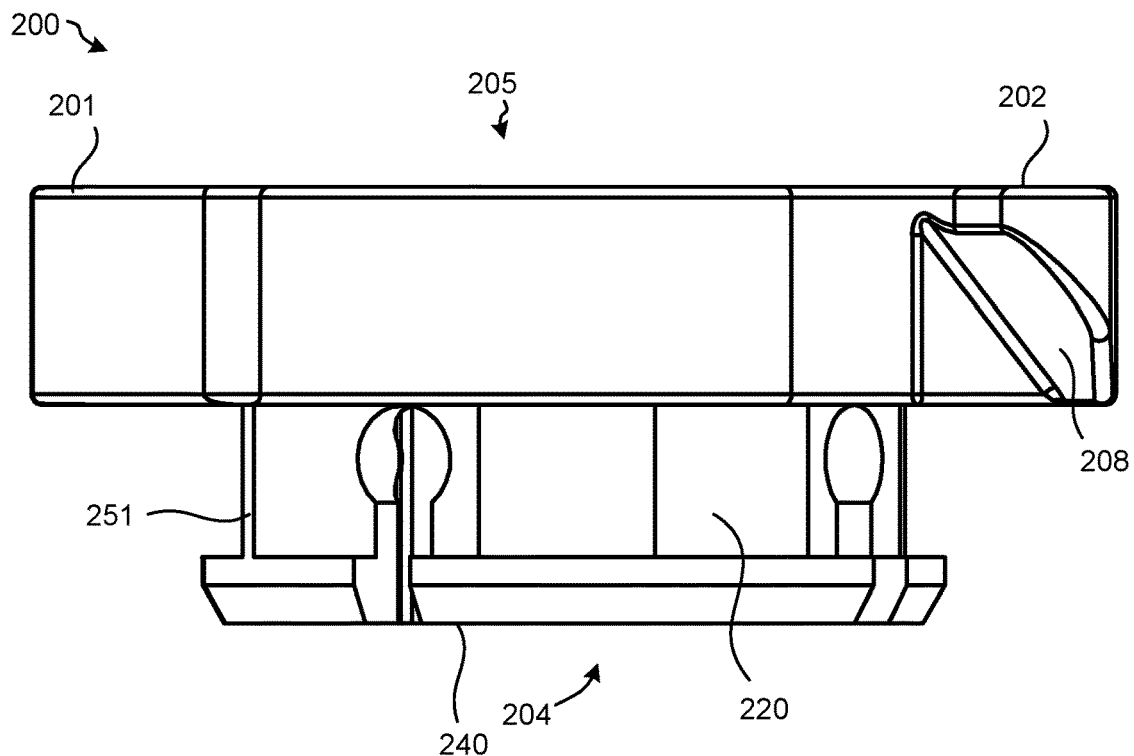
FIG. 2E illustrates a first side of the locking member 200 of FIG. 2A.
Figure 2F:
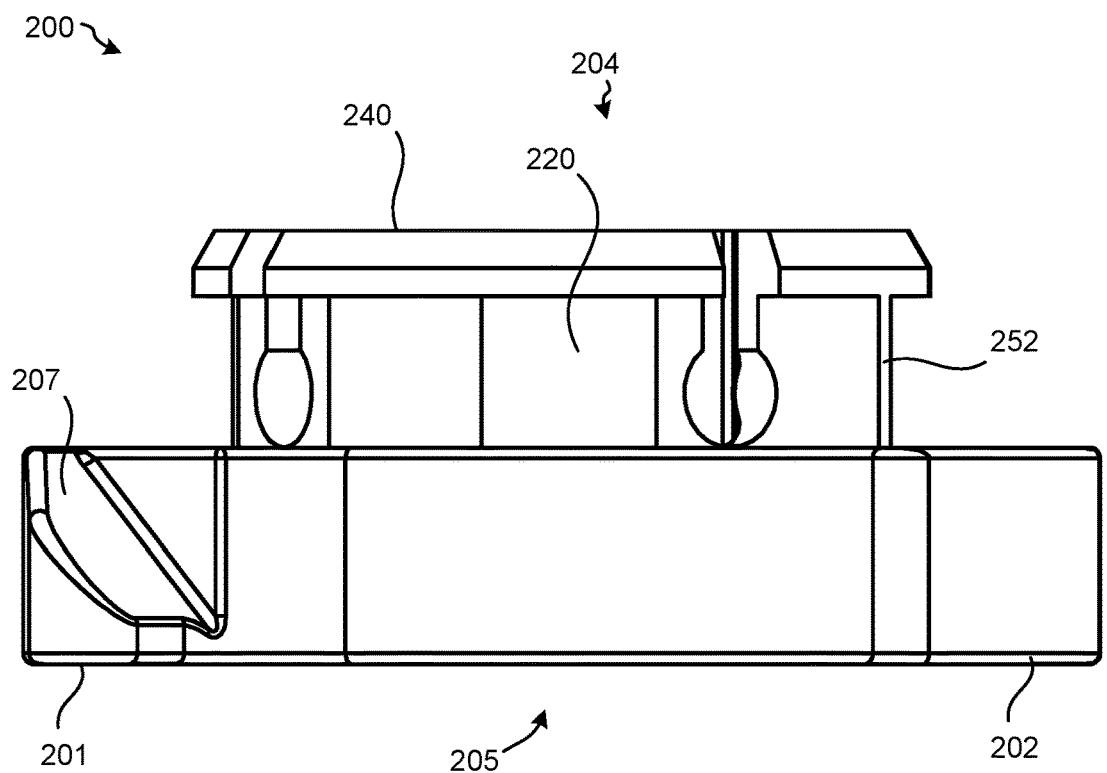
FIG. 2F illustrates a second side of the locking member 200 of FIG. 2A.

FIGS. 2A-2F illustrate various views of a locking member 200, according to an embodiment of the present disclosure. Specifically, FIG. 2A is a perspective top view of the locking member 200; FIG. 2B is a perspective bottom view of the locking member 200; FIG. 2C is a top view of the locking member 200; FIG. 2D is a bottom view of the locking member 200; FIG. 2E illustrates a first side of the locking member 200; and FIG. 2F illustrates a second side of the locking member 200 of FIG. 2A.

The locking member 200 may generally include a proximal end 205 with a first anti-backout member 201 and a second anti-backout member 202, a distal end 204 including a collet 210, and a driver engagement channel 260 that extends through the proximal and distal ends 205, 204 of the locking member 200.

The first and second anti-backout members 201, 202 may protrude radially away from the locking member 200. The first and second anti-backout members 201, 202 may also include angled engagement surfaces 207, 208 configured to engage the second pair of stop surfaces 148 formed in the intervertebral spacer 100. The second pair of stop surfaces 148 may also include complementarily shaped angled surfaces configured to receive the angled engagement surfaces 207, 208 of the first and second anti-backout members 201, 202.

The collet 210 may include a peripheral wall 220 with one or more slits 230 formed therein. In the example shown in FIGS. 2A-2F, the peripheral wall 220 of the collet 210 includes four slits 230 which are regularly spaced apart from each other. However, it will be understood that any number of slits 230 spaced apart from each other at any distance, arrangement, or pattern may also be utilized. The collet 210 may also include an annular flange 240 at its distal end which may be configured to be retained by the annular ridge 146 of the locking member channel 140 in order to rotatably couple the locking member 200 to the intervertebral spacer 100. For example, as the collet 210 of the locking member 200 is inserted into the locking member channel 140 of the intervertebral spacer 100 (e.g., see FIG. 4A), the slits 230 of the collet 210 will permit the collet 210 to compress inwardly to allow the annular flange 240 of the collet 210 to pass distally, beyond the annular ridge 146 that is formed in the inner wall 145 of the locking member channel 140. Once the annular flange 240 of the collet 210 has moved distal to the annular ridge 146, the collet 210 will expand outwardly again and the annular ridge 146 will retain the annular flange 240 of the collet 210 in order to rotatably couple the locking member 200 to the intervertebral spacer 100.

However, other embodiments for rotatably coupling the locking member 200 to the intervertebral spacer 100 are also contemplated herein. For example, in one embodiment contemplated herein (not shown), the locking member channel 140 may include an integral collet member configured to couple a shaft protruding from a locking member. The shaft protruding from the locking member may further include a ridge that may interact with the integral collet member within the intervertebral spacer in order to rotatably couple the locking member to the intervertebral spacer. In another example embodiment contemplated herein (not shown), a shaft protruding from a locking member may be rotatably coupled to an intervertebral spacer via a fastening member that can couple the locking member to the intervertebral spacer while allowing for rotation of the locking member (e.g., a rivet, a nut, a bolt, a screw, etc.).

Returning to FIGS. 2A-2F, the peripheral wall 220 of the collet 210 may include a first stop protrusion 251 projecting from a first side of the peripheral wall 220, and a second stop protrusion 252 projecting from a second side of the peripheral wall 220, opposite the first stop protrusion 251. Once the locking member 200 is rotatably coupled to the intervertebral spacer 100, as discussed above, the locking member 200 can be rotated within the locking member channel 140 between at least two stable positions comprising an unlocked position and a locked position. In the unlocked position, the first and second stop protrusions 251, 252 may protrude into the first pair of recesses 141 in order to retain the locking member 200 in the unlocked position, such that the first and second anti-backout members 201, 202 do not obstruct the first and second fastener channels 131, 132 (e.g., see FIG. 5A). In the locked position, the first and second stop protrusions 251, 252 may protrude into the second pair of recesses 142 in order to retain the locking member 200 in the locked position, such that the first and second anti-backout members 201, 202 obstruct the first and second fastener channels 131, 132 and prevent the first and second fasteners or bone screws 501, 502 from backing out of the first and second fastener channels 131, 132 (e.g., see FIGS. 5B and 5C for two example locked positions).

However, it will also be understood that other embodiments are contemplated herein in order to position and maintain the locking member 200 in either the unlocked or locked positions. For example, the inner wall 145 of the locking member channel 140 may comprise one or more inner wall engagement features that may engage with one or more collet engagement features formed on the collet 210 in order to retain the locking member 200 in either the unlocked or locked position, independently of any additional component besides the locking member 200 and the intervertebral spacer 100, such that one or more anti-backout members 201, 201 may selectively obstruct one or more fastener channels 131, 132. In this example, the one or more inner wall engagement features may comprise one or more recesses or one or more protrusions. Likewise, the one or more collet engagement features may comprise one or more recesses or one or more protrusions that are complementarily shaped to the one or more inner wall engagement features. In this manner, in the unlocked position, the one or more collet engagement features may engage with the one or more inner wall engagement features in order to retain the locking member 200 in the unlocked position, independently of any additional component besides the locking member 200 and the intervertebral spacer 100, and the one or more anti-backout members 201, 202 may not obstruct the one or more fastener channels 131, 132. Likewise, in the locked position, the one or more collet engagement features may engage with the one or more inner wall engagement features to retain the locking member 200 in the locked position, independently of any additional component besides the locking member 200 and the intervertebral spacer 100, and the one or more anti-backout members 201, 202 may obstruct the one or more fastener channels 131, 132 in order to prevent one or more fasteners or bone screws 501, 502 from backing out of the one or more fastener channels 131, 132.

FIGS. 6A-23H illustrate various views of differently sized intervertebral spacers, according to embodiments of the present disclosure. Specifically, FIGS. 6A-6H illustrate various views of an intervertebral spacer 600 having a height "H" (see FIG. 6E) of about 5 mm and a length "L" (see FIG. 6E) of about 14 mm; FIGS. 7A-7H illustrate various views of an intervertebral spacer 700 having a height of about 6 mm and a length of about 14 mm; FIGS. 8A-8H illustrate various views of an intervertebral spacer 800 having a height of about 7 mm and a length of about 14 mm; FIGS. 9A-9H illustrate various views of an intervertebral spacer 900 having a height of about 8 mm and a length of about 14 mm; FIGS. 10A-10H illustrate various views of an intervertebral spacer 1000 having a height of about 9 mm and a length of about 14 mm; FIGS. 11A-11H illustrate various views of an intervertebral spacer 1100 having a height of about 10 mm and a length of about 14 mm; FIGS. 12A-12H illustrate various views of an intervertebral spacer 1200 having a height of about 5 mm and a length of about 16 mm; FIGS. 13A-13H illustrate various views of an intervertebral spacer 1300 having a height of about 5 mm and a length of about 16 mm; FIGS. 14A-14H illustrate various views of an intervertebral spacer 1400 having a height of about 7 mm and a length of about 16 mm; FIGS. 15A-15H illustrate various views of an intervertebral spacer 1500 having a height of about 8 mm and a length of about 16 mm; FIGS. 16A-16H illustrate various views of an intervertebral spacer 1600 having a height of about 9 mm and a length of about 16 mm; FIGS. 17A-17H illustrate various views of an intervertebral spacer 1700 having a height of about 10 mm and a length of about 16 mm; FIGS. 18A-18H illustrate various views of an intervertebral spacer 1800 having a height of about 5 mm and a length of about 18 mm; FIGS. 19A-19H illustrate various views of an intervertebral spacer 1900 having a height of about 6 mm and a length of about 18 mm; FIGS. 20A-20H illustrate various views of an intervertebral spacer 2000 having a height of about 7 mm and a length of about 18 mm; FIGS. 21A-21H illustrate various views of an intervertebral spacer 2100 having a height of about 8 mm and a length of about 18 mm; FIGS. 22A-22H illustrate various views of an intervertebral spacer 2200 having a height of about 9 mm and a length of about 18 mm; and FIGS. 23A-23H illustrate various views of an intervertebral spacer 2300 having a height of about 10 mm and a length of about 18 mm.

FIGS. 24A-37 illustrate various views of surgical instruments, tools, and assemblies that may be utilized to implant an intervertebral spacer of the present disclosure.

FIGS. 24A and 24B are perspective top and bottom views of an example trial tool 2400 which may be utilized during a surgical procedure to implant an intervertebral spacer 100. For example, once a surgeon has created a space between two vertebral bodies for the intervertebral spacer 100 (e.g., by removing at least a portion of an intervertebral disc), the surgeon may utilize the trial tool 2400 (or another trial tool from a set of trial tools having different sizes) in order to ascertain which size of intervertebral spacer 100 should be implanted in the disc space between the two vertebral bodies.

As shown in FIGS. 24A and 24B, the trial tool 2400 may generally comprise a shaft 2410, a handle portion 2420, a first trial component 2401 having a first size, a first depth stop 2431 adjacent the first trial component 2401, a second trial component 2402 having a second size, and a second depth stop 2432 adjacent the second trial component 2402. The first and second depth stops 2431, 2432 may contact at least one of the vertebral bodies in order to prevent the first and second trial components 2401, 2401 from being inserted too far inside the prepared disc space.

FIGS. 25A-25E illustrate various views of an inserter tool 2500, according to an embodiment of the present disclosure. Specifically, FIG. 25A is a perspective top view of the inserter tool 2500; FIG. 25B is a perspective bottom view of the inserter tool 2500; FIG. 25C is a top view of the inserter tool 2500; FIG. 25D is a side view of the inserter tool 2500; and FIG. 25E is a bottom view of the inserter tool 2500. The inserter tool 2500 may generally include a shaft 2510 having a proximal end 2505 and a distal end 2504, a first flat surface 2511, a second flat surface 2512, recesses 2520, ridges 2540, and second threading 2530.

FIGS. 26A and 26B illustrate how the inserter tool 2500 and the intervertebral spacer 100 may be coupled together to form an insertion assembly 2600. Specifically, the distal end 2504 of the inserter tool 2500 (comprising the second threading 2530) may pass through the driver engagement channel 260 formed through the locking member 200 to engage with the first threading 144 formed in the locking member channel 140 of the intervertebral spacer 100 in order to couple the intervertebral spacer 100 to the inserter tool 2500. In at least one embodiment, the insertion assembly 2600 comprises the intervertebral spacer 100 preassembled onto the inserter tool 2500, which may then be packaged within a sterile container.

FIGS. 27A-27F illustrate various views of a Drill, Tap, and Screw guide (hereinafter "DTS guide" 2700, according to an embodiment of the present disclosure. Specifically, FIG. 27A is a perspective top view of the DTS guide 2700; FIG. 27B is a perspective bottom view of the DTS guide 2700; FIG. 27C is a top view of the DTS guide 2700; FIG. 27D is a bottom view of the DTS guide 2700; FIG. 27E is a proximal end view of the DTS guide 2700; and FIG. 27F is a distal end view of the DTS guide 2700. The DTS guide 2700 may generally include a proximal end 2705, a distal end 2704, a shaft 2710, a first guide 2701 having a first guide channel 2721, a second guide 2702 having a second guide channel 2722, an intermediate channel 2750, a first guide wing 2731, a second guide wing 2732, a first depth stop surface 2741, and a second depth stop surface 2742. Each different size of intervertebral spacer disclosed herein may be paired with a corresponding different size of DTS guide.

The shaft 2710 of the DTS guide 2700 may be hollow and have a "double D" shaped lumen 2760 that is configured to receive the shaft 2510 of the inserter tool 2500, which may also have a complementary "double D" shape due to the first and second flat surfaces 2511, 2512 formed in the inserter tool shaft 2510. The shaft 2710 of the DTS guide 2700 may also include one or more shaft splines 2715, as will be discussed in more detail below with respect to FIGS. 32A and 32B. FIGS. 28A and 28B illustrate how the DTS guide 2700 may be coupled with the inserter tool 2500 and the intervertebral spacer 100 to form an insertion assembly 2800. The first and second guide wings 2731, 2732 of the DTS guide 2700 may help correctly orient the DTS guide 2700 with respect to the intervertebral spacer 100 during assembly. In this manner, the DTS guide 2700 can correctly align with the first and second fastener channels 131, 132 of the intervertebral spacer 100. Moreover, the ridges 2540 formed on the inserter tool 2500 may couple with a recess (not shown) that is formed within the lumen 2760 of the DTS guide 2700 in order to couple the DTS guide 2700 to the inserter tool 2500. In at least one embodiment, the insertion assembly 2800 comprises the intervertebral spacer 100 and the DTS guide 2700 preassembled onto the inserter tool 2500, which may then be packaged within a sterile container.

FIGS. 29A and 29B illustrate perspective top and bottom views of a handle 2900 that may be utilized with the insertion assembly 2800 of FIGS. 28A and 28B, according to an embodiment of the present disclosure. The handle 2900 may have a "double D" shaped lumen 2960 that is configured to receive the "double D" shaped shaft 2510 of the inserter tool 2500. FIGS. 30A and 30B illustrate how the handle 2900 may be coupled with the inserter tool 2500, which itself may be coupled with the intervertebral spacer 100 and the DTS guide, in order to form an insertion assembly 3000. The surgeon may then utilize the insertion assembly 3000 to insert the intervertebral spacer 100 between two vertebral bodies of a patient by using the handle to manipulate the intervertebral spacer 100 into place. The surgeon may also utilize an impact tool (not shown) to strike the proximal end of the handle 2900 and drive the intervertebral spacer 100 into place. The first and second depth stop surfaces 2741, 2742 of the DTS guide may help prevent the surgeon from inserting the intervertebral spacer 100 too far into the disc space between the two vertebral bodies. Once the intervertebral spacer 100 has been properly placed between the two vertebral bodies, the surgeon may remove the handle 2900 from the insertion assembly 3000.

FIGS. 31A-31D illustrate various views of a U-support tool 3100 that may be utilized with the insertion assembly 2800 of FIG. 28B. Specifically, FIG. 31A is a perspective view of the U-support tool 3100; FIG. 31B is a front side view of the U-support tool 3100; FIG. 31C is a top view of the U-support tool 3100; and FIG. 31D is a left side view of the U-support tool 3100. The U-support tool 3100 may generally include a first arm 3110 having a first U-support 3130, a second arm 3120 having a second U-support 3140, and a ring member 3150 intermediate the first and second arms 3110, 3120 including a ring channel 3160 with one or more ring splines 3170 formed therein. FIGS. 32A and 32B illustrate how the U-support tool 3100 may be coupled to the DTS guide 2700 (which itself may be coupled to the inserter tool 2500 and the intervertebral spacer 100) in order to form an insertion assembly 3200. The one or more ring splines 3170 may be configured to engage the one or more shaft splines 2715 formed on the DTS guide 2700 in order to couple the U-support tool 3100 to the DTS guide 2700 at a selected orientation. The U-support tool 3100 may be coupled to the DTS guide 2700 at one or more discrete orientations or angles by rotating the one or more ring splines 3170 relative to the one or more shaft splines 2715 before sliding the U-support tool 3100 onto the DTS guide 2700. The one or more ring splines 3170 and the one or more shaft splines 2715 may be shaped and spaced apart from each other according to any desired distance in order to achieve a desired set of discrete angles between the U-support tool 3100 and the DTS guide 2700. As one non-limiting example, the shape and spacing of the one or more ring splines 3170 and the one or more shaft splines 2715 may be chosen to achieve a set of different orientations that are about 15 degrees apart from each other.

FIGS. 33A and 33B illustrate two side views of a flexible awl tool 3300, according to an embodiment of the present disclosure. In general, the flexible awl tool 3300 may include a proximal end 3305, a distal end 3304, a shaft 3310, a handle 3320, an awl sleeve 3330, an awl depth stop ring 3350, and a drill tip 3340. The awl sleeve 3330 may translate in the proximal to distal direction along the shaft 3310 in order to selectively prevent or allow the shaft 3310 from bending at the flexible portion 3360 of the shaft 3310. For example, FIG. 33A shows the awl sleeve 3330 translated distally in order to provide rigid support to the shaft 3310 over the flexible portion 3360 of the shaft, and FIG. 33B shows the awl sleeve 3330 translated proximally in order to allow the flexible portion 3360 of the shaft 3310 the freedom to bend and flex. The shaft 3310 may also include a first notch 3311, a second notch 3312, and a third notch 3313 which may interact with corresponding protrusions formed on the proximal and distal ends of the awl sleeve 3330 in order to selectively retain the awl sleeve 3330 in a locked position (e.g., the awl sleeve 3330 is translated to the proximal position) and an unlocked position (e.g., the awl sleeve 3330 is translated to the distal position). A tactile and/or audible "click" may be felt and/or heard by the surgeon when the awl sleeve 3330 reaches the unlocked and/or locked positions. The flexible portion 3360 of the shaft 3310 may include a plurality of slots 3370 that are configured to allow the flexible portion 3360 of the shaft 3310 to bend and flex. However, it will be understood that any suitable structure or arrangement may also be utilized to achieve a flexible shaft.

FIG. 34 illustrates an insertion assembly 3400 including the inserter tool 2500, the intervertebral spacer 100, the DTS guide 2700, the U-support tool 3100, and the flexible awl tool 3300 assembled together in order to form bone tunnels within vertebral bodies (not shown) adjacent the intervertebral spacer 100. The drill tip 3340 of the flexible awl tool 3300 can be guided by the DTS guide 2700 through the first and second guide channels 2721, 2722. The awl depth stop ring 3350 may abut the first and second depth stops 133, 134 formed in the intervertebral spacer 100 to control the depth of the drill tip 3340 that may protrude into the vertebral bodies adjacent the intervertebral spacer 100. The surgeon may also utilize the U-support tool 3100 to help guide the shaft 3310 of the flexible awl tool 3300. For example, the surgeon may press the shaft 3310 of the flexible awl tool 3300 against the U-support tool 3100 while he/she rotates the flexible awl tool 3300 to drill bone tunnels into the vertebral bodies adjacent the intervertebral spacer 100. In this manner, a proximal portion the shaft 3310 may remain closer to the shaft 2510 of the inserter tool 2500 and the shaft 2710 of the DTS guide 2700 and a smaller incision may be utilized during the procedure. In one embodiment, a proximal portion the shaft 3310 may be substantially parallel to the shaft 2510 of the inserter tool 2500 and/or substantially parallel to the shaft 2710 of the DTS guide 2700. Once the bone tunnels are formed in the vertebral bodies adjacent the intervertebral spacer 100, the flexible awl tool 3300 may be removed from the patient in preparation for the next step in the procedure.

However, it will also be understood that in an alternative surgical procedure, the U-support and DTS guide 2700 may be decoupled and removed from the patient, the awl sleeve 3330 may be moved to the locked position in order to prevent the flexible awl tool 3300 from bending, and a second and third incision may be made in the patient in order to approach the first and second fastener channels 131, 132 of the intervertebral spacer 100 via the second and third incisions with the flexible awl tool 3300 in its straight configuration in order to drill the bone tunnels.

FIGS. 35A and 35B illustrate two side views of a flexible driver tool 3500, according to an embodiment of the present disclosure. In general, the flexible driver tool 3500 may include a proximal end 3505, a distal end 3504, a shaft 3510, a handle 3520, a driver sleeve 3530, a driver depth stop ring 3550, and a driver engagement feature 3540. The driver sleeve 3530 likewise may translate in the proximal to distal direction along the shaft 3510 in order to selectively prevent or allow the shaft 3510 from bending at the flexible portion 3560 of the shaft 3510. For example, FIG. 35A shows the driver sleeve 3530 translated distally in order to provide rigid support to the shaft 3510 over the flexible portion 3560 of the shaft 3510, and FIG. 35B shows the driver sleeve 3530 translated proximally in order to allow the flexible portion 3560 of the shaft 3510 the freedom to bend and flex. The shaft 3510 may also include a first notch 3511, a second notch 3512, and a third notch 3513 which may interact with corresponding protrusions formed on the proximal and distal ends of the driver sleeve 3530 in order to selectively retain the driver sleeve 3530 in a locked position (e.g., the driver sleeve 3530 is translated to the proximal position) and an unlocked position (e.g., the driver sleeve 3530 is translated to the distal position). The flexible portion 3560 of the shaft 3510 may include a plurality of slots 3570 configured to allow the flexible portion 3560 of the shaft 3510 to bend and flex. However, it will be understood that any suitable structure or arrangement may be utilized to achieve a flexible shaft.

FIG. 36 illustrates an insertion assembly 3600 including the inserter tool 2500, the intervertebral spacer 100, the DTS guide 2700, the U-support tool 3100, and the flexible driver tool 3500 assembled together in order to drive a bone screw 502 into a vertebral body (not shown). The driver engagement feature 3540 of the flexible driver tool 3500 can be any suitable style (e.g., Torx, hex, etc.) and can include the ability to retainably couple with the bone screw 502 (e.g., via a magnetic coupling, a mechanical coupling, such with tapered surfaces, etc.). The driver engagement feature 3540 of the flexible driver tool 3500 can be guided by the DTS guide 2700 through the first and second guide channels 2721, 2722. The driver depth stop ring 3550 may abut the first and second depth stops 133, 134 formed in the intervertebral spacer 100 to control the depth of the bone screw 502 into the vertebral body. The surgeon may also utilize the U-support tool 3100 to help guide the shaft 3510 of the flexible driver tool 3500. For example, the surgeon may press the shaft 3510 of the flexible driver tool 3500 against the U-support tool 3100 while he/she rotates the flexible driver tool 3500 to drive the bone screw 502 into the vertebral body. In this manner, a proximal portion the shaft 3510 may likewise remain closer to the shaft 2510 of the inserter tool 2500 and/or the shaft 2710 of the DTS guide 2700 and a smaller incision may be utilized during the procedure. In one embodiment, a proximal portion the shaft 3510 may be substantially parallel to the shaft 2510 of the inserter tool 2500 and/or substantially parallel to the shaft 2710 of the DTS guide 2700. Once the bone screws are driven into the vertebral bodies adjacent the intervertebral spacer 100, the flexible driver tool 3500 may be removed from the patient in preparation for the next step in the procedure.

However, it will also be understood that in an alternative surgical procedure, the U-support and DTS guide 2700 may be decoupled and removed from the patient, the driver sleeve 3530 may be moved to the locked position in order to prevent the flexible driver tool 3500 from bending, and a second and third incision may be made in the patient in order to approach the first and second fastener channels 131, 132 of the intervertebral spacer 100 via the second and third incisions with the flexible driver tool 3500 in its straight configuration in order to drive the bone screws into the vertebral bodies.

Once the bone screws have been properly placed into the vertebral bodies adjacent the intervertebral spacer 100, the surgeon may remove all of the tools from the patient in preparation for the next step of the procedure. In this step, the driver sleeve 3530 may be moved distally to prevent the flexible driver tool 3500 from bending. FIG. 37 illustrates how the driver tool 3500 of FIG. 35A may be moved in the direction of arrow 2601 to couple with the locking member 200 in order to rotate the locking member 200 between an unlocked position and a locked position and prevent the bone screws 501, 502 from backing out of the intervertebral spacer 100. A tactile and/or audible "click" may be felt and/or heard by the surgeon when the locking member 200 reaches the unlocked and/or locked positions.

FIG. 38 illustrates a flowchart of a method 3800 for preventing a fastener from backing out of an intervertebral spacer, according to an embodiment of the present disclosure. In general, the method 3800 may include the use of an intervertebral spacer comprising a locking member channel with an inner wall having first and second recesses formed therein. The intervertebral spacer may also comprise a locking member that is rotatably coupled within the locking member channel and may include an anti-backout member and a stop protrusion configured to protrude into the first and second recesses in order to selectively retain the locking member in an unlocked position and a locked position.

The method 3800 may begin with a step 3810 in which a driver engagement feature of a driver tool may be aligned with a driver engagement channel formed in the locking member.

Once the driver engagement feature of the driver tool has been aligned with a driver engagement channel formed in the locking member, the method 3800 may proceed to a step 3820 in which the driver engagement feature may be moved into engagement with the driver engagement channel.

Once the driver engagement feature has been moved into engagement with the driver engagement channel, the method 3800 may proceed to a step 3830 in which the locking member may be rotated relative to the intervertebral spacer from the unlocked position to the locked position, such that the locking member is retained in the locked position, independently of any additional component besides the locking member and the intervertebral spacer, and the anti-backout member is placed in a path of the fastener to prevent the fastener from backing out of the intervertebral spacer.

Alternatively, or in addition thereto, the method 3800 may also include any one or more of the following steps, which may be performed in any order: (1) a step 3840 in which the intervertebral spacer may be inserted between two vertebral bodies of a patient; (2) a step 3850 in which an awl tool may be inserted into a fastener channel of the intervertebral spacer and a bone tunnel may be drilled into a vertebral body of the patient with the awl tool; and (3) a step 3860 in which a fastener may be inserted into the fastener channel formed in the intervertebral spacer and the fastener may be driven into the bone tunnel with the driver tool.

Any methods disclosed herein comprise one or more steps or actions for performing the described method. One or more of the method steps and/or actions may be omitted from and of the methods disclosed herein. Moreover, any of the method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

As defined herein, "substantially equal to" means "equal to," or within about a + or − 10% relative variance from one another.

While specific embodiments and applications of the present disclosure have been illustrated and described, it is to be understood that the scope of the appended claims is not limited to the precise configuration and components disclosed herein. Various modifications, changes, and variations which will be apparent to those skilled in the art may be made in the arrangement, operation, and details of the systems, methods, and devices disclosed herein.

What is claimed is:

1. An intervertebral spacer assembly comprising:
   an intervertebral spacer, the intervertebral spacer comprising:
      a superior surface configured to engage a superior vertebral body;
      an inferior surface configured to engage an inferior vertebral body;
      a proximal surface comprising:
         a first fastener channel configured to receive a first fastener, the first fastener channel oriented to pass through the proximal and superior surfaces of the intervertebral spacer at a first angle;
         a second fastener channel configured to receive a second fastener, the second fastener channel oriented to pass through the proximal and inferior surfaces of the intervertebral spacer at a second angle; and
         a locking member channel intermediate the first and second fastener channels, the locking member channel comprising:
            an inner wall;
            an annular ridge formed in the inner wall;
            a first pair of recesses formed in the inner wall; and
            a second pair of recesses formed in the inner wall and angularly offset from the first pair of recesses about a longitudinal axis of the locking member channel; and
   a locking member comprising:
      a first anti-backout member;
      a second anti-backout member; and
      a collet comprising:
         an annular flange configured to be retained by the annular ridge of the locking member channel in order to rotatably couple the locking member to the intervertebral spacer;
         a peripheral wall;
         a first stop protrusion projecting from a first side of the peripheral wall; and
         a second stop protrusion projecting from a second side of the peripheral wall, opposite the first stop protrusion;
      wherein:
         the locking member is rotatable within the locking member channel between two stable positions comprising an unlocked position and a locked position;
         in the unlocked position, the first and second stop protrusions protrude into the first pair of recesses in order to retain the locking member in the unlocked position, and the first and second anti-backout members do not obstruct the first and second fastener channels; and
         in the locked position, the first and second stop protrusions protrude into the second pair of recesses in order to retain the locking member in the locked position, and the first and second anti-backout members obstruct the first and second fastener channels in order to prevent the first and second fasteners from backing out of the first and second fastener channels.

2. The intervertebral spacer assembly of claim 1, wherein:
   the locking member channel comprises first threading configured to engage second threading formed on an inserter tool; and
   the locking member comprises a driver engagement channel configured to allow the inserter tool to pass through the locking member and couple with the intervertebral spacer.

3. The intervertebral spacer assembly of claim 2, wherein the driver engagement channel is configured to receive a driver engagement feature of a driver tool in order to selectively rotate the locking member between the unlocked and locked positions.

4. The intervertebral spacer assembly of claim 1, wherein the proximal surface of the intervertebral spacer comprises:
   a first pair of stop surfaces configured to prevent the locking member from rotating in a first direction past the unlocked position; and
   a second pair of stop surfaces configured to prevent the locking member from rotating in a second direction past the locked position.

5. The intervertebral spacer assembly of claim 1, wherein:
   the first fastener channel comprises a first depth stop; and
   the second fastener channel comprises a second depth stop.

6. The intervertebral spacer assembly of claim 1, further comprising at least one bone graft channel oriented to pass through opposing ends of the intervertebral spacer.

7. An intervertebral spacer comprising:
   a superior surface configured to engage a superior vertebral body;
   an inferior surface configured to engage an inferior vertebral body;
   a proximal end comprising:
      at least one fastener channel configured to receive a fastener, the at least one fastener channel oriented to pass through the proximal end of the intervertebral spacer and the superior and/or inferior surface of the intervertebral spacer; and
      a locking member channel comprising:
         an inner wall; and
         one or more inner wall engagement features; and
   a locking member comprising:
      an anti-backout member;
      a collet retainable within the locking member channel; and
      one or more collet engagement features;
   wherein:
      the locking member is rotatable within the locking member channel between an unlocked position and a locked position;
      in the unlocked position, the one or more collet engagement features engage the one or more inner wall engagement features in order to retain the locking member in the unlocked position, independently of any additional component besides the locking member and the intervertebral spacer, and the anti-backout member does not obstruct the fastener channel; and
      in the locked position, the one or more collet engagement features engage the one or more inner wall engagement features to retain the locking member in the locked position, independently of any additional component besides the locking member and the intervertebral spacer, and the anti-backout member obstructs the fastener channel in order to prevent the fastener from backing out of the fastener channel;

wherein:
- the locking member channel comprises first threading configured to engage second threading formed on an inserter tool; and
- the locking member comprises a driver engagement channel configured to allow the inserter tool to pass through the locking member and couple with the intervertebral spacer.

8. The intervertebral spacer of claim 7, wherein the driver engagement channel is configured to receive a driver engagement feature of a driver tool in order to selectively rotate the locking member between the unlocked and locked positions.

9. The intervertebral spacer of claim 7, wherein the proximal end of the intervertebral spacer comprises:
- a first stop surface configured to prevent the locking member from rotating in a first direction past the unlocked position; and
- a second stop surface configured to prevent the locking member from rotating in a second direction past the locked position.

10. The intervertebral spacer of claim 7, wherein the fastener channel comprises a depth stop.

11. The intervertebral spacer of claim 7, further comprising at least one bone graft channel oriented to pass through opposing ends of the intervertebral spacer.

12. The intervertebral spacer of claim 7, wherein the at least one fastener channel comprises:
- a first fastener channel configured to receive a first fastener, the first fastener channel oriented to pass through the proximal end and the superior surface of the intervertebral spacer at a first angle; and
- a second fastener channel configured to receive a second fastener, the second fastener channel oriented to pass through the proximal end and the inferior surface of the intervertebral spacer at a second angle.

13. An intervertebral spacer comprising:
- a superior surface configured to engage a superior vertebral body;
- an inferior surface configured to engage an inferior vertebral body;
- a proximal end comprising:
  - at least one fastener channel configured to receive a fastener, the at least one fastener channel oriented to pass through the proximal end of the intervertebral spacer and the superior and/or inferior surface of the intervertebral spacer; and
  - a locking member channel comprising:
    - an inner wall; and
    - one or more inner wall engagement features; and
- a locking member comprising:
  - an anti-backout member;
  - a collet retainable within the locking member channel; and
  - one or more collet engagement features;

wherein:
- the locking member is rotatable within the locking member channel between an unlocked position and a locked position;
- in the unlocked position, the one or more collet engagement features engage the one or more inner wall engagement features in order to retain the locking member in the unlocked position, independently of any additional component besides the locking member and the intervertebral spacer, and the anti-backout member does not obstruct the fastener channel; and
- in the locked position, the one or more collet engagement features engage the one or more inner wall engagement features to retain the locking member in the locked position, independently of any additional component besides the locking member and the intervertebral spacer, and the anti-backout member obstructs the fastener channel in order to prevent the fastener from backing out of the fastener channel;

wherein the collet is compressible.

14. The intervertebral spacer of claim 13, wherein:
- the locking member channel comprises first threading configured to engage second threading formed on an inserter tool; and
- the locking member comprises a driver engagement channel configured to allow the inserter tool to pass through the locking member and couple with the intervertebral spacer.

15. The intervertebral spacer of claim 14, wherein the driver engagement channel is configured to receive a driver engagement feature of a driver tool in order to selectively rotate the locking member between the unlocked and locked positions.

16. The intervertebral spacer of claim 13, wherein the proximal end of the intervertebral spacer comprises:
- a first stop surface configured to prevent the locking member from rotating in a first direction past the unlocked position; and
- a second stop surface configured to prevent the locking member from rotating in a second direction past the locked position.

17. The intervertebral spacer of claim 13, wherein the fastener channel comprises a depth stop.

18. The intervertebral spacer of claim 13, further comprising at least one bone graft channel oriented to pass through opposing ends of the intervertebral spacer.

19. The intervertebral spacer of claim 13, wherein the at least one fastener channel comprises:
- a first fastener channel configured to receive a first fastener, the first fastener channel oriented to pass through the proximal end and the superior surface of the intervertebral spacer at a first angle; and
- a second fastener channel configured to receive a second fastener, the second fastener channel oriented to pass through the proximal end and the inferior surface of the intervertebral spacer at a second angle.

\* \* \* \* \*